United States Patent
Jagasia et al.

(10) Patent No.: US 12,104,153 B2
(45) Date of Patent: *Oct. 1, 2024

(54) ANTISENSE OLIGONUCLEOTIDE FOR TARGETING PROGRANULIN

(71) Applicant: Hoffmann-La Roche Inc., Little Falls, NJ (US)

(72) Inventors: Ravi Jagasia, Basel (CH); Lars Jonson, Horsholm (DK); Soren Rasmussen, Horsholm (DK); Jacob Ravn, Horsholm (DK); Disa Tehler, Horsholm (DK); Dorthe Vang, Horsholm (DK); Jesper Worm, Horsholm (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/552,804

(22) Filed: Dec. 16, 2021

(65) Prior Publication Data

US 2022/0204973 A1   Jun. 30, 2022

(30) Foreign Application Priority Data

Dec. 18, 2020 (EP) .................................. 20215791

(51) Int. Cl.
*C12N 15/113* (2010.01)
*C12N 15/67* (2006.01)

(52) U.S. Cl.
CPC ............ *C12N 15/113* (2013.01); *C12N 15/67* (2013.01); *C12N 2310/11* (2013.01); *C12N 2310/315* (2013.01); *C12N 2310/3231* (2013.01); *C12N 2310/3341* (2013.01); *C12N 2310/346* (2013.01)

(58) Field of Classification Search
CPC .. C12N 15/113; C12N 15/67; C12N 2310/11; C12N 2310/315; C12N 2310/3231; C12N 2310/3341; C12N 2310/346; C12N 2310/321; C12N 2320/33
See application file for complete search history.

(56) References Cited

U.S. PATENT DOCUMENTS

2019/0070213 A1* 3/2019 Aznarez ............. C12N 15/1136

FOREIGN PATENT DOCUMENTS

| JP | 2019-500348 A | 1/2019 |
|---|---|---|
| WO | 98/39352 A1 | 9/1998 |
| WO | 99/14226 A2 | 3/1999 |
| WO | 00/47599 A1 | 8/2000 |
| WO | 00/66604 A2 | 11/2000 |
| WO | 01/23613 A1 | 4/2001 |
| WO | 2004/046160 A2 | 6/2004 |
| WO | 2007/090071 A2 | 8/2007 |
| WO | 2007/134181 A2 | 11/2007 |
| WO | 2008/150729 A2 | 12/2008 |
| WO | 2008/154401 A2 | 12/2008 |
| WO | 2009/006478 A2 | 1/2009 |
| WO | 2009/067647 A1 | 5/2009 |
| WO | 2010/036698 A1 | 4/2010 |
| WO | 2010/077578 A1 | 7/2010 |
| WO | WO201088668 * | 8/2010 |
| WO | 2011/017521 A2 | 2/2011 |
| WO | 2011/156202 A1 | 12/2011 |
| WO | 2013/154798 A1 | 10/2013 |
| WO | 2014/076195 A1 | 5/2014 |
| WO | 2015/113922 A1 | 8/2015 |
| WO | 2017/106370 A1 | 6/2017 |
| WO | 2020/191212 A1 | 9/2020 |
| WO | 2021/229036 A1 | 11/2021 |

OTHER PUBLICATIONS

Shimo et al. Design and evaluation of locked nucleic acid-based splice-switching oligonucleotides in vitro, Nucleic Acids Research, 2014, 42, 8174-8187 (Year: 2014).*

Alexandros et al., "Genetic variants in progranulin upstream open reading frames increase downstream protein expression", Neurobiology of Aging, vol. 110, Sep. 10, 2021, pp. 113-121.

Eriksen et al., "Progranulin: normal function and role in neurodegeneration", Journal of Neurochemistry, vol. 104, No. 0, Jan. 1, 2008, pp. 287-297.

He et al., "Progranulin (granulin-epithelin precursor, PC-cell-derived growth factor, acrogranin) mediates tissue repair and tumorigenesis", Journal of Molecular Medicine, vol. 81, No. 10, Oct. 1, 2003, pp. 600-612.

International Search Report and Written Opinion received for PCT Patent Application No. PCT/EP2021/086167, mailed on Mar. 30, 2022, 21 pages.

Bergstrom, D.E., "Unnatural nucleosides with unusual base pairing properties," Current Protocols in Nucleic Acid Chemistry, vol. 37, 2009, pp. 1.4.1.-1.4.32.

Capell, A., et al., "Progranulin Transcripts with Short and Long 5' Untranslated Regions (UTRs) Are Differentially Expressed via Posttranscriptional and Translational Repression," The Journal of Biological Chemistry, vol. 289, Issue 37, 2014, pp. 25879-25889.

Deleavey, G.F., et al., "Designing Chemically Modified Oligonucleotides for Targeted Gene Silencing," Chemistry and Biology, vol. 19, Issue 8, 2012, pp. 937-954.

Freier, S.M., et al., "The ups and downs of nucleic acid duplex stability: structure-stability studies on chemically-modified DNA:RNA duplexes," Nucl. Acid Res, vol. 25, Issue 22, 1997, pp. 4429-4443.

Hansen, L.D., et al., "Entropy titration. A calorimetric method for the determination of ?G°(K), ?H° and ?S°," Chem. Comm, 1965, pp. 36-38.

Hirao, I., et al., "Natural versus Artificial Creation of Base Pairs in DNA: Origin of Nucleobases from the Perspectives of Unnatural Base Pair Studies," Accounts of Chemical Research, vol. 45, Issue 12, 2012, pp. 2055-2065.

(Continued)

*Primary Examiner* — J. E. Angell
*Assistant Examiner* — Keyur A Vyas
(74) *Attorney, Agent, or Firm* — Smith, Gambrell & Russell, LLP; Judy Jarecki-Black; Sharon Ngwenya

(57) ABSTRACT

The present invention relates to oligonucleotides which alter the splicing pattern of progranulin in cells, and their use in the treatment of neurological disorders.

10 Claims, 19 Drawing Sheets

Specification includes a Sequence Listing.

(56) References Cited

OTHER PUBLICATIONS

Holdgate, G.A., et al., "Measurements of binding thermodynamics in drug discovery," Drug Discov. Today, vol. 10, Issue 22, 2005, pp. 1543-1550.

Manoharan, M., "Oligonucleotide Conjugates as Potential Antisense Drugs with Improved Uptake, Biodistribution, Targeted Delivery, and Mechanism of Action," Antisense and Nucleic Acid Drug Development, vol. 12, Issue 103, (2002).

McTigue, P.M., et al., "Sequence-Dependent Thermodynamic Parameters for Locked Nucleic Acid (LNA)-DNA Duplex Formation," Biochemistry, vol. 43, Issue 18, 2004, pp. 5388-5405.

Mergny, J.L., et al., "Analysis of Thermal Melting Curves," Oligonucleotides, vol. 13, Issue 6, 2003, pp. 515-537.

Mitsuoka, Y., et al., "A bridged nucleic acid, 2',4'-BNA COC : synthesis of fully modified oligonucleotides bearing thymine, 5-methylcytosine, adenine and guanine 2',4'-BNA COC monomers and RNA-selective nucleic-acid recognition," Nucleic Acids Research, vol. 37, Issue 4, 2009, pp. 1225-1238.

Morita, K., et al., "2'-O,4'-C-ethylene-bridged nucleic acids (ENA): highly nuclease-resistant and thermodynamically stable oligonucleotides for antisense drug," Bioorganic & Med. Chem. Lett., vol. 12, Issue 1, 2002, pp. 73-76.

Petkau, T.L., et al., "Progranulin Expression in the Developing Adult Murine Brain", The J. of Comp. Neurology, vol. 518, 2010, pp. 3931-3947.

Santalucia, J., "A unified view of polymer, dumbbell, and oligonucleotide DNA nearest-neighbor?thermodynamics," Proc. Natl. Acad. Sci. USA, vol. 95, 1998, pp. 1460-1465.

Seth, P.P., et al., "Synthesis and Biophysical Evaluation of 2',4'-Constrained 2'O-Methoxyethyl and 2',4'-Constrained 2'O-Ethyl Nucleic Acid Analogues," J. Org. Chem, vol. 75, issue 5, 2010, pp. 1569-1581.

Sugimoto, N., et al., "Thermodynamic Parameters To Predict Stability of RNA/DNA Hybrid Duplexes," Biochemistry, vol. 34, 1995, pp. 11211-11216.

Townley, R.A., et al., "Progranulin Functions and neurologic correlations," Neurology, vol. 90, Issue 24, 2018, pp. 118-125.

Uhlmann,"Recent advances in the medicinal chemistry of antisense oligonucleotides," Curr. Opinion in Drug Development, vol. 3, Issue 2, 2000, pp. 203-213.

Wan, W.B., et al., "The Medicinal Chemistry of Therapeutic Oligonucleotides," Medical Chemistry, vol. 59, Issue 21, 2016, pp. 9645-9667.

Office Action received for Taiwanese Patent Application No. 110147220, mailed on Feb. 22, 2023, 16 pages (6 pages of English Translation and 10 pages of Original Document).

\* cited by examiner

```
                                                              SEQ ID#134
GTAGGAGAGCGGGCCGCCAGACCTCTCGCCTGCTCCTGCCCAGGGCCCCCCAGGGCCATGTGAGCTTGAGGTTCCCCTG

SEQ ID#73, 74, 75
GAGTCTCAGCCCGGAGACAACAGAAGAACCGCTTACTGAAACTCCTTGGGGTTCTGATACACTAGGGGGAGTTTTATGGG

AAAGAGGAAGCAGTAATTGCAGTGACGCCCCGTTAGAGCTTTCTACCCCCCAGCATTCCCCCAAAGCAGGAGGACCACACC

ATTCTTGACCCAGCTCCACCCCCTGTCGgtaggtg
```

FIG. 4

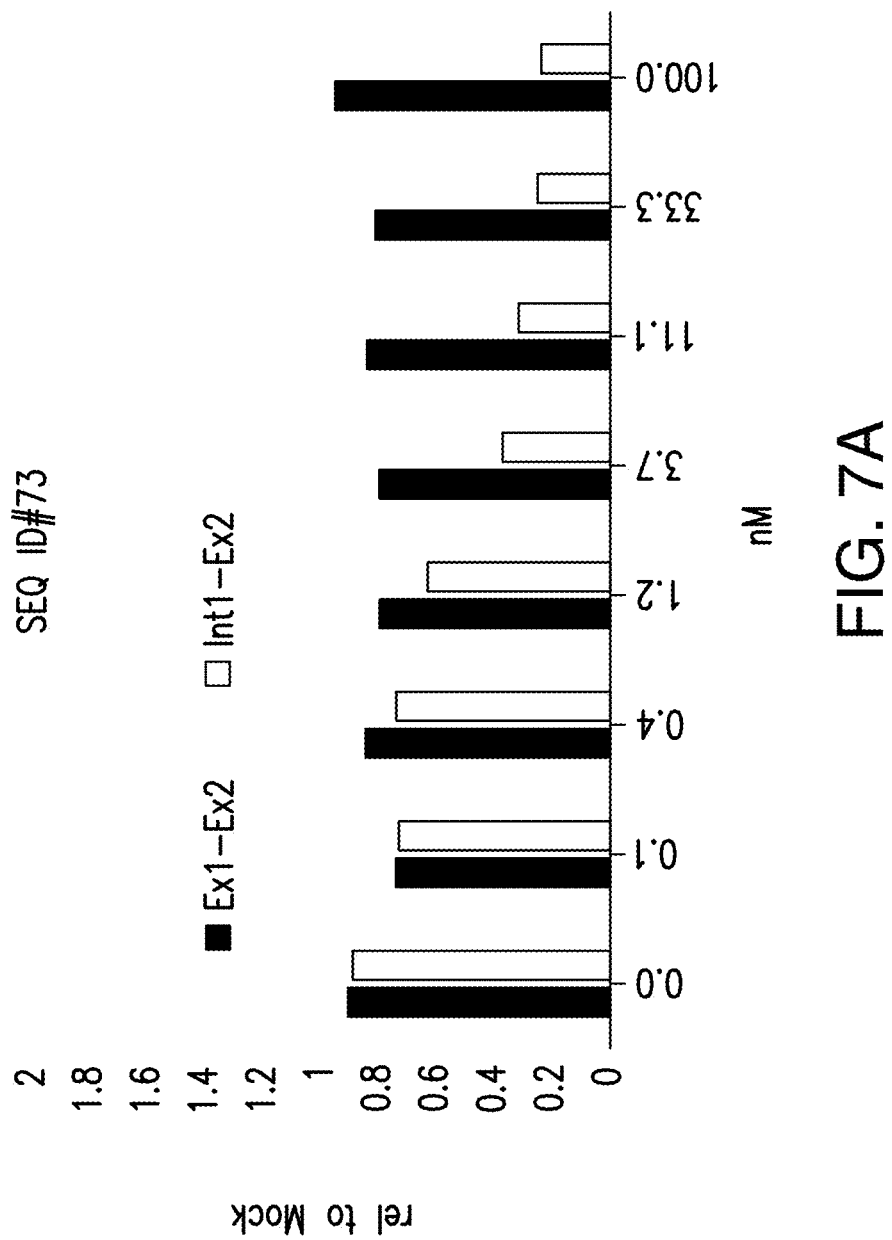

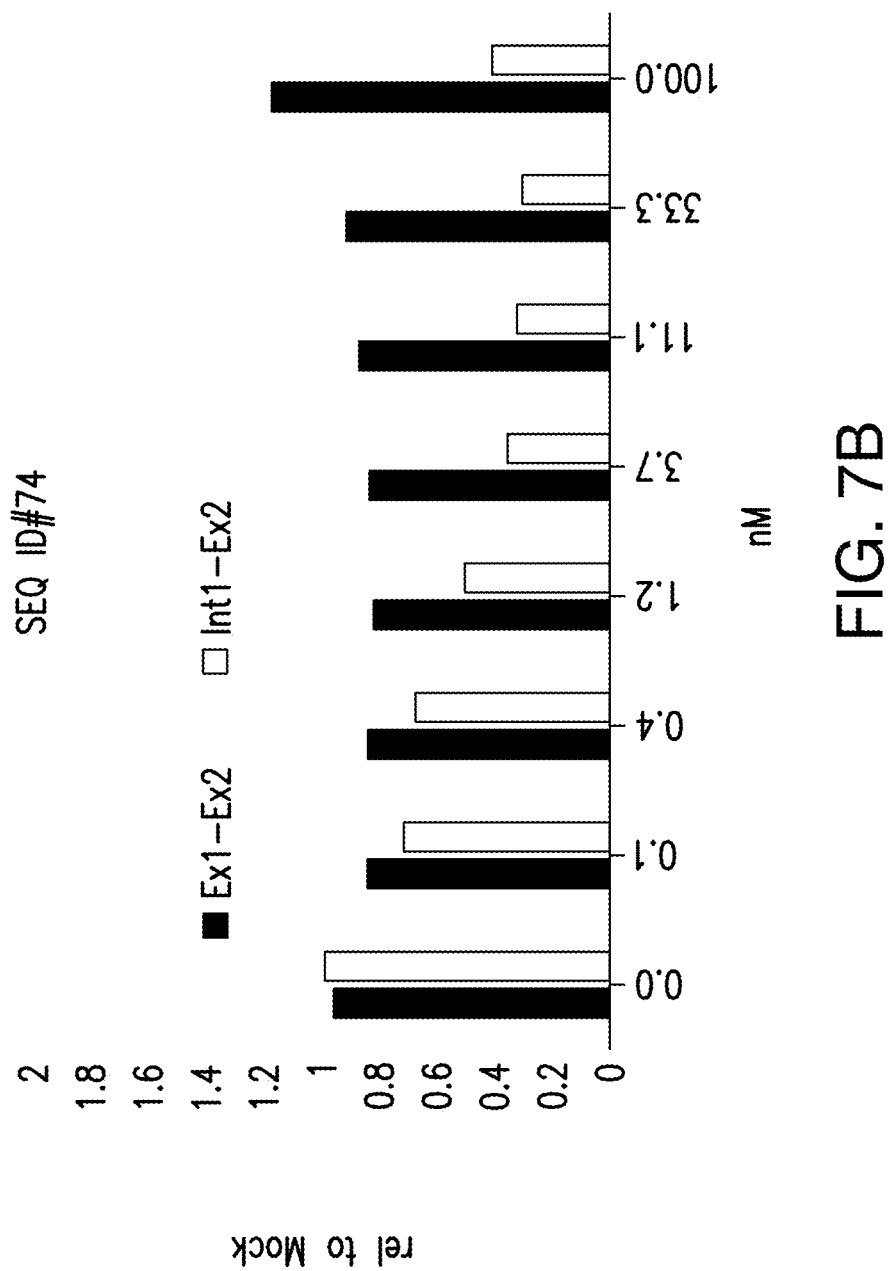

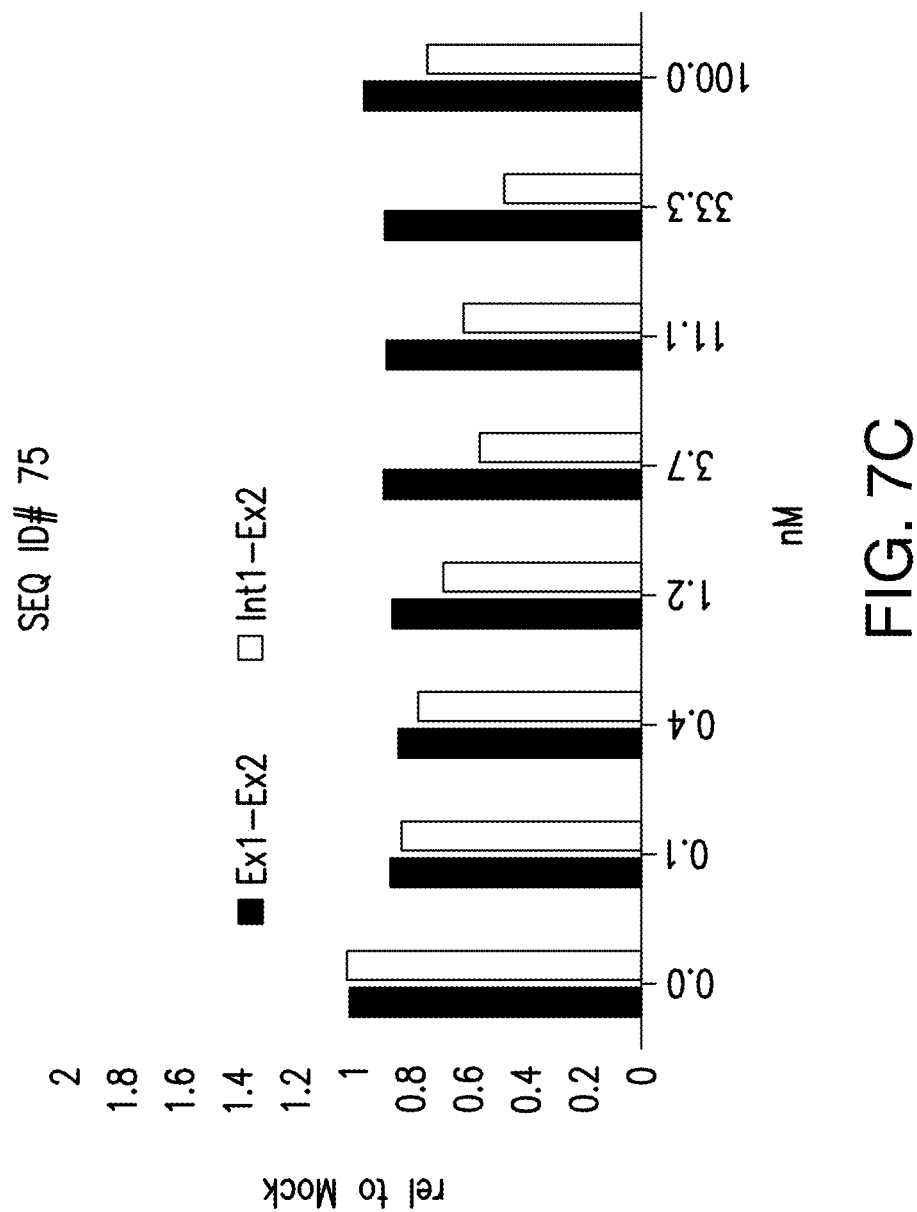

SEQUENCE LISTING

<160> NUMBER OF SEQ ID NOS: 292

<210> SEQ ID NO 1
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 1
tgcgtccgac tccgcg                                                    16

```
<210> SEQ ID NO 2
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 2
gtccgactcc gcggtc                                                       16

<210> SEQ ID NO 3
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 3
cgactccgcg gtcctt                                                       16

<210> SEQ ID NO 4
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 4
ctccgcggtc cttggg                                                       16

<210> SEQ ID NO 5
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 5
cgcggtcctt gggcag                                                       16

<210> SEQ ID NO 6
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 6
ggtccttggg cagcag                                                       16

<210> SEQ ID NO 7
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 7
ccttgggcag cagcaa                                                       16

<210> SEQ ID NO 8
<211> LENGTH: 16
<212> TYPE: DNA
<213> ORGANISM: Artificial Sequence
<220> FEATURE:
```

```
<223> OTHER INFORMATION: antisense oligonucleotide

<400> SEQUENCE: 8
tgggcagcag caaccg                                                    16

<210> SEQ ID NO 9
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 9
gcagcagcaa ccgggt                                                    16

<210> SEQ ID NO 10
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 10
gcagcaaccg ggtagc                                                    16

<210> SEQ ID NO 11
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 11
gcaaccgggt agcgct                                                    16

<210> SEQ ID NO 12
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 12
accgggtagc gctcag                                                    16

<210> SEQ ID NO 13
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 13
gggtagcgct cagact                                                    16

<210> SEQ ID NO 14
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 14
tagcgctcag actaca                                                    16
```

```
<210> SEQ ID NO 15
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 15
cgctcagact acagac                                                    16

<210> SEQ ID NO 16
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 16
tcagactaca gacccc                                                    16

<210> SEQ ID NO 17
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 17
gactacagac cccagc                                                    16

<210> SEQ ID NO 18
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 18
tacagacccc agcgcg                                                    16

<210> SEQ ID NO 19
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 19
agtccctact accttc                                                    16

<210> SEQ ID NO 20
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 20
ccctactacc ttcgag                                                    16

<210> SEQ ID NO 21
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 21
tactaccttc gagaag                                              16

<210> SEQ ID NO 22
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 22
taccttcgag aagcca                                              16

<210> SEQ ID NO 23
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 23
cttcgagaag ccaagg                                              16

<210> SEQ ID NO 24
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 24
cgagaagcca aggtct                                              16

<210> SEQ ID NO 25
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 25
gaagccaagg tctcag                                              16

<210> SEQ ID NO 26
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 26
gccaaggtct caggtc                                              16

<210> SEQ ID NO 27
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 27
aaggtctcag gtctcg                                              16

<210> SEQ ID NO 28
<211> LENGTH: 16
```

```
<212> TYPE: DNA
<213> ORGANISM: Artificial Sequence
<220> FEATURE:
<223> OTHER INFORMATION: antisense oligonucleotide

<400> SEQUENCE: 28
gtctcaggtc tcgttc                                                        16

<210> SEQ ID NO 29
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 29
tcaggtctcg ttccca                                                        16

<210> SEQ ID NO 30
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 30
ggtctcgttc ccaggc                                                        16

<210> SEQ ID NO 31
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 31
ctcgttccca ggccct                                                        16

<210> SEQ ID NO 32
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 32
gttcccaggc cctcgg                                                        16

<210> SEQ ID NO 33
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 33
cccaggccct cggagc                                                        16

<210> SEQ ID NO 34
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 34
```

```
aggccctcgg agctcc                                                   16

<210> SEQ ID NO 35
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 35
ccctcggagc tcccag                                                   16

<210> SEQ ID NO 36
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 36
tcggagctcc cagccc                                                   16

<210> SEQ ID NO 37
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 37
gagctcccag cccagg                                                   16

<210> SEQ ID NO 38
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 38
ctcccagccc agggtc                                                   16

<210> SEQ ID NO 39
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 39
ccagcccagg gtcgcg                                                   16

<210> SEQ ID NO 40
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 40
gcccagggtc gcgcgc                                                   16

<210> SEQ ID NO 41
<211> LENGTH: 16
<212> TYPE: DNA
<213> ORGANISM: Artificial Sequence
```

```
<220> FEATURE:
<223> OTHER INFORMATION: antisense oligonucleotide

<400> SEQUENCE: 41
cagggtcgcg cgcccc                                                    16

<210> SEQ ID NO 42
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 42
ggtcgcgcgc ccctcc                                                    16

<210> SEQ ID NO 43
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 43
cgcgcgcccc tccggc                                                    16

<210> SEQ ID NO 44
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 44
gcgcccctcc ggctcc                                                    16

<210> SEQ ID NO 45
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 45
cccctccggc tccagg                                                    16

<210> SEQ ID NO 46
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 46
ctccggctcc aggccg                                                    16

<210> SEQ ID NO 47
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 47
cggctccagg ccgccg                                                    16
```

```
<210> SEQ ID NO 48
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 48
ctccaggccg ccgcgg                                                    16

<210> SEQ ID NO 49
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 49
caggccgccg cgggaa                                                    16

<210> SEQ ID NO 50
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 50
gccgcgggaa ccaccc                                                    16

<210> SEQ ID NO 51
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 51
gcgggaacca cccacc                                                    16

<210> SEQ ID NO 52
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 52
ggaaccaccc accacc                                                    16

<210> SEQ ID NO 53
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 53
accacccacc accacc                                                    16

<210> SEQ ID NO 54
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 54
acccaccacc accagg                                                    16

<210> SEQ ID NO 55
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 55
caccaccacc aggaga                                                    16

<210> SEQ ID NO 56
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 56
caccaccagg agaggg                                                    16

<210> SEQ ID NO 57
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 57
caccaggaga ggggaa                                                    16

<210> SEQ ID NO 58
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 58
caggagaggg gaagaa                                                    16

<210> SEQ ID NO 59
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 59
gagaggggaa gaagcc                                                    16

<210> SEQ ID NO 60
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 60
aggggaagaa gccagc                                                    16

<210> SEQ ID NO 61
```

```
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 61
ggaagaagcc agcacc                                                    16

<210> SEQ ID NO 62
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 62
agaagccagc acctac                                                    16

<210> SEQ ID NO 63
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 63
agccagcacc taccga                                                    16

<210> SEQ ID NO 64
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 64
cagcacctac cgacag                                                    16

<210> SEQ ID NO 65
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 65
cacctaccga cagggg                                                    16

<210> SEQ ID NO 66
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 66
ctaccgacag gggtgg                                                    16

<210> SEQ ID NO 67
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 67
```
ccgacagggg tggagc                                                       16

<210> SEQ ID NO 68
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 68 acagggtgg agctgg                                                        16

<210> SEQ ID NO 69
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 69
ggggtggagc tgggtc                                                       16

<210> SEQ ID NO 70
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 70
gtggagctgg gtcaag                                                       16

<210> SEQ ID NO 71
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 71
gagctgggtc aagaat                                                       16

<210> SEQ ID NO 72
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 72
ctgggtcaag aatggt                                                       16

<210> SEQ ID NO 73
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 73
ggtcaagaat ggtgtg                                                       16

<210> SEQ ID NO 74
<211> LENGTH: 16
<212> TYPE: DNA

```
<213> ORGANISM: Artificial Sequence
<220> FEATURE:
<223> OTHER INFORMATION: antisense oligonucleotide

<400> SEQUENCE: 74
caagaatggt gtggtc                                                      16

<210> SEQ ID NO 75
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 75
gaatggtgtg gtccct                                                      16

<210> SEQ ID NO 76
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 76
tggtgtggtc cctgct                                                      16

<210> SEQ ID NO 77
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 77
tgtggtccct gctttg                                                      16

<210> SEQ ID NO 78
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 78
ggtccctgct ttgggg                                                      16

<210> SEQ ID NO 79
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 79
ccctgctttg ggggaa                                                      16

<210> SEQ ID NO 80
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 80
tgctttgggg gaatgc                                                      16
```

```
<210> SEQ ID NO 81
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 81
tttgggggaa tgctgg                                                   16

<210> SEQ ID NO 82
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 82 ggggaatgc tgggga                                                    16

<210> SEQ ID NO 83
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 83
ggaatgctgg ggaggt                                                   16

<210> SEQ ID NO 84
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 84
atgctgggga ggtaga                                                   16

<210> SEQ ID NO 85
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 85
ctggggaggt agaaag                                                   16

<210> SEQ ID NO 86
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 86
gggaggtaga aagccc                                                   16

<210> SEQ ID NO 87
<211> LENGTH: 16
<212> TYPE: DNA
<213> ORGANISM: Artificial Sequence
<220> FEATURE:
```

<223> OTHER INFORMATION: antisense oligonucleotide

<400> SEQUENCE: 87
aggtagaaag cccctt                                                        16

<210> SEQ ID NO 88
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 88
tagaaagccc cttcta                                                        16

<210> SEQ ID NO 89
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 89
aaagcccctt ctaacg                                                        16

<210> SEQ ID NO 90
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 90
gccccttcta acgggg                                                        16

<210> SEQ ID NO 91
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 91
ccttctaacg gggcgt                                                        16

<210> SEQ ID NO 92
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 92
tctaacgggg cgtcac                                                        16

<210> SEQ ID NO 93
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 93
aacggggcgt cactgc                                                        16

```
<210> SEQ ID NO 94
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 94
ggggcgtcac tgcaat                                                       16

<210> SEQ ID NO 95
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 95
gcgtcactgc aattac                                                       16

<210> SEQ ID NO 96
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 96
tcactgcaat tactgc                                                       16

<210> SEQ ID NO 97
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 97
ctgcaattac tgcttc                                                       16

<210> SEQ ID NO 98
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 98
caattactgc ttcctc                                                       16

<210> SEQ ID NO 99
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 99
ttactgcttc ctcttt                                                       16

<210> SEQ ID NO 100
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 100
ctgcttcctc tttccc                                                    16

<210> SEQ ID NO 101
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 101
cttcctcttt cccata                                                    16

<210> SEQ ID NO 102
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 102
cctctttccc ataaaa                                                    16

<210> SEQ ID NO 103
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 103
ctttcccata aaactc                                                    16

<210> SEQ ID NO 104
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 104
tcccataaaa ctcccc                                                    16

<210> SEQ ID NO 105
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 105
cataaaactc cccta                                                     16

<210> SEQ ID NO 106
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 106
aaaactcccc ctagtg                                                    16

<210> SEQ ID NO 107
<211> LENGTH: 16
```

```
<212> TYPE: DNA
<213> ORGANISM: Artificial Sequence
<220> FEATURE:
<223> OTHER INFORMATION: antisense oligonucleotide

<400> SEQUENCE: 107
actcccccta gtgtat                                                         16

<210> SEQ ID NO 108
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 108 cccctagtg tatcag                                                          16

<210> SEQ ID NO 109
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 109
cctagtgtat cagaac                                                         16

<210> SEQ ID NO 110
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 110
agtgtatcag aacccc                                                         16

<210> SEQ ID NO 111
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 111
gtatcagaac ccccaa                                                         16

<210> SEQ ID NO 112
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 112
tcagaacccc caagga                                                         16

<210> SEQ ID NO 113
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 113
``` gaaccccccaa ggagtt                                                  16

<210> SEQ ID NO 114
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 114
cccccaagga gtttca                                                   16

<210> SEQ ID NO 115
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 115
ccaaggagtt tcagta                                                   16

<210> SEQ ID NO 116
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 116
aggagtttca gtaagc                                                   16

<210> SEQ ID NO 117
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 117
agtttcagta agcggt                                                   16

<210> SEQ ID NO 118
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 118
ttcagtaagc ggttct                                                   16

<210> SEQ ID NO 119
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 119
agtaagcggt tcttct                                                   16

<210> SEQ ID NO 120
<211> LENGTH: 16
<212> TYPE: DNA
<213> ORGANISM: Artificial Sequence

```
<220> FEATURE:
<223> OTHER INFORMATION: antisense oligonucleotide

<400> SEQUENCE: 120
aagcggttct tctgtt                                               16

<210> SEQ ID NO 121
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 121
cggttcttct gttgtc                                               16

<210> SEQ ID NO 122
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 122
ttcttctgtt gtctcc                                               16

<210> SEQ ID NO 123
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 123
ttctgttgtc tccggc                                               16

<210> SEQ ID NO 124
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 124
tgttgtctcc ggctga                                               16

<210> SEQ ID NO 125
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 125
tgtctccggc tgagac                                               16

<210> SEQ ID NO 126
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 126
ctccggctga gactcc                                               16
```

```
<210> SEQ ID NO 127
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 127
cggctgagac tccagg                                                      16

<210> SEQ ID NO 128
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 128
ctgagactcc agggga                                                      16

<210> SEQ ID NO 129
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 129
agactccagg ggaacc                                                      16

<210> SEQ ID NO 130
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 130
ctccagggga acctca                                                      16

<210> SEQ ID NO 131
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 131
caggggaacc tcaagc                                                      16

<210> SEQ ID NO 132
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 132
gggaacctca agctca                                                      16

<210> SEQ ID NO 133
<211> LENGTH: 16
<212> TYPE: DNA
<213> ORGANISM: Artificial Sequence
<220> FEATURE:
<223> OTHER INFORMATION: antisense oligonucleotide
```

-continued

```
<400> SEQUENCE: 133
aacctcaagc tcacat                                                    16

<210> SEQ ID NO 134
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 134
ctcaagctca catggc                                                    16

<210> SEQ ID NO 135
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 135
aagctcacat ggccct                                                    16

<210> SEQ ID NO 136
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 136
ctcacatggc cctggc                                                    16

<210> SEQ ID NO 137
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 137
acatggccct ggcggg                                                    16

<210> SEQ ID NO 138
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 138
tggccctggc gggccc                                                    16

<210> SEQ ID NO 139
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 139
ccctggcggg ccctg                                                     16

<210> SEQ ID NO 140
```

```
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 140
tggcgggccc ctgggc                                                     16

<210> SEQ ID NO 141
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 141
cgggcccctg ggcagg                                                     16

<210> SEQ ID NO 142
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 142
gcccctgggc aggagc                                                     16

<210> SEQ ID NO 143
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 143
cctgggcagg agcagg                                                     16

<210> SEQ ID NO 144
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 144
gggcaggagc aggcga                                                     16

<210> SEQ ID NO 145
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 145
caggagcagg cgagag                                                     16

<210> SEQ ID NO 146
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 146
```

-continued gagcaggcga gaggtc				16

<210> SEQ ID NO 147
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 147
caggcgagag gtctgc				16

<210> SEQ ID NO 148
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 148
gcgagaggtc tgcgcg				16

<210> SEQ ID NO 149
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 149
agaggtctgc gcggcc				16

<210> SEQ ID NO 150
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 150
ggtctgcgcg gccgct				16

<210> SEQ ID NO 151
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 151
ctgcgcggcc gctctc				16

<210> SEQ ID NO 152
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 152
cgcggccgct ctccta				16

<210> SEQ ID NO 153
<211> LENGTH: 16
<212> TYPE: DNA

```
<213> ORGANISM: Artificial Sequence
<220> FEATURE:
<223> OTHER INFORMATION: antisense oligonucleotide

<400> SEQUENCE: 153
ggccgctctc ctacct                                                      16

<210> SEQ ID NO 154
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 154
cgctctccta cctgcg                                                      16

<210> SEQ ID NO 155
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 155
tctcctacct gcgtcc                                                      16

<210> SEQ ID NO 156
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 156
cctacctgcg tccgac                                                      16

<210> SEQ ID NO 157
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 157
acctgcgtcc gactcc                                                      16

<210> SEQ ID NO 158
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 158
ggggaagaag ccagca                                                      16

<210> SEQ ID NO 159
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 159
gggaagaagc cagcac                                                      16
```

```
<210> SEQ ID NO 160
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 160
gaagaagcca gcacct                                                      16

<210> SEQ ID NO 161
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 161
aagaagccag caccta                                                      16

<210> SEQ ID NO 162
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 162
gaagccagca cctacc                                                      16

<210> SEQ ID NO 163
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 163
aagccagcac ctaccg                                                      16

<210> SEQ ID NO 164
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 164
gccagcacct accgac                                                      16

<210> SEQ ID NO 165
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 165
ccagcaccta ccgaca                                                      16

<210> SEQ ID NO 166
<211> LENGTH: 16
<212> TYPE: DNA
<213> ORGANISM: Artificial Sequence
<220> FEATURE:
```

<223> OTHER INFORMATION: antisense oligonucleotide

<400> SEQUENCE: 166
agcacctacc gacagg                                                    16

<210> SEQ ID NO 167
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 167
gcacctaccg acaggg                                                    16

<210> SEQ ID NO 168
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 168
acctaccgac aggggt                                                    16

<210> SEQ ID NO 169
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 169
cctaccgaca ggggtg                                                    16

<210> SEQ ID NO 170
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 170
taccgacagg ggtgga                                                    16

<210> SEQ ID NO 171
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 171
accgacaggg gtggag                                                    16

<210> SEQ ID NO 172
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 172
cgacaggggt ggagct                                                    16

```
<210> SEQ ID NO 173
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 173
gacaggggtg gagctg                                                   16

<210> SEQ ID NO 174
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 174
caggggtgga gctggg                                                   16

<210> SEQ ID NO 175
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 175
aggggtggag ctgggt                                                   16

<210> SEQ ID NO 176
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 176
gggtggagct gggtca                                                   16

<210> SEQ ID NO 177
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 177
ggtggagctg ggtcaa                                                   16

<210> SEQ ID NO 178
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 178
tggagctggg tcaaga                                                   16

<210> SEQ ID NO 179
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 179
ggagctgggt caagaa                                              16

<210> SEQ ID NO 180
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 180
cagaagggga cggcag                                              16

<210> SEQ ID NO 181
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 181
aaggggacgg cagcag                                              16

<210> SEQ ID NO 182
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 182
gggacggcag cagctg                                              16

<210> SEQ ID NO 183
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 183
acggcagcag ctgtag                                              16

<210> SEQ ID NO 184
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 184
gcagcagctg tagctg                                              16

<210> SEQ ID NO 185
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 185
gcagctgtag ctggct                                              16

<210> SEQ ID NO 186
<211> LENGTH: 16
```

```
<212> TYPE: DNA
<213> ORGANISM: Artificial Sequence
<220> FEATURE:
<223> OTHER INFORMATION: antisense oligonucleotide

<400> SEQUENCE: 186
gctgtagctg gctcct                                                     16

<210> SEQ ID NO 187
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 187
gtagctggct cctccg                                                     16

<210> SEQ ID NO 188
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 188
gctggctcct ccgggg                                                     16

<210> SEQ ID NO 189
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 189
ggctcctccg gggtcc                                                     16

<210> SEQ ID NO 190
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 190
tcctccgggg tccagg                                                     16

<210> SEQ ID NO 191
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 191
tccggggtcc aggcag                                                     16

<210> SEQ ID NO 192
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 192
```

```
ggggtccagg cagcag                                                          16

<210> SEQ ID NO 193
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 193
gtccaggcag caggcc                                                          16

<210> SEQ ID NO 194
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 194
caggcagcag gccaca                                                          16

<210> SEQ ID NO 195
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 195
gcagcaggcc acaggg                                                          16

<210> SEQ ID NO 196
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 196
gcaggccaca gggcag                                                          16

<210> SEQ ID NO 197
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 197
ggccacaggg cagaac                                                          16

<210> SEQ ID NO 198
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 198
cacagggcag aactga                                                          16

<210> SEQ ID NO 199
<211> LENGTH: 16
<212> TYPE: DNA
<213> ORGANISM: Artificial Sequence
```

```
<220> FEATURE:
<223> OTHER INFORMATION: antisense oligonucleotide

<400> SEQUENCE: 199
agggcagaac tgacca                                                    16

<210> SEQ ID NO 200
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 200
gcagaactga ccatct                                                    16

<210> SEQ ID NO 201
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 201
gaactgacca tctggg                                                    16

<210> SEQ ID NO 202
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 202
ctgaccatct gggcac                                                    16

<210> SEQ ID NO 203
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 203
accatctggg caccgc                                                    16

<210> SEQ ID NO 204
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 204
atctgggcac cgcgtt                                                    16

<210> SEQ ID NO 205
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 205
tgggcaccgc gttcca                                                    16
```

<210> SEQ ID NO 206
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 206
gcaccgcgtt ccagcc    16

<210> SEQ ID NO 207
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 207
ccgcgttcca gccacc    16

<210> SEQ ID NO 208
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 208
cgttccagcc accagc    16

<210> SEQ ID NO 209
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 209
tccagccacc agccct    16

<210> SEQ ID NO 210
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 210
agccaccagc cctgct    16

<210> SEQ ID NO 211
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 211
caccagccct gctgtt    16

<210> SEQ ID NO 212
<211> LENGTH: 16
<212> TYPE: DNA
<213> ORGANISM: Artificial Sequence
<220> FEATURE:
<223> OTHER INFORMATION: antisense oligonucleotide

```
<400> SEQUENCE: 212
cagccctgct gttaag                                                   16

<210> SEQ ID NO 213
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 213
ccctgctgtt aaggcc                                                   16

<210> SEQ ID NO 214
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 214
tgctgttaag gccacc                                                   16

<210> SEQ ID NO 215
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 215
tgttaaggcc acccag                                                   16

<210> SEQ ID NO 216
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 216
taaggccacc cagctc                                                   16

<210> SEQ ID NO 217
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 217
ggccacccag ctcacc                                                   16

<210> SEQ ID NO 218
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 218
cacccagctc accagg                                                   16

<210> SEQ ID NO 219
```

```
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 219
ccagctcacc agggtc                                                     16

<210> SEQ ID NO 220
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 220
gctcaccagg gtccac                                                     16

<210> SEQ ID NO 221
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 221
caccagggtc cacatg                                                     16

<210> SEQ ID NO 222
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 222
cagggtccac atggtc                                                     16

<210> SEQ ID NO 223
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 223
ggtccacatg gtctgc                                                     16

<210> SEQ ID NO 224
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 224
ccacatggtc tgcctg                                                     16

<210> SEQ ID NO 225
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 225
```

-continued catggtctgc ctgcaa                                              16

<210> SEQ ID NO 226
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 226
ggtctgcctg caaagt                                              16

<210> SEQ ID NO 227
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 227
ctgcctgcaa agtacc                                              16

<210> SEQ ID NO 228
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 228
cctgcaaagt accaag                                              16

<210> SEQ ID NO 229
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 229
gcaaagtacc aaggaa                                              16

<210> SEQ ID NO 230
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 230
aagtaccaag gaacgt                                              16

<210> SEQ ID NO 231
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 231
taccaaggaa cgtctg                                              16

<210> SEQ ID NO 232
<211> LENGTH: 16
<212> TYPE: DNA

```
<213> ORGANISM: Artificial Sequence
<220> FEATURE:
<223> OTHER INFORMATION: antisense oligonucleotide

<400> SEQUENCE: 232
caaggaacgt ctggca                                                     16

<210> SEQ ID NO 233
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 233
ggaacgtctg gcaact                                                     16

<210> SEQ ID NO 234
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 234
acgtctggca actgct                                                     16

<210> SEQ ID NO 235
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 235
tctggcaact gcttaa                                                     16

<210> SEQ ID NO 236
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 236
ggcaactgct taagcc                                                     16

<210> SEQ ID NO 237
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 237
aactgcttaa gcccac                                                     16

<210> SEQ ID NO 238
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 238
tgcttaagcc cacgcc                                                     16
```

<210> SEQ ID NO 239
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 239
ttaagcccac gccacc                                                       16

<210> SEQ ID NO 240
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 240
agcccacgcc accctt                                                       16

<210> SEQ ID NO 241
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 241
ccacgccacc cttgat                                                       16

<210> SEQ ID NO 242
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 242
cgccaccctt gattct                                                       16

<210> SEQ ID NO 243
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 243
cacccttgat tctagg                                                       16

<210> SEQ ID NO 244
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 244
ccttgattct agggtc                                                       16

<210> SEQ ID NO 245
<211> LENGTH: 16
<212> TYPE: DNA
<213> ORGANISM: Artificial Sequence
<220> FEATURE:

```
<223> OTHER INFORMATION: antisense oligonucleotide

<400> SEQUENCE: 245
tgattctagg gtcact                                                   16

<210> SEQ ID NO 246
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 246
ttctagggtc actcag                                                   16

<210> SEQ ID NO 247
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 247
tagggtcact cagtac                                                   16

<210> SEQ ID NO 248
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 248
ggtcactcag taccct                                                   16

<210> SEQ ID NO 249
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 249
cactcagtac cctagc                                                   16

<210> SEQ ID NO 250
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 250
tcagtaccct agcccc                                                   16

<210> SEQ ID NO 251
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 251
gtaccctagc cccagg                                                   16
```

```
<210> SEQ ID NO 252
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 252
ccctagcccc aggcca                                                     16

<210> SEQ ID NO 253
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 253
tagccccagg ccaagg                                                     16

<210> SEQ ID NO 254
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 254
ccccaggcca aggtcc                                                     16

<210> SEQ ID NO 255
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 255
caggccaagg tcctgg                                                     16

<210> SEQ ID NO 256
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 256
gccaaggtcc tggccc                                                     16

<210> SEQ ID NO 257
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 257
aaggtcctgg cccagg                                                     16

<210> SEQ ID NO 258
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 258
gtcctggccc aggact                                                16

<210> SEQ ID NO 259
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 259
ctggcccagg actgcc                                                16

<210> SEQ ID NO 260
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 260
gcccaggact gcctga                                                16

<210> SEQ ID NO 261
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 261
caggactgcc tgagcc                                                16

<210> SEQ ID NO 262
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 262
gactgcctga gccttc                                                16

<210> SEQ ID NO 263
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 263
tgcctgagcc ttctca                                                16

<210> SEQ ID NO 264
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 264
ctgagccttc tcaaca                                                16

<210> SEQ ID NO 265
<211> LENGTH: 16
```

```
<212> TYPE: DNA
<213> ORGANISM: Artificial Sequence
<220> FEATURE:
<223> OTHER INFORMATION: antisense oligonucleotide

<400> SEQUENCE: 265
agccttctca acacct                                                    16

<210> SEQ ID NO 266
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 266
cttctcaaca cctccc                                                    16

<210> SEQ ID NO 267
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 267
ctcaacacct ccctgt                                                    16

<210> SEQ ID NO 268
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 268
aacacctccc tgtcca                                                    16

<210> SEQ ID NO 269
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 269
acctccctgt ccaggc                                                    16

<210> SEQ ID NO 270
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 270
tccctgtcca ggcagg                                                    16

<210> SEQ ID NO 271
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 271
```

```
ctgtccaggc aggcag                                                    16

<210> SEQ ID NO 272
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 272
tccaggcagg cagaaa                                                    16

<210> SEQ ID NO 273
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 273
aggcaggcag aaatct                                                    16

<210> SEQ ID NO 274
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 274
caggcagaaa tctgca                                                    16

<210> SEQ ID NO 275
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 275
gcagaaatct gcaggg                                                    16

<210> SEQ ID NO 276
<211> LENGTH: 4180
<212> TYPE: DNA
<213> ORGANISM: Homo sapiens

<400> SEQUENCE: 276
ggcgagagga agcagggagg agagtgattt gagtagaaaa gaaacacagc attccaggct    60
ggccccacct ctatattgat aagtagccaa tgggagcggg tagccctgat ccctggccaa   120
tggaaactga ggtaggcggg tcatcgcgct ggggtctgta gtctgagcgc tacccggttg   180
ctgctgccca aggaccgcgg agtcggacgc aggtaggaga gcggccgcgc agacctctcg   240
cctgctcctg cccaggggcc cgccagggcc atgtgagctt gaggttcccc tggagtctca   300
gccggagaca acagaagaac cgcttactga aactccttgg gggttctgat acactagggg   360
gagttttatg ggaaagagga agcagtaatt gcagtgacgc cccgttagaa ggggcttttct   420 acctccccag cattccccca aagcagggac cacaccattc ttgacccagc tccacccctg   480
tcggtaggtg ctggcttctt cccctctcct ggtggtggtg ggtggttccc gcggcggcct   540
ggagccggag gggcgcgcga ccctgggctg ggagctccga gggcctggga acagacctg    600 agaccttggc ttctcgaagg tagtagggac ttggagtggg tgactgaacc tggtctggct   660
```

```
cctccttact tcctcttgtt gcgggtggga cgagctagct tccgcctctc ccagccactt      720
tttcctgctc atttgcagct aggttggctc ccctttgggg aatttcctct ccccttggca      780
ctcggagttg gggggtgcca cctagtggaa gataacggag ctagggtctt gaagaggctg      840
ctgtcccctc tggctgtttt ggcggtgtag ggtggcatga gagactgcga ctcgcctcct      900
catccctgtt tctgtatgcg agtgcttgta ttcagtagaa gcatacacta tactccctca      960
atttagggta aacaggaggg gccacatgca caggtaattc accagggagc cgaacactcc     1020
tgtgcagaca gactccccct cccagcaagc catggcagcg gacagcctgc tgagaacacc     1080
caggaagcag gcggtgccag ctgcaggtgc tttgcctggg agctgtgggg ctgaggagag     1140
ggtccactgt ccaggaccag tgaacttcat ccttatctgt ccaggaggtg gcctcttggg     1200
gatgctgagt taggggaggg gcacttgagg aaagccaggt ggagcagaga ggatgtgagt     1260
gactgggtgg gtgagatttc ctgcccctcc ccccgcagtg gtatccacac ctagactcgt     1320
ggggtaactg aggcacagac agagagcaac ttctcaggcc ctcacagttg gcaattctag     1380
gattaggacc caagtgcgat tttcaggcag tccctgtacc ctgtttctgt tgtacctgtt     1440
gcaccattcc caggcactgc ccatcgtgcc actagtgata tgaacccagg tccaatacgc     1500
tctgggccca tcaaagcctg acgtcaccat gacctgatgt gtgacgtgtt ataggtgtcc     1560
cttggtatct tcacggaact ggttccagga ccccaaaatc tgtgggtgct caagcccctg     1620
agataaaatg gtgtaatatt tgcatataac ctatacatac tttaaatcat ttctagatta     1680
cttataccta atacaatgga aatgacatgt cggctgggcg tggtggctca tgcctgtaat     1740
cccaccactt tgggaggccg tggcaggtgg atcacctgag gtctggagtt tgagaccagc     1800
ctgaccaaca tggtgaaacc cccatctcta ctaaaaatac aaaaattagc caggtgtggt     1860
agcgcacacc tataatccca cctacttggg aggctgaggc aggagaattg cttgaacctg     1920
ggaggcggag ttcgcagtaa gctgagatcg cgccactgta ctacagcctg ggtgacagag     1980
caggactcca tctcaaaaaa aaaagagaaa aagaaaaaga aatgccatgt aaatagttgt     2040
gatcctgaat tgtttaggga ataataagaa agaactatct gtagatgttc agtatagatg     2100
cacccatcgt aagcctaact acattgtata actcagcaac gatgtaacat ttcaggggt      2160 ttttttgttt tgtttttga gacagaatct cagtctcact ctgtcaccca ggctggagta     2220
tgttggcgtg atctctgctc actgcaacct ccacctcctg ggctcaagcg attctcctgc     2280
ctcagcctct tgagtagctg ggattgcagg tgtgcgctac cacgcatggc taattttgt      2340 attttaata gagatggggt tttaccacgt tggtcaggct ggtcttgaac tcctgacctt      2400
gggatccgcc cacctgggcc tcccaaagtg ctgggattac aggcgttagc caccgcgccc     2460
aatatatttt gatccctggt tggatatgga gggctgactg tacttaacat ctctaagctt     2520
cagtttcctc ctttaaaata aaggtgtggc tgggtgtggt ggttcaagcc tgtaatccca     2580
gcacttaggg aggctgaggt gggtggatca gctgaggtca ggagttcaag accagcctga     2640
ccaatatggt gaaaccccct ctctgctaaa aatacaaaaa ttagccaggc gtggtggcga     2700
gcgcctgtag tcccagctac ttgcttgaac ttgggaggca gaggttgcag tgagctgaga     2760
tcgtgccact gaactcgagc atgggcaaca gagcaagact gtctcaaaaa aaaaaaaaaa     2820 aaggggggtga gcagacgtgg tggcacgctc ccacagtccc agctacttag taggaggcca     2880
aggttggagg attgcttgat cccaggagtc tgagtccagc ctgggcaaca tggcaatacc     2940
tcatctctaa aaataaaata aaagtaaagg tattaattac tactttggat ggttgttgca     3000
```

-continued

```
aagaaatata tataaaataa tggagagtct tgtaactggc tcccaagagg ctcaacagac   3060
attactgttt ttgcttcttc attatgagtt acctctctgg ccacccccact gaactagctg  3120 ggctagctga gcctgggaga agagttgttt aggaagtgag aggctgctct ccacagagac   3180
tcaaggctca gttcctcctg gtgactcaga tgggcagccc agtgggcaca cgtggtctct   3240
ctccacatgt ggctgagttt cacttccaga atagatggag aggcaagggc agggtttagc   3300
atgcttgagg aatctcagag ggccctggtg gtgtggggga ccctcagaac acaggtgtct   3360
caagggctga cccagcttct gtgtccttt tctctgggtga ggaggggaca ttcatgggca   3420
gatggtgacc tctggggaag gcagcccaga ctccactggc caccatattt cctttttcac   3480
aactttctca cccctgtggt ttcccatgtc atcatgtggc cgcttcccgc aaggccttag   3540
cggggtgcag gtatgaacat agtgtcaggc aaggaggcat ctggagggga accctggctt   3600
ttcctggggg gactccctcc ctgcacccta gccctgtcct ctcccatggc tactgatgcc   3660
ttcccctcac cccagaggtg gcccacatct gcacagatca gacccacaaa aatcacgtct   3720
tcctgactct cataagcctg cccagtgagg cccaggcatt aggccatgtg ctggggactc   3780
agacccacac atatacgcat gtcagcattc atgcttacag gtccgcacat gctggggcaa   3840
gtgtcacaca cggggcgctg taggaagctg actctcagcc cctgcagatt tctgcctgcc   3900
tggacaggga ggtgttgaga aggctcaggc agtcctgggc caggaccttg gcctggggct   3960
agggtactga gtgaccctag aatcaagggt ggcgtgggct taagcagttg ccagacgttc   4020
cttggtactt tgcaggcaga ccatgtggac cctggtgagc tgggtggcct taacagcagg   4080
gctggtggct ggaacgcggt gcccagatgg tcagttctgc cctgtggcct gctgcctgga   4140
ccccggagga gccagctaca gctgctgccg tccccttctg                         4180
```

```
<210> SEQ ID NO 277
<211> LENGTH: 16
<212> TYPE: DNA
<213> ORGANISM: Artificial Sequence
<220> FEATURE:
<223> OTHER INFORMATION: target site for SEQ ID NO: 71

<400> SEQUENCE: 277
attcttgacc cagctc                                                      16

<210> SEQ ID NO 278
<211> LENGTH: 16
<212> TYPE: DNA
<213> ORGANISM: Artificial Sequence
<220> FEATURE:
<223> OTHER INFORMATION: target site for SEQ ID NO: 73

<400> SEQUENCE: 278
cacaccattc ttgacc                                                      16

<210> SEQ ID NO 279
<211> LENGTH: 16
<212> TYPE: DNA
<213> ORGANISM: Artificial Sequence
<220> FEATURE:
<223> OTHER INFORMATION: target site for SEQ ID NO: 74

<400> SEQUENCE: 279
gaccacacca ttcttg                                                      16

<210> SEQ ID NO 280
<211> LENGTH: 16
```

```
<212> TYPE: DNA
<213> ORGANISM: Artificial Sequence
<220> FEATURE:
<223> OTHER INFORMATION: target site for SEQ ID NO: 75

<400> SEQUENCE: 280
agggaccaca ccattc                                                    16

<210> SEQ ID NO 281
<211> LENGTH: 16
<212> TYPE: DNA
<213> ORGANISM: Artificial Sequence
<220> FEATURE:
<223> OTHER INFORMATION: target site for SEQ ID NO: 134

<400> SEQUENCE: 281
gccatgtgag cttgag                                                    16

<210> SEQ ID NO 282
<211> LENGTH: 22
<212> TYPE: DNA
<213> ORGANISM: Artificial Sequence
<220> FEATURE:
<223> OTHER INFORMATION: GRN Exon1-Exon2 (FAM) Primer 1

<400> SEQUENCE: 282
gctgctgccc aaggaccgcg ga                                             22

<210> SEQ ID NO 283
<211> LENGTH: 22
<212> TYPE: DNA
<213> ORGANISM: Artificial Sequence
<220> FEATURE:
<223> OTHER INFORMATION: GRN Exon1-Exon2 (FAM) Primer 2

<400> SEQUENCE: 283
gccctgctgt taaggccacc ca                                             22

<210> SEQ ID NO 284
<211> LENGTH: 27
<212> TYPE: DNA
<213> ORGANISM: Artificial Sequence
<220> FEATURE:
<223> OTHER INFORMATION: GRN Exon1-Exon2 (FAM) Probe
<220> FEATURE:
<221> NAME/KEY: misc_feature
<222> LOCATION: (9)..(10)
<223> OTHER INFORMATION: internal ZEN quencher between nucleotides 9 and
      10

<400> SEQUENCE: 284
ggacgcaggc agaccatgtg gaccctg                                        27

<210> SEQ ID NO 285
<211> LENGTH: 25
<212> TYPE: DNA
<213> ORGANISM: Artificial Sequence
<220> FEATURE:
<223> OTHER INFORMATION: GRN Intron1-Exon2 (HEX) Primer 1

<400> SEQUENCE: 285
ccaaagcagg gaccacacca ttctt                                          25

<210> SEQ ID NO 286
<211> LENGTH: 22
<212> TYPE: DNA
<213> ORGANISM: Artificial Sequence
```

<220> FEATURE:
<223> OTHER INFORMATION: GRN Intron1-Exon2 (HEX) Primer 2

<400> SEQUENCE: 286
gccctgctgt taaggccacc ca                                           22

<210> SEQ ID NO 287
<211> LENGTH: 29
<212> TYPE: DNA
<213> ORGANISM: Artificial Sequence
<220> FEATURE:
<223> OTHER INFORMATION: GRN Intron1-Exon2 (HEX) Probe
<220> FEATURE:
<221> NAME/KEY: misc_feature
<222> LOCATION: (9)..(10)
<223> OTHER INFORMATION: internal ZEN quencher between nucleotides 9 and
      10

<400> SEQUENCE: 287
cccagctcca ccctgtcgg cagaccatg                                     29

<210> SEQ ID NO 288
<211> LENGTH: 274
<212> TYPE: DNA
<213> ORGANISM: Homo sapiens

<400> SEQUENCE: 288
gtaggagagc ggccgcgcag acctctcgcc tgctcctgcc caggggcccg ccagggccat    60
gtgagcttga ggttcccctg gagtctcagc cggagacaac agaagaaccg cttactgaaa   120
ctccttgggg gttctgatac actaggggga gttttatggg aaagaggaag cagtaattgc   180
agtgacgccc cgttagagct ttctacctcc ccagcattcc cccaaagcag ggaccacacc   240
attcttgacc cagctccacc cctgtcggta ggtg                              274

<210> SEQ ID NO 289
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 289
tcaagaatgg tgtggtcc                                                18

<210> SEQ ID NO 290
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 290
ggtcaagaat ggtgtggt                                                18

<210> SEQ ID NO 291
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 291
ggaccacacc attcttga                                                18

```
<210> SEQ ID NO 292
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 292
accacaccat tcttgacc                                                    18
```

ANTISENSE OLIGONUCLEOTIDE FOR TARGETING PROGRANULIN

CROSS REFERENCE TO RELATED APPLICATIONS

This application claims benefit of and priority to the European Patent Application EP 20215791.3 filed on Dec. 18, 2020, which is incorporated by reference in its entirety where permissible.

TECHNICAL FIELD OF THE INVENTION

The present invention relates to antisense oligonucleotides which alter the splicing pattern of progranulin, and their use in the treatment of neurological disorders. Such antisense oligonucleotides may up-regulate or restore expression of the Exon1-Exon2 progranulin splice variant in cells.

REFERENCE TO SEQUENCE LISTING

The instant application contains a Sequence Listing which has been submitted electronically in ASCII format and is hereby incorporated by reference in its entirety. Said ASCII copy, created on Dec. 14, 2021, is named 067211_016US1_SL.txt and is 64,354 bytes in size.

BACKGROUND OF THE INVENTION

Progranulin (PGRN) is a highly conserved secreted protein that is expressed in multiple cell types, both in the CNS and in peripheral tissues.

Deficiency of the secreted protein progranulin in the central nervous system causes the neurodegenerative disease fronto temporal dementia (FTD). Pathogenic progranulin mutations lead to a loss of about 50% in progranulin levels through haploinsufficiency and to intraneuronal aggregation of TDP-43 protein. Progranulin plays a supportive and protective role in numerous processes within the brain, including neurite outgrowth, synapse biology, response to exogenous stressors, lysosomal function, neuroinflammation, and angiogenesis in both cell autonomous and non-autonomous manners.

Both directly and via its conversion to granulins, progranulin regulates lysosomal function, cell growth, survival, repair, and inflammation. Progranulin has a major role in regulation of lysosomal function associated microglial responses in the CNS. Autosomal dominant mutations of the progranulin gene leading to protein haploinsufficiency are linked to familial frontotemporal dementia with neuropathologic frontotemporal lobar degeneration (FTLD) associated with accumulation of TAR-DNA binding protein of 43 kDA (TDP-43) inclusions (FTLD-TDP). Homozygous GRN mutations are linked to neuronal ceroid lipofuscinosis (NCL) (Townley, et al., Neurology, 2018 Jun. 12; 90(24): 1127).

Mutations in the progranulin gene have recently been identified as a cause of about 5% of all FTD, including some sporadic cases. Recent studies using mouse models have defined the expression of progranulin in the brain (Petkau et al., 2010). Progranulin is expressed late in neurodevelopment, localizing with markers of mature neurons. Progranulin is expressed in neurons in most brain regions, with highest expression in the thalamus, hippocampus, and cortex. Microglia cells also express progranulin, and the level of expression is upregulated by microglial activation. Around 70 different progranulin gene mutations have been identified in FTD and all reduce progranulin levels or result in loss of progranulin function.

There is therefore an urgent need for therapeutic agents which can increase the expression and/or activity of progranulin.

SUMMARY OF THE INVENTION

A splice variant of progranulin which retains the 5' part of Intron 1 is expressed in the brain such as in neurons or microglia cells (Capell et al. The Journal of Biological Chemistry, 2014, 289(37), 25879-25889). This splice variant include the 5' most 271 nucleotides of intron 1, which totals 3823 nucleotides. The 271 nucleotide fragment of intron 1 includes two AUG sites upstream of the canonical downstream AUG (open reading frame) in exon 2. Translation from these two upstream AUG sites will not encode the progranulin protein, and due to premature termination codons the transcript may undergo non-sense mediated mRNA decay (NMD).

WO2020/191212 describes specific oligonucleotides which can target the progranulin mRNA. Here the inventors have determined that reducing the splice variant which retains the 5' part of intron 1 increases the Exon1 and Exon2 splice variant and further increases progranulin protein expression.

The present invention provides antisense oligonucleotides of progranulin. These antisense oligonucleotides are capable of altering the splicing pattern of progranulin, In particular the antisense oligonucleotides may up-regulate expression of the Exon1-Exon2 progranulin splice variant, reducing production of the progranulin Intron1-Exon2 splice variant which retains the 5' part of intron 1, increasing the expression of the progranulin protein. These antisense oligonucleotides could be described as modulators of progranulin splicing, or as agonists of progranulin Exon1-Exon 2.

The antisense oligonucelotides of the invention may be used to restore or enhance expression of the progranulin Exon1-Exon2 splice variant in cells.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a splice regulation site of the human progranulin pre-mRNA.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a splice regulation site of the exon 1, intron 1 and exon 2 sequence of the human progranulin pre-mRNA. The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a human progranulin pre-mRNA transcript that comprises the exon1, intron 1 and exon 2 sequence of the human progranulin pre-mRNA transcript (SEQ ID NO: 276).

The progranulin exon 1, intron 1 and exon 2 sequence is shown below as SEQ ID NO: 276. The progranulin exon1 sequence (in capital letters) corresponds to genome Ensemble (www.ensemble.org) chromosome 17 position 44,345,123; to position 44,345,334. Intron 1 corresponds to genome Ensemble chromosome 17 position 44,345,335 to 44,349,157 and Exon 2 sequence (in capital letters) corresponds to genome Ensemble chromosome 17 position 44,349,158 to position 44,349,302.

Exon 1, intron 1 and exon 2 sequence of the human progranulin pre-mRNA (SEQ ID NO: 276):
GGCGAGAGGAAGCAGGGAGGAGAGTGATTTGAGTAGAAAAGAAACACAGCATTCC

AGGCTGGCCCCACCTCTATATTGATAAGTAGCCAATGGGAGCGGGTAGCCCTGATCC

CTGGCCAATGGAAACTGAGGTAGGCGGGTCATCGCGCTGGGGTCTGTAGTCTGAGC

GCTACCCGGTTGCTGCTGCCCAAGGACCGCGGAGTCGGACGCAGgtaggagagcggccgcgc agacctctcgcctgctcctgcccaggggcccgccagggccatgtgagcttgaggttccctggagtctcagccggagacaacagaagaa ccgcttactgaaactccttgggggttctgatacactaggggagttttatgggaaagaggaagcagtaattgcagtgacgccccgttagaag gggcttctacctccccagcattcccccaaagcagggaccacaccattcttgacccagctccacccctgtcggtaggtgctggcttcttcccc tctcctggtggtggtgggtggttcccgcggcggcctggagcggaggggcgcgcgaccctgggctgggagctccgagggcctgggaa cgagacctgagaccttggcttctcgaaggtagtagggacttgggagtggtgactgaacctggtctggctcctccttacttcctcttgttgcggg tgggacgagctagcttccgcctctcccagccacttttcctgctcatttgcagctaggttggctccccttttgggaatttcctctccccttggcact cggagttgggggtgccacctagtggaagataacggagctagggtcttgaagaggctgctgtcccctctggctgttttggcggtgtagggt ggcatgagagactgcgactcgcctcctcatccctgtttctgtatgcgagtgcttgtattcagtagaagcatacactatactccctcaatttagggt aaacaggaggggccacatgcacaggtaattcaccagggagccgaacactcctgtgcagacagactccccttcccagcaagccatggcag cggacagcctgctgagaacacccaggaagcaggcggtgccagctgcaggtgctttgcctgggagctgtggggctgaggagagggtcca ctgtccaggaccagtgaacttcatccttatctgtccaggaggtggcctcttggggatgctgagttaggggagggcacttgaggaaagcca ggtggagcagagaggatgtgagtgactgggtgggtgagatttcctgcccctcccccgcagtggtatccacacctagactcgtggggtaa ctgaggcacagacagagagcaacttctcaggccctcacagttggcaattctaggattaggacccaagtgcgattttcaggcagtccctgtac cctgtttctgttgtacctgttgcaccattcccaggcactgcccatcgtgccactagtgatatgaacccaggtccaatacgctctggggccatca aagcctgacgtcaccatgacctgatgtgtgacgtgttataggtgtcccttggtatcttcacggaactggttccaggaccccaaaatctgtgggt gctcaagcccctgagataaaatggtgtaatatttgcatataacctatacatactttaaatcatttctagattacttatacctaatacaatggaaatga catgtcggctgggcgtggtggctcatgcctgtaatcccaccactttgggaggccgtggcaggtggatcacctgaggtctggagtttgagac cagcctgaccaacatggtgaaaccccatctctactaaaaatacaaaaattagccaggtgtggtagcgcacacctataatcccacctacttgg gaggctgaggcaggagaattgcttgaacctgggaggcggagttcgcagtaagctgagatcgcgccactgtactacagcctgggtgacag agcaggactccatctcaaaaaaaaagagaaaaagaaaaagaaatgccatgtaaatagttgtgatcctgaattgtttagggaataataagaa agaactatctgtagatgttcagtatagatgcacccatcgtaagcctaactacattgtataactcagcaacgatgtaacatttcaggggttttttttg tttgttttttgagacagaatctcagtctcactctgtcacccaggctggagtatgttggcgtgatctctgctcactgcaacctccacctcctgggct caagcgattctcctgcctcagcctcttgagtagctgggattgcaggtgtgcgctaccacgcatggctaattttttgtattttaatagagatggggt tttaccacgttggtcaggctggtcttgaactcctgaccttgggatccgcccacctgggcctcccaaagtgctgggattacaggcgttagccac cgcgcccaatatattttgatccctggttggatatggagggctgactgtacttaacatctctaagcttcagtttcctcctttaaaataaaggtgtggc tgggtgtggtggttcaagcctgtaatcccagcacttagggaggctgaggtgggtggatcagctgaggtcaggagttcaagaccagcctgac caatatggtgaaaccccctctctgctaaaaatacaaaaattagccaggcgtggtggcgagcgcctgtagtcccagctacttgcttgaacttgg gaggcagaggttgcagtgagctgagatcgtgccactgaactcgagcatgggcaacagagcaagactgtctcaaaaaaaaaaaaaaaag ggggtgagcagacgtggtggcacgctcccacagtcccagctacttagtaggaggccaaggttggaggattgcttgatcccaggagtctga gtccagcctgggcaacatggcaatacctcatctctaaaaataaaataaaagtaaaggtattaattactactttggatggttgttgcaaagaaata tatataaaataatggagagtcttgtaactggctcccaagaggctcaacagacattactgtttttgcttcttcattatgagttacctctctggccacc ccactgaactagctgggctagctgagcctgggagaagagttgtttaggaagtgagaggctgctctccacagagactcaaggctcagttcct cctggtgactcagatgggcagcccagtgggcacacgtggtctctctccacatgtggctgagtttcacttccagaatagatggagaggcaag ggcagggtttagcatgcttgaggaatctcagagggccctggtggtgtgggggaccctcagaacacaggtgtctcaagggctgacccagct tctgtgtcctttctctggtgaggaggggacattcatgggcagatggtgacctctggggaaggcagcccagactccactggccaccatattt cctttttcacaactttctcaccccctgtggtttcccatgtcatcatgtggccgcttcccgcaaggccttagcggggtgcaggtatgaacatagtgt -continued

```
caggcaaggaggcatctggaggggaaccctggatttcctggggggactccctccctgcaccctagccctgtcctctcccatggctactgat gccttcccctcaccccagaggtggcccacatctgcacagatcagacccacaaaaatcacgtcttcctgactctcataagcctgcccagtgag gcccaggcattaggccatgtgctggggactcagacccacacatatacgcatgtcagcattcatgcttacaggtccgcacatgctggggcaa gtgtcacacacggggcgctgtaggaagctgactctcagccctgcagatttctgcctgcctggacagggaggtgttgagaaggctcaggc agtcctgggccaggaccttggcctggggctagggtactgagtgacccagaatcaagggtggcgtgggcttaagcagttgccagacgttc cttggtactttgcagGCAGACCATGTGGACCCTGGTGAGCTGGGTGGCCTTAACAGCAGGGCT

GGTGGCTGGAACGCGGTGCCCAGATGGTCAGTTCTGCCCTGTGGCCTGCTGCCTGGA

CCCCGGAGGAGCCAGCTACAGCTGCTGCCGTCCCCTTCTG
```

The invention provides an antisense oligonucleotide, wherein the antisense oligonucleotide is 8-40 nucleotides in length and comprises a contiguous nucleotide sequence of at least 12 nucleotides in length which is complementary, such as fully complementary, to a splice regulation site of the human progranulin pre-mRNA.

The invention provides an antisense oligonucleotide, wherein the antisense oligonucleotide is 8-40 nucleotides in length and comprises a contiguous nucleotide sequence of 12-16 nucleotides in length which is complementary, such as fully complementary, to a splice regulation site of the human progranulin pre-mRNA.

The invention provides an antisense oligonucleotide, wherein the antisense oligonucleotide is 12-16 nucleotides in length and comprises a contiguous nucleotide sequence of 12-16 nucleotides in length which is complementary, such as fully complementary, to a splice regulation site of the human progranulin pre-mRNA.

The invention provides an antisense oligonucleotide, wherein the antisense oligonucleotide is 8-40 nucleotides in length and comprises a contiguous nucleotide sequence of 12-18 nucleotides in length which is complementary, such as fully complementary, to a splice regulation site of the human progranulin pre-mRNA.

The invention provides an antisense oligonucleotide, wherein the antisense oligonucleotide is 12-18 nucleotides in length and comprises a contiguous nucleotide sequence of 12-18 nucleotides in length which is complementary, such as fully complementary, to a splice regulation site of the human progranulin pre-mRNA.

The invention provides an antisense oligonucleotide, wherein the antisense oligonucleotide is 8-40 nucleotides in length and comprises a contiguous nucleotide sequence of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length which is complementary, such as fully complementary, to a splice regulation site of the human progranulin pre-mRNA.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a nucleotide sequence comprised within SEQ ID NO: 276.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a nucleotide sequence comprised within nucleotides 441-468 of SEQ ID NO: 276.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a nucleotide sequence comprised within nucleotides 441-462 of SEQ ID NO: 276.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a sequence selected from the group consisting of: SEQ ID NO: 277, SEQ ID NO: 278, SEQ ID NO: 279 and SEQ ID NO: 280.

```
Target site for SEQ ID NO: 71
                                        (SEQ ID NO: 277)
ATTCTTGACCCAGCTC.

Target site for SEQ ID NO: 73
                                        (SEQ ID NO: 278)
CACACCATTCTTGACC.

Target site for SEQ ID NO: 74
                                        (SEQ ID NO: 279)
GACCACACCATTCTTG.

Target site for SEQ ID NO: 75
                                        (SEQ ID NO: 280)
AGGGACCACACCATTC.
```

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a nucleotide sequence comprised within nucleotides 268-283 of SEQ ID NO: 276.

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to SEQ ID NO: 281.

```
Target site for SEQ ID NO: 134
                                        (SEQ ID NO: 281)
GCCATGTGAGCTTGAG.
```

The invention provides an antisense oligonucleotide, wherein the antisense oligonucleotide is 8-40 nucleotides in length and comprises a contiguous nucleotide sequence of 8-40 nucleotides in length which is complementary, such as fully complementary, to a sequence selected from the group consisting of: SEQ ID NO: 291 and SEQ ID NO: 292.

The antisense oligonucleotide may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments the antisense oligonucleotide is 8-40, 12-40, 12-20, 10-20, 14-18, 12-18 or 16-18 nucleotides in length.

The contiguous nucleotide sequence may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the contiguous nucleotide sequence is of a length of at least 12 nucleotides in length, such as 12-16 or 12-18 nucleotides in length.

In some embodiments, the contiguous nucleotide sequence is the same length as the antisense oligonucleotide.

In some embodiments the antisense oligonucleotide consists of the contiguous nucleotide sequence.

In some embodiments the antisense oligonucleotide is the contiguous nucleotide sequence.

In some embodiments, the contiguous nucleotide sequence is fully complementary to a nucleotide sequence comprised within SEQ ID NO: 276.

In some embodiments, the contiguous nucleotide sequence is fully complementary to a nucleotide sequence comprised within nucleotides 441-468 of SEQ ID NO: 276.

In some embodiments, the contiguous nucleotide sequence is fully complementary to a nucleotide sequence comprised within nucleotides 441-462 of SEQ ID NO: 276.

In some embodiments, the contiguous nucleotide sequence is fully complementary to a sequence selected from the group consisting of SEQ ID NO: 277, SEQ ID NO:278, SEQ ID NO:279 and SEQ ID NO:280.

In some embodiments, the contiguous nucleotide sequence is fully complementary to SEQ ID NO:277.

In some embodiments, the contiguous nucleotide sequence is fully complementary to SEQ ID NO:278.

In some embodiments, the contiguous nucleotide sequence is fully complementary to SEQ ID NO:279.

In some embodiments, the contiguous nucleotide sequence is fully complementary to SEQ ID NO:280.

In some embodiments, the contiguous nucleotide sequence is fully complementary to a nucleotide sequence comprised within nucleotides 256-283 of SEQ ID NO: 276.

In some embodiments, the contiguous nucleotide sequence is fully complementary to SEQ ID NO:281.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO: 134, SEQ ID NO: 135, SEQ ID NO: 196, SEQ ID NO:220, SEQ ID NO:228 and SEQ ID NO:252, or at least 8 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO:100, SEQ ID NO:134, SEQ ID NO:135, SEQ ID NO:196, SEQ ID NO:220, SEQ ID NO:228 and SEQ ID NO:252, or at least 9 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO: 134, SEQ ID NO:135, SEQ ID NO:196, SEQ ID NO:220, SEQ ID NO:228 and SEQ ID NO:252, or at least 10 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO:134, SEQ ID NO: 135, SEQ ID NO: 196, SEQ ID NO:220, SEQ ID NO:228 and SEQ ID NO:252, or at least 11 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO: 134, SEQ ID NO: 135, SEQ ID NO: 196, SEQ ID NO:220, SEQ ID NO:228 and SEQ ID NO:252, or at least 12 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO: 134, SEQ ID NO: 135, SEQ ID NO: 196, SEQ ID NO:220, SEQ ID NO:228 and SEQ ID NO:252, or at least 13 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO: 100, SEQ ID NO: 134, SEQ ID NO: 135, SEQ ID NO: 196, SEQ ID NO:220, SEQ ID NO:228 and SEQ ID NO:252, or at least 14 contiguous nucleotides thereof.

In some embodiments, the contiguous nucleotide sequence is a sequence selected from the group consisting of SEQ ID NO:51, SEQ ID NO:52, SEQ ID NO:53, SEQ ID NO:54, SEQ ID NO:55, SEQ ID NO: 62. SEQ ID NO:63, SEQ ID NO:67, SEQ ID NO:71, SEQ ID NO: 73, SEQ ID NO:74, SEQ ID NO:75, SEQ ID NO: 100, SEQ ID NO: 134, SEQ ID NO:135, SEQ ID NO: 196, SEQ ID NO:220, SEQ ID NO:228 and SEQ ID NO:252, or at least 15 contiguous nucleotides thereof.

In some embodiments the contiguous nucleotide sequence is selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO: 67, SEQ ID NO:71, SEQ ID NO:73, SEQ ID NO: 74, SEQ ID NO:75, SEQ ID NO: 100, SEQ ID NO: 134, SEQ ID NO: 135, SEQ ID NO:196, SEQ ID NO:220, SEQ ID NO:228 and SEQ ID NO:252.

In some embodiments the contiguous nucleotide sequence is SEQ ID NO:71.

In some embodiments the contiguous nucleotide sequence is SEQ ID NO:73.

In some embodiments the contiguous nucleotide sequence is SEQ ID NO:74.

In some embodiments the contiguous nucleotide sequence is SEQ ID NO:75.

In some embodiments the contiguous nucleotide sequence is SEQ ID NO:134.

The invention provides an antisense oligonucleotide, wherein the antisense oligonucleotide is 8-40 nucleotides in length and comprises a contiguous nucleotide sequence of 8-40 nucleotides in length, wherein the contiguous nucleotide sequence is selected from the group consisting of: SEQ ID NO: 289 and SEQ ID NO: 290.

The invention provides for an antisense oligonucleotide which is isolated, purified or manufactured.

In some embodiments, the antisense oligonucleotide is or comprises an antisense oligonucleotide mixmer or totalmer. In some embodiments, the contiguous nucleotide sequence is a mixmer or a tolalmer.

The invention provides for a conjugate comprising the antisense oligonucleotide according to the invention, and at least one conjugate moiety covalently attached to said antisense oligonucleotide.

The invention provides an antisense oligonucleotide covalently attached to at least one conjugate moiety.

The invention provides for a pharmaceutically acceptable salt of the antisense oligonucleotide according to the invention, or the conjugate according to the invention.

The invention provides for an antisense oligonucleotide according to the invention wherein the antisense oligonucleotide is in the form of a pharmaceutically acceptable salt. In some embodiments the pharmaceutically acceptable salt may be a sodium salt, a potassium salt or an ammonium salt.

The invention provides for a pharmaceutically acceptable sodium salt of the antisense oligonucleotide according to the invention, or the conjugate according to the invention.

The invention provides for a pharmaceutically acceptable potassium salt of the antisense oligonucleotide according to the invention, or the conjugate according to the invention.

The invention provides for a pharmaceutically acceptable ammonium salt of the antisense oligonucleotide according to the invention, or the conjugate according to the invention.

The invention provides for a pharmaceutical composition comprising the antisense oligonucleotide of the invention, or the conjugate of the invention, and a pharmaceutically acceptable diluent, solvent, carrier, salt and/or adjuvant.

The invention provides for a pharmaceutical composition comprising the antisense oligonucleotide of the invention, or the conjugate of the invention, and a pharmaceutically acceptable salt. For example, the salt may comprise a metal cation, such as a sodium salt, a potassium salt or an ammonium salt.

The invention provides for a pharmaceutical composition according to the invention, wherein the pharmaceutical composition comprises the antisense oligonucleotide of the invention or the conjugate of the invention, or the pharmaceutically acceptable salt of the invention; and an aqueous diluent or solvent.

The invention provides for a solution, such as a phosphate buffered saline solution of the antisense oligonucleotide of the invention, or the conjugate of the invention, or the pharmaceutically acceptable salt of the invention. Suitably the solution, such as phosphate buffered saline solution, of the invention, is a sterile solution.

The invention provides for a method for enhancing the expression of the Exon1-Exon2 progranulin splice variant in a cell which is expressing progranulin, said method comprising administering an antisense oligonucleotide of the invention, or a conjugate of the invention, or a salt of the invention, or a pharmaceutical composition of the invention in an effective amount to said cell. In some embodiments the method is an in vitro method. In some embodiments the method is an in vivo method.

In some embodiments, the cell is either a human cell or a mammalian cell.

The invention provides for a method for treating or preventing progranulin haploinsufficiency or a related disorder, comprising administering a therapeutically or prophylactically effective amount of an antisense oligonucleotide of the invention, or a conjugate of the invention, or a salt of the invention, or a pharmaceutical composition of the invention to a subject suffering from or susceptible to progranulin haploinsufficiency or a related disorder.

The invention provides for a method for treating or preventing neurological disease, comprising administering a therapeutically or prophylactically effective amount of an antisense oligonucleotide of the invention, or a conjugate of the invention, or a salt of the invention, or a pharmaceutical composition of the invention to a subject suffering from or susceptible to neurological disease. In one embodiment the neurological disease may be a TDP-43 pathology.

The invention provides for an antisense oligonucleotide of the invention, for use as a medicament.

The invention provides for an antisense oligonucleotide of the invention, for use in therapy.

The invention provides for the antisense oligonucleotide of the invention or the conjugate of the invention, or the salt of the invention, or the pharmaceutical composition of the invention, for use as a medicament.

The invention provides the antisense oligonucleotide of the invention or the conjugate of the invention, or the salt of the invention, or the pharmaceutical composition of the invention for use in therapy.

The invention provides for the antisense oligonucleotide of the invention or the conjugate of the invention, or the salt of the invention, or the pharmaceutical composition of the invention for use in the treatment of a neurological disease. In one embodiment the neurological disease may be a TDP-43 pathology.

The invention provides for the antisense oligonucleotide of the invention or the conjugate of the invention, or the salt of the invention, or the pharmaceutical composition of the invention for use in the treatment or prevention of progranulin haploinsufficiency or a related disorder.

The invention provides for the use of the antisense oligonucleotide of the invention or the conjugate of the invention, or the salt of the invention, or the pharmaceutical composition of the invention, for the preparation of a medicament for treatment or prevention of a neurological disease. In one embodiment the neurological disease may be a TDP-43 pathology.

The invention provides for the use of the antisense oligonucleotide of the invention or the conjugate of the invention, or the salt of the invention, or the pharmaceutical composition of the invention, for the preparation of a medicament for treatment or prevention of progranulin haploinsufficiency or a related disorder.

In some embodiments the method, use, or antisense oligonucleotide for use, of the invention is for the treatment of fronto temporal dementia (FTD), neuropathologic frontotemporal lobar degeneration or neuroinflammation. In other embodiments the method, use, or antisense oligonucleotide for use, of the invention is for the treatment of amyotrophic lateral sclerosis (ALS), Alzheimer's disease, Parkinson's disease, Autism, Hippocampal sclerosis dementia, Down syndrome, Huntington's disease, polyglutamine diseases, spinocerebellar ataxia 3, myopathies or Chronic Traumatic Encephalopathy.

In one aspect the invention includes an oligonucleotide progranulin agonist having the structure corresponding to SEQ ID NO:71:
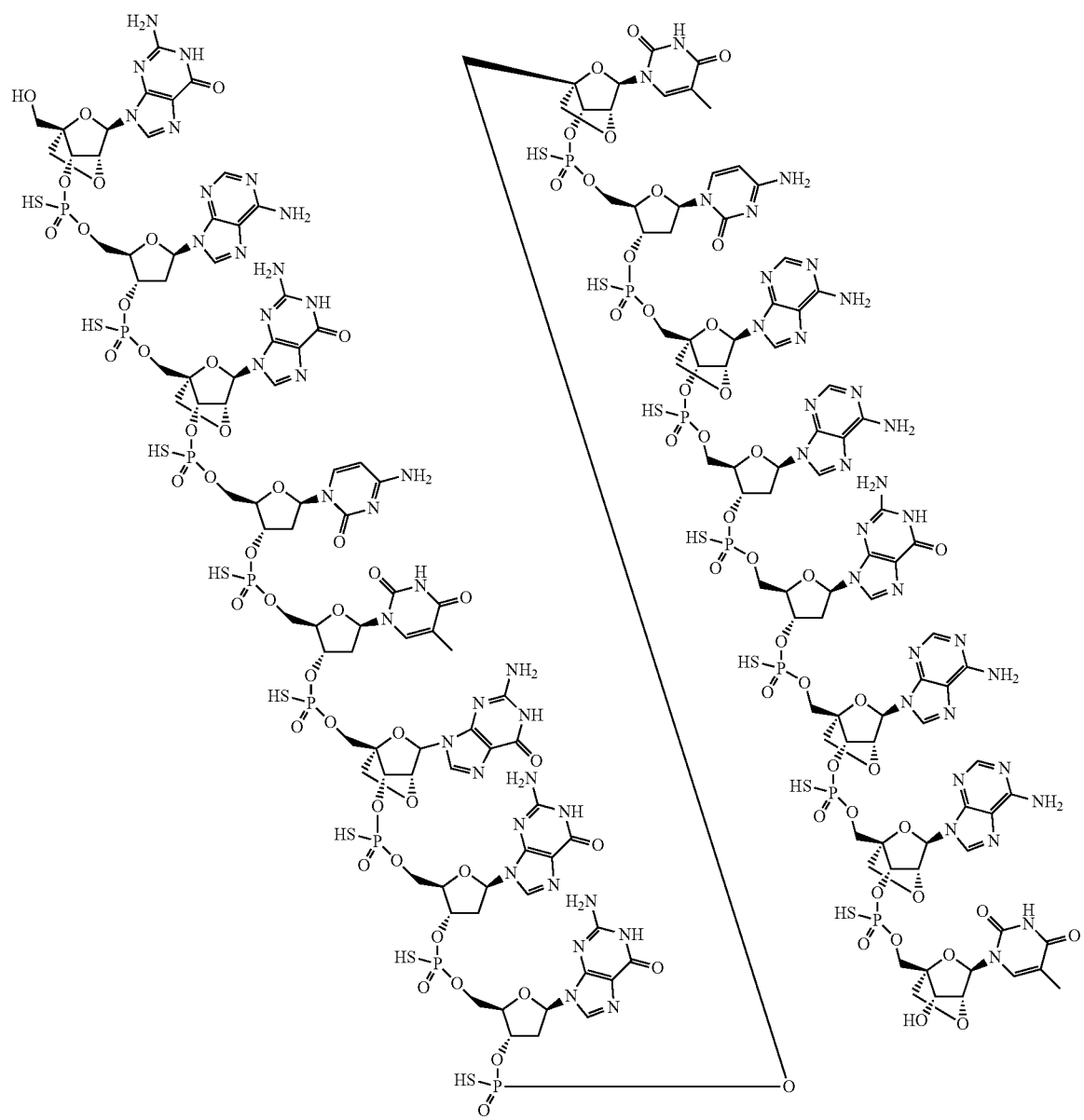

In another aspect the invention includes an oligonucleotide progranulin agonist having the structure corresponding to SEQ ID NO:73:
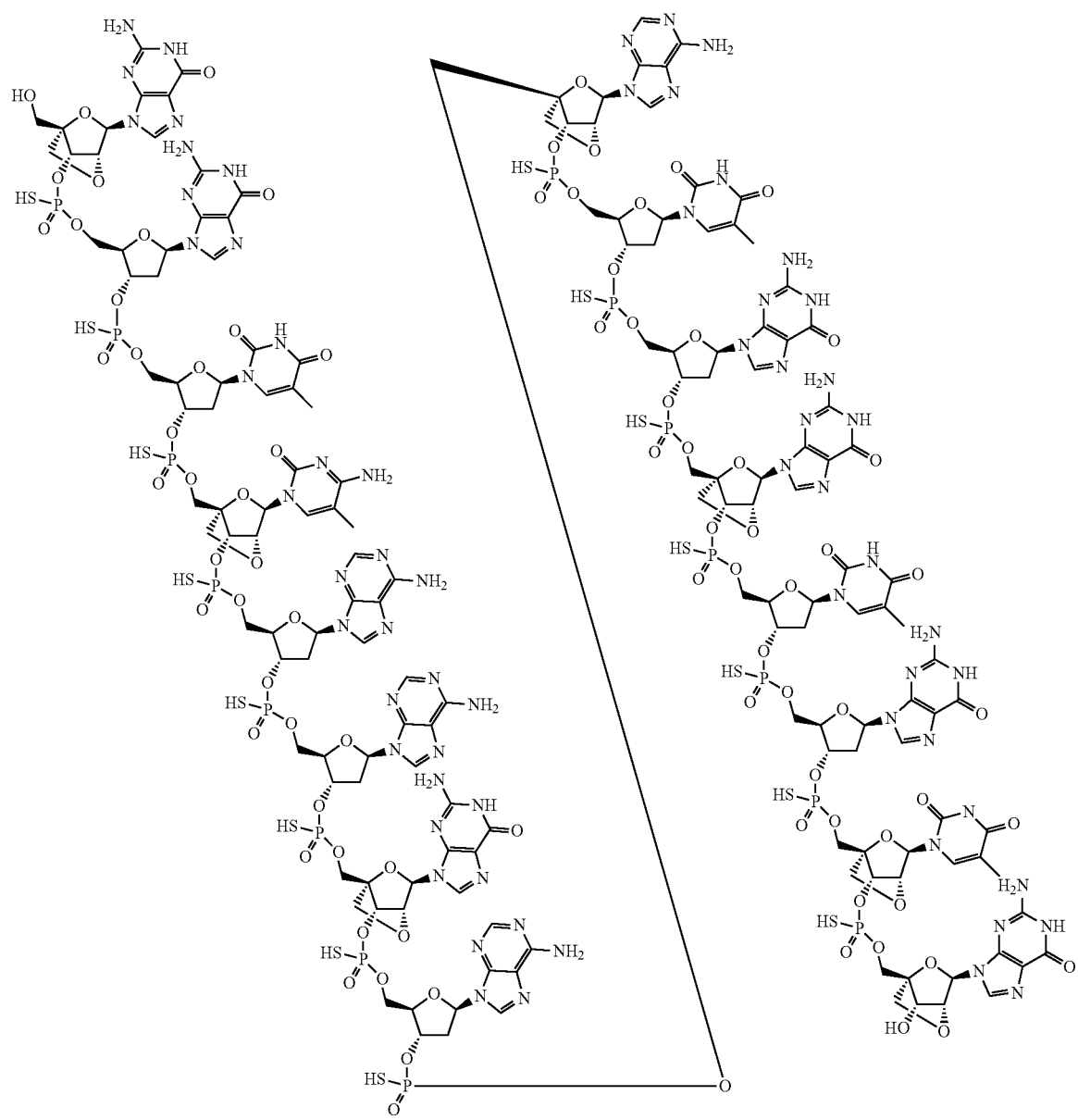

In another aspect the invention includes an oligonucleotide progranulin agonist having the structure corresponding to SEQ ID NO: 74:
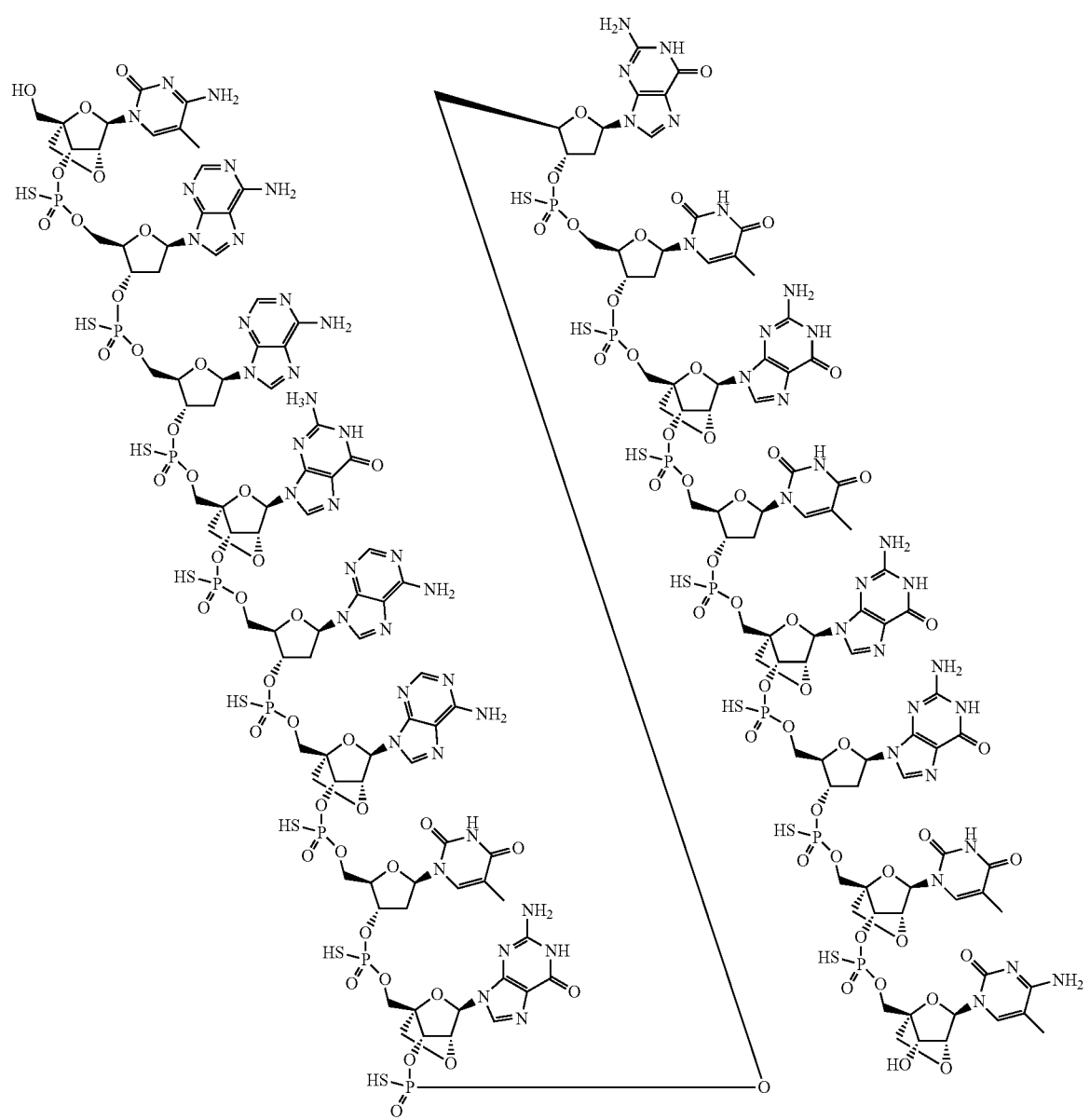

In another aspect the invention includes an oligonucleotide progranulin agonist having the structure corresponding to SEQ ID NO:75:
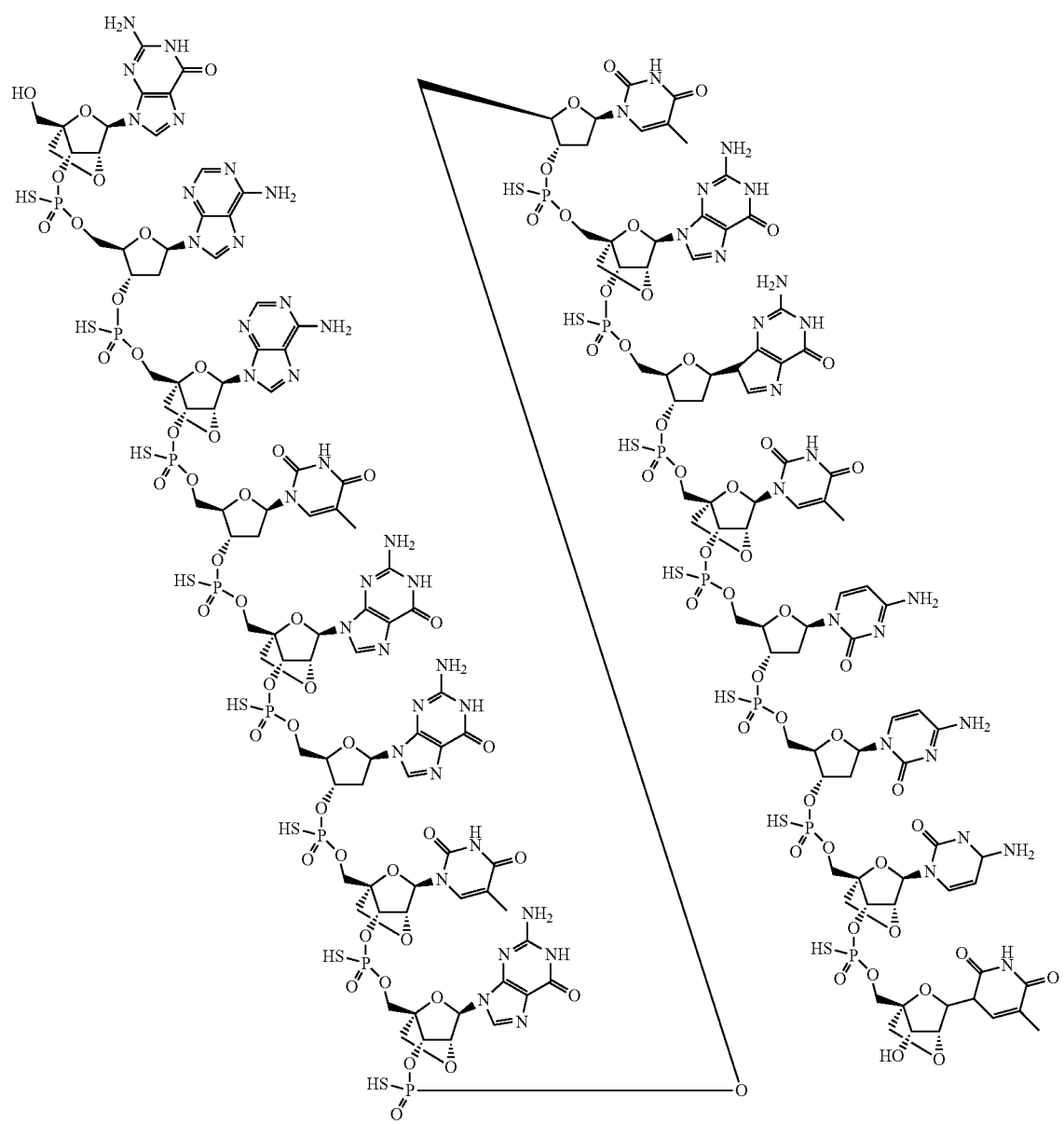

In another aspect the invention includes an oligonucleotide progranulin agonist having the structure corresponding to SEQ ID NO: 134:

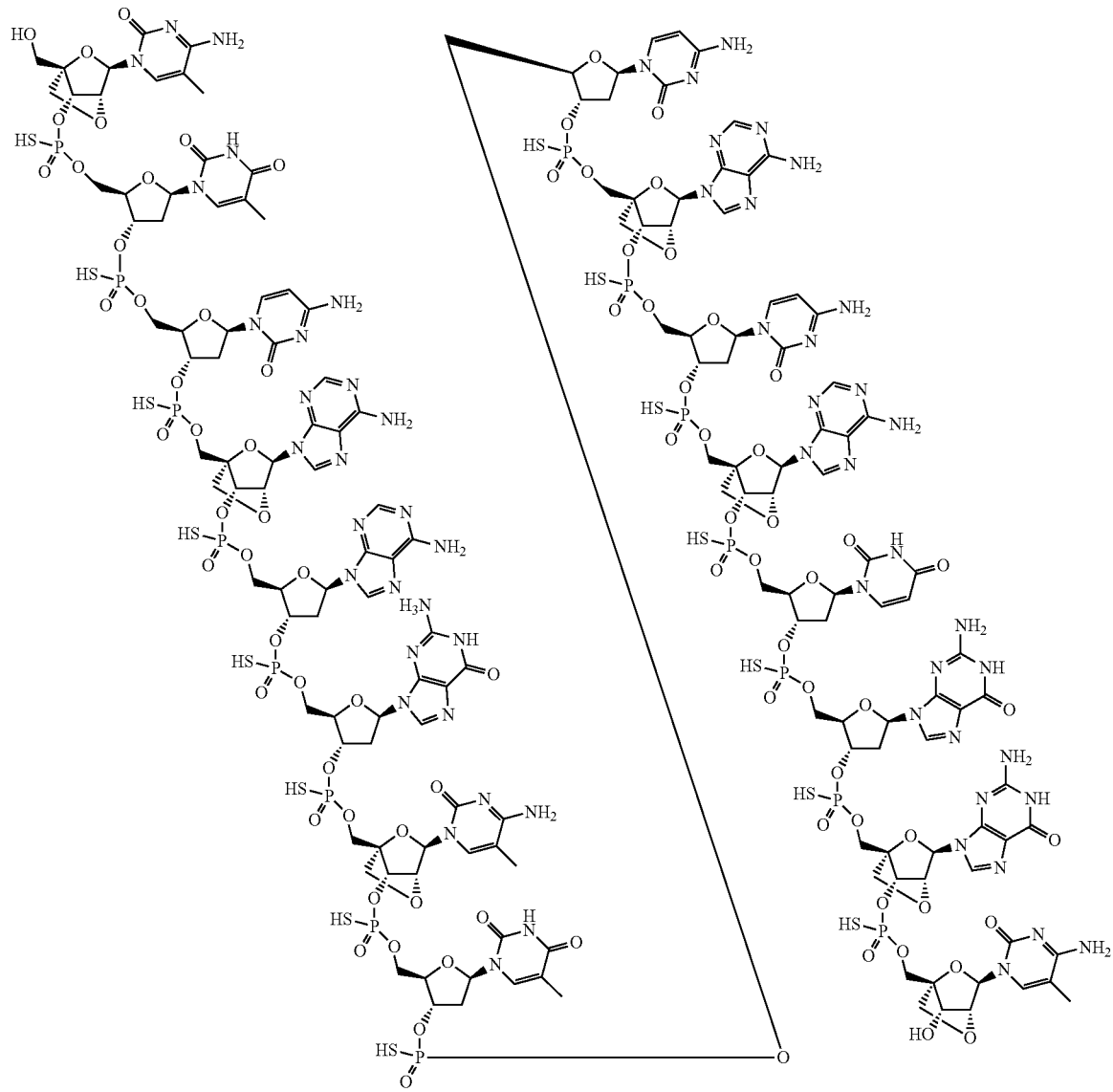

In another aspect the invention includes an antisense oligonucleotide wherein the oligonucleotide is the oligonucleotide compound GaGctGggTcAagAAT (SEQ ID NO: 71) wherein capital letters represent beta-D-oxy LNA nucleosides, lowercase letters represent DNA nucleosides, all LNA C are 5-methyl cytosine, and all internucleoside linkages are phosphorothioate internucleoside linkages.

In another aspect the invention includes an antisense oligonucleotide wherein the oligonucleotide is the oligonucleotide compound GgtCaaGaAtgGtgTG (SEQ ID NO: 73) wherein capital letters represent beta-D-oxy LNA nucleosides, lowercase letters represent DNA nucleosides, all LNA C are 5-methyl cytosine, and all internucleoside linkages are phosphorothioate internucleoside linkages.

In another aspect the invention includes an antisense oligonucleotide wherein the oligonucleotide is the oligonucleotide compound CaGaAtGgtGtGgTC (SEQ ID NO:74) wherein capital letters represent beta-D-oxy LNA nucleosides, lowercase letters represent DNA nucleosides, all LNA C are 5-methyl cytosine, and all internucleoside linkages are phosphorothioate internucleoside linkages.

In another aspect the invention includes an antisense oligonucleotide wherein the oligonucleotide is the oligonucleotide compound GaAtGgtGtGgTccC (SEQ ID NO:75) wherein capital letters represent beta-D-oxy LNA nucleosides, lowercase letters represent DNA nucleosides, all LNA C are 5-methyl cytosine, and all internucleoside linkages are phosphorothioate internucleoside linkages.

In another aspect the invention includes an antisense oligonucleotide wherein the oligonucleotide is the oligonucleotide compound CtcAagCtcAcAtgGC (SEQ ID NO:134) wherein capital letters represent beta-D-oxy LNA nucleosides, lowercase letters represent DNA nucleosides, all LNA C are 5-methyl cytosine, and all internucleoside linkages are phosphorothioate internucleoside linkages.

BRIEF DESCRIPTION OF THE DRAWINGS

FIG. 4 shows an overall sequence (SEQ ID NO: 288). The first boxed sequence (SEQ ID NO: 281) is complimentary to SEQ ID NO: 134. Residues seven through twenty-two of the second box (SEQ ID NO: 278) are complementary to SEQ ID NO: 73. Residues four through nineteen of the second box (SEQ ID NO: 279) are complementary to SEQ ID NO: 74. Residues one through sixteen of the second box (SEQ ID NO: 280) are complementary to SEQ ID NO: 75.

FIGS. 7A-7D shows ddPCR data quantifying the abundance of the 5 UTR splice variants in GRN mRNA 48h after transfection in H4 cells relative to Mock transfected cells. Grey bars quantify the abundance of the splice variant with retention of intron1 (Int1-Ex2) and the black bars the splice variant with the splicing of Ex1-Ex2 (Ex1-Ex2). SEQ ID NO: 73 (FIG. 7A), SEQ ID NO: 74 (FIG. 7B) and SEQ ID NO: 75 (FIG. 7C) show dose-dependent skipping of intron1 retention (Int1-Ex2) and an increase in Ex1-Ex2 splice-variant. The S10 compound from WO 2020/191212 (FIG. 7D) shows no/limited effects on skipping of intron1 retention.

DETAILED DESCRIPTION OF THE INVENTION

I. Definitions

Figure 1A:
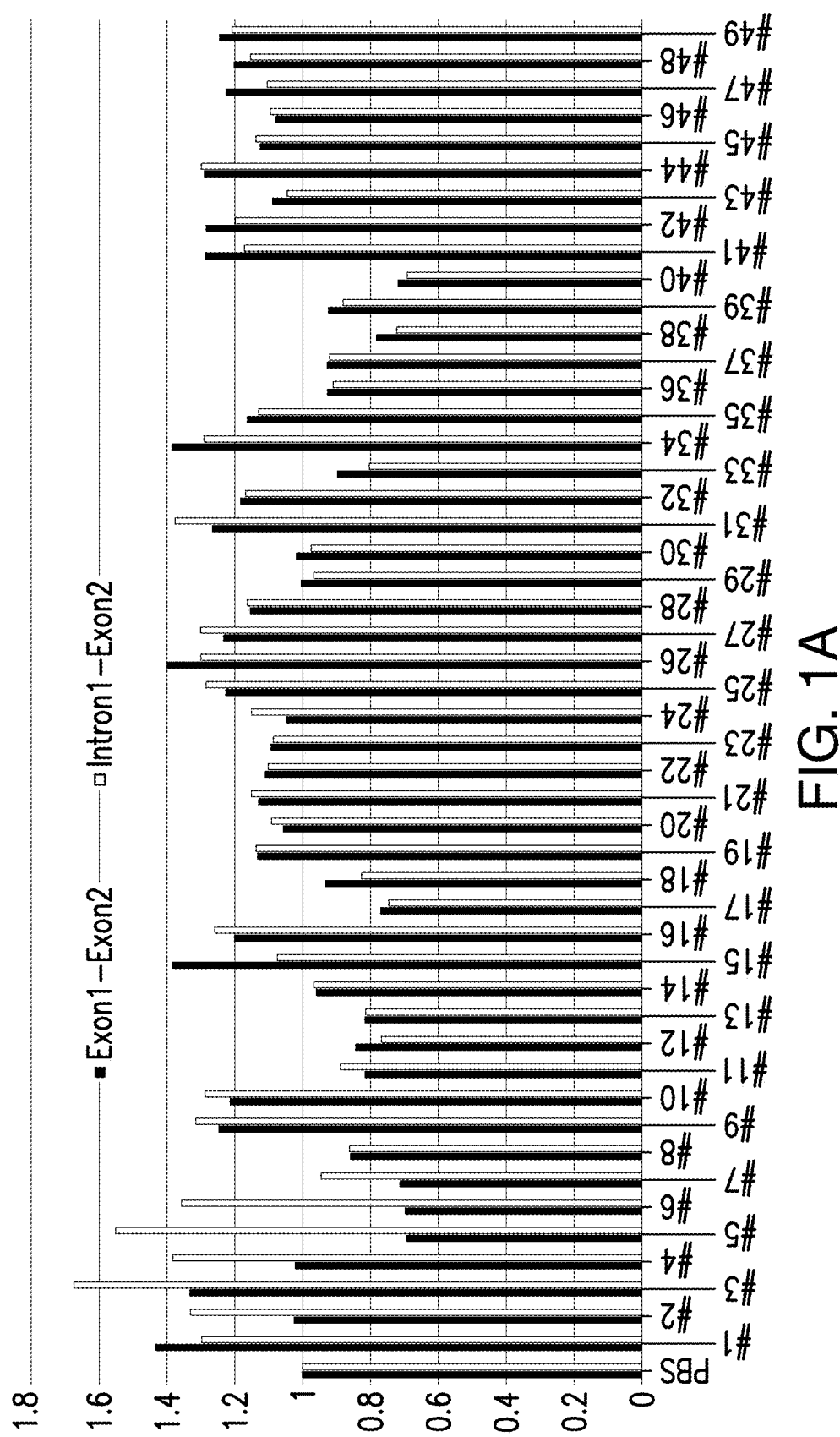
FIGS. 1A-1E shows expression levels of the Exon1-Exon2 mRNA splice form of progranulin relative to HPRT1 and Intron1-Exon2 relative to HPRT1. SEQ ID NOs: 1-49 are shown in FIG. 1A. SEQ ID NOs: 50-109 are shown in FIG. 1B. SEQ ID NOs: 110-169 are shown in FIG. 1C. SEQ ID NOs: 170-229 are shown in FIG. 1D. SEQ ID Nos: 230-275 are shown in FIG. 1E.
Figure 1B:
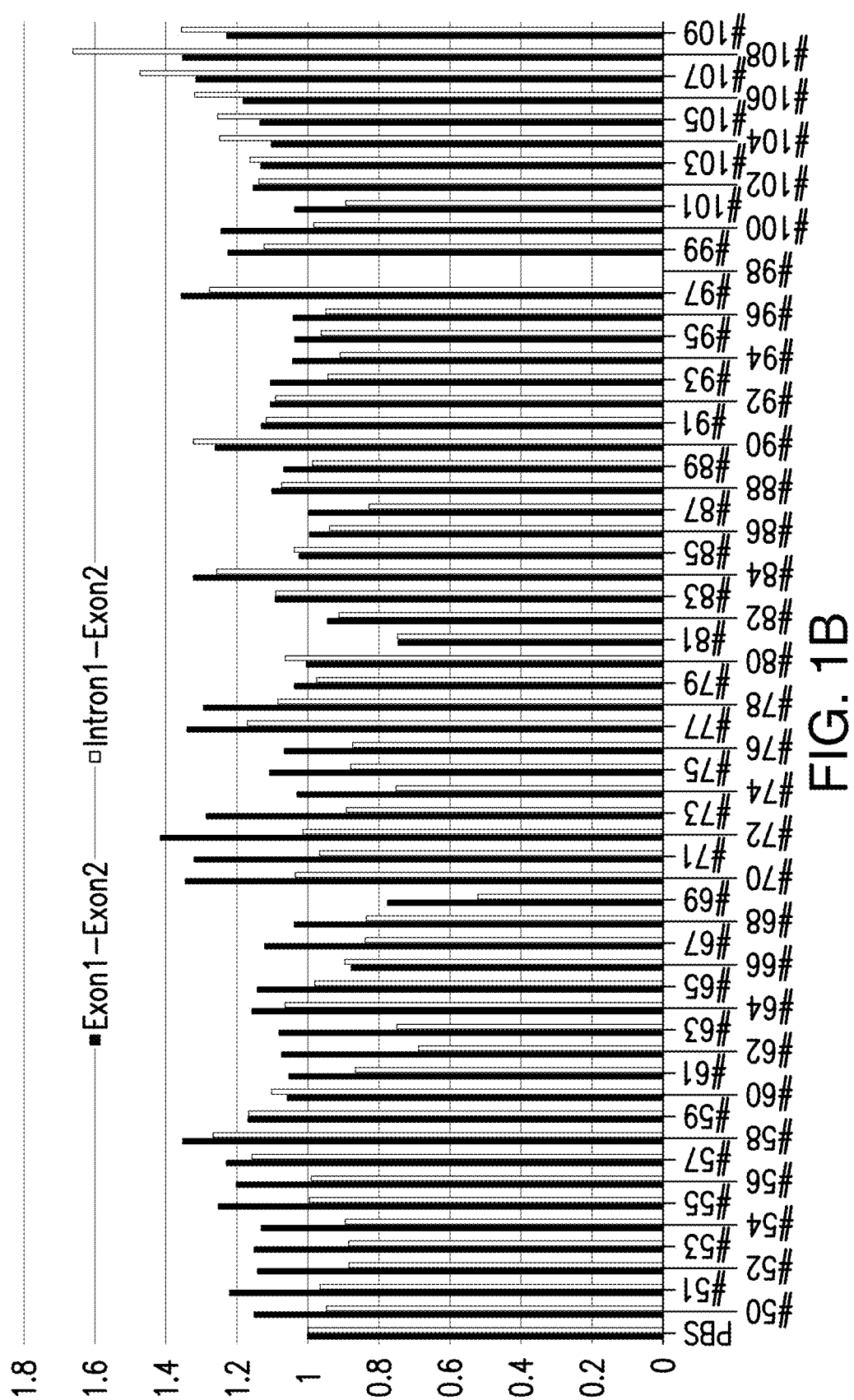
Figure 1C:
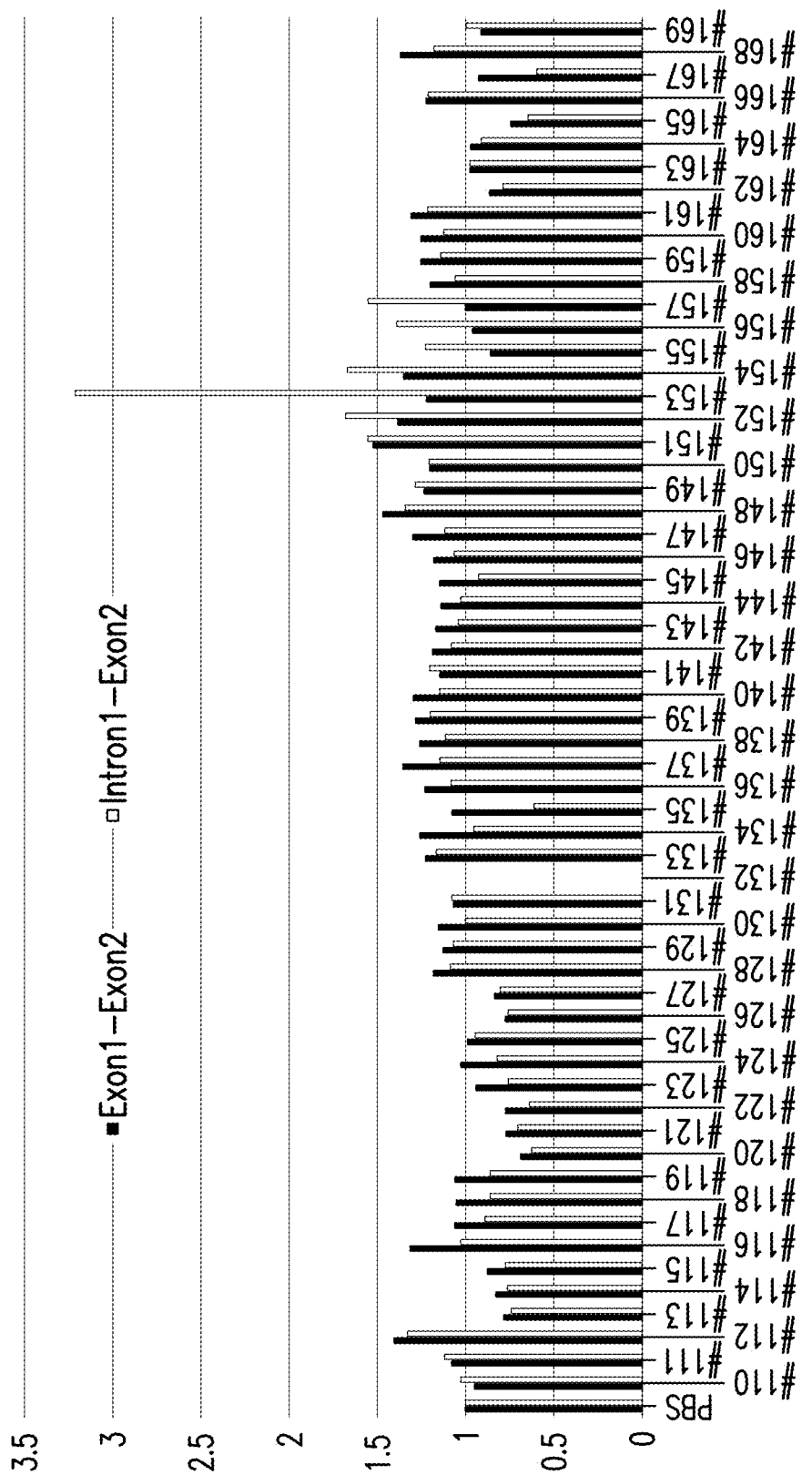
Figure 1D:
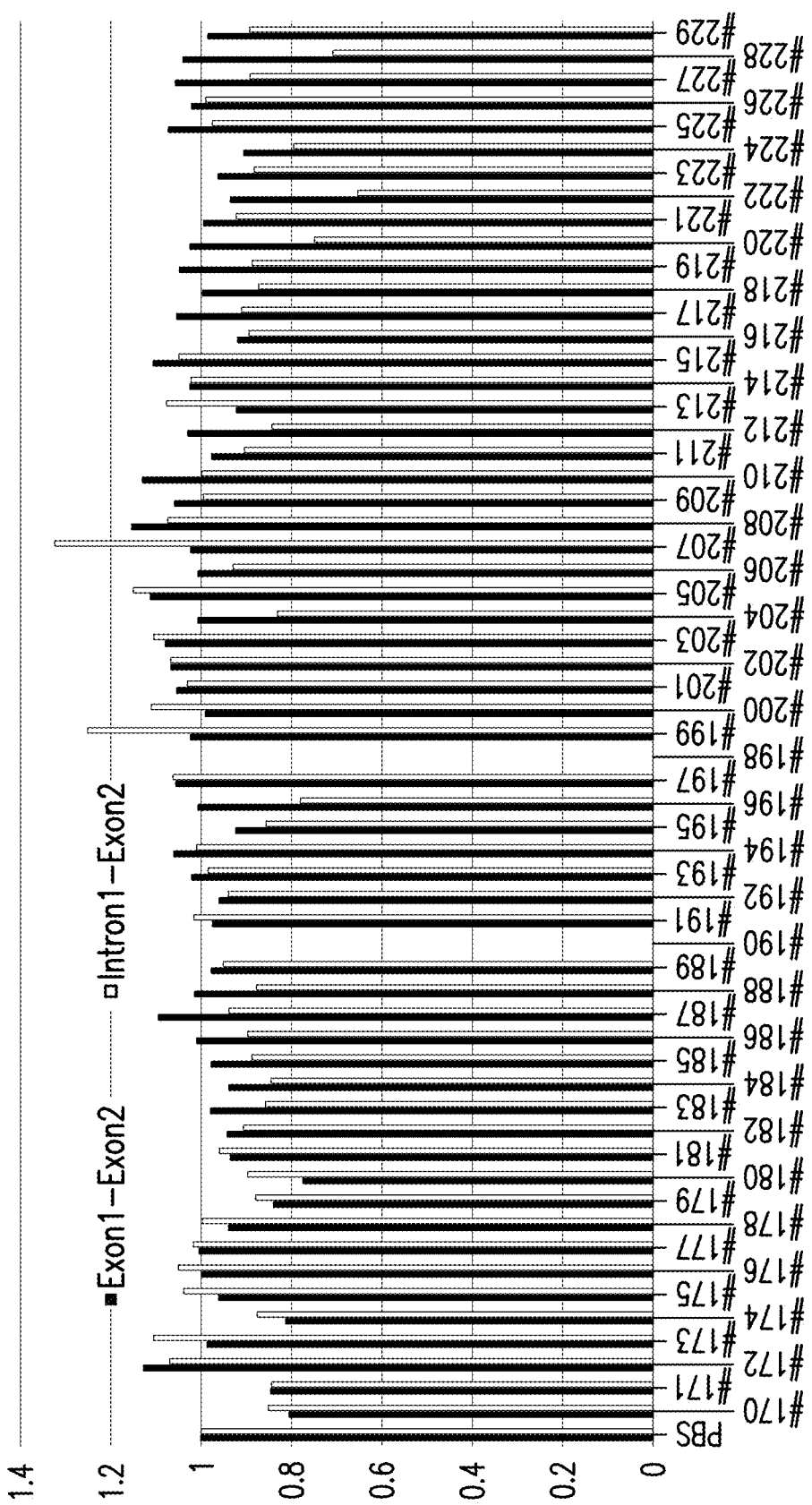
Figure 1E:
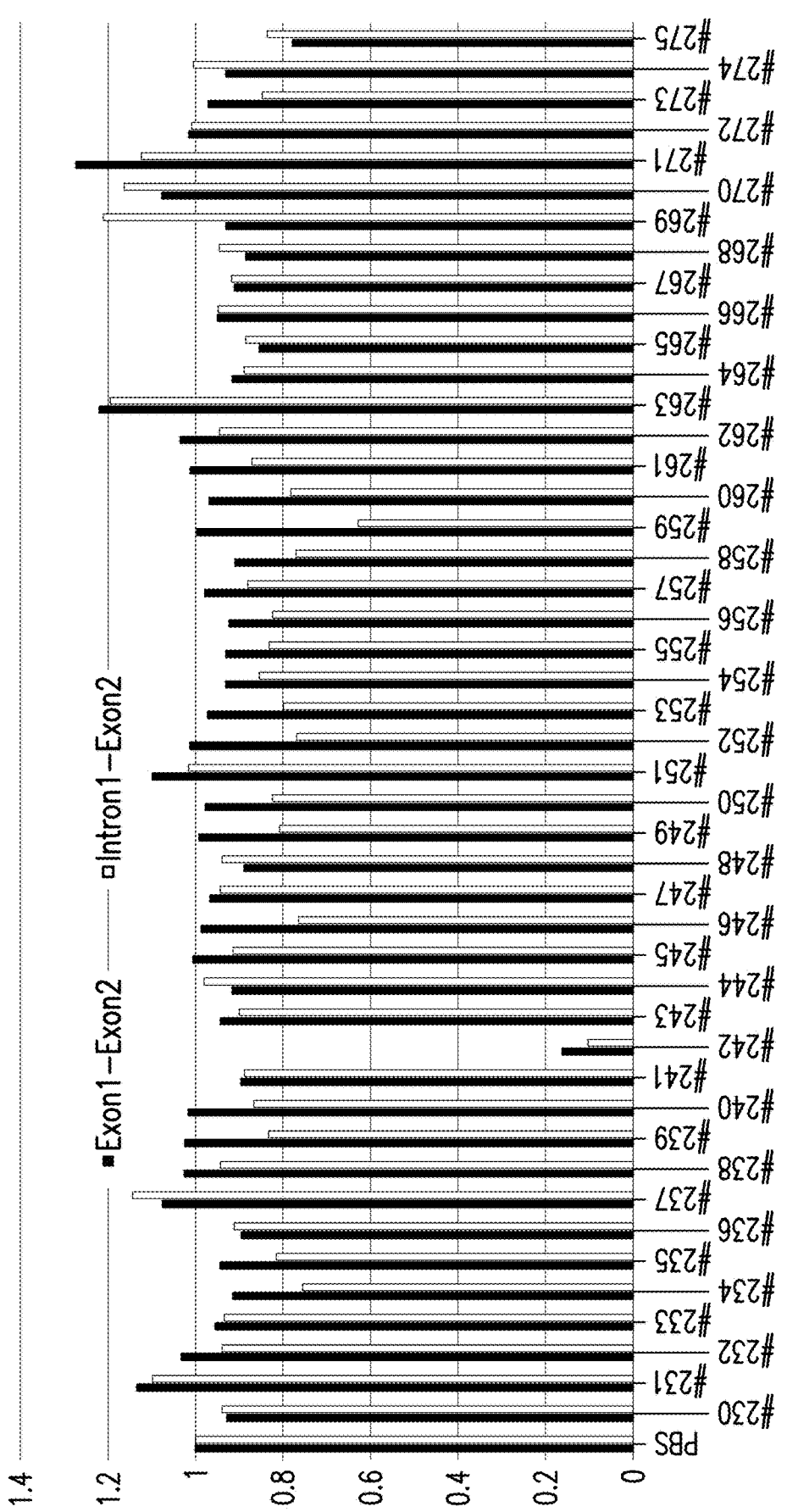

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "treat," "treating," "treatment" and "therapeutic use" refer to the elimination, reduction or amelioration of one or more symptoms of a disease or disorder. Specifically, the term "treatment" may refer to both treatment of an existing disease (e.g. a disease or disorder as herein referred to), or prevention of a disease (i.e. prophylaxis). It will therefore be recognized that treatment as referred to herein may, in some embodiments, be prophylactic. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers.

Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotides of the invention are man-made, and are chemically synthesized, and are typically purified or isolated. The oligonucleotides of the invention may comprise one or more modified nucleosides such as 2' sugar modified nucleosides. The oligonucleotides of the invention may comprise one or more modified internucleoside linkages, such as one or more phosphorothioate internucleoside linkages.

Antisense Oligonucleotide

The term "antisense oligonucleotide" as used herein is defined as an oligonucleotide capable of modulating expression of a target gene by hybridizing to a target nucleic acid, in particular to a contiguous sequence on a target nucleic acid. Antisense oligonucleotides are not essentially double stranded and are therefore not siRNAs or shRNAs. The antisense oligonucleotides of the present invention may be single stranded. It is understood that single stranded oligonucleotides of the present invention can form hairpins or intermolecular duplex structures (duplex between two molecules of the same oligonucleotide), as long as the degree of intra or inter self-complementarity is less than approximately 50% across of the full length of the oligonucleotide.

In certain contexts the antisense oligonucleotides of the invention may be referred to as oligonucleotides.

In some embodiments, the single stranded antisense oligonucleotides of the invention may not contain RNA nucleosides.

Advantageously, the antisense oligonucleotides of the invention comprise one or more modified nucleosides or nucleotides, such as 2' sugar modified nucleosides. Furthermore, in some antisense oligonucleotides of the invention, it may be advantageous that the nucleosides which are not modified are DNA nucleosides.

Contiguous Nucleotide Sequence

The term "contiguous nucleotide sequence" refers to the region of the oligonucleotide which is complementary to a target nucleic acid, which may be or may comprise an oligonucleotide motif sequence. The term is used interchangeably herein with the term "contiguous nucleobase sequence". In some embodiments all the nucleosides of the oligonucleotide constitute the contiguous nucleotide sequence. The contiguous nucleotide sequence is the sequence of nucleotides in the oligonucleotide of the invention which is complementary to, and in some instances fully complementary to, the target nucleic acid or target sequence, or target site sequence.

In some embodiments the target sequence is SEQ ID NO:276.

SEQ ID NO:276 is the sequence of exon 1, intron 1 and exon 2 of the human progranulin pre-mRNA transcript.

In some embodiments the target sequence is or comprises nucleotides 441-468 of SEQ ID NO:276.

In some embodiments the target sequence is or comprises nucleotides 441-462 of SEQ ID NO:276.

In some embodiments the target sequence is or comprises SEQ ID NO:277.

In some embodiments the target sequence is or comprises SEQ ID NO:278 In some embodiments the target sequence is or comprises SEQ ID NO:279.

In some embodiments the target sequence is or comprises SEQ ID NO:280.

In some embodiments the target sequence is or comprises nucleotides 268-283 of SEQ ID NO:276.

In some embodiments the target sequence is or comprises SEQ ID NO:281.

In some embodiments the target sequence is or comprises SEQ ID NO:291.

In some embodiments the target sequence is or comprises SEQ ID NO:292.

In some embodiments the oligonucleotide comprises the contiguous nucleotide sequence, and may optionally comprise further nucleotide(s), for example a nucleotide linker region which may be used to attach a functional group (e.g. a conjugate group) to the contiguous nucleotide sequence. The nucleotide linker region may or may not be complementary to the target nucleic acid. It is understood that the contiguous nucleotide sequence of the oligonucleotide cannot be longer than the oligonucleotide as such and that the oligonucleotide cannot be shorter than the contiguous nucleotide sequence.

Nucleotides and Nucleosides

Nucleotides and nucleosides are the building blocks of oligonucleotides and polynucleotides, and for the purposes of the present invention include both naturally occurring and non-naturally occurring nucleotides and nucleosides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleotide

Advantageously, the antisense oligonucleotide of the invention may comprise one or more modified nucleosides.

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. Advantageously, one or more of the modified nucleosides of the antisense oligonucleotides of the invention may comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing. Exemplary modified nucleosides which may be used in the antisense oligonucleotides of the invention include LNA, 2'-O-MOE and morpholino nucleoside analogues.

Modified Internucleoside Linkage

Advantageously, the antisense oligonucleotide of the invention comprises one or more modified internucleoside linkage.

The term "modified internucleoside linkage" is defined as generally understood by the skilled person as linkages other than phosphodiester (PO) linkages, that covalently couple two nucleosides together. The antisense oligonucleotides of the invention may therefore comprise one or more modified internucleoside linkages such as one or more phosphorothioate internucleoside linkages.

In some embodiments at least 50% of the internucleoside linkages in the antisense oligonucleotide, or contiguous nucleotide sequence thereof, are phosphorothioate, such as at least 60%, such as at least 70%, such as at least 75%, such as at least 80%, such as at least 90% or more of the internucleoside linkages in the antisense oligonucleotide, or contiguous nucleotide sequence thereof, are phosphorothioate. In some embodiments all of the internucleoside linkages of the antisense oligonucleotide, or contiguous nucleotide sequence thereof, are phosphorothioate.

Advantageously, all the internucleoside linkages of the contiguous nucleotide sequence of the antisense oligonucleotide may be phosphorothioate, or all the internucleoside linkages of the antisense oligonucleotide may be phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but which are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al. (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The antisense oligonucleotide of the invention may be a modified oligonucleotide.

The term modified oligonucleotide describes an oligonucleotide comprising one or more sugar-modified nucleosides and/or modified internucleoside linkages. The term "chimeric oligonucleotide" is a term that has been used in the literature to describe oligonucleotides comprising sugar modified nucleosides and DNA nucleosides. In some embodiments, it may be advantageous for the antisense oligonucleotide of the invention to be a chimeric oligonucleotide.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U).

It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pairs) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

Within the present invention the term "complementary" requires the antisense oligonucleotide to be at least about 80% complementary, or at least about 90% complementary, to a human progranulin pre-mRNA transcript. In some embodiments the antisense oligonucleotide may be at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% complementary to a human progranulin pre-mRNA transcript. Put another way, for some embodiments, an antisense oligonucleotide of the invention may include one, two, three or more mis-matches, wherein a mis-match is a nucleotide within the antisense oligonucleotide of the invention which does not base pair with its target.

The term "fully complementary" refers to 100% complementarity.

The antisense oligonucleotides of the invention are complementary to the human progranulin pre-mRNA. The antisense oligonucleotides of the invention are advantageously complementary to the intron 1 sequence of the human progranulin pre-mRNA transcript. The sequence of exon 1, intron 1 and exon 2 of the human progranulin pre-mRNA transcript is exemplified herein as SEQ ID NO:276. SEQ ID NO:276 is provided herein as a reference sequence and it will be understood that the target progranulin nucleic acid may be an allelic variant of SEQ ID NO:276, such as an allelic variant which comprises one or more polymorphism in the human progranulin nucleic acid sequence.

Identity

The term "identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif).

The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The terms "hybridizing" or "hybridizes" as used herein are to be understood as two nucleic acid strands (e.g. an antisense oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature (Tm) defined as the temperature at which half of the oligonucleotides are duplexed with the target nucleic acid. At physiological conditions Tm is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RT\ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405.

In some embodiments, antisense oligonucleotides of the present invention hybridize to a target nucleic acid with estimated $\Delta G°$ values below-10 kcal for oligonucleotides that are 10-30 nucleotides in length.

In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal, or −16 to −27 kcal such as −18 to −25 kcal.

High Affinity Modified Nucleosides

A high affinity modified nucleoside is a modified nucleotide which, when incorporated into the oligonucleotide enhances the affinity of the oligonucleotide for its complementary target, for example as measured by the melting temperature (Tm). A high affinity modified nucleoside of the present invention preferably results in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The antisense oligonucleotides of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been given to developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

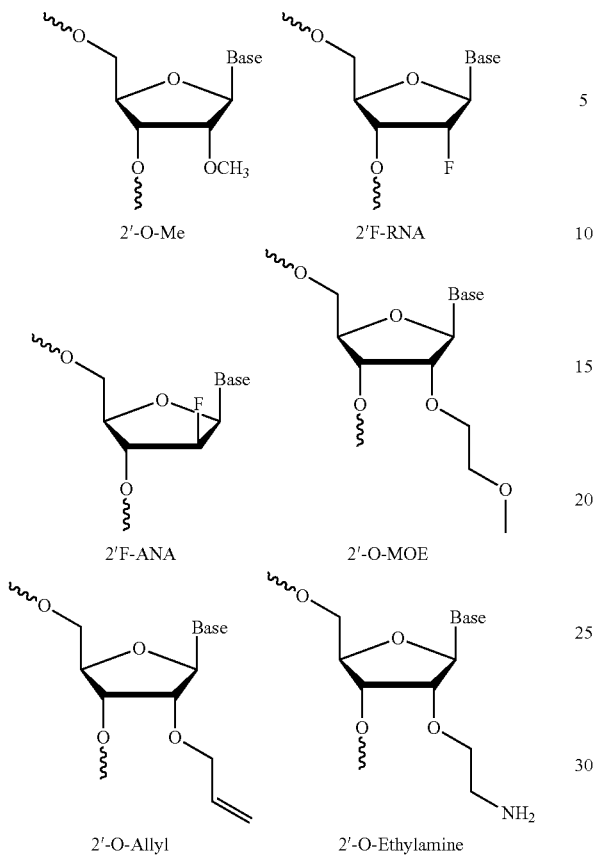

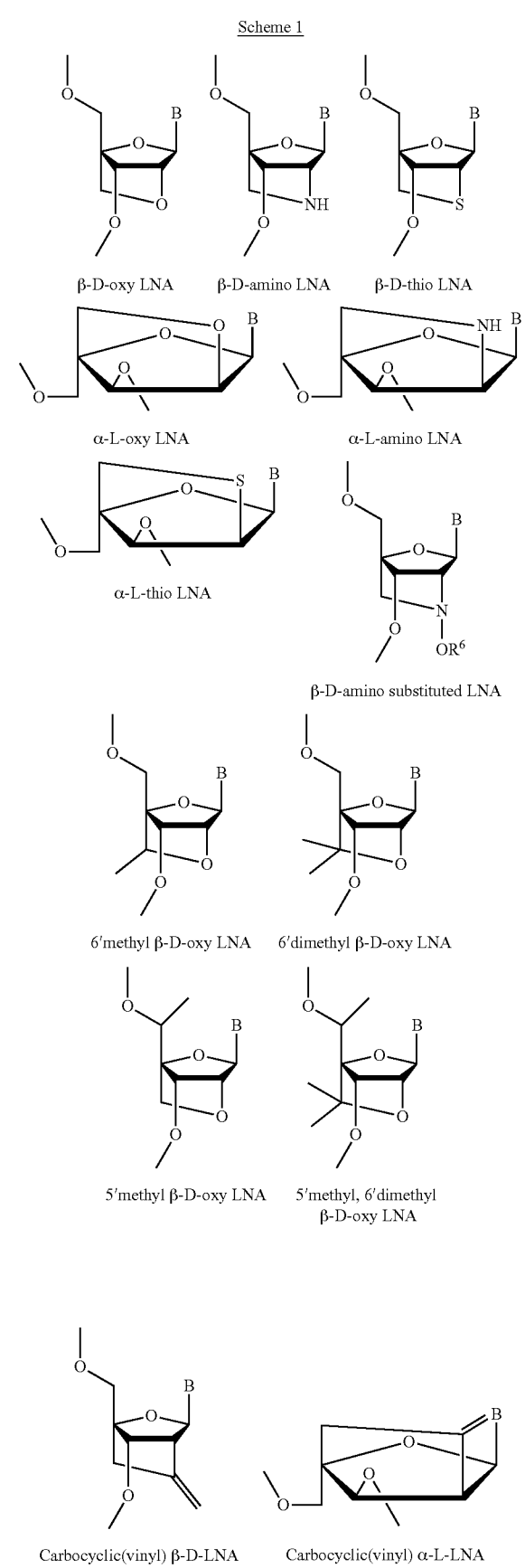

Scheme 1

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

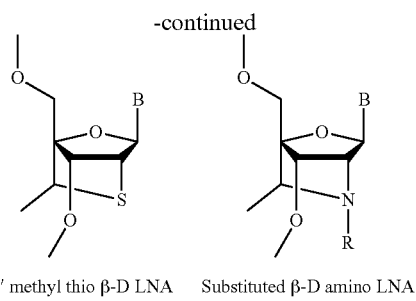

6' methyl thio β-D LNA   Substituted β-D amino LNA

Particular LNA nucleosides are beta-D-oxy-LNA, 6'-methyl-beta-D-oxy LNA such as (S)-6'-methyl-beta-D-oxy-LNA (ScET) and ENA.

A particularly advantageous LNA is beta-D-oxy-LNA.

Morpholino Oligonucleotides

In some embodiments, the antisense oligonucleotide of the invention comprises or consists of morpholino nucleosides (i.e. is a Morpholino oligomer and as a phosphorodiamidate Morpholino oligomer (PMO)). Splice modulating morpholino oligonucleotides have been approved for clinical use-see for example eteplirsen, a 30 nt morpholino oligonucleotide targeting a frame shift mutation in DMD, used to treat Duchenne muscular dystrophy. Morpholino oligonucleotides have nucleobases attached to six membered morpholine rings rather ribose, such as methylenemorpholine rings linked through phosphorodiamidate groups, for example as illustrated by the following illustration of 4 consecutive morpholino nucleotides:

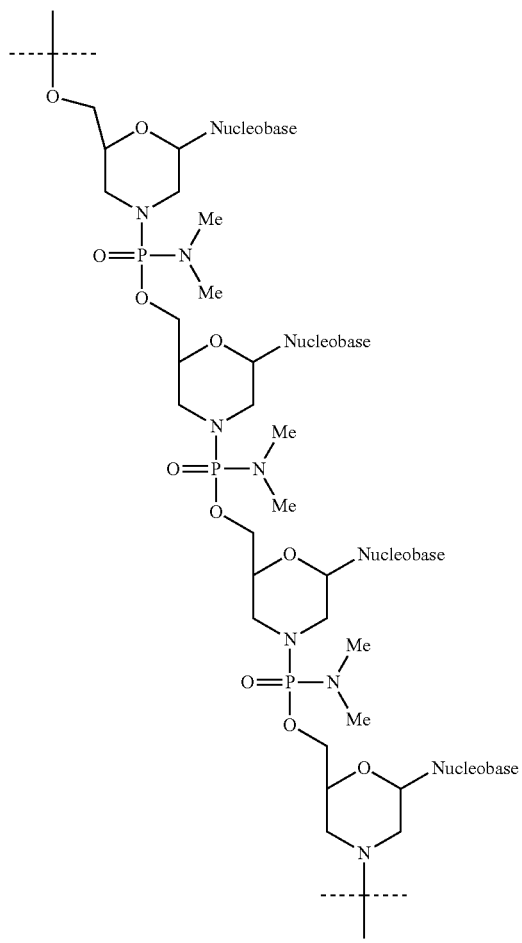

In some embodiments, morpholino oligonucleotides of the invention may be, for example 20-40 morpholino nucleotides in length, such as morpholino 25-35 nucleotides in length.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10%, at least 20% or more than 20%, of the initial rate determined when using an oligonucleotide having the same base sequence as the modified oligonucleotide being tested, but containing only DNA monomers with phosphorothioate linkages between all monomers in the oligonucleotide, and using the methodology provided by Examples 91-95 of WO01/23613 (hereby incorporated by reference). For use in determining RHase H activity, recombinant RNase H1 is available from Lubio Science GmbH, Lucerne, Switzerland.

DNA oligonucleotides are known to effectively recruit RNaseH, as are gapmer oligonucleotides which comprise a region of DNA nucleosides (typically at least 5 or 6 contiguous DNA nucleosides), flanked 5' and 3' by regions comprising 2' sugar modified nucleosides, typically high affinity 2' sugar modified nucleosides, such as 2-O-MOE and/or LNA. For effective modulation of splicing, degradation of the pre-mRNA is not desirable, and as such it is preferable to avoid the RNaseH degradation of the target. Therefore, the antisense oligonucleotides of the invention are not RNaseH recruiting gapmer oligonucleotide.

RNaseH recruitment may be avoided by limiting the number of contiguous DNA nucleotides in the oligonucleotide-therefore mimxes and totalmer designs may be used. Advantageously the antisense oligonucleotides of the invention, or the contiguous nucleotide sequence thereof, do not comprise more than 3 contiguous DNA nucleosides. Further, advantageously the antisense oligonucleotides of the invention, or the contiguous nucleotide sequence thereof, do not comprise more than 4 contiguous DNA nucleosides. Further advantageously, the antisense oligonucleotides of the invention, or contiguous nucleotide sequence thereof, do not comprise more than 2 contiguous DNA nucleosides.

Mixmers and Totalmers

For splice modulation it is often advantageous to use antisense oligonucleotides which do not recruit RNAaseH. As RNaseH activity requires a contiguous sequence of DNA nucleotides, RNaseH activity of antisense oligonucleotides may be achieved by designing antisense oligonucleotides which do not comprise a region of more than 3 or more than 4 contiguous DNA nucleosides. This may be achieved by using antisense oligonucleotides or contiguous nucleoside regions thereof with a mixmer design, which comprise sugar modified nucleosides, such as 2' sugar modified nucleosides, and short regions of DNA nucleosides, such as 1, 2 or 3 DNA nucleosides. Mixmers are exemplified herein by every second design, wherein the nucleosides alternate between 1 LNA and 1 DNA nucleoside, e.g. LDLDLDLDLDLD-LDLL, with 5' and 3' terminal LNA nucleosides, and every third design, such as LDDLDDLDDLDDLDDL, where every third nucleoside is a LNA nucleoside.

A totalmer is an antisense oligonucleotide or a contiguous nucleotide sequence thereof which does not comprise DNA or RNA nucleosides, and may for example comprise only 2'-O-MOE nucleosides, such as a fully MOE phosphorothioate, e.g. MMMMMMMMMMMMMMMMMMMMM, where M=2'-O-MOE, which are reported to be effective splice modulators for therapeutic use.

Alternatively, a mixmer may comprise a mixture of modified nucleosides, such as MLMLMLMLMLMLMLMLMLML, wherein L=LNA and M=2'-O-MOE nucleosides.

Advantageously, the internucleoside nucleosides in mixmers and totalmers may be phosphorothioate, or a majority of nucleoside linkages in mixmers may be phosphorothioate. Mixmers and totalmers may comprise other internucleoside linkages, such as phosphodiester or phosphorodithioate, by way of example.

Region D' or D" in an Oligonucleotide

The antisense oligonucleotide of the invention may in some embodiments comprise or consist of the contiguous nucleotide sequence of the oligonucleotide which is complementary to the target nucleic acid, such as a mixmer or toalmer region, and further 5' and/or 3' nucleosides. The further 5' and/or 3' nucleosides may or may not be complementary, such as fully complementary, to the target nucleic acid. Such further 5' and/or 3' nucleosides may be referred to as region D' and D" herein.

The addition of region D' or D" may be used for the purpose of joining the contiguous nucleotide sequence, such as the mixmer or totoalmer, to a conjugate moiety or another functional group. When used for joining the contiguous nucleotide sequence with a conjugate moiety it can serve as a biocleavable linker. Alternatively, it may be used to provide exonuclease protection or for case of synthesis or manufacture.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D" region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs within a single oligonucleotide.

In one embodiment the antisense oligonucleotide of the invention comprises a region D' and/or D" in addition to the contiguous nucleotide sequence which constitutes a mixmer or a totalmer.

In some embodiments the internucleoside linkage positioned between region D' or D" and the mixmer or totalmer region is a phosphodiester linkage.

Conjugate

The invention encompasses an antisense oligonucleotide covalently attached to at least one conjugate moiety. In some embodiments this may be referred to as a conjugate of the invention.

The term "conjugate" as used herein refers to an antisense oligonucleotide which is covalently linked to a non-nucleotide moiety (conjugate moiety or region C or third region). The conjugate moiety may be covalently linked to the antisense oligonucleotide, optionally via a linker group, such as region D' or D".

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103.

In some embodiments, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the antisense oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or antisense oligonucleotide conjugate of the invention may optionally comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In some embodiments the nuclease susceptible linker comprises between 1 and 5 nucleosides, such as DNA nucleoside(s) comprising at least two consecutive phosphodiester linkages. Phosphodiester containing biocleavable linkers are described in more detail in WO 2014/076195.

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups. The antisense oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In some embodiments the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

TDP-43 Pathologies

A TDP-43 pathology is a disease which is associated with reduced or aberrant expression of TDP-43, often associated with an increase in cytoplasmic TDP-43, particularly hyperphosphorylated and ubiquitinated TDP-43.

Diseases associated with TDP-43 pathology include amyotrophic lateral sclerosis (ALS), frontotemporal lobar degeneration (FTLD), Alzheimer's disease, Parkinson's disease, Autism, Hippocampal sclerosis dementia, Down syndrome, Huntington's disease, polyglutamine diseases, such as spinocerebellar ataxia 3, myopathies and Chronic Traumatic Encephalopathy.

The inventors have identified that targeting the progranulin pre-mRNA transcript with antisense oligonucleotides can increase expression of the progranulin Exon1-Exon 2 spliced mRNA, decrease expression of the progranulin Intron1-Exon2 spliced mRNA (which retains the 271 nucleotide 5' fragment of intron 1) and/or alter the ratio of Exon1-Exon2 vs Intron1-Exon2 mRNA. This is particularly the case when antisense oligonucleotides which comprise high affinity sugar modified nucleosides, such as high affinity 2' sugar modified nucleosides, such as LNA nucleosides or 2'-O-methoxyethyl (MOE) nucleosides are used.

Described herein are target sites present on the human progranulin pre-mRNA which can be targeted by antisense oligonucleotides. Also described are antisense oligonucleotides which are complementary, such as fully complementary, to these target sites.

Without wishing to be bound by theory, it is considered that the antisense oligonucleotides of the invention can increase expression of the progranulin Exon1-Exon2 spliced mRNA, decrease expression of the progranulin Intron1-Exon1 spliced mRNA and/or alter the ratio of Exon1-Exon2 vs Intron1-Exon2 mRNA by binding to these regions and affecting, such as increasing, production of the Exon1-Exon2 splice variant.

Oligonucleotides, such as RNaseH recruiting single stranded antisense oligonucleotides or siRNAs are used extensively in the art to inhibit target RNAs—i.e. are used as antagonists of their complementary nucleic acid target.

The antisense oligonucleotides of the present invention may be described as modulators, i.e. they alter the expression of a particular splice variant of their complementary target, progranulin pre-mRNA, and thereby increase the production of active progranulin protein.

Reduced expression of the progranulin Intron1-Exon2 splice variant is desirable because the inclusion of an intron, such as Intron 1, within a mature mRNA sequence leads to nonsense-mediated mRNA decay (NMD).

Enhanced expression of the progranulin Exon1-Exon2 over the splice variant which retains the 5' part of intron 1 is desirable because the Exon1-Exon2 splice variant does not include the 271 nucleotide fragment of intron 1 with two AUG sites upstream of the canonical downstream AUG in Exon 2 (open reading frame). Translation from these two upstream AUG sites will not encode the progranulin protein and due to premature termination codons the transcript may undergo non-sense mediated mRNA decay (NMD). Changing the splicing to the Exon1-Exon2 splice variant will instead lead to translation of an active version of the progranulin protein. Progranulin is a neuroprotective protein, and increasing its production can be used to treat a range of neurological disorders, such as TDP-43 pathologies.

In certain embodiments the antisense oligonucleotides of the present invention may enhance the production of the Exon1-Exon2 progranulin splice variant.

In certain embodiments the antisense oligonucleotides of the present invention may enhance the production of the Exon1-Exon2 progranulin splice variant mRNA by at least about 10% relative to the production of the Exon1-Exon2 progranulin splice variant mRNA in the absence of an antisense oligonucleotide of the invention. In other embodiments the antisense oligonucleotides of the present invention may enhance the production of the Exon1-Exon2 progranulin splice variant mRNA by at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 300%, at least about 400%, at least about 500% or more relative to the production of the Exon1-Exon2 progranulin splice variant mRNA in the absence of an antisense oligonucleotide of the invention.

In certain embodiments the antisense oligonucleotides of the present invention may reduce the production of the Intron1-Exon2 progranulin splice variant mRNA.

In certain embodiments the antisense oligonucleotides of the present invention may reduce the production of the Intron1-Exon2 progranulin splice variant mRNA by at least about 10% relative to the production of the Intron1-Exon2 progranulin splice variant mRNA in the absence of an antisense oligonucleotide of the invention. In other embodiments the antisense oligonucleotides of the present invention may reduce the production of the Intron1-Exon2 progranulin splice variant mRNA by at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 300%, at least about 400%, at least about 500% or more relative to the production of the Intron1-Exon2 progranulin splice variant mRNA in the absence of an antisense oligonucleotide of the invention.

Enhanced expression of the progranulin Exon1-Exon2 splice variant should lead to translation of an active version of the progranulin protein. In certain embodiments the antisense oligonucleotides of the present invention may increase production of the progranulin protein by at least about 10% relative to the production of the progranulin protein in the absence of an antisense oligonucleotide of the invention. In other embodiments the antisense oligonucleotides of the present invention may increase the production of the progranulin protein by at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 300%, at least about 400%, at least about 500% or more relative to the production of the progranulin protein in the absence of an antisense oligonucleotide of the invention.

In certain embodiments, the antisense oligonucleotides of the present invention may alter the ratio of Exon 1-Exon2 vs Intron-Exon2 progranulin mRNA.

In certain embodiments, the antisense oligonucleotides of the present invention may alter the ratio of Exon1-Exon2 vs Intron1-Exon2 progranulin mRNA by at least about 10% relative to the ratio of Exon1-Exon2 vs Intron1-Exon2 progranulin mRNA in the absence of an antisense oligonucleotide of the invention. In other embodiments the antisense oligonucleotides of the present invention may alter the ratio of Exon1-Exon2 vs Intron1-Exon2 progranulin mRNA by at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100% or more, relative to the ratio of Exon1-Exon2 vs Intron1-Exon2 progranulin mRNA in the absence of an antisense oligonucleotide of the invention.

In certain embodiments, the antisense oligonucleotides of the present invention may alter the ratio of Exon1-Exon2 vs Intron1-Exon2 progranulin mRNA to at least about 1.2. In certain embodiments, the antisense oligonucleotides of the present invention may alter the ratio of Exon1-Exon2 vs Intron1-Exon2 progranulin mRNA to at least about 1.3, at least about 1.4, at least about 1.5, at least about 1.6, at least about 1.7, at least about 1.8, at least about 1.9, at least about 2.0 or more.

In some embodiments, the antisense oligonucleotides of the invention or the contiguous nucleotide sequence thereof comprises or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 contiguous nucleotides in length.

In some embodiments, the entire nucleotide sequence of the antisense oligonucleotide is the contiguous nucleotide sequence.

In one embodiment the contiguous nucleotide sequence may a sequence selected from the group consisting of SEQ ID NO:71, SEQ ID NO:73, SEQ ID NO:74, SEQ ID NO:75 and SEQ ID NO:134. The invention also contemplates fragments of these contiguous nucleotide sequences, including fragments of at least 8, at least 9, at least 10, at least 11, at least 12, at least 13, at least 14, or at least 15 contiguous nucleotides thereof.

In some embodiments, the antisense oligonucleotide or contiguous nucleotide sequence comprises or consists of a sequence selected from the group consisting of SEQ ID NO:71, SEQ ID NO:73, SEQ ID NO:74, SEQ ID NO:75 and SEQ ID NO:134. It will be understood that the sequences shown in SEQ ID NO:71, SEQ ID NO:73, SEQ ID NO:74, SEQ ID NO:75 and SEQ ID NO:134 may include modified nucleobases which function as the shown nucleobase in base pairing, for example 5-methyl cytosine may be used in place of methyl cytosine. Inosine may be used as a universal base.

In some embodiments, the antisense oligonucleotide or contiguous nucleotide sequence comprises or consists of 8 to 30 or 8 to 40 nucleotides in length with at least 90% identity, preferably 100% identity, to a sequence selected from the group consisting of SEQ ID NO:71, SEQ ID NO:73, SEQ ID NO:74, SEQ ID NO:75 and SEQ ID NO:134. In some embodiments the antisense oligonucleotide may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In some embodiments, the antisense oligonucleotide or contiguous nucleotide sequence comprises or consists of 8 to 30 or 8 to 40 nucleotides in length with at least 90% identity, preferably 100% identity, to a sequence selected from the group consisting of SEQ ID NO:289 and SEQ ID NO:290. In some embodiments the antisense oligonucleotide may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

It is understood that the contiguous nucleobase sequences (motif sequence) can be modified to, for example, increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The antisense oligonucleotides of the invention are designed with modified nucleosides and DNA nucleosides. Advantageously, high affinity modified nucleosides are used.

In an embodiment, the antisense oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides.

In an embodiment the antisense oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the antisense oligonucleotide comprises one or more sugar modified nucleosides, such as 2' sugar modified nucleosides. Preferably the antisense oligonucleotide of the invention comprises one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the antisense oligonucleotide comprises at least one modified internucleoside linkage. Suitable internucleoside modifications are described in the "Definitions" section under "Modified internucleoside linkage". It is advantageous if at least 75%, such as all, the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In one embodiment, the invention presents an antisense oligonucleotide, wherein the antisense oligonucleotide is 8-40 nucleotides in length and comprises a contiguous nucleotide sequence of 8-40 nucleotides in length which is complementary to a splice regulation site of the human progranulin pre-mRNA transcript.

In another embodiment, the human progranulin pre-mRNA transcript comprises the exon 1, intron 1 and exon 2 sequence of the human progranulin pre-mRNA transcript (SEQ ID NO:276).

In another embodiment, the contiguous nucleotide sequence is of a length of at least 12 nucleotides in length.

In another embodiment, the contiguous nucleotide sequence is 12-16 nucleotides in length.

In another embodiment, the contiguous nucleotide sequence is 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In another embodiment, the contiguous nucleotide sequence is the same length as the antisense oligonucleotide.

In another embodiment, the contiguous nucleotide sequence is fully complementary to the human progranulin pre-mRNA transcript.

In another embodiment, the contiguous nucleotide sequence is complementary to a nucleotide sequence comprised within nucleotides 441-468 of SEQ ID NO: 276.

In another embodiment, the contiguous nucleotide sequence is complementary to a nucleotide sequence comprised within nucleotides 441-462 of SEQ ID NO: 276.

In another embodiment, the contiguous nucleotide sequence is complementary to SEQ ID NO:277, SEQ ID NO:278, SEQ ID NO:279 or SEQ ID NO:280.

In another embodiment, the contiguous nucleotide sequence is fully complementary to SEQ ID NO:277, SEQ ID NO:278, SEQ ID NO:279 or SEQ ID NO:280.

In another embodiment, the contiguous nucleotide sequence is selected from SEQ ID NO:71, SEQ ID NO:73, SEQ ID NO:74 and SEQ ID NO:75, or at least 8 or at least 10 contiguous nucleotides thereof.

In another embodiment, the contiguous nucleotide sequence SEQ ID NO:71.

In another embodiment, the contiguous nucleotide sequence SEQ ID NO:73.

In another embodiment, the contiguous nucleotide sequence SEQ ID NO:74.

In another embodiment, the contiguous nucleotide sequence SEQ ID NO:75.

In another embodiment, the contiguous nucleotide sequence is complementary to a nucleotide sequence comprised within nucleotides 268-283 of SEQ ID NO: 276.

In another embodiment, the contiguous nucleotide sequence is complementary to SEQ ID NO:281.

In another embodiment, the contiguous nucleotide sequence is fully complementary to SEQ ID NO:281.

In another embodiment, the contiguous nucleotide sequence is SEQ ID NO:134, or at least 8 or at least 10 contiguous nucleotides thereof.

In another embodiment, the contiguous nucleotide sequence is selected from the group consisting of SEQ ID NO:51, SEQ ID NO:52, SEQ ID NO:53, SEQ ID NO:54, SEQ ID NO:55, SEQ ID NO:62, SEQ ID NO:63, SEQ ID NO:67, SEQ ID NO:71, SEQ ID NO:73, SEQ ID NO:74, SEQ ID NO:75, SEQ ID NO:100, SEQ ID NO:134, SEQ ID NO:135, SEQ ID NO:196, SEQ ID NO:220, SEQ ID NO:228 and SEQ ID NO:252.

In some embodiments, the antisense oligonucleotide is isolated, purified or manufactured.

In other embodiments, the antisense oligonucleotide or contiguous nucleotide sequence thereof comprises one or more modified nucleotides or one or more modified nucleosides.

In another embodiment, the antisense oligonucleotide or contiguous nucleotide sequence thereof, comprises one or more modified nucleosides, such as one or more modified nucleotides independently selected from the group consisting of 2'-O-alkyl-RNA; 2'-O-methyl RNA (2'-OMe); 2'-alkoxy-RNA; 2'-O-methoxyethyl-RNA (2'-MOE); 2'-amino-DNA; 2'-fluro-RNA; 2'-fluoro-DNA; arabino nucleic acid (ANA); 2'-fluoro-ANA; bicyclic nucleoside analog (LNA); or any combination thereof.

In some embodiments, one or more of the modified nucleosides is a sugar modified nucleoside.

In another embodiment, one or more of the modified nucleosides comprises a bicyclic sugar.

In yet another embodiment, one or more of the modified nucleosides is an affinity enhancing 2' sugar modified nucleoside.

In another embodiment, one or more of the modified nucleosides is an LNA nucleoside, such as one or more beta-D-oxy LNA nucleosides.

In another embodiment, the antisense oligonucleotide or contiguous nucleotide sequence thereof, comprises one or more 5'-methyl-cytosine nucleobases.

In another embodiment, one or more of the internucleoside linkages within the contiguous nucleotide sequence of the antisense oligonucleotide is modified.

In another embodiment, at least about 75%, at least about 80%, at least about 85%, at least about 90%, at least about 95% or about 100% of the internucleoside linkages are modified.

In another embodiment, the one or more modified internucleoside linkages comprise a phosphorothioate linkage.

In another embodiment, the antisense oligonucleotide is a morpholino modified antisense oligonucleotide.

In another embodiment, the antisense oligonucleotide is or comprises an antisense oligonucleotide mixmer or totalmer.

In another embodiment, the antisense oligonucleotide or contiguous nucleotide sequence thereof is 10-20 nucleotides in length.

In another embodiment, the antisense oligonucleotide or contiguous nucleotide sequence thereof is 16 nucleotides in length.

In some embodiments, the invention presents an antisense oligonucleotide having the structure:
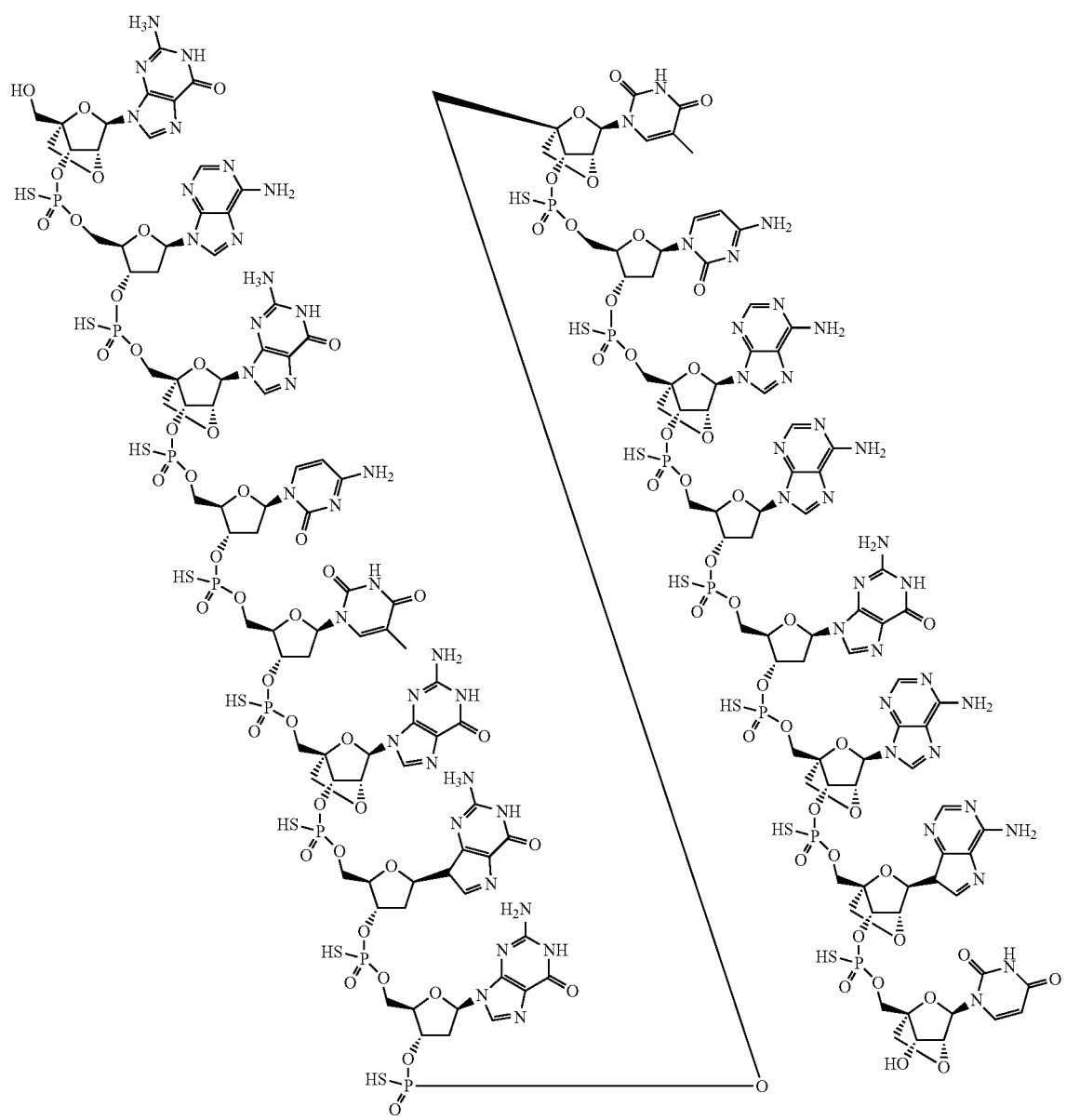

In some embodiments, the invention presents an antisense oligonucleotide having the structure:
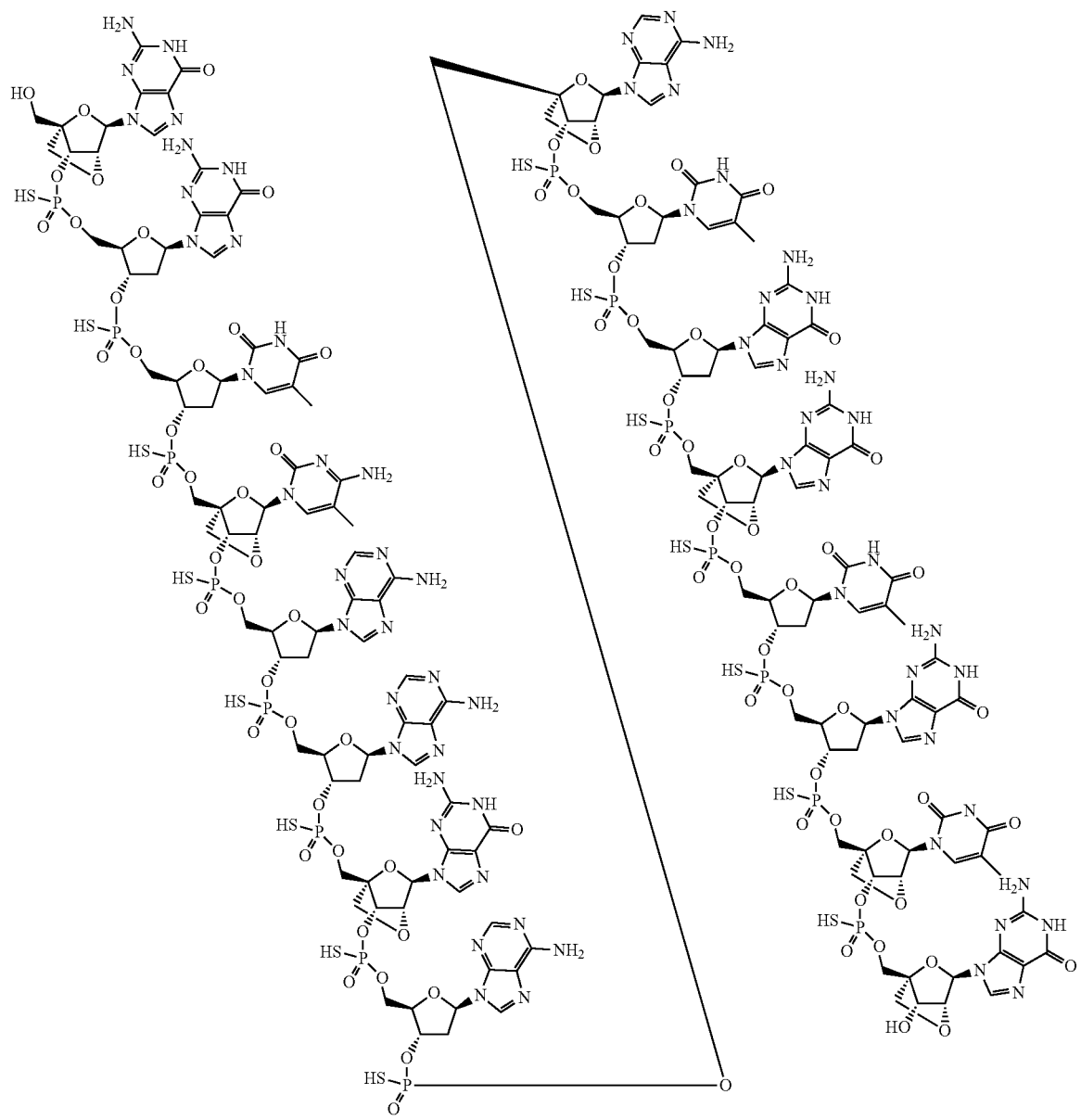

In some embodiments, the invention presents an antisense oligonucleotide having the structure:
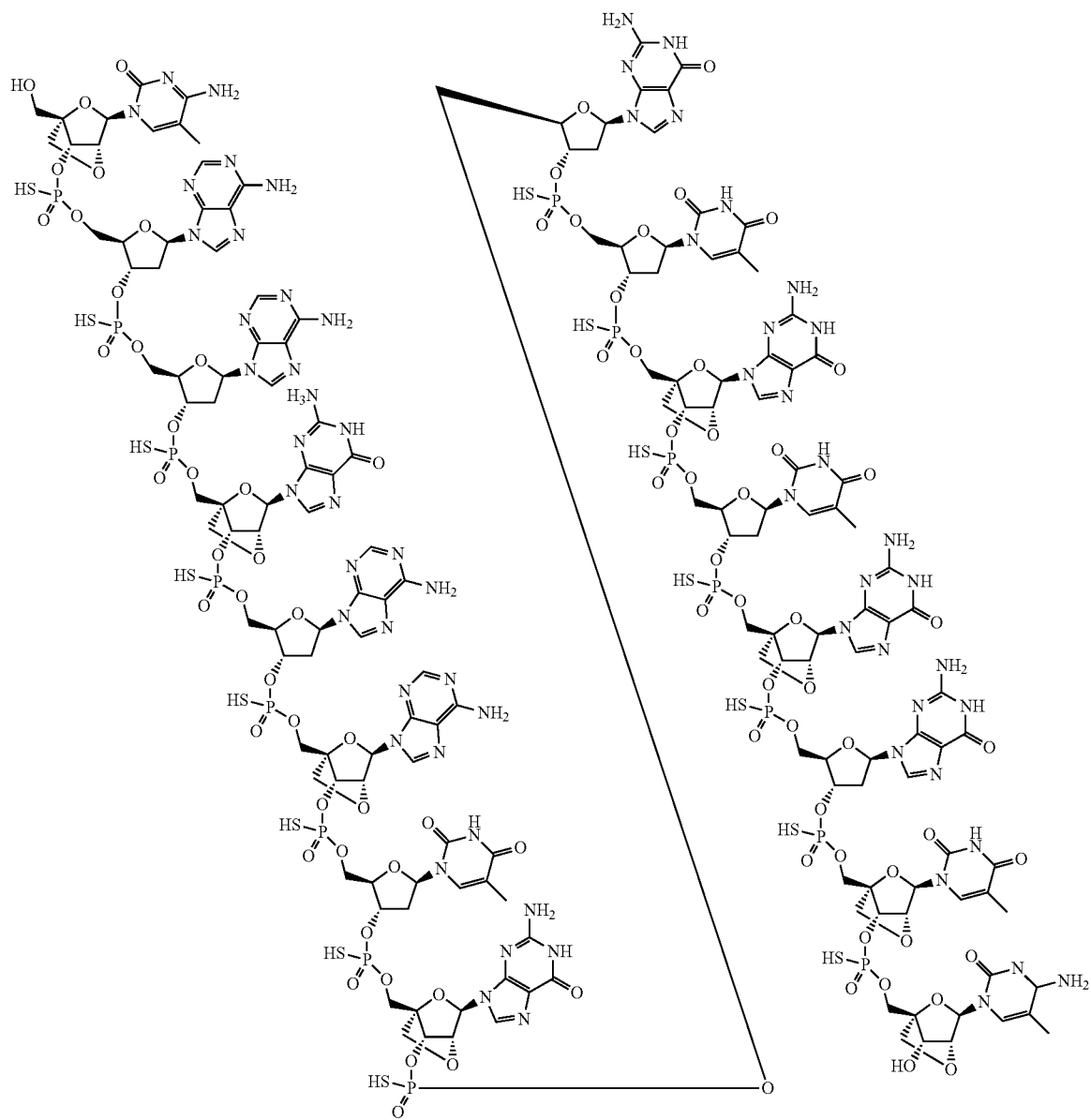

In another embodiment, the invention presents an antisense oligonucleotide having the structure:
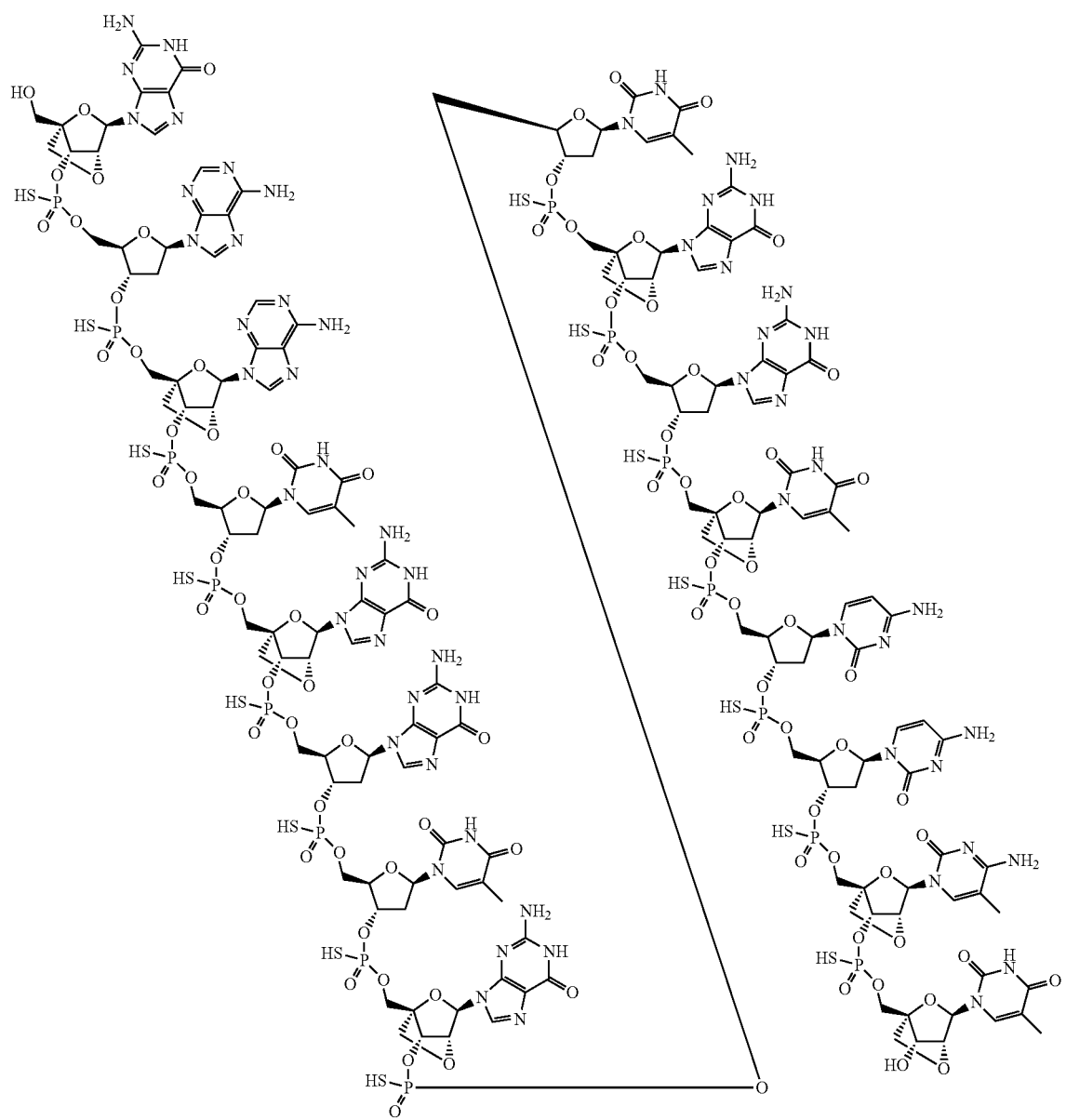

In another embodiment, the invention presents an antisense oligonucleotide having the structure:

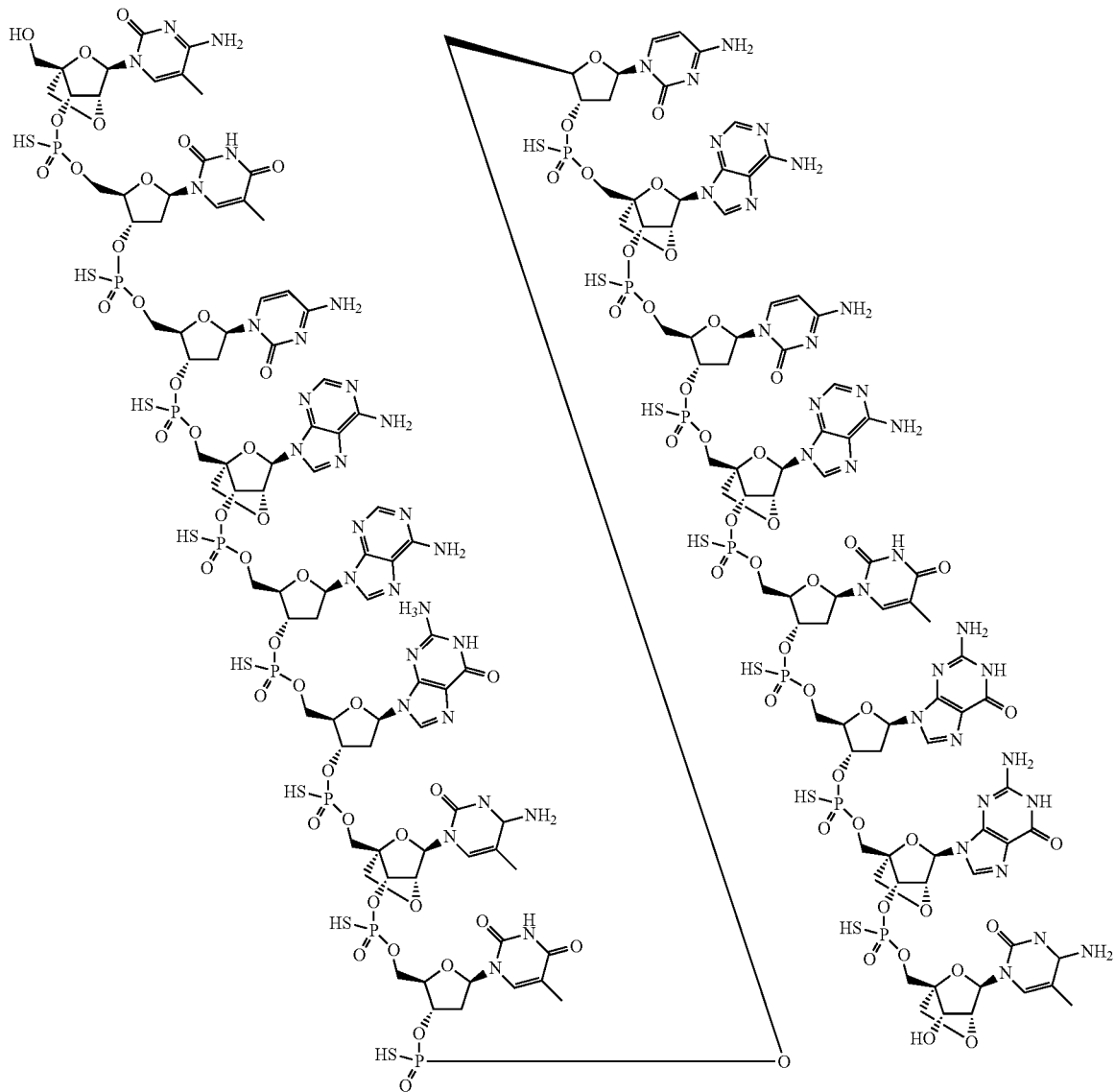

In another embodiment, the invention presents an antisense oligonucleotide wherein the oligonucleotide is the oligonucleotide compound GaGctGggTcAagAAT (SEQ ID NO: 71) wherein capital letters represent beta-D-oxy LNA nucleosides, lowercase letters represent DNA nucleosides, all LNA C are 5-methyl cytosine, and all internucleoside linkages are phosphorothioate internucleoside linkages.

In some embodiments, the invention presents an antisense oligonucleotide wherein the oligonucleotide is the oligonucleotide compound GgtCaaGaAtgGtgTG (SEQ ID NO: 73) wherein capital letters represent beta-D-oxy LNA nucleosides, lowercase letters represent DNA nucleosides, all LNA C are 5-methyl cytosine, and all internucleoside linkages are phosphorothioate internucleoside linkages.

Another embodiment presents an antisense oligonucleotide wherein the oligonucleotide is the oligonucleotide compound CaGaAtGgtGtGgTC (SEQ ID NO:74) wherein capital letters represent beta-D-oxy LNA nucleosides, lowercase letters represent DNA nucleosides, all LNA C are 5-methyl cytosine, and all internucleoside linkages are phosphorothioate internucleoside linkages.

Another embodiment presents an antisense oligonucleotide wherein the oligonucleotide is the oligonucleotide compound GaAtGgtGtGgTccC (SEQ ID NO:75) wherein capital letters represent beta-D-oxy LNA nucleosides, lowercase letters represent DNA nucleosides, all LNA C are 5-methyl cytosine, and all internucleoside linkages are phosphorothioate internucleoside linkages.

Another embodiment presents an antisense oligonucleotide wherein the oligonucleotide is the oligonucleotide compound CtcAagCtcAcAtgGC (SEQ ID NO:134) wherein capital letters represent beta-D-oxy LNA nucleosides, lowercase letters represent DNA nucleosides, all LNA C are 5-methyl cytosine, and all internucleoside linkages are phosphorothioate internucleoside linkages.

Some embodiments present an antisense oligonucleotide covalently attached to at least one conjugate moiety.

In some embodiments, the antisense oligonucleotide is in the form of a pharmaceutically acceptable salt.

In some embodiments, the salt is a sodium salt, a potassium salt or an ammonium salt.

In other embodiments, the invention presents a pharmaceutical composition comprising the antisense oligonucleotide and a pharmaceutically acceptable diluent, solvent, carrier, salt and/or adjuvant.

In other embodiments the pharmaceutical composition comprises an aqueous diluent or solvent, such as phosphate buffered saline.

In other embodiments, the invention presents an in vivo or in vitro method for enhancing the expression of the Exon1-Exon2 progranulin splice variant in a cell which is expressing progranulin, said method comprising administering an antisense oligonucleotide, or a pharmaceutical composition in an effective amount to said cell.

In some embodiments, the cell is either a human cell or a mammalian cell.

In yet another embodiment, the invention presents a method for treating or preventing neurological disease comprising administering a therapeutically or prophylactically effective amount of an antisense oligonucleotide or the pharmaceutical composition to a subject suffering from or susceptible to neurological disease.

In yet another embodiment, the invention presents a method for treating or preventing progranulin haploinsufficiency or a related disorder comprising administering a therapeutically or prophylactically effective amount of an antisense oligonucleotide or the pharmaceutical composition to a subject suffering from or susceptible to progranulin haploinsufficiency or a related disorder.

In some embodiments, the antisense oligonucleotide or the pharmaceutical composition are used as a medicament.

In another embodiment, the antisense oligonucleotide, or the pharmaceutical composition are used in the treatment of a neurological disease.

In another embodiment, the antisense oligonucleotide or pharmaceutical composition for use in the treatment of a neurological disease, wherein the neurological disease is a TDP-43 pathology.

In some embodiments, the antisense oligonucleotide or the pharmaceutical composition are used in the treatment of progranulin haploinsufficiency or a related disorder.

In yet another embodiment, the invention presents the use of the antisense oligonucleotide or the pharmaceutical composition for the preparation of a medicament for treatment or prevention of a neurological disease. In some embodiments, the neurological disease is a TDP-43 pathology.

Another embodiments presents the use of the antisense oligonucleotide or the pharmaceutical composition for the preparation of a medicament for treatment or prevention of progranulin haploinsufficiency or a related disorder.

EXAMPLES

Example 1: 275 Oligonucleotides Screened for Effects on Intron 1 Skipping

H4 neuroglioma cells were seeded 15000 pr well in 96-well plates the day before transfection in medium (DMEM Sigma: D0819, 15% FBS, 1 mM Sodium Pyruvate, 25 µg/ml Gentamicin).

Microglia cells were chosen for analysis because these cells produce high levels of progranulin. Reduction of progranulin in microglia cells alone is sufficient to recapitulate inflammation, lysosomal dysfunction, and hyperproliferation in a cell-autonomous manner. Therefore, targeting microglial dysfunction caused by progranulin insufficiency represents a potential therapeutic strategy to manage neurodegeneration in Frontotemporal dementia. To study effects on Progranulin in cellular systems, H4 cells (ATCC HTB-148) a commercial available glial cell line derived from a cancer patient have been used for identifying oligonucleotides capable of increasing progranulin production.

To further use Microglia that exhibit functional characteristics similar to human microglia, including phagocytosis and cytokine-mediated inflammatory responses, and express relevant microglial markers, hiPSC derived microglia iCell® Microglia from FujiFilm Cellular Dynamics Inc. (Cat. no R1131) have been used for investigating effects of selected oligonucleotides on progranulin production.

Transfection was performed using Lipofectamine 2000 (Invitrogen) using the following procedure.

Medium was removed from cells and 80 µL Optimem reduced serum medium (Gibco) containing 6.25 µg/mL Lipofectamine 2000 (Invitrogen) was added, 20 µL Optimem with compounds (125 nM) were added to each well (25 nM final). As control PBS was used instead of compound. After 5 hours, transfection solution was removed from wells and full growth medium was added. The day after transfection, RNA was extracted by adding 125 µL RLT buffer (Qiagen) and using RNeasy 97 kit and protocols from Qiagen. cDNA synthesis was performed using 4 µL input RNA was performed using IScript Advanced cDNA Synthesis Kit for RT-qPCR (Bio-Rad) and 2 µL was used as input for digital droplet PCR using ddPCR supermix for probes (no dUTP) (Bio-Rad) according to Manufactor's protocol. The following Primers and Probes (IDT) were used:

```
GRN Exon1-Exon2 (FAM):
Primer 1:
                                       (SEQ ID NO: 282)
GCTGCTGCCCAAGGACCGCGGA Primer 2:
                                       (SEQ ID NO: 283)
GCCCTGCTGTTAAGGCCACCCA Probe
                                       (SEQ ID NO: 284)
/56-FAM/GGACGCAGG/ZEN/CAGACCATGTGGACCCTG/3IABkFQ/

GRN Intron1-Exon2 (HEX):
Primer 1:
                                       (SEQ ID NO: 285)
CCAAAGCAGGGACCACACCATTCTT Primer 2:
                                       (SEQ ID NO: 286)
GCCCTGCTGTTAAGGCCACCCA Probe
                                       (SEQ ID NO: 287)
/5HEX/CCCAGCTCC/ZEN/ACCCCTGTCGGCAGACCATG/3IABkFQ/
```

HPRT1: HPRT1 (FAM, PT.58v.45621572, IDT) and HPRT1 (HEX, Hs.PT.58v.45621572) IDT.

Exon1-Exon2 GRN mRNA and Intron1-Exon2 GRN mRNA concentrations were quantified relative to the housekeeping gene HPRT1 using QuantaSoft Software (Bio-Rad).

The compounds were profiled and ranked according to expression of Exon 1-Exon2 mRNA splice form relative to HPRT1 and Intron1-Exon2 relative to HPRT1 and results are shown in FIGS. 1A-1E.

The following compounds relative to PBS transfected cells show an increased expression of Exon1-Exon 2 spliced mRNA, a reduced expression of Intron1-Exon 1 spliced mRNA and a more than 25% shift in ratio Exon 1-Exon2 vs Intron1-Exon2: SEQ ID NOS: 51, SEQ ID NO: 52, SEQ ID NO: 53, SEQ ID NO: 54, SEQ ID NO: 55, SEQ ID NO: 62, SEQ ID NO: 63, SEQ ID NO: 67, SEQ ID NO: 71, SEQ ID NO: 73, SEQ ID NO: 74, SEQ ID NO: 75, SEQ ID NO: 100, SEQ ID NO: 134, SEQ ID NO: 135, SEQ ID NO: 196, SEQ ID NO: 220, SEQ ID NO: 228 and SEQ ID NO: 252 as shown in FIGS. 1A-1E.

TABLE 1

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every 2$^{nd}$ or 3$^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| SEQ ID NO: 1 | TGCGTCCGACTCCGCG | 1.43 | 1.30 | 1.11 |
| 2 | GTCCGACTCCGCGGTC | 1.02 | 1.33 | 0.77 |
| 3 | CGACTCCGCGGTCCTT | 1.33 | 1.67 | 0.80 |
| 4 | CTCCGCGGTCCTTGGG | 1.02 | 1.38 | 0.74 |
| 5 | CGCGGTCCTTGGGCAG | 0.69 | 1.55 | 0.45 |
| 6 | GGTCCTTGGGCAGCAG | 0.70 | 1.36 | 0.51 |
| 7 | CCTTGGGCAGCAGCAA | 0.71 | 0.95 | 0.75 |
| 8 | TGGGCAGCAGCAACCG | 0.86 | 0.86 | 1.00 |
| 9 | GCAGCAGCAACCGGGT | 1.25 | 1.31 | 0.95 |
| 10 | GCAGCAACCGGGTAGC | 1.21 | 1.29 | 0.94 |
| 11 | GCAACCGGGTAGCGCT | 0.82 | 0.89 | 0.92 |
| 12 | ACCGGGTAGCGCTCAG | 0.84 | 0.77 | 1.10 |
| 13 | GGGTAGCGCTCAGACT | 0.82 | 0.81 | 1.00 |
| 14 | TAGCGCTCAGACTACA | 0.96 | 0.97 | 0.99 |
| 15 | CGCTCAGACTACAGAC | 1.38 | 1.07 | 1.29 |
| 16 | TCAGACTACAGACCCC | 1.20 | 1.26 | 0.95 |
| 17 | GACTACAGACCCCAGC | 0.77 | 0.75 | 1.03 |
| 18 | TACAGACCCCAGCGCG | 0.93 | 0.83 | 1.13 |
| 19 | AGTCCCTACTACCTTC | 1.13 | 1.14 | 1.00 |
| 20 | CCCTACTACCTTCGAG | 1.06 | 1.09 | 0.97 |
| 21 | TACTACCTTCGAGAAG | 1.13 | 1.15 | 0.98 |
| 22 | TACCTTCGAGAAGCCA | 1.11 | 1.10 | 1.01 |
| 23 | CTTCGAGAAGCCAAGG | 1.09 | 1.09 | 1.01 |
| 24 | CGAGAAGCCAAGGTCT | 1.05 | 1.15 | 0.91 |
| 25 | GAAGCCAAGGTCTCAG | 1.23 | 1.28 | 0.95 |
| 26 | GCCAAGGTCTCAGGTC | 1.40 | 1.30 | 1.08 |
| 27 | AAGGTCTCAGGTCTCG | 1.23 | 1.30 | 0.95 |
| 28 | GTCTCAGGTCTCGTTC | 1.15 | 1.16 | 0.99 |
| 29 | TCAGGTCTCGTTCCCA | 1.00 | 0.97 | 1.04 |
| 30 | GGTCTCGTTCCCAGGC | 1.02 | 0.97 | 1.05 |
| 31 | CTCGTTCCCAGGCCCT | 1.27 | 1.38 | 0.92 |
| 32 | GTTCCCAGGCCCTCGG | 1.18 | 1.17 | 1.01 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 33 | CCCAGGCCCTCGGAGC | 0.90 | 0.80 | 1.12 |
| 34 | AGGCCCTCGGAGCTCC | 1.38 | 1.29 | 1.07 |
| 35 | CCCTCGGAGCTCCCAG | 1.16 | 1.13 | 1.03 |
| 36 | TCGGAGCTCCCAGCCC | 0.93 | 0.91 | 1.02 |
| 37 | GAGCTCCCAGCCCAGG | 0.93 | 0.92 | 1.01 |
| 38 | CTCCCAGCCCAGGGTC | 0.78 | 0.72 | 1.08 |
| 39 | CCAGCCCAGGGTCGCG | 0.92 | 0.88 | 1.05 |
| 40 | GCCCAGGGTCGCGCGC | 0.72 | 0.69 | 1.04 |
| 41 | CAGGGTCGCGCGCCCC | 1.29 | 1.17 | 1.10 |
| 42 | GGTCGCGCGCCCCTCC | 1.28 | 1.20 | 1.07 |
| 43 | CGCGCGCCCCTCCGGC | 1.09 | 1.05 | 1.04 |
| 44 | GCGCCCCTCCGGCTCC | 1.29 | 1.30 | 0.99 |
| 45 | CCCCTCCGGCTCCAGG | 1.12 | 1.14 | 0.99 |
| 46 | CTCCGGCTCCAGGCCG | 1.08 | 1.09 | 0.99 |
| 47 | CGGCTCCAGGCCGCCG | 1.23 | 1.10 | 1.11 |
| 48 | CTCCAGGCCGCCGCGG | 1.20 | 1.15 | 1.04 |
| 49 | CAGGCCGCCGCGGGAA | 1.24 | 1.21 | 1.03 |
| 50 | GCCGCGGGAACCACCC | 1.15 | 0.95 | 1.21 |
| 51 | GCGGGAACCACCCACC | 1.22 | 0.97 | 1.26 |
| 52 | GGAACCACCCACCACC | 1.14 | 0.88 | 1.29 |
| 53 | ACCACCCACCACCACC | 1.15 | 0.89 | 1.30 |
| 54 | ACCCACCACCACCAGG | 1.13 | 0.89 | 1.26 |
| 55 | CACCACCACCAGGAGA | 1.25 | 1.00 | 1.26 |
| 56 | CACCACCAGGAGAGGG | 1.20 | 0.99 | 1.21 |
| 57 | CACCAGGAGAGGGGAA | 1.23 | 1.16 | 1.06 |
| 58 | CAGGAGAGGGGAAGAA | 1.35 | 1.27 | 1.07 |
| 59 | GAGAGGGGAAGAAGCC | 1.17 | 1.17 | 1.00 |
| 60 | AGGGGAAGAAGCCAGC | 1.06 | 1.10 | 0.96 |
| 61 | GGAAGAAGCCAGCACC | 1.05 | 0.87 | 1.22 |
| 62 | AGAAGCCAGCACCTAC | 1.07 | 0.69 | 1.56 |
| 63 | AGCCAGCACCTACCGA | 1.08 | 0.75 | 1.44 |
| 64 | CAGCACCTACCGACAG | 1.16 | 1.06 | 1.09 |
| 65 | CACCTACCGACAGGGG | 1.14 | 0.98 | 1.16 |
| 66 | CTACCGACAGGGGTGG | 0.88 | 0.90 | 0.98 |
| 67 | CCGACAGGGGTGGAGC | 1.12 | 0.84 | 1.34 |
| 68 | ACAGGGGTGGAGCTGG | 1.04 | 0.84 | 1.24 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
| --- | --- | --- | --- | --- |
| 69 | GGGGTGGAGCTGGGTC | 0.77 | 0.52 | 1.49 |
| 70 | GTGGAGCTGGGTCAAG | 1.34 | 1.04 | 1.30 |
| 71 | GAGCTGGGTCAAGAAT | 1.32 | 0.97 | 1.37 |
| 72 | CTGGGTCAAGAATGGT | 1.42 | 1.01 | 1.40 |
| 73 | GGTCAAGAATGGTGTG | 1.29 | 0.89 | 1.44 |
| 74 | CAAGAATGGTGTGGTC | 1.03 | 0.75 | 1.37 |
| 75 | GAATGGTGTGGTCCCT | 1.11 | 0.88 | 1.26 |
| 76 | TGGTGTGGTCCCTGCT | 1.07 | 0.87 | 1.22 |
| 77 | TGTGGTCCCTGCTTTG | 1.34 | 1.17 | 1.14 |
| 78 | GGTCCCTGCTTTGGGG | 1.29 | 1.08 | 1.19 |
| 79 | CCCTGCTTTGGGGAA | 1.04 | 0.98 | 1.06 |
| 80 | TGCTTTGGGGAATGC | 1.00 | 1.06 | 0.94 |
| 81 | TTTGGGGAATGCTGG | 0.75 | 0.75 | 1.00 |
| 82 | GGGGAATGCTGGGGA | 0.94 | 0.91 | 1.04 |
| 83 | GGAATGCTGGGGAGGT | 1.09 | 1.09 | 1.00 |
| 84 | ATGCTGGGGAGGTAGA | 1.32 | 1.26 | 1.05 |
| 85 | CTGGGGAGGTAGAAAG | 1.02 | 1.04 | 0.99 |
| 86 | GGGAGGTAGAAAGCCC | 0.99 | 0.94 | 1.06 |
| 87 | AGGTAGAAAGCCCCTT | 1.00 | 0.83 | 1.20 |
| 88 | TAGAAAGCCCCTTCTA | 1.10 | 1.07 | 1.02 |
| 89 | AAAGCCCCTTCTAACG | 1.07 | 0.99 | 1.08 |
| 90 | GCCCCTTCTAACGGGG | 1.26 | 1.32 | 0.95 |
| 91 | CCTTCTAACGGGGCGT | 1.13 | 1.12 | 1.01 |
| 92 | TCTAACGGGGCGTCAC | 1.10 | 1.09 | 1.01 |
| 93 | AACGGGGCGTCACTGC | 1.10 | 0.94 | 1.17 |
| 94 | GGGGCGTCACTGCAAT | 1.04 | 0.91 | 1.15 |
| 95 | GCGTCACTGCAATTAC | 1.04 | 0.96 | 1.08 |
| 96 | TCACTGCAATTACTGC | 1.04 | 0.95 | 1.10 |
| 97 | CTGCAATTACTGCTTC | 1.36 | 1.28 | 1.06 |
| 98 | CAATTACTGCTTCCTC | n.d. | n.d. | n.d. |
| 99 | TTACTGCTTCCTCTTT | 1.22 | 1.12 | 1.09 |
| 100 | CTGCTTCCTCTTTCCC | 1.24 | 0.98 | 1.26 |
| 101 | CTTCCTCTTTCCCATA | 1.04 | 0.89 | 1.16 |
| 102 | CCTCTTTCCCATAAAA | 1.15 | 1.14 | 1.01 |
| 103 | CTTTCCCATAAAACTC | 1.13 | 1.16 | 0.97 |
| 104 | TCCCATAAAACTCCCC | 1.10 | 1.25 | 0.88 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 105 | CATAAAACTCCCCCTA | 1.14 | 1.25 | 0.90 |
| 106 | AAAACTCCCCCTAGTG | 1.18 | 1.32 | 0.90 |
| 107 | ACTCCCCCTAGTGTAT | 1.31 | 1.47 | 0.89 |
| 108 | CCCCCTAGTGTATCAG | 1.35 | 1.66 | 0.81 |
| 109 | CCTAGTGTATCAGAAC | 1.23 | 1.36 | 0.91 |
| 110 | AGTGTATCAGAACCCC | 0.95 | 1.03 | 0.92 |
| 111 | GTATCAGAACCCCCAA | 1.08 | 1.12 | 0.96 |
| 112 | TCAGAACCCCCAAGGA | 1.40 | 1.33 | 1.06 |
| 113 | GAACCCCCAAGGAGTT | 0.78 | 0.74 | 1.06 |
| 114 | CCCCCAAGGAGTTTCA | 0.83 | 0.76 | 1.08 |
| 115 | CCAAGGAGTTTCAGTA | 0.88 | 0.77 | 1.13 |
| 116 | AGGAGTTTCAGTAAGC | 1.31 | 1.03 | 1.28 |
| 117 | AGTTTCAGTAAGCGGT | 1.06 | 0.89 | 1.19 |
| 118 | TTCAGTAAGCGGTTCT | 1.05 | 0.86 | 1.22 |
| 119 | AGTAAGCGGTTCTTCT | 1.06 | 0.86 | 1.23 |
| 120 | AAGCGGTTCTTCTGTT | 0.69 | 0.63 | 1.10 |
| 121 | CGGTTCTTCTGTTGTC | 0.77 | 0.70 | 1.09 |
| 122 | TTCTTCTGTTGTCTCC | 0.77 | 0.64 | 1.21 |
| 123 | TTCTGTTGTCTCCGGC | 0.94 | 0.76 | 1.24 |
| 124 | TGTTGTCTCCGGCTGA | 1.03 | 0.82 | 1.25 |
| 125 | TGTCTCCGGCTGAGAC | 0.99 | 0.95 | 1.04 |
| 126 | CTCCGGCTGAGACTCC | 0.77 | 0.76 | 1.02 |
| 127 | CGGCTGAGACTCCAGG | 0.83 | 0.80 | 1.04 |
| 128 | CTGAGACTCCAGGGGA | 1.18 | 1.09 | 1.09 |
| 129 | AGACTCCAGGGGAACC | 1.13 | 1.07 | 1.05 |
| 130 | CTCCAGGGGAACCTCA | 1.15 | 1.00 | 1.15 |
| 131 | CAGGGGAACCTCAAGC | 1.07 | 1.08 | 0.99 |
| 132 | GGGAACCTCAAGCTCA | n.d. | n.d. | n.d. |
| 133 | AACCTCAAGCTCACAT | 1.23 | 1.17 | 1.05 |
| 134 | CTCAAGCTCACATGGC | 1.26 | 0.95 | 1.32 |
| 135 | AAGCTCACATGGCCCT | 1.08 | 0.61 | 1.75 |
| 136 | CTCACATGGCCCTGGC | 1.23 | 1.08 | 1.13 |
| 137 | ACATGGCCCTGGCGGG | 1.35 | 1.15 | 1.18 |
| 138 | TGGCCCTGGCGGGCCC | 1.26 | 1.11 | 1.13 |
| 139 | CCCTGGCGGGCCCCTG | 1.28 | 1.20 | 1.07 |
| 140 | TGGCGGGCCCCTGGGC | 1.29 | 1.15 | 1.13 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 141 | CGGGCCCCTGGGCAGG | 1.14 | 1.20 | 0.95 |
| 142 | GCCCCTGGGCAGGAGC | 1.19 | 1.08 | 1.10 |
| 143 | CCTGGGCAGGAGCAGG | 1.17 | 1.04 | 1.12 |
| 144 | GGGCAGGAGCAGGCGA | 1.14 | 1.03 | 1.11 |
| 145 | CAGGAGCAGGCGAGAG | 1.15 | 0.93 | 1.24 |
| 146 | GAGCAGGCGAGAGGTC | 1.18 | 1.07 | 1.11 |
| 147 | CAGGCGAGAGGTCTGC | 1.30 | 1.12 | 1.16 |
| 148 | GCGAGAGGTCTGCGCG | 1.47 | 1.34 | 1.09 |
| 149 | AGAGGTCTGCGCGGCC | 1.23 | 1.29 | 0.96 |
| 150 | GGTCTGCGCGGCCGCT | 1.20 | 1.21 | 1.00 |
| 151 | CTGCGCGGCCGCTCTC | 1.52 | 1.56 | 0.98 |
| 152 | CGCGGCCGCTCTCCTA | 1.38 | 1.68 | 0.82 |
| 153 | GGCCGCTCTCCTACCT | 1.22 | 3.21 | 0.38 |
| 154 | CGCTCTCCTACCTGCG | 1.35 | 1.67 | 0.81 |
| 155 | TCTCCTACCTGCGTCC | 0.86 | 1.23 | 0.70 |
| 156 | CCTACCTGCGTCCGAC | 0.96 | 1.39 | 0.69 |
| 157 | ACCTGCGTCCGACTCC | 1.00 | 1.55 | 0.64 |
| 158 | GGGGAAGAAGCCAGCA | 1.20 | 1.06 | 1.13 |
| 159 | GGGAAGAAGCCAGCAC | 1.25 | 1.14 | 1.10 |
| 160 | GAAGAAGCCAGCACCT | 1.25 | 1.12 | 1.11 |
| 161 | AAGAAGCCAGCACCTA | 1.31 | 1.22 | 1.08 |
| 162 | GAAGCCAGCACCTACC | 0.86 | 0.79 | 1.10 |
| 163 | AAGCCAGCACCTACCG | 0.97 | 0.98 | 1.00 |
| 164 | GCCAGCACCTACCGAC | 0.97 | 0.91 | 1.06 |
| 165 | CCAGCACCTACCGACA | 0.74 | 0.65 | 1.15 |
| 166 | AGCACCTACCGACAGG | 1.22 | 1.21 | 1.01 |
| 167 | GCACCTACCGACAGGG | 0.93 | 0.60 | 1.55 |
| 168 | ACCTACCGACAGGGGT | 1.37 | 1.18 | 1.16 |
| 169 | CCTACCGACAGGGGTG | 0.91 | 1.00 | 0.92 |
| 170 | TACCGACAGGGGTGGA | 0.81 | 0.85 | 0.95 |
| 171 | ACCGACAGGGGTGGAG | 0.85 | 0.84 | 1.00 |
| 172 | CGACAGGGGTGGAGCT | 1.13 | 1.07 | 1.05 |
| 173 | GACAGGGGTGGAGCTG | 0.99 | 1.11 | 0.89 |
| 174 | CAGGGGTGGAGCTGGG | 0.81 | 0.88 | 0.93 |
| 175 | AGGGGTGGAGCTGGGT | 0.96 | 1.04 | 0.92 |
| 176 | GGGTGGAGCTGGGTCA | 1.00 | 1.05 | 0.95 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 177 | GGTGGAGCTGGGTCAA | 1.00 | 1.02 | 0.99 |
| 178 | TGGAGCTGGGTCAAGA | 0.94 | 1.00 | 0.94 |
| 179 | GGAGCTGGGTCAAGAA | 0.84 | 0.88 | 0.95 |
| 180 | CAGAAGGGGACGGCAG | 0.77 | 0.90 | 0.86 |
| 181 | AAGGGGACGGCAGCAG | 0.93 | 0.96 | 0.97 |
| 182 | GGGACGGCAGCAGCTG | 0.94 | 0.91 | 1.04 |
| 183 | ACGGCAGCAGCTGTAG | 0.98 | 0.86 | 1.14 |
| 184 | GCAGCAGCTGTAGCTG | 0.94 | 0.85 | 1.11 |
| 185 | GCAGCTGTAGCTGGCT | 0.98 | 0.89 | 1.10 |
| 186 | GCTGTAGCTGGCTCCT | 1.01 | 0.90 | 1.13 |
| 187 | GTAGCTGGCTCCTCCG | 1.09 | 0.94 | 1.17 |
| 188 | GCTGGCTCCTCCGGGG | 1.01 | 0.88 | 1.16 |
| 189 | GGCTCCTCCGGGGTCC | 0.98 | 0.95 | 1.03 |
| 190 | TCCTCCGGGGTCCAGG | n.d. | n.d. | n.d. |
| 191 | TCCGGGGTCCAGGCAG | 0.97 | 1.02 | 0.96 |
| 192 | GGGGTCCAGGCAGCAG | 0.96 | 0.94 | 1.02 |
| 193 | GTCCAGGCAGCAGGCC | 1.02 | 0.98 | 1.04 |
| 194 | CAGGCAGCAGGCCACA | 1.06 | 1.01 | 1.05 |
| 195 | GCAGCAGGCCACAGGG | 0.92 | 0.86 | 1.08 |
| 196 | GCAGGCCACAGGGCAG | 1.01 | 0.78 | 1.29 |
| 197 | GGCCACAGGGCAGAAC | 1.06 | 1.06 | 0.99 |
| 198 | CACAGGGCAGAACTGA | n.d. | n.d. | n.d. |
| 199 | AGGGCAGAACTGACCA | 1.02 | 1.25 | 0.82 |
| 200 | GCAGAACTGACCATCT | 0.99 | 1.11 | 0.89 |
| 201 | GAACTGACCATCTGGG | 1.05 | 1.03 | 1.02 |
| 202 | CTGACCATCTGGGCAC | 1.07 | 1.07 | 1.00 |
| 203 | ACCATCTGGGCACCGC | 1.08 | 1.11 | 0.98 |
| 204 | ATCTGGGCACCGCGTT | 1.01 | 0.83 | 1.21 |
| 205 | TGGGCACCGCGTTCCA | 1.11 | 1.15 | 0.97 |
| 206 | GCACCGCGTTCCAGCC | 1.01 | 0.93 | 1.08 |
| 207 | CCGCGTTCCAGCCACC | 1.02 | 1.32 | 0.77 |
| 208 | CGTTCCAGCCACCAGC | 1.15 | 1.07 | 1.07 |
| 209 | TCCAGCCACCAGCCCT | 1.06 | 1.00 | 1.06 |
| 210 | AGCCACCAGCCCTGCT | 1.13 | 1.00 | 1.13 |
| 211 | CACCAGCCCTGCTGTT | 0.98 | 0.90 | 1.08 |
| 212 | CAGCCCTGCTGTTAAG | 1.03 | 0.84 | 1.22 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 213 | CCCTGCTGTTAAGGCC | 0.92 | 1.08 | 0.86 |
| 214 | TGCTGTTAAGGCCACC | 1.02 | 1.02 | 1.00 |
| 215 | TGTTAAGGCCACCCAG | 1.11 | 1.05 | 1.05 |
| 216 | TAAGGCCACCCAGCTC | 0.92 | 0.89 | 1.03 |
| 217 | GGCCACCCAGCTCACC | 1.05 | 0.91 | 1.16 |
| 218 | CACCCAGCTCACCAGG | 1.00 | 0.87 | 1.14 |
| 219 | CCAGCTCACCAGGGTC | 1.05 | 0.89 | 1.18 |
| 220 | GCTCACCAGGGTCCAC | 1.02 | 0.75 | 1.37 |
| 221 | CACCAGGGTCCACATG | 0.99 | 0.92 | 1.08 |
| 222 | CAGGGTCCACATGGTC | 0.94 | 0.65 | 1.43 |
| 223 | GGTCCACATGGTCTGC | 0.96 | 0.88 | 1.09 |
| 224 | CCACATGGTCTGCCTG | 0.91 | 0.80 | 1.14 |
| 225 | CATGGTCTGCCTGCAA | 1.07 | 0.98 | 1.10 |
| 226 | GGTCTGCCTGCAAAGT | 1.02 | 0.99 | 1.03 |
| 227 | CTGCCTGCAAAGTACC | 1.06 | 0.89 | 1.18 |
| 228 | CCTGCAAAGTACCAAG | 1.04 | 0.71 | 1.47 |
| 229 | GCAAAGTACCAAGGAA | 0.99 | 0.89 | 1.10 |
| 230 | AAGTACCAAGGAACGT | 0.93 | 0.94 | 0.99 |
| 231 | TACCAAGGAACGTCTG | 1.13 | 1.10 | 1.03 |
| 232 | CAAGGAACGTCTGGCA | 1.03 | 0.94 | 1.10 |
| 233 | GGAACGTCTGGCAACT | 0.95 | 0.93 | 1.02 |
| 234 | ACGTCTGGCAACTGCT | 0.91 | 0.75 | 1.21 |
| 235 | TCTGGCAACTGCTTAA | 0.94 | 0.82 | 1.16 |
| 236 | GGCAACTGCTTAAGCC | 0.90 | 0.91 | 0.98 |
| 237 | AACTGCTTAAGCCCAC | 1.08 | 1.14 | 0.94 |
| 238 | TGCTTAAGCCCACGCC | 1.03 | 0.94 | 1.09 |
| 239 | TTAAGCCCACGCCACC | 1.02 | 0.83 | 1.23 |
| 240 | AGCCCACGCCACCCTT | 1.02 | 0.87 | 1.17 |
| 241 | CCACGCCACCCTTGAT | 0.90 | 0.89 | 1.01 |
| 242 | CGCCACCCTTGATTCT | 0.16 | 0.10 | 1.57 |
| 243 | CACCCTTGATTCTAGG | 0.94 | 0.90 | 1.05 |
| 244 | CCTTGATTCTAGGGTC | 0.92 | 0.98 | 0.93 |
| 245 | TGATTCTAGGGTCACT | 1.01 | 0.91 | 1.10 |
| 246 | TTCTAGGGTCACTCAG | 0.99 | 0.76 | 1.29 |
| 247 | TAGGGTCACTCAGTAC | 0.97 | 0.94 | 1.02 |
| 248 | GGTCACTCAGTACCCT | 0.89 | 0.94 | 0.95 |

TABLE 1-continued

All the antisense oligonucleotides are designed as 16-mers DNA-LNA mixmers with a phosphorothioate backbone, DNA-LNA mixmers with a phosphorothioate backbone, LNA at the very 5' and 3' position and e.g. LNA for every $2^{nd}$ or $3^{rd}$ nucleotide (see Compound table Table 2).

| Oligo (SEQ ID NO) | Sequence | Exon 1-Exon 2 | Intron1-Exon2 | Ratio: Exon1-2/ Intron1-Exon2 |
|---|---|---|---|---|
| 249 | CACTCAGTACCCTAGC | 0.99 | 0.81 | 1.23 |
| 250 | TCAGTACCCTAGCCCC | 0.98 | 0.82 | 1.19 |
| 251 | GTACCCTAGCCCCAGG | 1.10 | 1.02 | 1.08 |
| 252 | CCCTAGCCCCAGGCCA | 1.01 | 0.77 | 1.32 |
| 253 | TAGCCCCAGGCCAAGG | 0.97 | 0.80 | 1.22 |
| 254 | CCCCAGGCCAAGGTCC | 0.93 | 0.85 | 1.09 |
| 255 | CAGGCCAAGGTCCTGG | 0.93 | 0.83 | 1.12 |
| 256 | GCCAAGGTCCTGGCCC | 0.92 | 0.82 | 1.12 |
| 257 | AAGGTCCTGGCCCAGG | 0.98 | 0.88 | 1.11 |
| 258 | GTCCTGGCCCAGGACT | 0.91 | 0.77 | 1.18 |
| 259 | CTGGCCCAGGACTGCC | 1.00 | 0.63 | 1.58 |
| 260 | GCCCAGGACTGCCTGA | 0.97 | 0.78 | 1.24 |
| 261 | CAGGACTGCCTGAGCC | 1.01 | 0.87 | 1.16 |
| 262 | GACTGCCTGAGCCTTC | 1.03 | 0.95 | 1.09 |
| 263 | TGCCTGAGCCTTCTCA | 1.22 | 1.20 | 1.02 |
| 264 | CTGAGCCTTCTCAACA | 0.92 | 0.89 | 1.03 |
| 265 | AGCCTTCTCAACACCT | 0.85 | 0.88 | 0.96 |
| 266 | CTTCTCAACACCTCCC | 0.95 | 0.95 | 1.00 |
| 267 | CTCAACACCTCCCTGT | 0.91 | 0.92 | 0.99 |
| 268 | AACACCTCCCTGTCCA | 0.88 | 0.95 | 0.94 |
| 269 | ACCTCCCTGTCCAGGC | 0.93 | 1.21 | 0.77 |
| 270 | TCCCTGTCCAGGCAGG | 1.08 | 1.16 | 0.93 |
| 271 | CTGTCCAGGCAGGCAG | 1.27 | 1.12 | 1.13 |
| 272 | TCCAGGCAGGCAGAAA | 1.01 | 1.01 | 1.01 |
| 273 | AGGCAGGCAGAAATCT | 0.97 | 0.85 | 1.15 |
| 274 | CAGGCAGAAATCTGCA | 0.93 | 1.00 | 0.93 |
| 275 | GCAGAAATCTGCAGGG | 0.78 | 0.84 | 0.93 |

Example 2: Oligonucleotides Tested for Effect on Progranulin Expression

Figure 2:
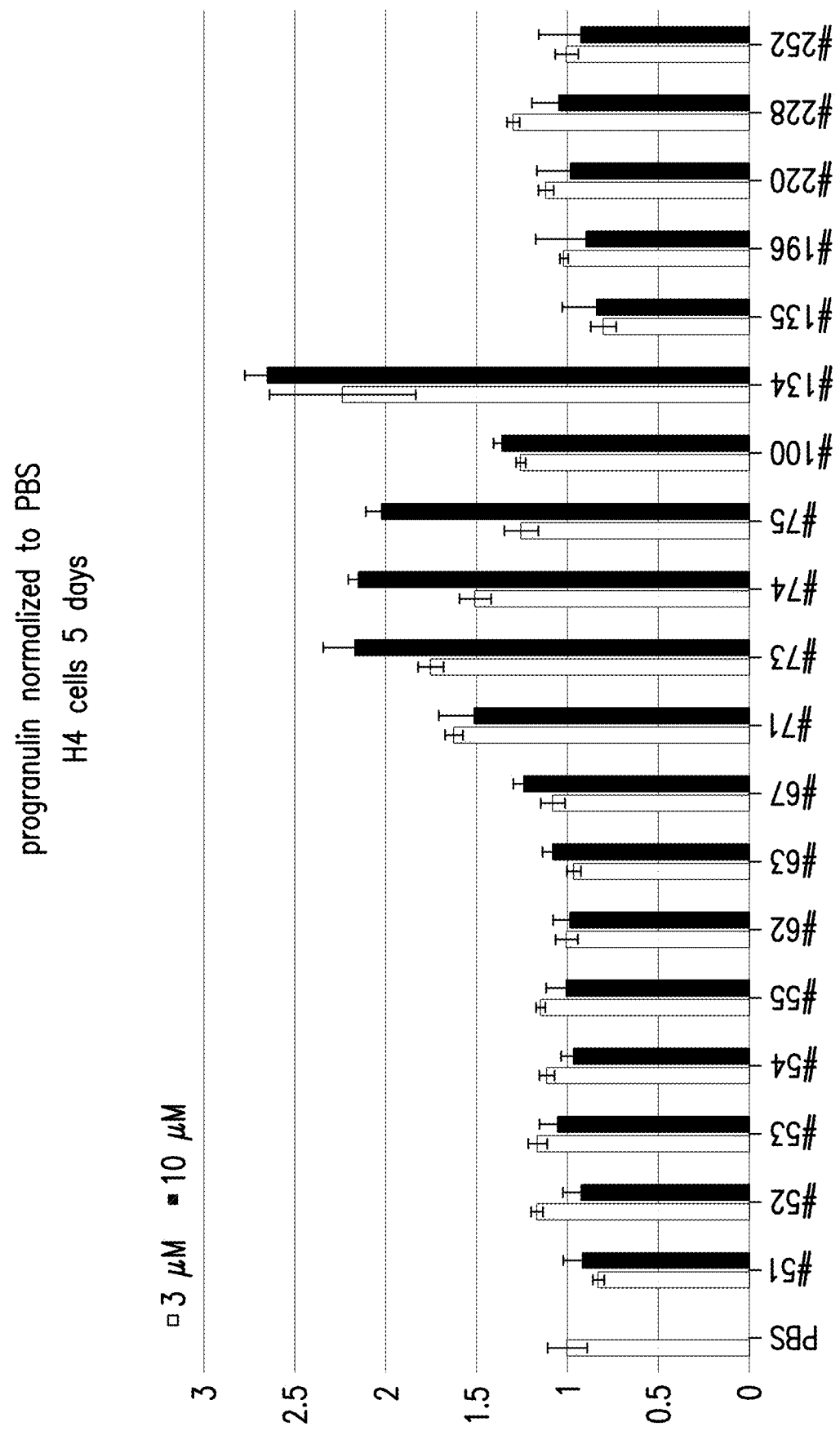
FIG. 2 shows progranulin expression levels following treatment with an oligonucleotide for 5 days.
Figure 3:
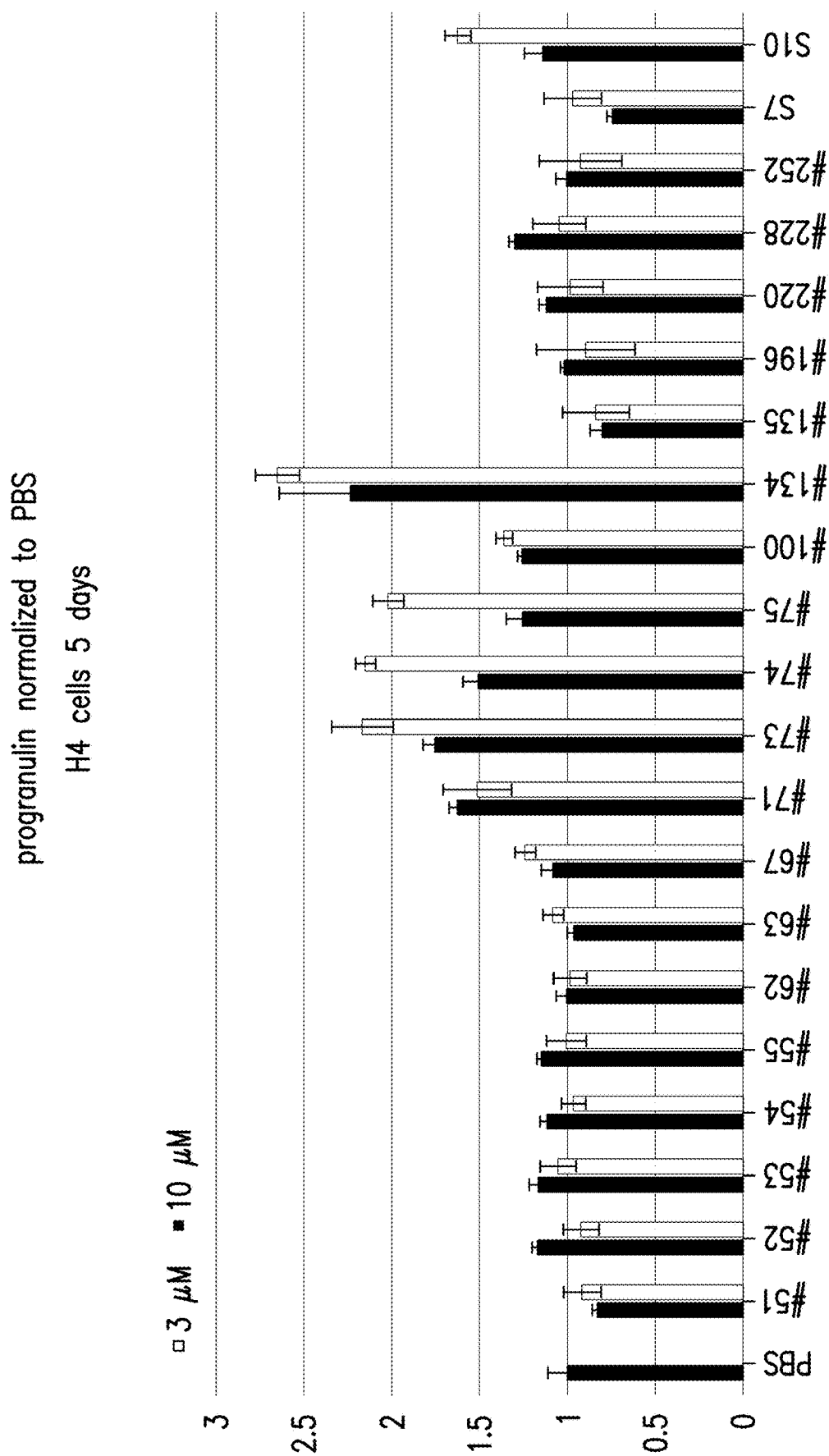
FIG. 3 shows progranulin expression levels following treatment with an oligonucleotide for 5 days compared to oligonucleotides S7 and S10 from WO 2020/191212.

H4 neuroglioma cells seeded in 96 well plates 5000 pr well, were treated with either 3 µM or 10 µM final concentration of oligo for 5 days in 200 µL medium. Progranulin expression levels were evaluated in media after dilution 1:8 by ELISA from Abcam (ab252364). SEQ ID NOs: 71, 73, 74, 75 and 134 induced progranulin secretion more than 1.5 fold compared to PBS as shown in FIG. 2. For comparison effects of oligonucleotides S7 and S10 from patent (WO 2020/191212A1) are shown in FIG. 3.

Example 3: Sequence Localization of Oligos

Sequence localization of SEQ ID NO: 73, SEQ ID NO: 74, SEQ ID NO: 75 and SEQ ID NO: 134 are shown in FIG. 4.

Figure 5:
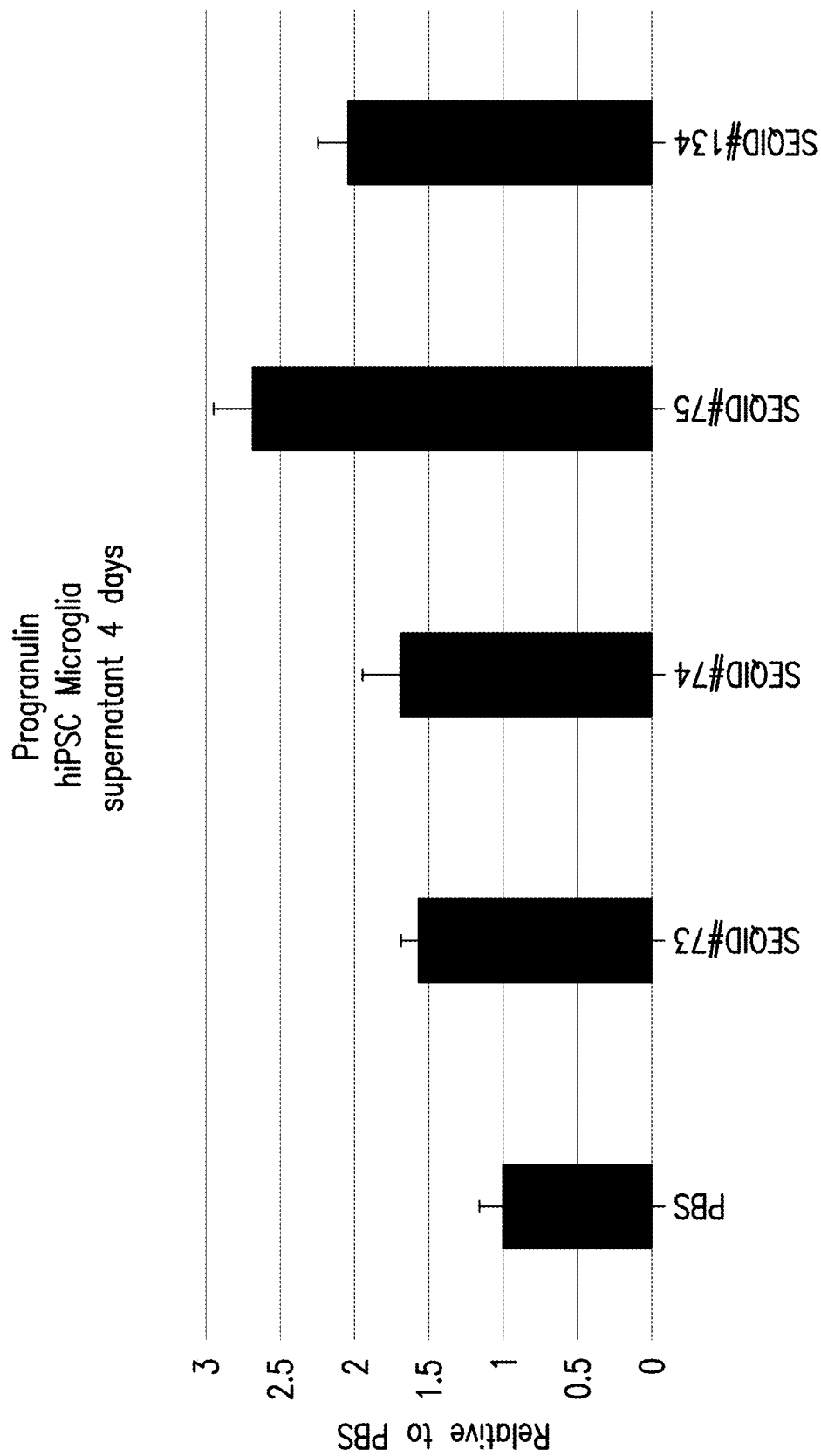
FIG. 5 shows progranulin expression levels following treatment with an oligonucleotide for 4 days.
Figure 6:
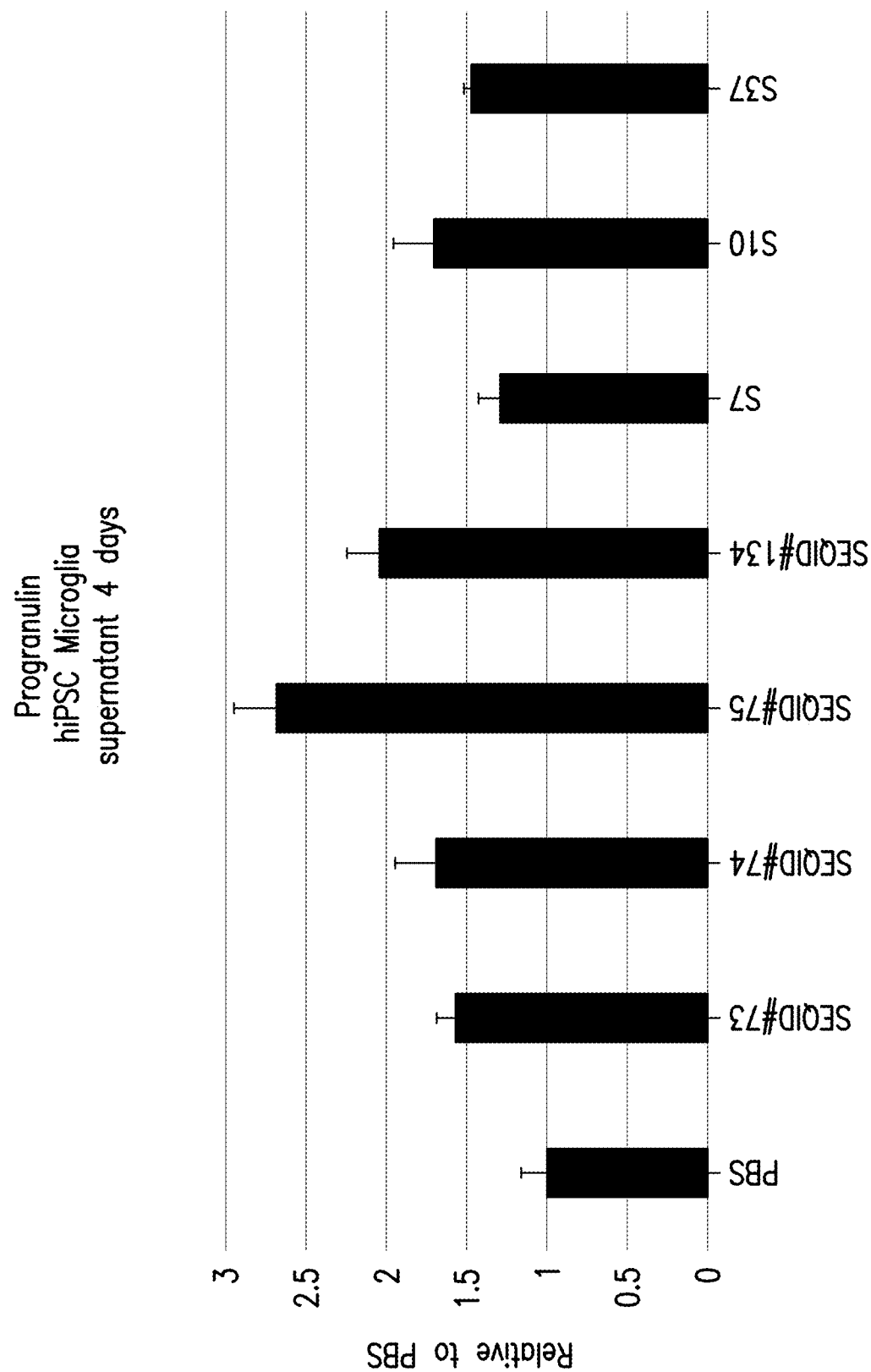
FIG. 6 shows progranulin expression levels following treatment with an oligonucleotide for 4 days compared to oligonucleotides S7, S10 and S37 from WO 2020/191212.
Figure 7D:
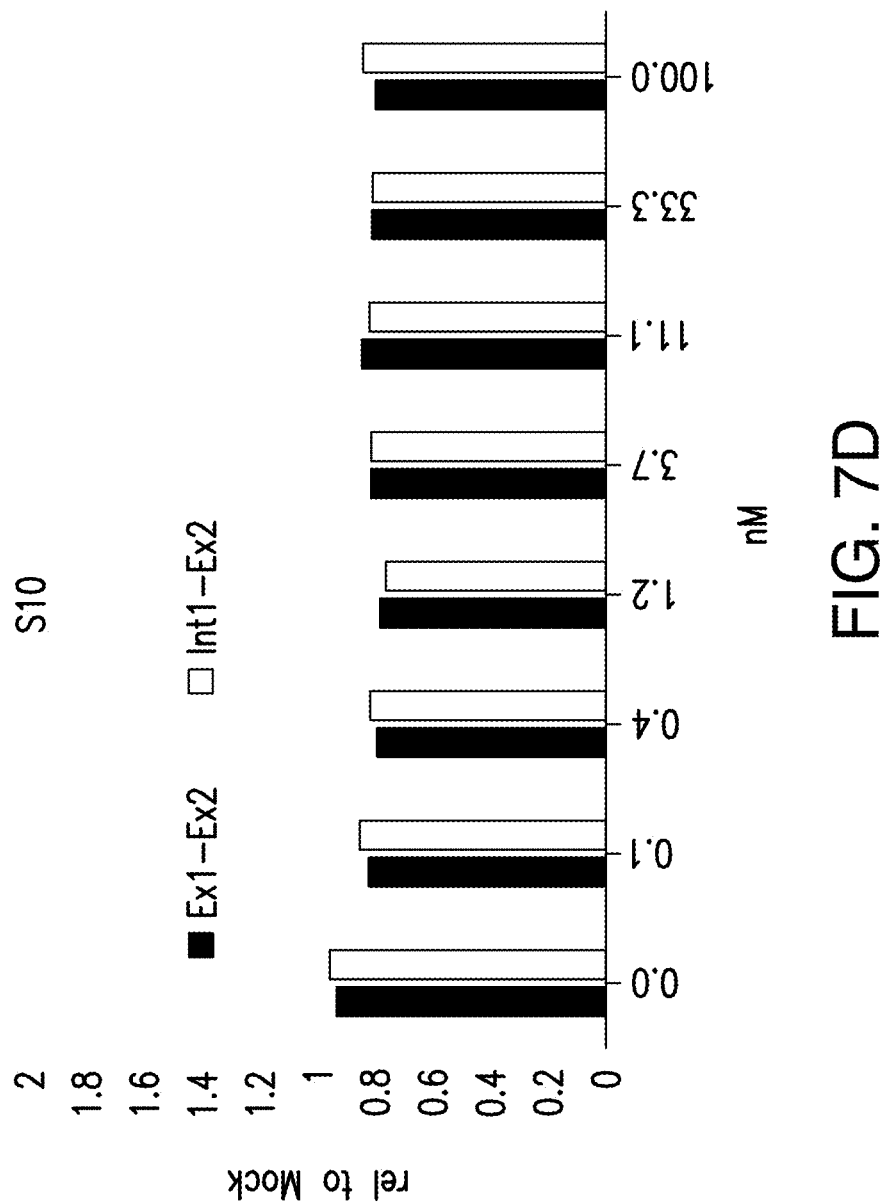

Example 4: Oligonucleotides Tested for Effect on Progranulin Expression in hiPSC Derived Microglia hiPSC derived microglia (iCell Microglia Kit, 01279, Cat. no R1131) were seeded (n=3) in Poly-D-lysine coated 96-well plates (Greiner Catalog No. 655946) with 20000 cells pr well in 200 µL and were treated with indicated concentrations of SEQ ID NO: 73, SEQ ID NO: 74, SEQ ID NO: 75 and SEQ ID NO: 134 for 4 days. Progranulin protein expression levels were evaluated in media after dilution 1:8 using ELISA from Abcam (ab252364). SEQ ID NO: 73, SEQ ID NO: 74, SEQ ID NO: 75 and SEQ ID NO: 134 induced progranulin secretion more than 1.5 fold compared to PBS as shown in FIG. 5. For comparison effects of oligonucleotides S7, S10 and S37 from WO 2020/191212 are shown in FIG. 6.

Example 5: Oligonucleotides Tested for Effect on Progranulin Expression in H4 Neuroglioma Cells H4 neuroglioma cells were seeded 15000 pr well in 96-well plates the day before transfection in medium (DMEM Sigma: D0819, 15% FBS, 1 mM Sodium Pyruvate, 25 µg/ml Gentamicin). Transfection was performed using Lipofectamine 2000 (Invitrogen) using the following procedure. Medium was removed from cells and 80 µL Optimem reduced serum medium (Gibco) containing 6.25 µg/mL Lipofectamine 2000 (Invitrogen) was added, 20 µL Optimem with compounds (125 nM) were added to each well (25 nM final). As control PBS was used instead of compound. After 5 hours, transfection solution was removed from wells and full growth medium was added. The day after transfection, RNA was extracted by adding 125 µL RLT buffer (Qiagen) and using RNeasy 97 kit and protocols from Qiagen. cDNA synthesis was performed using 4 µL input RNA was performed using IScript Advanced cDNA Synthesis Kit for RT-qPCR (Bio-Rad) and 2 µL was used as input for digital droplet PCR using ddPCR supermix for probes (no dUTP) (Bio-Rad) according to Manufactor's protocol.

The following Primers and Probes (IDT) were used

```
GRN Exon1-Exon2 (FAM):
Primer 1:
GCTGCTGCCCAAGGACCGCGGA,

Primer 2:
GCCCTGCTGTTAAGGCCACCCA
and

Probe
/56-FAM/GGACGCAGG/ZEN/CAGACCATGTGGACCCTG/3IABkFQ/

GRN Intron1-Exon2 (HEX):
Primer 1:
CCAAAGCAGGGACCACACCATTCTT,

Primer 2:
GCCCTGCTGTTAAGGCCACCCA
and

Probe
/5HEX/CCCAGCTCC/ZEN/ACCCCTGTCGGCAGACCATG/3IABkFQ/
```

HPRT1: HPRT1 (FAM, PT.58v.45621572, IDT) and HPRT1 (HEX, Hs.PT.58v.45621572) IDT.

Exon1-Exon2 GRN mRNA and Intron1-Exon2 GRN mRNA concentrations were quantified relative to the housekeeping gene HPRT1 using QuantaSoft Software (Bio-Rad).

The results for SEQ ID NO: 73, SEQ ID NO: 74 and SEQ ID NO: 75 are show in FIGS. 7A-7D. SEQ ID NO: 73, SEQ ID NO: 74 and SEQ ID NO: 75 show dose-dependent skipping of intron1 retention (Int1-Ex2) and an increase in Ex1-Ex2 splice-variant. The S10 compound from WO 2020/191212 showed no/limited effects on skipping of intron1 retention.

Example 6-Oligonucleotides Tested for Effect on Progranulin Expression in H4 Neuroglioma Cells H4 neuroglioma cells were seeded 15000 pr well in 96-well plates the day before transfection in medium (DMEM Sigma: D0819, 15% FBS, 1 mM Sodium Pyruvate, 25 µg/ml Gentamicin). Transfection was performed using Lipofectamine 2000 (Invitrogen) using the following procedure. Medium was removed from cells and 80 µL Optimem reduced serum medium (Gibco) containing 6.25 µg/mL Lipofectamine 2000 (Invitrogen) was added, 20 µL Optimem with compounds (125 nM) were added to each well (25 nM final). As control PBS was used instead of compound. After 5 hours, transfection solution was removed from wells and full growth medium was added. The day after transfection, RNA was extracted by adding 125 µL RLT buffer (Qiagen) and using RNeasy 97 kit and protocols from Qiagen. cDNA synthesis was performed using 4 µL input RNA was performed using IScript Advanced cDNA Synthesis Kit for RT-qPCR (Bio-Rad) and 2 µL was used as input for digital droplet PCR using ddPCR supermix for probes (no dUTP) (Bio-Rad) according to Manufactor's protocol. The following Primers and Probes (IDT) were used

```
GRN Exon1-Exon2 (FAM):
Primer 1:
GCTGCTGCCCAAGGACCGCGGA,

Primer 2:
GCCCTGCTGTTAAGGCCACCCA
and

Probe
/56-FAM/GGACGCAGG/ZEN/CAGACCATGTGGACCCTG/3IABkFQ/

GRN Intron1-Exon2 (HEX):
Primer 1:
CCAAAGCAGGGACCACACCATTCTT,

Primer 2:
GCCCTGCTGTTAAGGCCACCCA
and

Probe
/5HEX/CCCAGCTCC/ZEN/ACCCCTGTCGGCAGACCATG/3IABkFQ/
```

HPRT1: HPRT1 (FAM, PT.58v.45621572, IDT) and HPRT1 (HEX, Hs.PT.58v.45621572) IDT.

Exon1-Exon2 GRN mRNA and Intron1-Exon2 GRN mRNA concentrations were quantified relative to the housekeeping gene HPRT1 using QuantaSoft Software (Bio-Rad).

Figure 8A:
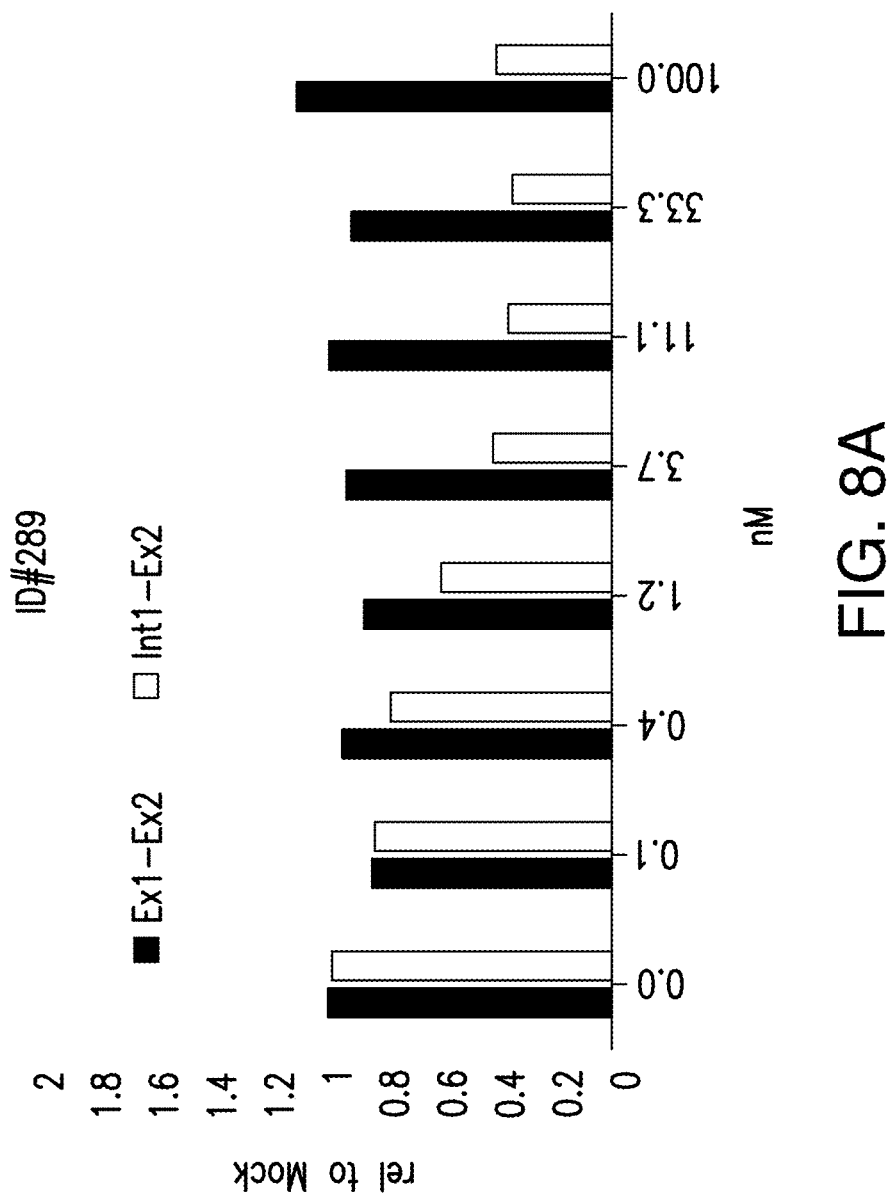
FIGS. 8A-8C shows ddPCR data quantifying the abundance of the 5 UTR splice variants in GRN mRNA 48h after transfection in H4 cells relative to Mock transfected cells. Grey bars quantify the abundance of the splice variant with retention of intron1 (Int1-Ex2) and the black bars the splice variant with the splicing of Ex1-Ex2 (Ex1-Ex2). SEQ ID NO: 289 (FIG. 8A) and SEQ ID NO: 290 (FIG. 8B) show dose-dependent skipping of intron1 retention (Int1-Ex2) and an increase in Ex1-Ex2 splice-variant. The S10 compound from WO 2020/191212 showed no/limited effects on skipping of intron1 retention (FIG. 8C).
Figure 8B:
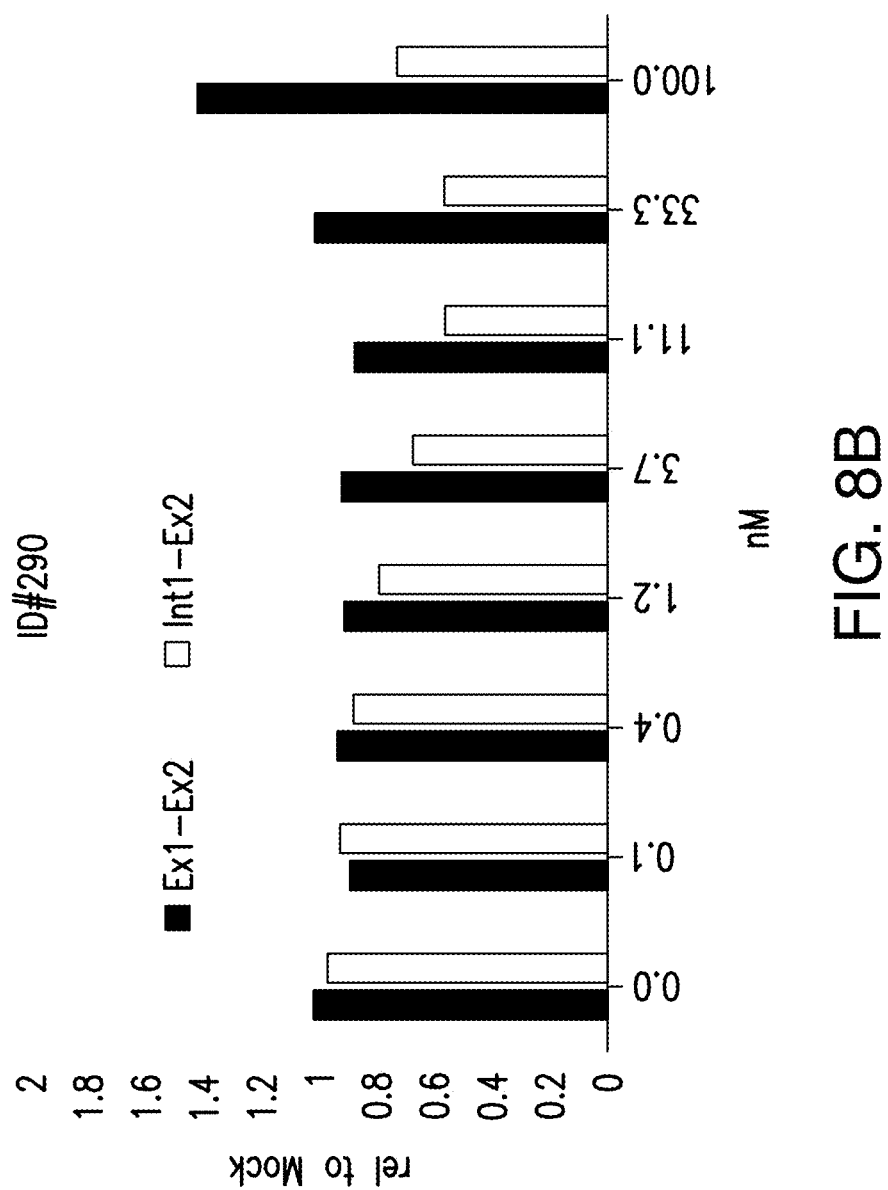
Figure 8C:
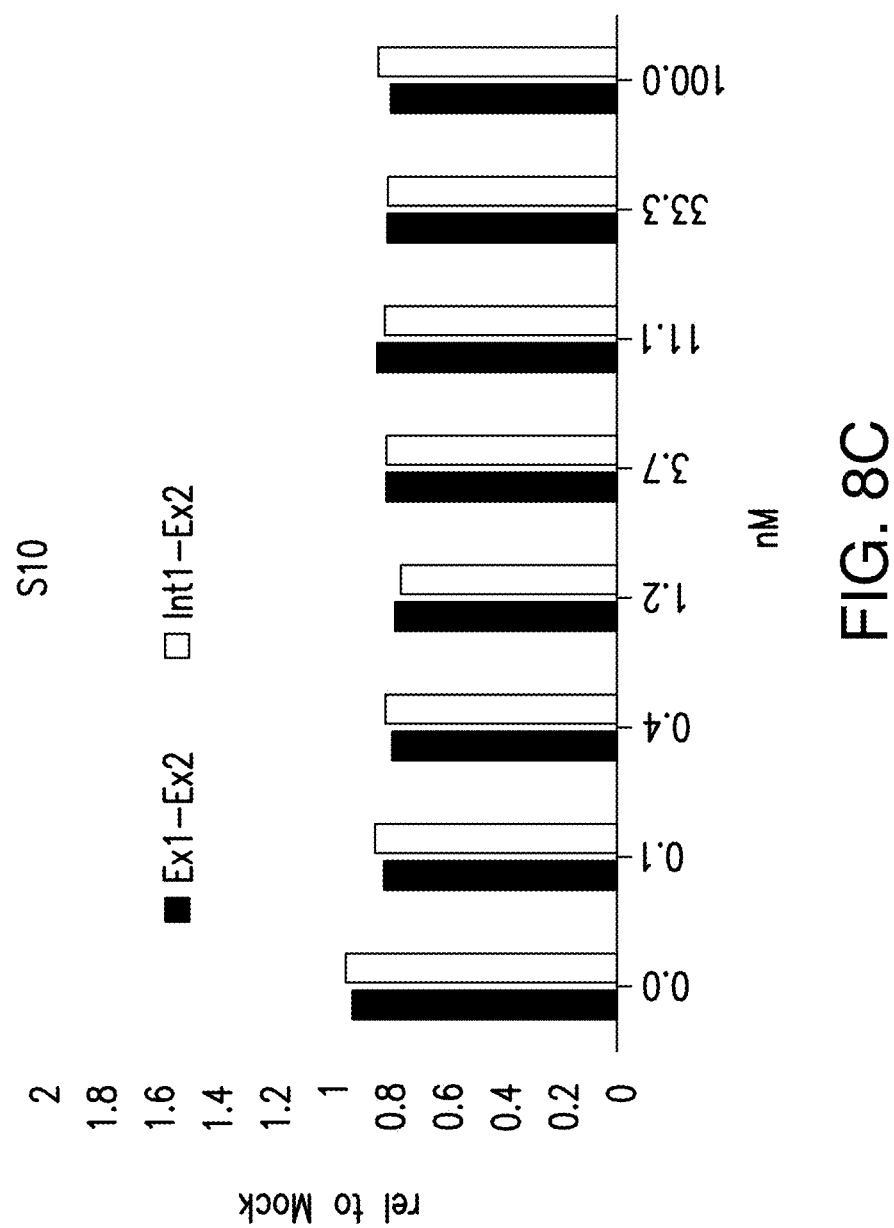

The results for SEQ ID NO: 289 and SEQ ID NO: 290 are show in FIGS. 8A-8C. SEQ ID: 289 and 290 show dose-dependent skipping of intron1 retention (Int1-Ex2) and an increase in Ex1-Ex2 splice-variant. The S10 compound from WO 2020/191212 showed no/limited effects on skipping of intron1 retention.

Example 7-Oligonucleotides Tested for Effect on Progranulin Expression in hiPSC Derived Microglia hiPSC derived microglia (iCell Microglia Kit, 01279, Cat. no R1131) were seeded (n=3) in Poly-D-lysine coated 96-well plates (Greiner Catalog No. 655946) with 20000 cells pr well in 200 µL and were treated with indicated concentrations of Compound S10 and SEQ ID NO: 290 for 5 days.

RNA was extracted by adding 125 µL RLT buffer (Qiagen) and using RNeasy 97 kit and protocols from Qiagen.

cDNA synthesis was performed using 4 µL input RNA was performed using IScript Advanced cDNA Synthesis Kit for RT-qPCR (Bio-Rad) and 2 µL was used as input for digital droplet PCR using ddPCR supermix for probes (no dUTP) (Bio-Rad) according to Manufactor's protocol. The following Primers and Probes (IDT) were used

```
GRN Exon1-Exon2 (FAM):
Primer 1:
GCTGCTGCCCAAGGACCGCGGA,

Primer 2:
GCCCTGCTGTTAAGGCCACCCA
and

Probe
/56-FAM/GGACGCAGG/ZEN/CAGACCATGTGGACCCTG/3IABkFQ/

GRN Intron1-Exon2 (HEX):
Primer 1:
CCAAAGCAGGGACCACACCATTCTT,

Primer 2:
GCCCTGCTGTTAAGGCCACCCA
and

Probe
/5HEX/CCCAGCTCC/ZEN/ACCCCTGTCGGCAGACCATG/3IABkFQ/
```

GAPDH: GAPDH (FAM, Hs.PT.39a.22214836, IDT) and GAPDH (HEX, Hs.PT.39a.22214836, IDT).

Exon1-Exon2 GRN mRNA and Intron1-Exon2 GRN mRNA concentrations were quantified relative to the housekeeping gene GAPDH using QuantaSoft Software (Bio-Rad).

Figure 9:
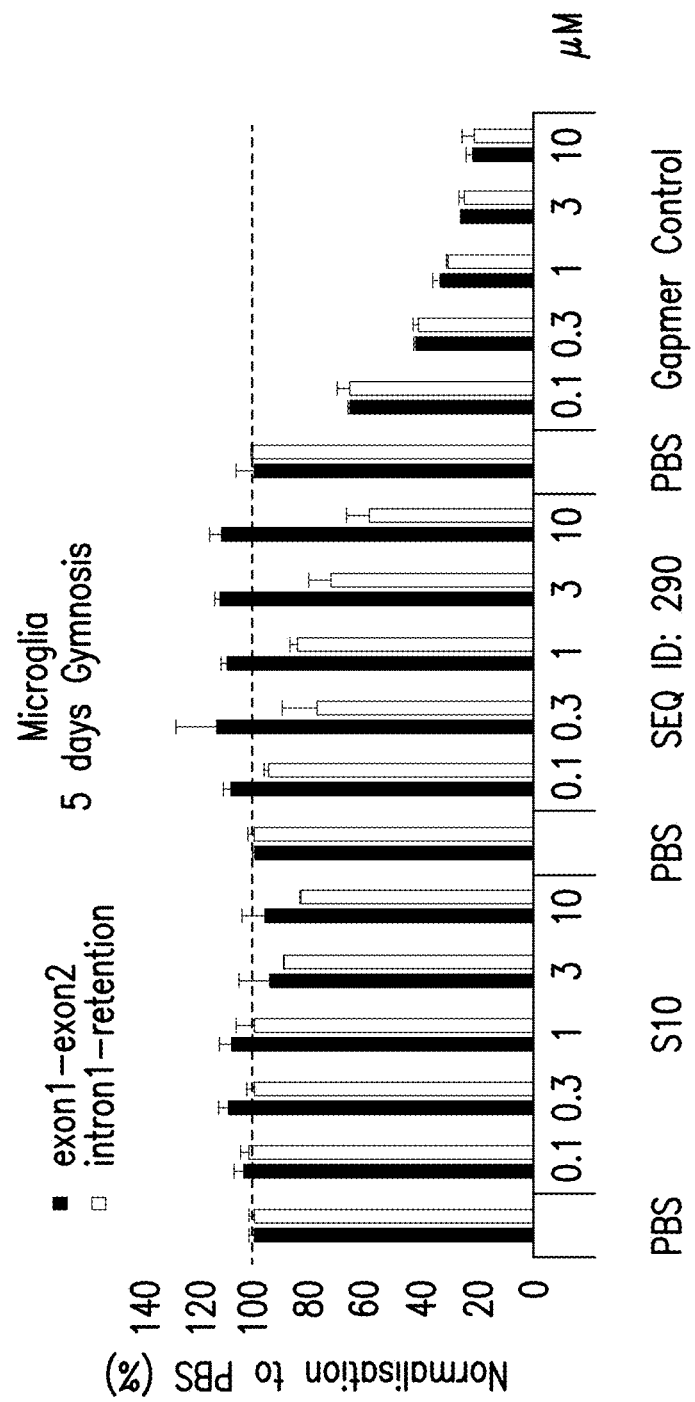
FIG. 9 shows ddPCR data quantifying the abundance of the 5 UTR splice variants in GRN mRNA after 5 days gymnosis in Microglia cells relative to PBS transfected cells. Grey bars quantify the abundance of the splice variant with retention of intron1 (Intron 1 retention) and the black bars the splice variant with the splicing of Exon1-Exon 2 (exon1-exon2). SEQ ID NO: 290 showed dose-dependent skipping of intron1 retention and an increase in Exon1-Exon2 splice-variant. The S10 compound from WO 2020/191212 showed no/limited effects on skipping of intron1 retention. The gapmer control show the expected dose-dependent knockdown of both splice variants.

The results for SEQ ID NO: 290 are show in FIG. 9. SEQ ID: 290 showed dose-dependent skipping of intron1 retention (Int1-Ex2) and an increase in Ex1-Ex2 splice-variant. The S10 compound from WO 2020/191212 showed no/limited effects on skipping of intron1 retention, a gapmer was included as control showing the expected dose-dependent knockdown of both splice variants.

Example 8—Splice Switch Analysis Using SEQ ID NO: 290

Figure 10:
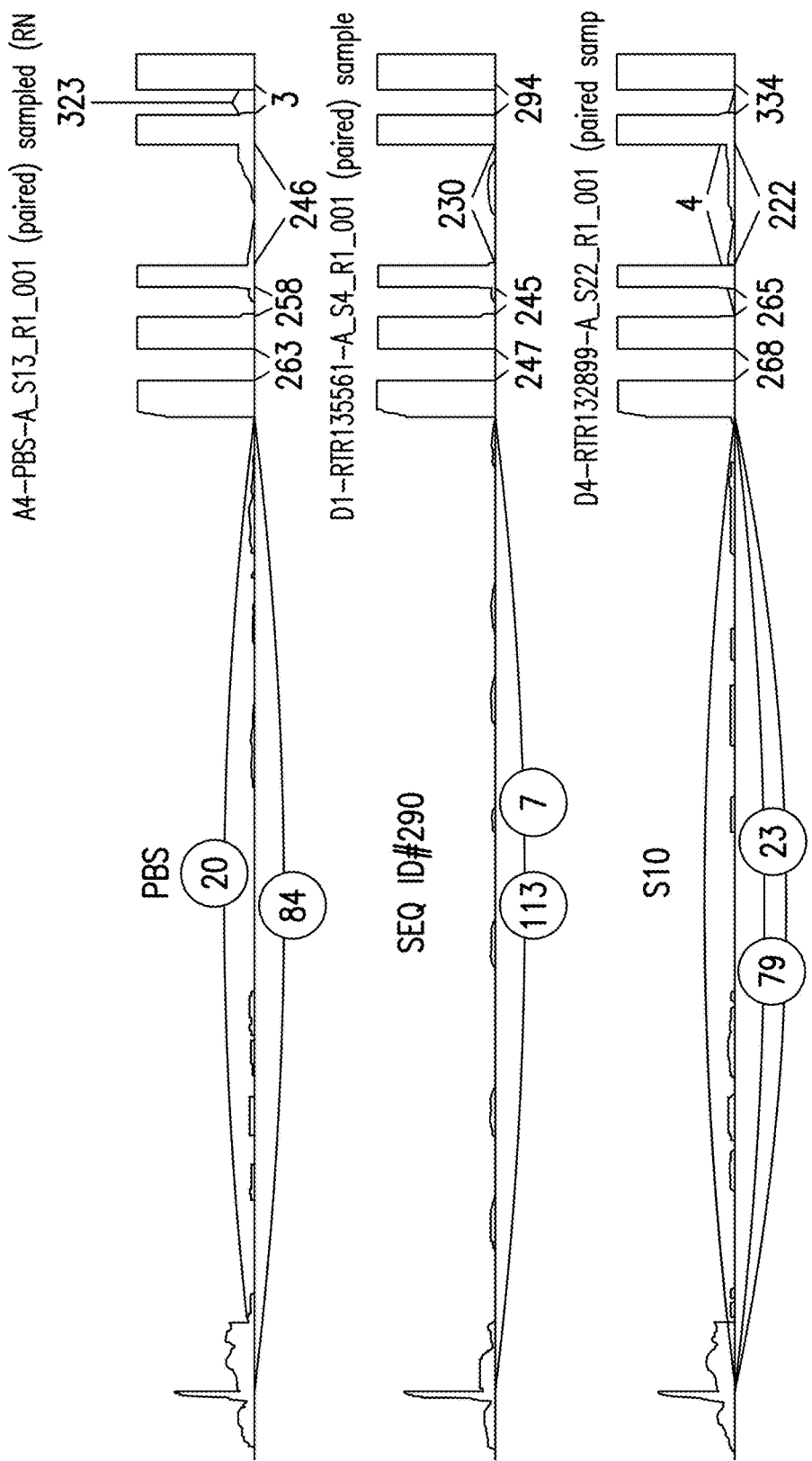
FIG. 10 shows a Sashimi plot corresponding to the splice-switch occurring with SEQ ID NO: 290, and not occurring with compound S10 according to WO 2020/191912.

H4 neuroglioma cells were seeded 15000 pr well in 96-well plates the day before transfection in medium (DMEM Sigma: D0819, 15% FBS, 1 mM Sodium Pyruvate, 25 µg/ml Gentamicin). Transfection was performed using Lipofectamine 2000 (Invitrogen) using the following procedure. Medium was removed from cells and 80 µL Optimem reduced serum medium (Gibco) containing 6.25 µg/mL Lipofectamine 2000 (Invitrogen) was added, 20 µL Optimem with compounds (125 nM) were added to each well (25 nM final). As control PBS was used instead of compound. After 5 hours, transfection solution was removed from wells and full growth medium was added. Two days after transfection, RNA was extracted by adding 350 µL Magnapure lysis buffer (Roche) and using the Magnapure system and protocols (including DNase treatment) from Roche. Total RNA was eluted in 50 µL elution buffer. KAPA mRNA HyperPrep Kits (Roche) was used to generate next generation sequencing (NGS) libraries using 100 ng of total RNA as input. Sequencing was performed on the Illumina NextSeq 550 system to obtain more than 30 million paired end reads (2×151 bp) per sample. Reads were trimmed by removal of 1 nucleotide at the 3'end, and subsampled to 30 million reads per sample prior to RNA-Seq analysis using CLC Genomic Workbench (Qiagen). To generate the Sashimi plots (showing the number of reads spanning the exon junctions), the Bam files was exported from CLC Genomic Workbench (Qiagen) and imported into The Integrative Genomics Viewer (IGV) (version IGV_2.8.2) from Broad Institute. Sashimi plots showing the splice-switching to obtain the correct splicing from exon 1 to exon 2 with the SEQ ID NO: 290 and not with S10 compound from WO 2020/191212. This is shown in FIG. 10.

TABLE 2

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 1 | TGCGTCC GACTCCG CG | RNA1{[LR](T)[sP].[dR](G)[sP].[dR](C)[sP].[LR](G)[sP].[dR](T)[sP].[dR](C)[sP].[LR]([5meC])[sP].[dR](G)[sP].[LR](A)[sP].[dR](C)[sP].[dR](T)[sP].[LR]([5meC])[sP].[dR]([5meC])[sP].[dR](G)[sP].[LR]([5meC])[sP].[LR](G)}$$$$V2.0 | CGCGGAGT CGGACGCA | 196 | 211 | 44345318 | 44345333 |
| 2 | GTCGAC TCCGCGG TC | RNA1{[LR](G)[sP].[dR](T)[sP].[LR]([5meC])[sP].[dR](C)[sP].[LR](G)[sP].[dR](A)[sP].[dR](C)[sP].[LR](T)[sP].[dR](C)[sP].[dR](C)[sP].[LR](G)[sP].[dR](C)[sP].[LR](G)[sP].[dR](G)[sP].[LR](T)[sP].[LR]([5meC])}$$$$V2.0 | GACCGCGG AGTCGGAC | 193 | 208 | 44345315 | 44345330 |
| 3 | CGACTCC GCGGTCC TT | RNA1{[LR]([5meC])[sP].[dR](G)[sP].[LR](A)[sP].[dR](C)[sP].[dR](T)[sP].[LR]([5meC])[sP].[dR]([5meC])sP].[dR](G)[sP].[LR]([5meC])[sP].[dR](G)[sP].[dR](G)[sP].[LR](T)[sP].[dR](C)[sP].[dR](C)[sP].[LR](T)[sP].[LR](T)}$$$$V2.0 | AAGGACCG CGGAGTCG | 190 | 205 | 44345312 | 44345327 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 4 | CTCCGCG GTCCTTG GG | RNA1{[LR]([5meC])[sP].[dR](T) [sP].[dR](C)[sP].[LR]([5meC]) [sP].[dR](G)[sP].[dR](C)[sP]. [LR](G)[sP].[dR](G)[sP].[LR] (T)[sP].[dR](C)[sP].[dR](C) [sP].[LR](T)[sP].[dR](T)[sP]. [dR](G)[sP].[LR](G)[sP].[LR] (G)}$$$$V2.0 | CCCAAGGA CCGCGGAG | 187 | 202 | 44345309 | 44345324 |
| 5 | CGCGGT CCTTGG GCAG | RNA1{[LR]([5meC])[sP].[dR](G) [sP].[dR](C)[sP].[LR](G)[sP]. [dR](G)[sP].[dR](T)[sP].[LR] ([5meC])[sP].[dR[(C)[sP].[dR] (T)[sP].[LR](T)[sP].[dR](G) [sP].[dR](G)[sP].[LR](G)[sP]. [dR](C)[sP].[LR](A)[sP].[LR] (G)}$$$$V2.0 | CTGCCCAA GGACCGC | 184 | 199 | 44345306 | 44345321 |
| 6 | GGTCCTT GGGCAGC AG | RNA1{[LR](G)[sP].[dR](G)[sP]. [dR](T)[sP].[LR]([5meC])[sP]. [dR](C)[sP].[dR](T)[sP].[LR] (T)[sP].[dR](G)[sP].[cR](G) [sP].[LR](G)[sP].[dR](C)[sP]. [LR](A)[sP].[dR](G)[sP].[dR] (C)[sP].[LR](A)[sP].[LR](G)}$ $$$V2.0 | CTGCTGCC CAAGGACC | 181 | 196 | 44345303 | 44345318 |
| 7 | CCTTGGG CAGCAGC AA | RNA1{[LR]([5meC])[sP].[dR](C) [sP].[dR](T)[sP].[LR](T)[sP]. [dR](G)[sP].[dR](G)[sP].[LR] (G)[sP].[dR](C)[sP].[LR](A) [sP].[dR](G)[sP].[dR](C)[sP]. [LR](A)[sP].[dR](G)[sP].[dR] (C)[sP].[LR](A)[sP].[LR](A)} $$$$V2.0 | TTGCTGCT GCCCAAGG | 178 | 193 | 44345300 | 44345315 |
| 8 | TGGGCAG CAGCAAC CG | RNA1{[LR](T)[sP].[dR](G)[sP]. [dR](G)[sP].[LR](G)[sP].[dR] (C)[sP].[LR](A)[sP].[dR](G) [sP].[dR](C)[sP].[LR](A)[sP]. [dR](G)[sP].[dR](C)[sP].[LR] (A)[sP].[dR](A)[sP].[dR](C) [sP].[LR]([5meC])[sP].[LR](G)} $$$$V2.0 | CGGTTGCT GCTGCCCA | 175 | 190 | 44345297 | 44345312 |
| 9 | GCAGCAG CAACCGG GT | RNA1{[LR](G)[sP].[dR](C)[sP]. [LR](A)[sP].[dR](G)[sP].[dR] (C)[sP].[LR](A)[sP].[dR](G) [sP].[dR](C)[sP].[LR](A)[sP]. [dR](A)[sP].[dR](C)[sP].[LR] ([5meC])[sP].[dR](G)[sP].[dR] (G)[sP].[LR](G)[sP].[LR](T)}$ $$$V2.0 | ACCCGGTT GCTGCTGC | 172 | 187 | 44345294 | 44345309 |
| 10 | GCAGCAA CCGGGTA GC | RNA1{[LR](G)[sP].[dR](C)[sP]. [LR](A)[sP].[dR](G)[sP].[dR] (C)[sP].[LR](A)[sP].[dR](A) [sP].[dR](C)[sP].[LR]([5meC]) [sP].[dR](G)[sP].[dR](G)[sP]. [LR](G)[sP].[dR](T)[sP].[dR] (A)[sP].[LR](G)[sP].[LR] ([5meC])}$$$$V2.0 | GCTACCCG GTTGCTGC | 169 | 184 | 44345291 | 44345306 |
| 11 | GCAACCG GGTAGCG CT | RNA1{[LR](G)[sP].[dR](C)[sP]. [LR](A)[sP].[dR](A)[sP].[dR] (C)[sP].[LR]([5meC])[sP].[dR] (G)[sP].[dR](G)[sP].[LR](G) [sP].[dR](T)[sP].[dR](A)[sP]. [LR](G)[sP].[dR]([5meC])[sP]. [dR](G)[sP].[LR]([5meC])[sP]. [LR](T)}$$$$V2.0 | AGCGCTAC CCGGTTGC | 166 | 181 | 44345288 | 44345303 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 12 | ACCGGGT AGCGCTC AG | RNA1{[LR](A)[sP].[dR](C)[sP].[LR]([5meC])[sP].[dR](G)[sP].[dR](G)[sP].[LR](G)[sP].[dR](T)[sP].[LR](A)[sP].[dR](G)[sP].[dR](C)[sP].[LR](G)[sP].[dR](C)[sP].[LR](T)[sP].[dR](C)[sP].[LR](A)[sP].[LR](G)}$$$$V2.0 | CTGAGCGC TACCCGGT | 163 | 178 | 44345285 | 44345300 |
| 13 | GGGTAGC GCTCAGA CT | RNA1{[LR](G)[sP].[dR](G)[sP].[LR](G)[sP].[dR](T)[sP].[LR](A)[sP].[dR](G)[sP].[dR](C)[sP].[LR](G)[sP].[dR](C)[sP].[LR](T)[sP].[dR](C)[sP].[LR](A)[sP].[dR](G)[sP].[dR](A)[sP].[LR]([5meC])[sP].[LR](T)}$$$$V2.0 | AGTCTGAG CGCTACCC | 160 | 175 | 44345282 | 44345297 |
| 14 | TAGCGCT CAGACTA CA | RNA1{[LR](T)[sP].[dR](A)[sP].[dR](G)[sP].[LR]([5meC])[sP].[dR](G)[sP].[dR](C)[sP].[LR](T)[sP].[dR](C)[sP].[LR](A)[sP].[dR](G)[sP].[dR](A)[sP].[LR]([5meC])[sP].[dR](T)[sP].[dR](A)[sP].[LR]([5meC])[sP].[LR](A)}$$$$V2.0 | TGTAGTCT GAGCGCTA | 157 | 172 | 44345279 | 44345294 |
| 15 | CGCTCAG ACTACAG AC | RNA1{[LR]([5meC])[sP].[dR](G)[sP].[dR](C)[sP].[LR](T)[sP].[dR](C)[sP].[LR](A)[sP].[dR](G)[sP].[LR](A)[sP].[dR](C)[sP].[dR](T)[sP].[LR](A)[sP].[dR](C)[sP].[LR](A)[sP].[dR](G)[sP].[LR](A)[sP].[LR]([5meC])}$$$$V2.0 | GTCTGTAG TCTGAGCG | 154 | 169 | 44345276 | 44345291 |
| 16 | TCAGACT ACAGACC CC | RNA1{[LR](T)[sP].[dR](C)[sP].[LR](A)[sP].[dR](G)[sP].[LR](A)[sP].[dR](C)[sP].[dR](T)[sP].[LR](A)[sP].[dR](C)[sP].[LR](A)[sP].[dR](G)[sP].[LR](A)[sP].[dR](C)[sP].[dR](C)[sP].[LR]([5meC])[sP].[LR]([5meC])}$$$$V2.0 | GGGGTCTG TAGTCTGA | 151 | 166 | 44345273 | 44345288 |
| 17 | GACTACA GACCCCA GC | RNA1{[LR](G)[sP].[dR](A)[sP].[dR](C)[sP].[LR](T)[sP].[dR](A)[sP].[dR](C)[sP].[LR](A)[sP].[dR](G)[sP].[LR](A)[sP].[dR](C)[sP].[dR](C)[sP].[LR]([5meC])[sP].[dR](C)[sP].[dR](A)[sP].[LR](G)[sP].[LR]([5meC])}$$$$V2.0 | GCTGGGGT CTGTAGTC | 148 | 163 | 44345270 | 44345285 |
| 18 | TACAGAC CCCAGCG CG | RNA1{[LR](T)[sP].[dR](A)[sP].[dR](C)[sP].[LR](A)[sP].[dR](G)[sP].[LR](A)[sP].[dR](C)[sP].[dR](C)[sP].[LR]([5meC])[sP].[dR](C)[sP].[dR](A)[sP].[LR](G)[sP].[dR]([5meC])[sP].[dR](G)[sP].[LR]([5meC])[sP].[LR](G)}$$$$V2.0 | CGCGCTGG GGTCTGTA | 145 | 160 | 44345267 | 44345282 |
| 19 | AGTTCCC TACTACC TCC | RNA1{[LR](A)[sP].[dR](G)[sP].[LR](T)[sP].[dR](C)[sP].[LR]([5meC])[sP].[dR](C)[sP].[dR](T)[sP].[LR](A)[sP].[dR](C)[sP].[dR](T)[sP].[LR](A)[sP].[dR](C)[sP].[LR]([5meC])[sP].[dR](T)[sP].[LR](T)[sP].[LR]([5meC])}$$$$V2.0 | GAAGGTAG TAGGGACT | 616 | 631 | 44345738 | 44345753 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 20 | CCCTACT ACCTTCG AG | RNA1{[LR]([5meC])[sP].[dR](C) [sP].[LR]([5meC])[sP].[dR](T) [sP].[LR](A)[sP].[dR](C)[sP]. [dR](T)[sP].[LR](A)[sP].[dR] (C)[sP].[LR]([5meC])[sP].[dR] (T)[sP].[LR](T)[sP].[dR] ([5meC][sP].[dR](G)[sP].[LR] (A).[LR](G)}$$$$V2.0 | CTCGAAGG TAGTAGGG | 613 | 628 | 44345735 | 44345750 |
| 21 | TACTACC TTCGAGA AG | RNA1{[LR](T)[sP].[dR](A)[sP]. [LR]([5meC])[sP].[dR](T)[sP]. [LR](A)[sP].[dR](C)[sP].[dR] (C)[sP].[LR](T)[sp].[c1R](T) [sP].[dR](C)[sP].[LR](G)[sP]. [dR](A)[sP].[dR](G)[sP].[LR] (A)[sP].[LR](A)[sP].[LR](G)} $$$$V2.0 | CTTCTCGA AGGTAGTA | 610 | 625 | 44345732 | 44345747 |
| 22 | TACCTTC GAGAAGC CA | RNA1{[LR](T)[sP].[dR](A)[sP]. [LR]([5meC])[sP].[dR](C)[sP]. [dR](T)[sP].[LR](T)[sP].[dR] (C)[sP].[LR](G)[sP].[dR](A) [sP].[dR](G)[sP].[LR](A)[sP]. [dR](A)[sP].[dR](G)[sP].[dR] (C)[sP].[LR]([5meC])[sP].[LR] (A)}$$$$V2.0 | TGGCTTCT CGAAGGTA | 607 | 622 | 44345729 | 44345744 |
| 23 | CTTCGAG AAGCCAA GG | RNA1{[LR]([5meC])[sP].[dR](T) [sP].[LR](T)[sP].[dR](C)[sP]. [LR](G)[sP].[dR](A)[sP].[dR] (G)[sP].[LR](A)[sp].[dR](A) [sP].[LR](G)[sP].[dR](C)[sP]. [dR](C)[sP].[LR](A)[sP].[dR] (A)[sP].[LR](G)[sP].[LR](G)} $$$$V2.0 | CCTTGGCT TCTCGAAG | 604 | 619 | 44345726 | 44345741 |
| 24 | CGAGAAG CCAAGGT CT | RNA1{[LR]([5meC])[sP].[dR](G) [sP].[dR](A)[sP].[LR](G)[sP]. [dR](A)[sP].[dR](A)[sP].[LR] (G)[sP].[dR](C)[sP].[dR](C) [sP].[LR](A)[sP].[dR](A)[sP]. [dR](G)[sP].[LR](G)[sP].[dR] (T)[sP].[LR]([5meC])[sP].[LR] (T)}$$$$V2.0 | AGACCTTG GCTTCTCG | 601 | 616 | 44345723 | 44345738 |
| 25 | GAAGCCA AGGTCTC AG | RNA1{[LR](G)[sP].[dR](A)[sP]. [dR](A)[sP].[LR](G)[sP].[dR] (C)[sP].[dR](C)[sP].[LR](A) [sP].[dR](A)[sP].[dR](G)[sP]. [LR](G)[sP].[dR](T)[sP].[dR] (C)[sP].[LR](T)[sP].[dR](C) [sP].[LR](A)[sP].[LR](G)}$$$ $V2.0 | CTGAGACC TTGGCTTC | 598 | 613 | 44345720 | 44345735 |
| 26 | GCCAAGG TCTCAGG TC | RNA1{[LR](G)[sP].[dR](C)[sP]. [dR](C)[sP].[LR](A)[sP].[dR] (A)[sP].[dR](G)[sP].[LR](G) [sP].[dR](T)[sP].[dR](C)[sP]. [LR](T)[sP].[dR](C)[sP].[LR] (A)[sP].[dR](G)[sP].[dR](G) [sP].[LR](T)[sP].[LR] ([5meC])}$$$$V2.0 | GACCTGAG ACCTTGGC | 595 | 610 | 44345717 | 44345732 |
| 27 | AAGGTCT CAGGTCT CG | RNA1{[LR](A)[sP].[dR](A)[sP]. [dR](G)[sP].[LR](G)[sP].[dR] (T)[sP].[dR](C)[sP].[LR](T) [sP].[dR](C)[sP].[LR](A)[sP]. [dR](G)[sP].[dR](G)[sP].[LR] (T)[sP].[dR](C)[sP].[dR](T) [sP].[LR]([5meC])[sP].[LR] (G)}$$$$V2.0 | CGAGACCT GAGACCTT | 592 | 607 | 44345714 | 44345729 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 28 | GTCTCAG GTCTCG TTC | RNA1{[LR](G)[sP].[dR](T)[sP].[dR](C)[sP].[LR](T)[sP].[dR](C)[sP].[dR](A)[sP].[dR](G)[sP].[LR](G)[sP].[dR](T)[sP].[dR](C)[sP].[dR](T)[sP].[LR]([5meC])[sP].[dR](G)[sP].[dR](T)[sP].[LR](T)[sP].[LR]([5meC])}$$$$V2.0 | GAACGAGA CCTGAGAC | 589 | 604 | 44345711 | 44345726 |
| 29 | TCAGGTC TCGTTCC CA | RNA1{[LR](T)[sP].[dR](C)[sP].[LR](A)[sP].[dR](G)[sP].[dR](G)[sP].[LR](T)[sP].[dR](C)[sP].[dR](T)[sP].[LR]([5meC])[sP].[dR](G)[sP].[dR](T)[sP].[LR](T)[sP].[dR](C)[sP].[dR](C)[sP].[LR]([5meC])[sP].[LR](A)}$$$$V2.0 | TGGGAACG AGACCTGA | 586 | 601 | 44345708 | 44345723 |
| 30 | GGTCTCG TTCCCAG GC | RNA1{[LR](G)[sP].[dR](G)[sP].[dR](T)[sP].[LR]([5meC])[sP].[dR](T)[sP].[dR](C)[sP].[LR](G)[sP].[dR](T)[sP].[LR](T)[sP].[dR](C)[sP].[dR](C)[sP].[LR]([5meC])[sP].[dR](A)[sP].[dR](G)[sP].[LR](G)[sP].[LR]([5meC])}$$$$V2.0 | GCCTGGGA ACGAGACC | 583 | 598 | 44345705 | 44345720 |
| 31 | CTCGTTC CCAGGCC CT | RNA1{[LR]([5meC])[sP].[dR](T)[sP].[dR](C)[sP].[LR](G)[sP].[dR](T)[sP].[LR](T)[sP].[dR](C)[sP].[dR](C)[sP].[LR]([5meC])[sP].[dR](A)[sP].[dR](G)[sP].[LR](G)[sP].[dR](C)[sP].[dR](C)[sP].[LR]([5meC])[sP].[LR](T)}$$$$V2.0 | AGGGCCTG GGAACGAG | 580 | 595 | 44345702 | 44345717 |
| 32 | GTTCCCA GGCCCTC GG | RNA1{[LR](G)[sP].[dR](T)[sP].[LR](T)[sP].[dR](C)[sP].[dR](C)[sP].[LR]([5meC])[sP].[dR](A)[sP].[dR](G)[sP].[LR](G)[sP].[dR](C)[sP].[dR](C)[sP].[LR]([5meC])[sP].[dR](T)[sP].[dR](C)[sP].[LR](G)[sP].[LR](G)}$$$$V2.0 | CCGAGGGC CTGGGAAC | 577 | 592 | 44345699 | 44345714 |
| 33 | CCCAGGC CCTCGGA GC | RNA1{[LR]([5meC])[sP].[dR](C)[sP].[dR](C)[sP].[LR](A)[sP].[dR](G)[sP].[dR](G)[sP].[LR]([5meC])[sP].[dR](C)[sP].[dR](C)[sP].[LR](T)[sP].[dR]([5meC])[sP].[dR](G)[sP].[LR](G)[sP].[dR](A)[sP].[LR](G)[sP].[LR]([5meC])}$$$$V2.0 | GCTCCGAG GGCCTGGG | 574 | 589 | 44345696 | 44345711 |
| 34 | AGGCCCT CGGAGCT CC | RNA1{[LR](A)[sP].[dR](G)[sP].[dR](G)[sP].[LR]([5meC])[sP].[dR](C)[sP].[dR](C)[sP].[LR](T)[sP].[dR]([5meC])[sP].[dR](G)[sP].[LR](G)[sP].[dR](A)[sP].[LR](G)[sP].[dR](C)[sP].[dR](T)[sP].[LR]([5meC])[sP].[LR]([5meC])}$$$$V2.0 | GGAGCTCC GAGGGCCT | 571 | 586 | 44345693 | 44345708 |
| 35 | CCCTCGG AGCTCCC AG | RNA1{[LR]([5meC])[sP].[dR](C)[sP].[dR](C)[sP].[LR](T)[sP].[dR]([5meC])[sP].[dR](G)[sP].[LR](G)[sP].[dR](A)[sP].[LR](G)[sP].[dR](C)[sP].[dR](T)[sP].[LR]([5meC])[sP].[dR](C)[sP].[dR](C)[sP].[LR](A)[sP].[LR](G)}$$$$V2.0 | CTGGGAGC TCCGAGGG | 568 | 583 | 44345690 | 44345705 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 36 | TCGGAGC TCCCAGC CC | RNA1{[LR](T)[sP].[dR]([5meC]) [sP].[dR](G)[sP].[LR](G)[sP]. [dR](A)[sP].[LR](G)[sP].[dR] (C)[sP].[dR](T)[sP].[LR] ([5meC])[sP].[dR](C)[sP].[dR] (C)[sP].[LR](A)[sP].[dR](G) [sP].[dR](C)[sP].[LR]([5meC]) [sP].[LR]([5meC])}$$$$V2.0 | GGGCTGGG AGCTCCGA | 565 | 580 | 44345687 | 44345702 |
| 37 | GAGCTCC CAGCCCA GG | RNA1{[LR](G)[sP].[dR](A)[sP]. [LR](G)[sP].[dR](C)[sP].[dR] (T)[sP].[LR]([5meC])[sP].[dR] (C)[sP].[dR](C)[sP].[LR](A) [sP].[dR](G)[sP].[dR](C)[sP]. [LR]([5meC])[sP].[dR](C)[sP]. [dR](A)[sP].[LR](G)[sP].[LR] (G)}$$$$V2.0 | CCTGGGCT GGGAGCTC | 562 | 577 | 44345684 | 44345699 |
| 38 | CTCCCAG CCCAGGG TC | RNA1{[LR]([5meC])[sP].[dR](T) [sP].[dR](C)[sP].[LR]([5meC]) [sP].[dR](C)[sP].[LR](A)[sP]. [dR](G)[sP].[dR](C)[sP].[LR] ([5meC])[sP].[dR](C)[sP].[dR] (A)[sP].[LR](G)[sP].[dR](G) [sP].[dR](G)[sP].[LR](T)[sP]. [LR]([5meC])}$$$$V2.0 | GACCCTGG GCTGGGAG | 559 | 574 | 44345681 | 44345696 |
| 39 | CCAGCCC AGGGTCG CG | RNA1{[LR]([5meC][sP].[dR](C) [sP].[LR](A)[sP].[dR](G)[sP]. [dR](C)[sP].[LR]([5meC])[sP]. [dR](C)[sP].[dR](A)[sP].[LR] (G)[sP].[dR](G)[sP].[dR](G) [sP].[LR](T)[sP].[dR]([5meC]) [sP].[dR](G)[sP].[LR]([5meC]) [sP].[LR](G)}$$$$V2.0 | CGCGACCC TGGGCTGG | 556 | 571 | 44345678 | 44345693 |
| 40 | GCCCAGG GTCGCGC GC | RNA1{[LR](G)[sP].[dR](C)[sP]. [LR]([5meC])[sP].[dR](C)[sP]. [LR](A)[sP].[dR](G)[sP].[dR] (G)[sP].[LR](G)[sp].[dR](T) [sP].[dR](C)[sP].[LR](G)[sP]. [dR](C)[sP].[LR](G)[sP].[dR] (C)[sP].[LR](G)[sP].[LR] ([5meC])}$$$$V2.0 | GCGCGCGA CCCTGGGC | 553 | 568 | 44345675 | 44345690 |
| 41 | CAGGGTC GCGGCC CC | RNA1{[LR]([5meC])[sP].[dR](A) [sP].[dR](G)[sP].[LR](G)[sP]. [dR](G)[sP].[dR](T)[sP].[LR] ([5meC])[sP].[dm(G)[sP].[dR] (C)[sP].[LR](G)[sP].[dR](C) [sP].[LR](G)[sP].[dR](C)[sP]. [dR](C)[sP].[LR]([5meC])[sP]. [LR]([5meC])}$$$$V2.0 | GGGGCGCG CGACCCTG | 550 | 565 | 44345672 | 44345687 |
| 42 | GGTCGCG CGCCCCT CC | RNA1{[LR](G)[sP].[dR](G)[sP]. [dR](T)[sP].[LR]([5meC])[sP]. [dR](G)[sP].[dR](C)[sP].[LR] (G)[sP].[dR](C)[sP].[LR](G) [sP].[dR](C)[sP].[dR](C)[sP]. [LR]([5meC])[sP].[dR](C)[sP]. [dR](T)[sP].[LR]([5meC])[sP]. [LR]([5meC])}$$$$V2.0 | GGAGGGGC GCGCGACC | 547 | 562 | 44345669 | 44345684 |
| 43 | CGCGCGC CCCTCCG CC | RNA1{[LR]([5meC])[sP].[dR](G) [sP].[dR](C)[sP].[LR](G)[sP]. [dR](C)[sP].[dR](G)[sP].[LR] (C)[sP].[dR](C)[sP].[LR] ([5meC])[sP].[dR](C)[sP].[dR] (T)[sP].[LR]([5meC])[sP].[dR] ([5meC])[sP].[dR](G)[sP].[LR] (G)[sP].[LR]([5meC])}$$$$V2.0 | GCCGGAGG GCGCGCG | 544 | 559 | 44345666 | 44345681 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 44 | GCGCCCCTCCGGCTCC | RNA1{[LR](G)[sP].[dR](C)[sP].[LR](G)[sP].[dR](C)[sP].[dR](C)[sP].[LR]([5meC])[sP].[dR](C)[sP].[dR](T)[sP].[LR]([5meC])[sP].[dR]([5meC])[sP].[dR](G)[sP].[LR](G)[sP].[dR](C)[sP].[dR](T)[sP].[LR]([5meC])[sP].[LR]([5meC])}$$$$V2.0 | GGAGCCGGAGGGGCGC | 541 | 556 | 44345663 | 44345678 |
| 45 | CCCCTCCGGCTCCAGG | RNA1{[LR]([5meC])[sP].[dR](C)[sP].[LR]([5meC])[sP].[dR](C)[sP].[dR](T)[sP].[LR]([5meC])[sP].[dR]([5meC])[sP].[dR](G)[sP].[LR](G)[sP].[dR](C)[sP].[dR](T)[sP].[LR]([5meC])[sP].[dR](C)[sP].[dR](A)[sP].[LR](G)[sP].[LR](G)}$$$$V2.0 | CCTGGAGCCGGAGGGG | 538 | 553 | 44345660 | 44345675 |
| 46 | CTCCGGCTCCAGGCCG | RNA1{[LR]([5meC])[sP].[dR](T)[sP].[dR](C)[sP].[LR]([5meC])[sP].[dR](G)[sP].[dR](G)[sP].[LR]([5meC])[sp].[dR](T)[sP].[dR](C)[sP].[dR]([5meC])[sP].[dR](A)[sP].[dR](G)[sP].[LR](G)[sP].[dR](C)[sP].[LR]([5meC])[sP].[LR](G)}$$$$V2.0 | CGGCCTGGAGCCGGAG | 535 | 550 | 44345657 | 44345672 |
| 47 | CGGCTCCAGGCCGCCG | RNA1{[LR]([5meC])[sP].[dR](G)[sP].[dR](G)[sP].[LR]([5meC])[sP].[dR](T)[sP].[dR](C)[sP].[LR]([5meC])[sP].[dR](A)[sP].[dR](G)[sP].[LR](G)[sP].[dR](C)[sP].[dR](C)[sP].[LR](G)[sP].[dR](C)[sP].[LR]([5meC])[sP].[LR](G)}$$$$V2.0 | CGGCGGCCTGGAGCCG | 532 | 547 | 44345654 | 44345669 |
| 48 | CTCCAGGCCGCCGCGG | RNA1{[LR]([5meC])[sP].[dR](T)[sP].[dR](C)[sP].[LR]([5meC])[sP].[dR](A)[sP].[dR](G)[sP].[LR](G)[sP].[dR](C)[sP].[dR](C)[sP].[LR](G)[sP].[dR](C)[sP].[dR](C)[sP].[LR](G)[sP].[dR](C)[sP].[LR](G)[sP].[LR](G)}$$$$V2.0 | CCGCGGCGGCCTGGAG | 529 | 544 | 44345651 | 44345666 |
| 49 | CAGGCCGCCGCGGGAA | RNA1{[LR]([5meC])[sP].[dR](A)[sP].[dR](G)[sP].[LR](G)[sP].[dR](C)[sP].[dR](C)[sP].[LR](G)[sP].[dR](C)[sP].[dR](C)[sP].[LR](G)[sP].[dR](C)[sP].[dR](G)[sP].[LR](G)[sP].[dR](G)[sP].[LR](A)[sP].[LR](A)}$$$$V2.0 | TTCCCGCGGCGGCCTG | 526 | 541 | 44345648 | 44345663 |
| 50 | GCCGCGGGAACCACCC | RNA1{[LR](G)[sP].[dR](C)[sP].[dR](C)[sP].[LR](G)[sP].[dR](C)[sP].[LR](G)[sP].[dR](G)[sP].[dR](G)[sP].[dR](A)[sP].[dR](A)[sP].[dR](C)[sP].[LR]([5meC])[sP].[dR](A)[sP].[dR](C)[sP].[LR]([5meC])[sP].[LR]([5meC])}$$$$V2.0 | GGGTGGTTCCCGCGGC | 520 | 535 | 44345642 | 44345657 |
| 51 | GCGGGAACCACCCACC | RNA1{[LR](G)[sP].[dR]([5meC])[sP].[dR](G)[sP].[LR](G)[sP].[dR](G)[sP].[dR](A)[sP].[LR](A)[sP].[dR](C)[sP].[dR](C)[sP].[LR](A)[sP].[dR](C)[sP]. | GGTGGGTGGTTCCCGC | 517 | 532 | 44345639 | 44345654 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [dR](C)[sP].[LR]([5meC])[sP].[dR](A)[sP].[LR]([5meC])[sP].[LR]([5meC])}$$$V2.0 | | | | | |
| 52 | GGAACCA CCCACCA CC | RNA1{[LR](G)[sP].[dR](G)[sP].[dR](A)[sP].[dR](A)[sP].[dR](C)[sP].[dR](C)[sP].[LR](A)[sP].[dR](C)[sP].[dR](C)[sP].[LR]([5meC])[sP].[dR](A)[sP].[dR](C)[sP].[LR]([5meC])[sP].[dR](A)[sP].[LR]([5meC])[sP].[LR]([5meC])}$$$V2.0 | GGTGGTGG GTGGTTCC | 514 | 529 | 44345636 | 44345651 |
| 53 | ACCACCC ACCACCA CC | RNA1{[LR](A)[sP].[dR](C)[sP].[dR](C)[sP].[LR](A)[sP].[dR](C)[sP].[LR]([5meC])[sP].[dR](C)[sP].[LR](A)[sP].[dR](C)[sP].[dR](C)[sP].[LR](A)[sP].[dR](C)[sP].[dR](C)[sP].[LR](A)[sP].[LR]([5meC])[sP].[LR]([5meC])}$$$V2.0 | GGTGGTGG TGGGTGGT | 511 | 526 | 44345633 | 44345648 |
| 54 | ACCCACC ACCACCA GG | RNA1{[LR](A)[sP].[dR](C)[sP].[LR]([5meC])[sP].[dR](C)[sP].[LR](A)[sP].[dR](C)[sP].[dR](C)[sP].[LR](A)[sP].[dR](C)[sP].[dR](C)[sP].[LR](A)[sP].[dR](C)[sP].[LR]([5meC])[sP].[dR](A)[sP].[LR](G)[sP].[LR](G)}$$$V2.0 | CCTGGTGG TGGTGGGT | 508 | 523 | 44345630 | 44345645 |
| 55 | CACCACC ACCAGGA GA | RNA1{[LR]([5meC])[sP].[dR](A)[sP].[LR]([5meC])[sP].[dR](C)[sP].[LR](A)[sP].[dR](C)[sP].[dR](C)[sP].[LR](A)[sP].[dR](C)[sP].[dR](C)[sP].[LR](A)[sP].[dR](G)[sP].[LR](G)[sP].[dR](A)[sP].[LR](G)[sP].[LR](A)}$$$V2.0 | TCTCCTGG TGGTGGTG | 505 | 520 | 44345627 | 44345642 |
| 56 | CACCACC AGGAGAG GG | RNA1{[LR]([5meC])[sP].[dR](A)[sP].[dR](C)[sP].[LR]([5meC])[sP].[dR](A)[sP].[dR](C)[sP].[LR]([5meC])[sP].[dR](A)[sP].[dR](G)[sP].[LR](G)[sP].[dR](A)[sP].[dR](A)[sP].[dR](A)[sP].[LR](G)[sP].[LR](G)}$$$V2.0 | CCCTCTCC TGGTGGTG | 502 | 517 | 44345624 | 44345639 |
| 57 | CACCAGG AGAGGGG AA | RNA1{[LR]([5meC])[sP].[dR](A)[sP].[dR](C)[sP].[LR]([5meC])[sP].[dR](A)[sP].[dR](G)[sP].[LR](G)[sP].[dR](A)[sP].[LR](G)[sP].[dR](A)[sP].[dR](G)[sP].[LR](G)[sP].[dR](G)[sP].[dR](G)[sP].[dR](G)[sP].[LR](A)}$$$V2.0 | TTCCCCTCT CTGGTG | 499 | 514 | 44345621 | 44345636 |
| 58 | CAGGAGA GGGGAAG AA | RNA1{[LR]([5meC])[sP].[dR](A)[sP].[dR](G)[sP].[LR](G)[sP].[dR](A)[sP].[LR](G)[sP].[dR](A)[sP].[dR](G)[sP].[LR](G)[sP].[dR](G)[sP].[dR](G)[sP].[LR](A)[sP].[dR](A)[sP].[dR](G)[sP].[LR](A)[sP].[LR](A)}$$$V2.0 | TTCTTCCCC TCTCCTG | 496 | 511 | 44345618 | 44345633 |
| 59 | GAGAGGG GAAGAAG CC | RNA1{[LR](G)[sP].[dR](A)[sP].[LR](G)[sP].[dR](A)[sP].[dR](G)[sP].[LR](G)[sP].[dR](G)[sP].[dR](G)[sP].[LR](A)[sP].[dR](A)[sP].[dR](G)[sP].[LR] | GGCTTCTT CCCCTCTC | 493 | 508 | 44345615 | 44345630 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | (A)[sP].[dR](A)[sP].[dR](G) [sP].[LR]([5meC])[sP].[LR] ([5meC])}$$$$V2.0 | | | | | |
| 60 | AGGGGAA GAAGCCA GC | RNA1{[LR](A)[sP].[dR](G)[sP]. [LR](G)[sP].[dR](G)[sP].[dR] (G)[sP].[LR](A)[sP].[dR](A) [sP].[dR](G)[sP].[LR](A)[sP]. [dR](A)[sP].[dR](G)[sP].[LR] ([5meC])[sP].[dR](C)[sP].[dR] (A)[sP].[LR](G)[sP].[LR] ([5meC])}$$$$V2.0 | GCTGGCTT CTTCCCCT | 490 | 505 | 44345612 | 44345627 |
| 61 | GGAAGAA GCCAGCA CC | RNA1{[LR](G)[sP].[dR](G)[sP]. [LR](A)[sP].[dR](A)[sP].[dR] (G)[sP].[LR](A)[sP].[dR](A) [sP].[dR](G)[sP].[LR]([5meC]) [sP].[dR](C)[sP].[dR](A)[sP]. [LR](G)[sP].[dR](C)[sP].[dR] (A)[sP].[LR]([5meC])[sP].[LR] ([5meC])}$$$$V2.0 | GGTGCTGG CTTCTTCC | 487 | 502 | 44345609 | 44345624 |
| 62 | AGAAGCC AGCACCT AC | RNA1{[LR](A)[sP].[dR](G)[sP]. [LR](A)[sP].[dR](A)[sP].[LR] (G)[sP].[dR](C)[sP].[dR](C) [sP].[LR](A)[sP].[dR](G)[sP]. [dR](C)[sP].[LR](A)[sP].[dR] (C)[sP].[LR]([5meC])[sP].[dR] (T)[sP].[LR](A)[sP].[LR] ([5meC])}$$$$V2.0 | GTAGGTGC TGGCTTCT | 484 | 499 | 44345606 | 44345621 |
| 63 | AGCCAGC ACCTACC GA | RNA1{[LR](A)[sP].[dR](G)[sP]. [dR](C)[sP].[LR]([5meC])[sP]. [dR](A)[sP].[dR](G)[sP].[LR] ([5meC])[sP].[dR](A)[sP].[LR] ([5meC])[sP].[dR](C)[sP].[dR] (T)[sP].[LR](A)[sP].[dR](C) [sP].[dR](C)[sP].[LR](G)[sP]. [LR](A)}$$$$V2.0 | TCGGTAGG TGCTGCT | 481 | 496 | 44345603 | 44345618 |
| 64 | CAGCACC TACCGAC AG | RNA1{[LR]([5meC])[sP].[dR](A) [sP].[dR](G)[sP].[LR]([5meC]) [sP].[dR](A)[sP].[LR]([5meC]) [sP].[dR](C)[sP].[dR](T)[sP]. [LR](A)[sP].[dR](C)[sP].[dR] (C)[sP].[LR](G)[sP].[dR](A) [sP].[dR](C)[sP].[LR](A)[sP]. [LR](G)}$$$$V2.0 | CTGTCGGT AGGTGCTG | 478 | 493 | 44345600 | 44345615 |
| 65 | CACCTAC CGACAGG GG | RNA1{[LR]([5meC])[sP].[dR](A) [sP].[LR]([5meC])[sP].[dR](C) [sP].[dR](T)[sP].[LR](A)[sP]. [dR](C)[sP].[dR](C)[sP].[LR] (G)[sP].[dR](A)[sP].[dR](C) [sP].[LR](A)[sP].[dR](G)[sP]. [dR](G)[sP].[LR](G)[sP].[LR] (G)}$$$$V2.0 | CCCCTGTC GGTAGGTG | 475 | 490 | 44345597 | 44345612 |
| 66 | CTACCGA CAGGGGT GG | RNA1{[LR]([5meC])[sP].[dR](T) [sP].[LR](A)[sP].[dR](C)[sP]. [dR](C)[sP].[LR](G)[sP].[dR] (A)[sP].[dR](C)[sP].[LR](A) [sP].[dR](G)[sP].[dR](G)[sP]. [LR](G)[sP].[dR](G)[sP].[dR] (T)[sP].[LR](G)[sP].[LR](G)}$ $$$V2.0 | CCACCCCT GTCGGTAG | 472 | 487 | 44345594 | 44345609 |
| 67 | CCGACAG GGGTGGA GC | RNA1{[LR]([5meC][sP].[dR](C) [sP].[LR](G)[sP].[dR](A)[sP]. [dR](C)[sP].[LR](A)[sP].[dR] (G)[sP].[dR](G)[sP].[LR](G) [sP].[dR](G)[sP].[dR](T)[sP]. | GCTCCACC CCTGTCGG | 469 | 484 | 44345591 | 44345606 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [LR](G)[sP].[dR](G)[sP].[dR] (A)[sP].[LR](G)[sP].[LR] ([5meC])}$$$$V2.0 | | | | | |
| 68 | ACAGGGG TGGAGCT GG | RNA1{[LR](A)[sP].[dR](C)[sP]. [LR](A)[sP].[dR](G)[sP].[dR] (G)[sP].[LR](G)[sP].[dR](G) [sP].[dR](T)[sP].[LR](G)[sP]. [dR](G)[sP].[dR](A)[sP].[LR] (G)[sP].[dR](C)[sP].[dR](T) [sP].[LR](G)[sP].[LR](G)}$$$$ V2.0 | CCAGCTCC ACCCCTGT | 466 | 481 | 44345588 | 44345603 |
| 69 | GGGGTGG AGCTGGG TC | RNA1{[LR](G)[sP].[dR](G)[sP]. [dR](G)[sP].[LR](G)[sP].[dR] (T)[sP].[dR](G)[sP].[LR](G) [sP].[dR](A)[sP].[dR](G)[sP]. [dR](C)[sP].[dR](T)[sP].[LR] (G)[sP].[dR](G)[sP].[dR](G) [sP].[LR](T)[sP].[LR] ([5meC])}$$$$V2.0 | GACCCAGC TCCACCCC | 463 | 478 | 44345585 | 44345600 |
| 70 | GTGGAGC TGGGTCA AG | RNA1{[LR](G)[sP].[dR](T)[sP]. [dR](G)[sP].[LR](G)[sP].[dR] (A)[sP].[LR](G)[sP].[dR](C) [sP].[dR](T)[sP].[dR](G)[sP].[LR] (G)[sP].[dR](G)[sP].[dR](G)[sP].[LR] (T)[sP].[dR](C)[sP].[dR](A) [sP].[LR](A)[sP].[LR](G)}$$$$ V2.0 | CTTGACCC AGCTCCAC | 460 | 475 | 44345582 | 44345597 |
| 71 | GAGCTGG GTCAAGA AT | RNA1{[LR](G)[sP].[dR](A)[sP]. [LR](G)[sP].[dR](C)[sP].[dR] (T)[sP].[LR](G)[sP].[dR](G) [sP].[dR](G)[sP].[LR](T)[sP]. [dR](C)[sP].[LR](A)[sP].[dR] (A)[sP].[dR](G)[sP].[LR](A) [sP].[LR](A)[sP].[LR](T)}$$ $$V2.0 | ATTCTTGA CCCAGCTC | 457 | 472 | 44345579 | 44345594 |
| 72 | CTGGGTC AAGAATG GT | RNA1{[LR]([5meC])[sP].[dR](T) [sP].[LR](G)[sP].[dR](G)[sP]. [dR](G)[sP].[LR](T)[sP].[dR] (C)[sP].[LR](A)[sP].[dR](A) [sP].[dR](G)[sP].[LR](A)[sP]. [LR](A)[sP].[dR](T)[sP].[dR] (G)[sP].[LR](G)[sP].[LR](T)}$ $$$V2.0 | ACCATTCT TGACCCAG | 454 | 469 | 44345576 | 44345591 |
| 73 | GGTCAAG AATGGTG TG | RNA1{[LR](G)[sP].[dR](G)[sP]. [dR](T)[sP].[LR]([5meC])[sP]. [dR](A)[sP].[dR](A)[sP].[LR] (G)[sP].[dR](A)[sP].[LR](A) [sP].[dR](T)[sP].[dR](G)[sP]. [LR](G)[sP].[dR](T)[sP].[dR] (G)[sP].[LR](T)[sP].[LR](G)}$ $$$V2.0 | CACACCAT TCTTGACC | 451 | 466 | 44345573 | 44345588 |
| 74 | CAAGAAT GGTGTGG TC | RNA1{[LR]([5meC])[sP].[dR](A) [sP].[dR](A)[sP].[LR](G)[sP]. [dR](A)[sP].[LR](A)[sP].[dR] (T)[sP].[LR](G)[sP].[dR](G) [sP].[dR](T)[sP].[LR](G)[sP]. [dR](T)[sP].[LR](G)[sP].[dR] (G)[sP].[LR](T)[sP].[LR] ([5meC])}$$$$V2.0 | GACCACAC CATTCTTG | 448 | 463 | 44345570 | 44345585 |
| 75 | GAATGGT GTGGTCC CT | RNA1{[LR](G)[sP].[dR](A)[sP]. [LR](A)[sP].[dR](T)[sP].[LR] (G)[sP].[dR](G)[sP].[dR](T) [sP].[LR](G)[sP].[dR](T)[sP]. [LR](G)[sP].[dR](G)[sP].[LR] | AGGGACCA CACCATTC | 445 | 460 | 44345567 | 44345582 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | (T)[sP].[dR](C)[sP].[dR](C) [sP].[LR]([5meC])[sP].[LR] (T)}$$$$V2.0 | | | | | |
| 76 | TGGTGTG GTCCCTG CT | RNA1{[LR](T)[sP].[dR](G)[sP]. [dR](G)[sP].[LR](T)[sP].[dR] (G)[sP].[dR](T)[sP].[dR](G) [sP].[dR](G)[sP].[LR](T)[sP]. [dR](C)[sP].[dR](C)[sP].[LR] ([5meC])[sP].[dR](T)[sP].[dR] (G)[sP].[LR]([5meC])[sP].[LR] (T)}$$$$V2.0 | AGCAGGGA CACACCA | 442 | 457 | 44345564 | 44345579 |
| 77 | TGTGGTC CCTGCTT TG | RNA1{[LR](T)[sP].[dR](G)[sP]. [dR](T)[sP].[LR](G)[sP].[dR] (G)[sP].[LR](T)[sP].[dR](C) [sP].[LR]([5meC])[sP].[dR](C) [sP].[dR](T)[sP].[dR](G)[sP]. [dR](C)[sP].[LR](T)[sP].[dR] (T)[sP].[LR](T)[sP].[LR](G)}$ $$$V2.0 | CAAAGCAG GACCACA | 439 | 454 | 44345561 | 44345576 |
| 78 | GGTCCCT GCTTTGG GG | RNA1{[LR](G)[sP].[dR](G)[sP]. [LR](T)[sP].[dR](C)[sP].[LR] ([5meC])[sP].[dR](C)[sP].[dR] (T)[sP].[LR](G)[sP].[dR](C) [sP].[dR](T)[sP].[LR](T)[sP]. [dR](T)[sP].[LR](G)[sP].[dR] (G)[sP].[LR](G)[sP].[LR](G)}$ $$$V2.0 | CCCCAAAG CAGGGACC | 436 | 451 | 44345558 | 44345573 |
| 79 | CCCTGCT TTGGGGG AA | RNA1{[LR]([5meC][sP].[dR[(C) [sP].[dR](C)[sP].[LR](T) [sP].[dR](G)[sP].[dR](C) [sP].[LR](T)[sP].[dR](T) [sP].[LR](T)[sP].[dR](G) [sP].[dR](G)[sP].[LR](G) [sP].[dR](G)[sP].[dR](G) [sP].[LR](A)[sP].[LR](A)}$$$$ V2.0 | TTCCCCCA AAGCAGGG | 433 | 448 | 44345555 | 44345570 |
| 80 | TGCTTTG GGGGAAT GC | RNA1{[LR](T)[sP].[dR](G)[sP]. [dR](C)[sP].[LR](T)[sP].[dR] (T)[sP].[dR](T)[sP].[LR](G) [sP].[dR](G)[sP].[dR](G)[sP]. [LR](G)[sP].[dR](G)[sP].[dR] (A)[sP].[LR](A)[sP].[dR](T) [sP].[LR](G)[sP].[LR] ([5meC])}$$$$V2.0 | GCATTCCC CCAAAGCA | 430 | 445 | 44345552 | 44345567 |
| 81 | TTTGGGG GAATGCT GG | RNA1{[LR](T)[sP].[dR](T)[sP]. [dR](T)[sP].[LR](G)[sP].[dR] (G)[sP].[dR](G)[sP].[LR](G) [sP].[dR](G)[sP].[dR](A)[sP]. [LR](A)[sP].[dR](T)[sP].[LR] (G)[sP].[dR](C)[sP].[dR](T) [sP].[LR](G)[sP].[LR](G)}$$$$ V2.0 | CCAGCATT CCCCCAAA | 427 | 442 | 44345549 | 44345564 |
| 82 | GGGGGAA TGCTGGG GA | RNA1{[LR](G)[sP].[dR](G)[sP]. [dR](G)[sP].[LR](G)[sP].[dR] (G)[sP].[dR](A)[sP].[LR](A) [sP].[dR](T)[sP].[LR](G)[sP]. [dR](C)[sP].[dR](T)[sP].[LR] (G)[sP].[dR](G)[sP].[dR](G) [sP].[LR](G)[sP].[LR](A)}$$$$ V2.0 | TCCCCAGC ATTCCCCC | 424 | 439 | 44345546 | 44345561 |
| 83 | GGAATGC TGGGGAG GT | RNA1{[LR](G)[sP].[dR](G)[sP]. [dR](A)[sP].[LR](A)[sP].[dR] (T)[sP].[LR](G)[sP].[dR](C) [sP].[dR](T)[sP].[LR](G)[sP]. | ACCTCCCC AGCATTCC | 421 | 436 | 44345543 | 44345558 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [dR](G)[sP].[dR](G)[sP].[LR](G)[sP].[dR](A)[sP].[dR](G)[sP].[LR](G)[sP].[LR](T)}$$$$V2.0 | | | | | |
| 84 | ATGCTGGGGAGGTAGA | RNA1{[LR](A)[sP].[dR](T)[sP].[LR](G)[sP].[dR](C)[sP].[dR](T)[sP].[LR](G)[sP].[dR](G)[sP].[dR](G)[sP].[LR[(G)[sP].[dR](A)[sP].[dR](G)[sP].[LR](G)[sP].[dR](T)[sP].[dR](A)[sP].[LR](G)[sP].[LR](A)}$$$$V2.0 | TCTACCTCCCCAGCAT | 481 | 433 | 44345540 | 44345555 |
| 85 | CTGGGGAGGTAGAAAG | RNA1{[LR]([5meC])[sP].[dR](T)[sP].[LR](G)[sP].[dR](G)[sP].[dR](G)[sP].[dR](G)[sP].[dR](A)[sP].[dR](G)[sP].[LR](G)[sP].[dR](T)[sP].[dR](A)[sP].[LR](G)[sP].[dR](A)[sP].[dR](A)[sP].[LR](A)[sP].[LR](G)}$$$$V2.0 | CTTTCTACCTCCCCAG | 415 | 430 | 44345537 | 44345552 |
| 86 | GGGAGGTAGAAAGCCC | RNA1{[LR](G)[sP].[dR](G)[sP].[LR](G)[sP].[dR](A)[sP].[dR](G)[sP].[LR](G)[sP].[dR](T)[sP].[dR](A)[sP].[LR](G)[sP].[dR](A)[sP].[dR](A)[sP].[LR](A)[sP].[dR](G)[sP].[dR](C)[sP].[LR]([5meC])[sP].[LR]([5meC])}$$$$V2.0 | GGGCTTTCTACCTCCC | 412 | 427 | 44345534 | 44345549 |
| 87 | AGGTAGAAAGCCCCTT | RNA1{[LR](A)[sP].[dR](G)[sP].[dR](G)[sP].[LR](T)[sP].[dR](A)[sP].[dR](G)[sP].[LR](A)[sP].[dR](A)[sP].[LR](A)[sP].[dR](G)[sP].[dR](C)[sP].[LR]([5meC])[sP].[dR](C)[sP].[dR](C)[sP].[LR](T)[sP].[LR](T)}$$$$V2.0 | AAGGGGCTTTCTACCT | 409 | 424 | 44345531 | 44345546 |
| 88 | TAGAAAGCCCCTTCTA | RNA1{[LR](T)[sP].[dR](A)[sP].[dR](G)[sP].[LR](A)[sP].[dR](A)[sP].[dR](A)[sP].[dR](A)[sP].[LR](G)[sP].[dR](C)[sP].[dR](C)[sP].[LR]([5meC])[sP].[dR](C)[sP].[dR](T)[sP].[LR](T)[sP].[dR](C)[sP].[LR](T)[sP].[LR](A)}$$$$V2.0 | TAGAAGGGGCTTTCTA | 406 | 421 | 44345528 | 44345543 |
| 89 | AAAGCCCCTTCTAACG | RNA1{[LR](A)[sP].[dR](A)[sP].[dR](A)[sP].[LR](G)[sP].[dR](C)[sP].[dR](C)[sP].[LR]([5meC])[sP].[dR](C)[sP].[dR](T)[sP].[LR](T)[sP].[dR](C)[sP].[dR](T)[sP].[LR](A)[sP].[dR](A)[sP].[LR]([5meC])[sP].[LR](G)}$$$$V2.0 | CGTTAGAAGGGGCTTT | 403 | 418 | 44345525 | 44345540 |
| 90 | GCCCCTTCTAACGGGG | RNA1{[LR](G)[sP].[dR](C)[sP].[dR](C)[sP].[LR]([5meC])[sP].[dR](C)[sP].[dR](T)[sP].[LR](T)[sP].[dR](C)[sP].[dR](T)[sP].[LR](A)[sP].[dR](A)[sP].[LR]([5meC])[sP].[dR](G)[sP].[dR](G)[sP].[LR](G)[sP].[LR](G)}$$$$V2.0 | CCCCGTTAGAAGGGGC | 400 | 415 | 44345522 | 44345537 |
| 91 | CCTTCTAACGGGGCGT | RNA1{[LR]([5meC])[sP].[dR](C)[sP].[dR](T)[sP].[LR](T)[sP].[dR](C)[sP].[dR](T)[sP].[LR](A)[sP].[dR](A)[sP].[dR](C) | ACGCCCCGTTAGAAGG | 397 | 412 | 44345519 | 44345534 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [sP].[LR](G)[sP].[dR](G)[sP].[dR](G)[sP].[LR](G)[sP].[dR](C)[sP].[LR](G)[sP].[LR](T)}$$$$V2.0 | | | | | |
| 92 | TCTAACG GGGCGTC AC | RNA1{[LR](T)[sP].[dR](C)[sP].[dR](T)[sP].[LR](A)[sP].[dR](A)[sP].[dR](C)[sP].[LR](G)[sP].[dR](G)[sP].[dR](G)[sP].[LR](G)[sP].[dR](C)[sP].[LR](G)[sP].[dR](T)[sP].[dR](C)[sP].[LR](A)[sP].[LR]([5meC])}$$$$V2.0 | GTGACGCC CCGTTAGA | 394 | 409 | 44345516 | 44345531 |
| 93 | AACGGGG CGTCACT GC | RNA1{[LR](A)[sP].[dR](A)[sP].[dR](C)[sP].[LR](G)[sP].[dR](G)[sP].[dR](G)[sP].[LR](G)[sP].[dR](C)[sP].[LR](G)[sP].[dR](T)[sP].[dR](C)[sP].[LR](A)[sP].[dR](C)[sP].[dR](T)[sP].[LR](G)[sP].[LR]([5meC])}$$$$V2.0 | GCAGTGAC GCCCCGTT | 391 | 406 | 44345513 | 44345528 |
| 94 | GGGGCGT CACTGCA AT | RNA1{[LR](G)[sP].[dR](G)[sP].[dR](G)[sP].[LR](G)[sP].[dR](C)[sP].[LR](G)[sP].[dR](T)[sP].[dR](C)[sP].[LR](A)[sP].[dR](C)[sP].[dR](T)[sP].[LR](G)[sP].[dR](C)[sP].[dR](A)[sP].[LR](A)[sP].[LR](T)}$$$$V2.0 | ATTGCAGT GACGCCCC | 388 | 403 | 44345510 | 44345525 |
| 95 | GCGTCAC TGCAATT AC | RNA1{[LR](G)[sP].[dR](C)[sP].[LR](G)[sP].[dR](T)[sP].[dR](C)[sP].[LR](A)[sP].[dR](C)[sP].[dR](T)[sP].[LR](G)[sP].[dR](C)[sP].[dR](A)[sP].[LR](A)[sP].[dR](T)[sP].[dR](T)[sP].[LR](A)[sP].[LR]([5meC])}$$$$V2.0 | GTAATTGC AGTGACGC | 385 | 400 | 44345507 | 44345522 |
| 96 | TCACTGC AATTACT GC | RNA1{[LR](T)[sP].[dR](C)[sP].[LR](A)[sP].[dR](C)[sP].[dR](T)[sP].[LR](G)[sP].[dR](C)[sP].[dR](A)[sP].[LR](A)[sP].[dR](T)[sP].[dR](T)[sP].[LR](A)[sP].[dR](C)[sP].[dR](T)[sP].[LR](G)[sP].[LR]([5meC])}$$$$V2.0 | GCAGTAAT TGCAGTGA | 382 | 397 | 44345504 | 44345519 |
| 97 | CTGCAAT TACTGCT TC | RNA1{[LR]([5meC])[sP].[dR](T)[sP].[LR](G)[sP].[dR](C)[sP].[dR](A)[sP].[LR](A)[sP].[dR](T)[sP].[sP].[LR](A)[sP].[dR](C)[sP].[dR](T)[sP].[LR](G)[sP].[dR](C)[sP].[dR](T)[sP].[LR](T)[sP].[LR]([5meC])}$$$$V2.0 | GAAGCAGT AATTGCAG | 379 | 394 | 44345501 | 44345516 |
| 98 | CAATTAC TGCTTCC TC | RNA1{[LR]([5meC])[sP].[dR](A)[sP].[LR](A)[sP].[dR](T)[sP].[dR](T)[sP].[LR](A)[sP].[dR](C)[sP].[dR](T)[sP].[LR](G)[sP].[dR](C)[sP].[dR](T)[sP].[LR](T)[sP].[dR](C)[sP].[dR](C)[sP].[LR](T)[sP].[LR]([5meC])}$$$$V2.0 | GAGGAAGC AGTAATTG | 376 | 391 | 44345498 | 44345513 |
| 99 | TTACTGC TTCCTCT TT | RNA1{[LR](T)[sP].[dR](T)[sP].[LR](A)[sP].[dR](C)[sP].[dR](T)[sP].[LR](G)[sP].[dR](C)[sP].[dR](T)[sP].[LR](T)[sP]. | AAAGAGGA AGCAGTAA | 373 | 388 | 44345495 | 44345510 |

TABLE 2-continued

Compound Table

| SEQ ID NO | Oligo Sequence | Helm sequence | Target sequence | Start position in SEQ ID 276 | End position in SEQ ID 276 | chromo- some start (hg38 assembly) | Chromo- some end (hg38 assembly) |
|---|---|---|---|---|---|---|---|
| | | [dR](C)[sP].[dR](C)[sP].[LR] (T)[sP].[dR](C)[sP].[dR](T) [sP].[LR](T)[sP].[LR](T)}$$$$ V2.0 | | | | | |
| 100 | CTGCTTC CTCTTTC CC | RNA1{[LR]([5meC])[sP].[dR](T) [sP].[LR](G)[sP].[dR](C)[sP]. [dR](T)[sP].[LR](T)[sP].[dR] (C)[sP].[dR](C)[sP].[LR](T) [sP].[dR](C)[sP].[dR](T)[sP]. [LR](T)[sP].[dR](T)[sP].[dR] (C)[sP].[LR]([5meC])[sP].[LR] ([5meC])}$$$$V2.0 | GGGAAAGA GGAAGCAG | 370 | 385 | 44345492 | 44345507 |
| 101 | CTTCCTC TTTCCCA TA | RNA1{[LR]([5meC])[sP].[dR](T) [sP].[LR](T)[sP].[dR](C)[sP]. [dR](C)[sP].[LR](T)[sP].[dR] (C)[sP].[dR](T)[sP].[LR](T) [sP].[dR](T)[sP].[dR](C)[sP]. [LR]([5meC])[sP].[dR](C)[sP]. [dR](A)[sP].[LR](T)[sP].[LR] (A)}$$$$V2.0 | TATGGGAA AGAGGAAG | 367 | 382 | 44345489 | 44345504 |
| 102 | CCTCTTT CCCATAA AA | RNA1{[LR]([5meC])[sP].[dR](C) [sP].[LR](T)[sP].[dR](C)[sP]. [dR](T)[sP].[LR](T)[sP].[dR] (T)[sP].[dR](C)[sP].[LR] ([5meC])[sP].[dR](C)[sP].[LR] (A)[sP].[dR](T)[sP].[LR](A) [sP].[dR](A)[sP].[dR](A)[sP]. [LR](A)}$$$$V2.0 | TTTTATGG GAAAGAGG | 364 | 379 | 44345486 | 44345501 |
| 103 | CTTTCCC ATAAAAC TC | RNA1{[LR]([5meC])[sP].[dR](T) [sP].[dR](T)[sP].[LR](T)[sP]. [dR](C)[sP].[dR](C)[sP].[LR] ([5meC])[sP].[dR](A)[sP].[dR] (T)[sP].[LR](A)[sP].[dR](A) [sP].[LR](A)[sP].[dR](A)[sP]. [dR](C)[sP].[LR](T)[sP].[LR] ([5meC])}$$$$V2.0 | GAGTTTTA TGGGAAAG | 361 | 376 | 44345483 | 44345498 |
| 104 | TCCCATA AAACTCC CC | RNA1{[LR](T)[sP].[dR](C)[sP]. [dR](C)[sP].[LR]([5meC])[sP]. [dR](A)[sP].[dR](T)[sP].[LR] (A)[sP].[dR](A)[sP].[LR](A) [sP].[dR](A)[sP].[dR](C)[sP]. [LR](T)[sP].[dR](C)[sP].[dR] (C)[sP].[LR]([5meC])[sP].[LR] ([5meC])}$$$$V2.0 | GGGGAGTT TTATGGGA | 358 | 373 | 44345480 | 44345495 |
| 105 | CATAAAA CTCCCCC TA | RNA1{[LR]([5meC])[sP].[dR](A) [sP].[dR](T)[sP].[LR](A)[sP]. [dR](A)[sP].[LR](A)[sP].[dR] (A)[sP].[dR](C)[sP].[LR](T) [sP].[dR](C)[sP].[dR](C)[sP]. [LR]([5meC])[sP].[dR](C)[sP]. [dR](C)[sP].[LR](T)[sP].[LR] (A)}$$$$V2.0 | TAGGGGGA GTTTTATG | 355 | 370 | 44345477 | 44345492 |
| 106 | AAAACTC CCCCTAG TG | RNA1{[LR](A)[sP].[dR](A)[sP]. [dR](A)[sP].[LR](A)[sP].[dR] (C)[sP].[dR](T)[sP].[LR] ([5meC])[sP].[dR](C)[sP].[LR] ([5meC])[sP].[dR](C)[sP].[dR] (C)[sP].[dR](T)[sP].[LR](A) [sP].[dR](G)[sP].[LR](T)[sP]. [LR](G)}$$$$V2.0 | CACTAGGG GGAGTTTT | 352 | 367 | 44345474 | 44345489 |
| 107 | ACTCCCC CTAGTGT AT | RNA1{[LR](A)[sP].[dR](C)[sP]. [dR](T)[sP].[LR]([5meC])[sP]. [dR](C)[sP].[dR](C)[sP].[LR] ([5meC])[sP].[dR](C)[sP].[dR] | ATACACTA GGGGGAGT | 349 | 364 | 44345471 | 44345486 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | (T)[sP].[dR](A)[sP].[dR](G)[sP].[dR](T)[sP].[LR](G)[sP].[dR](T)[sP].[LR](A)[sP].[LR](T)}$$$$V2.0 | | | | | |
| 108 | CCCCCTAGTGTATCAG | RNA1{[LR]([5meC])[sP].[dR](C)[sP].[dR](C)[sP].[LR]([5meC])[sP].[dR](C)[sP].[dR](T)[sP].[LR](A)[sP].[dR](G)[sP].[dR](T)[sP].[LR](G)[sP].[dR](T)[sP].[LR](A)[sP].[dR](T)[sP].[dR](C)[sP].[LR](A)[sP].[LR](G)}$$$$V2.0 | CTGATACACTAGGGGG | 346 | 361 | 44345468 | 44345483 |
| 109 | CCTAGTGTATCAGAAC | RNA1{[LR]([5meC])[sP].[dR](C)[sP].[dR](T)[sP].[LR](A)[sP].[dR](G)[sP].[dR](T)[sP].[LR](G)[sP].[dR](T)[sP].[LR](A)[sP].[dR](T)[sP].[dR](C)[sP].[LR](A)[sP].[dR](G)[sP].[dR](A)[sP].[LR]([5meC])}$$$$V2.0 | GTTCTGATACACTAGG | 343 | 358 | 44345465 | 44345480 |
| 110 | AGTGTATCAGAACCCC | RNA1{[LR](A)[sP].[dR](G)[sP].[dR](T)[sP].[LR](G)[sP].[dR](T)[sP].[LR](A)[sP].[dR](T)[sP].[dR](C)[sP].[LR](A)[sP].[dR](G)[sP].[dR](A)[sP].[LR](A)[sP].[dR](C)[sP].[dR](C)[sP].[LR]([5meC])[sP].[LR]([5meC])}$$$$V2.0 | GGGGTTCTGATACACT | 340 | 355 | 44345462 | 44345477 |
| 111 | GTATCAGAACCCCCAA | RNA1{[LR](G)[sP].[dR](T)[sP].[LR](A)[sP].[dR](T)[sP].[dR](C)[sP].[LR](A)[sP].[dR](G)[sP].[dR](A)[sP].[LR](A)[sP].[dR](C)[sP].[dR](C)[sP].[LR]([5meC])[sP].[dR](C)[sP].[dR](C)[sP].[LR](A)[sP].[LR](A)}$$$$V2.0 | TTGGGGGTTCTGATAC | 337 | 352 | 44345459 | 44345474 |
| 112 | TCAGAACCCCCAAGGA | RNA1{[LR](T)[sP].[dR](C)[sP].[LR](A)[sP].[dR](G)[sP].[dR](A)[sP].[LR](A)[sP].[dR](C)[sP].[dR](C)[sP].[LR]([5meC])[sP].[dR](C)[sP].[dR](C)[sP].[LR](A)[sP].[dR](A)[sP].[dR](G)[sP].[LR](G)[sP].[LR](A)}$$$$V2.0 | TCCTTGGGGGTTCTGA | 334 | 349 | 44345456 | 44345471 |
| 113 | GAACCCCCAAGGAGTT | RNA1{[LR](G)[sP].[dR](A)[sP].[LR](A)[sP].[dR](C)[sP].[dR](C)[sP].[LR]([5meC])[sP].[dR](C)[sP].[dR](C)[sP].[LR](A)[sP].[dR](A)[sP].[dR](G)[sP].[LR](G)[sP].[dR](A)[sP].[dR](G)[sP].[LR](T)[sP].[LR](T)}$$$$V2.0 | AACTCCTTGGGGGTTC | 331 | 346 | 44345453 | 44345468 |
| 114 | CCCCCAAGGAGTTTCA | RNA1{[LR]([5meC])[sP].[dR](C)[sP].[LR]([5meC])[sP].[dR](C)[sP].[dR](C)[sP].[LR](A)[sP].[dR](A)[sP].[dR](G)[sP].[LR](G)[sP].[dR](A)[sP].[dR](G)[sP].[LR](T)[sP].[dR](T)[sP].[dR](T)[sP].[LR]([5meC])[sP].[LR](A)}$$$$V2.0 | TGAAACTCCTTGGGGG | 328 | 343 | 44345450 | 44345465 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 115 | CCAAGGA GTTTCAG TA | RNA1{[LR]([5meC])[sP].[dR](C) [sP].[LR](A)[sP].[dR](A)[sP]. [dR](G)[sP].[LR](G)[sP].[dR] (A)[sP].[dR](G)[sP].[LR](T) [sP].[dR](T)[sP].[dR](T) [sP].[LR]([5meC])[sP].[dR](A) [sP].[dR](G)[sP].[LR](T)[sP]. [LR](A)}$$$$V2.0 | TACTGAAA CTCCTTGG | 325 | 340 | 44345447 | 44345462 |
| 116 | AGGAGTT TCAGTAA GC | RNA1{[LR](A)[sP].[dR](G)[sP]. [dR](G)[sP].[LR](A)[sP].[dR] (G)[sP].[dR](T)[sP].[LR](T) [sP].[dR](T)[sP].[dm](C)[sP]. [LR](A)[sP].[dR](G)[sP].[dR] (T)[sP].[LR](A)[sP].[dR](A) [sP].[dR](G)[sP].[LR] ([5meC])}$$$$V2.0 | GCTTACTG AAACTCCT | 322 | 337 | 44345444 | 44345459 |
| 117 | AGTTTCA GTAAGCG GT | RNA1{[LR](A)[sP].[dR](G)[sP]. [dR](T)[sP].[LR](T)[sP].[dR] (T)[sP].[dR](C)[sP].[LR](A) [sP].[dR](G)[sP].[dR](T)[sP]. [LR](A)[sP].[dR](A)[sP].[LR] (G)[sP].[dR]([5meC])[sP].[dR] (G)[sP].[LR](G)[sP].[LR](T)}$ $$$V2.0 | ACCGCTTA CTGAAACT | 319 | 334 | 44345441 | 44345456 |
| 118 | TTCAGTA AGCGGTT CT | RNA1{[LR](T)[sP].[dR](T)[sP]. [dR](C)[sP].[LR](A)[sP].[dR] (G)[sP].[dR](T)[sP].[LR](A) [sP].[dR](A)[sP].[dR](G)[sP]. [LR]([5meC])[sP].[dR](G)[sP]. [dR](G)[sP].[LR](T)[sP].[dR] (T)[sP].[LR]([5meC])[sP].[LR] (T)}$$$$V2.0 | AGAACCGC TTACTGAA | 316 | 331 | 44345438 | 44345453 |
| 119 | AGTAAGC GGTTCTT CT | RNA1{[LR](A)[sP].[dR](G)[sP]. [dR](T)[sP].[LR](A)[sP].[dR] (A)[sP].[dR](G)[sP].[LR] ([5meC])[sP].[dR](G)[sP].[dR] (G)[sP].[LR](T)[sP].[dR](T) [sP].[dR](C)[sP].[LR](T)[sP]. [dR](T)[sP].[LR]([5meC])[sP]. [LR](T)}$$$$V2.0 | AGAAGAAC CGCTTACT | 313 | 328 | 44345435 | 44345450 |
| 120 | AAGCGGT TCTTCTG TT | RNA1{[LR](A)[sP].[dR](A)[sP]. [dR](G)[sP].[LR]([5meC])[sP]. [dR](G)[sP].[dR](G)[sP].[LR] (T)[sP].[dR](T)[sP].[dR](C) [sP].[LR](T)[sP].[dR](T)[sP]. [LR]([5meC])[sP].[dR](T)[sP]. [dR](G)[sP].[LR](T)[sP].[LR] (T)}$$$$V2.0 | AACAGAAG AACCGCTT | 310 | 325 | 44345432 | 44345447 |
| 121 | CGGTTCT TCTGTTG TC | RNA1{[LR]([5meC])[sP].[dR](G) [sP].[LR](G)[sP].[dR](T)[sP]. [LR](T)[sP].[dR](C)[sP].[dR] (T)[sP].[LR](T)[sP].[dR](C) [sP].[dR](T)[sP].[LR](G)[sP]. [dR](T)[sP].[LR](T)[sP].[dR] (G)[sP].[LR](T)[sP].[LR] ([5meC])}$$$$V2.0 | GACAACAG AAGAACCG | 307 | 322 | 44345429 | 44345444 |
| 122 | TTCTTCT GTTGTCT CC | RNA1{[LR](T)[sP].[LR](T)[sP]. [dR](C)[sP].[dR](T)[sP].[LR] (T)[sP].[dR](C)[sP].[dR](T) [sP].[LR](G)[sP].[dR](T)[sP]. [dR](T)[sP].[LR](G)[sP].[dR] (T)[sP].[LR]([5meC])[sP].[dR] (T)[sP].[LR]([5meC])[sP].[LR] ([5meC])}$$$$V2.0 | GGAGACAA CAGAAGAA | 304 | 319 | 44345426 | 44345441 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 123 | TTCTGTTGTCTCCGGC | RNA1{[LR](T)[sP].[LR](T)[sP].[dR](C)[sP].[dR](T)[sP].[LR](G)[sP].[dR](T)[sP].[dR](T)[sP].[LR](G)[sP].[dR](T)[sP].[dR](C)[sP].[LR](T)[sP].[dR](C)[sP].[LR]([5meC])[sP].[dR](G)[sP].[LR](G)[sP].[LR]([5meC])}$$$$V2.0 | GCCGGAGACAACAGAA | 301 | 316 | 44345423 | 44345438 |
| 124 | TGTTGTCTCCGGCTGA | RNA1{[LR](T)[sP].[dR](G)[sP].[LR](T)[sP].[dR](T)[sP].[dR](G)[sP].[LR](T)[sP].[dR](C)[sP].[dR](T)[sP].[LR]([5meC][sP].[dR]([5meC][sP].[dR](G)[sP].[LR](G)[sP].[dR](C)[sP].[dR](T)[sP].[LR](G)[sP].[LR](A)}$$$$V2.0 | TCAGCCGGAGACAACA | 298 | 313 | 44345420 | 44345435 |
| 125 | TGTCTCCGGCTGAGAC | RNA1{[LR](T)[sP].[dR](G)[sP].[LR](T)[sP].[dR](C)[sP].[dR](T)[sP].[LR]([5meC][sP].[dR]([5meC])[sP].[dR](G)[sP].[LR](G)[sP].[dR](C)[sP].[dR](T)[sP].[LR](G)[sP].[dR](A)[sP].[dR](G)[sP].[LR](A)[sP].[LR]([5meC])}$$$$V2.0 | GTCTCAGCCGGAGACA | 295 | 310 | 44345417 | 44345432 |
| 126 | CTCCGGCTGAGACTCC | RNA1{[LR]([5meC])[sP].[dR](T)[sP].[dR](C)[sP].[LR]([5meC])[sP].[dR](G)[sP].[LR](G)[sP].[dR](C)[sP].[dR](T)[sP].[LR](G)[sP].[dR](A)[sP].[dR](G)[sP].[LR](A)[sP].[dR](C)[sP].[dR](T)[sP].[LR]([5meC])[sP].[LR]([5meC])}$$$$V2.0 | GGAGTCTCAGCCGGAG | 292 | 307 | 44345414 | 44345429 |
| 127 | CGGCTGAGACTCCAGG | RNA1{[LR]([5meC])[sP].[dR](G)[sP].[LR](G)[sP].[dR](C)[sP].[dR](T)[sP].[LR](G)[sP].[dR](A)[sP].[dR](G)[sP].[LR](A)[sP].[dR](C)[sP].[dR](T)[sP].[LR]([5meC])[sP].[dR](C)[sP].[dR](A)[sP].[LR](G)[sP].[LR](G)}$$$$V2.0 | CCTGGAGTCTCAGCCG | 289 | 304 | 44345411 | 44345426 |
| 128 | CTGAGACTCCAGGGGA | RNA1{[LR]([5meC])[sP].[dR](T)[sP].[LR](G)[sP].[dR](A)[sP].[dR](G)[sP].[LR](A)[sP].[dR](C)[sP].[dR](T)[sP].[LR]([5meC])[sP].[dR](C)[sP].[dR](A)[sP].[LR](G)[sP].[dR](G)[sP].[dR](G)[sP].[LR](G)[sP].[LR](A)}$$$$V2.0 | TCCCCTGGAGTCTCAG | 286 | 301 | 44345408 | 44345423 |
| 129 | AGACTCCAGGGGAACC | RNA1{[LR](A)[sP].[dR](G)[sP].[dR](A)[sP].[LR]([5meC])[sP].[dR](T)[sP].[dR](C)[sP].[LR]([5meC])[sP].[dR](A)[sP].[dR](G)[sP].[LR](G)[sP].[dR](G)[sP].[dR](G)[sP].[LR](A)[sP].[dR](A)[sP].[LR]([5meC])[sP].[LR]([5meC])}$$$$V2.0 | GGTTCCCCTGGAGTCT | 283 | 298 | 44345405 | 44345420 |
| 130 | CTCCAGGGGAACCTCA | RNA1{[LR]([5meC])[sP].[dR](T)[sP].[dR](C)[sP].[LR]([5meC])[sP].[dR](A)[sP].[dR](G)[sP].[LR](G)[sP].[dR](G)[sP].[dR](G)[sP].[LR](A)[sP].[dR](A)[sP].[LR]([5meC])[sP].[dR](C)[sP].[dR](T)[sP].[LR]([5meC])[sP].[LR](A)}$$$$V2.0 | TGAGGTTCCCCTGGAG | 280 | 295 | 44345402 | 44345417 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 131 | CAGGGGA ACCTCAA GC | RNA1{[LR]([5meC])[sP].[dR](A) [sP].[dR](G)[sP].[LR](G)[sP]. [dR](G)[sP].[dR[(G)[sP].[LR] (A)[sP].[dR](A)[sP].[dR](C) [sP].[LR]([5meC])[sP].[dR](T) [sP].[dR](C)[sP].[LR](A)[sP]. [dR](A)[sP].[LR](G)[sP].[LR] ([5meC])}$$$$V2.0 | GCTTGAGG TTCCCCTG | 277 | 292 | 44345399 | 44345414 |
| 132 | GGGAACC TCAAGCT CA | RNA1{[LR](G)[sP].[dR](G)[sP]. [dR](G)[sP].[dR](A)[sP].[dR] (A)[sP].[dR](C)[sP].[LR] ([5meC])[sP].[dR](T)[sP].[dR] (C)[sP].[LR](A)[sP].[dR](A) [sP].[LR](G)[sP].[dR](C)[sP]. [dR](T)[sP].[LR]([5meC])[sP]. [LR](A)}$$$$V2.0 | TGAGCTTG AGGTTCCC | 274 | 289 | 44345396 | 44345411 |
| 133 | AACCTCA AGCTCAC AT | RNA1{[LR](A)[sP].[dR](A)[sP]. [dR](C)[sP].[LR]([5meC])[sP]. [dR[(T)[sP].[dR[(C)[sP].[LR] (A)[sP].[dR](A)[sP].[dR](G) [sP].[LR]([5meC])[sP].[dR](T) [sP].[dR(C)[sP].[LR](A)[sP]. [dR](C)[sP].[LR](A)[sP].[LR] (T)}$$$$V2.0 | ATGTGAGC TTGAGGTT | 271 | 286 | 44345393 | 44345408 |
| 134 | CTCAAGC TCACATG GC | RNA1{[LR]([5meC])[sP].[dR](T) [sP].[dR](C)[sP].[LR](A)[sP]. [dR](A)[sP].[dR](G)[sP].[LR] ([5meC])[sP].[dR](T)[sP].[dR [(C)[sP].[LR](A)[sP].[dR](C) [sP].[LR](A)[sP].[dR](T)[sP]. [dR](G)[sP].[LR](G)[sP].[LR] ([5meC])}$$$$V2.0 | GCCATGTG AGCTTGAG | 268 | 283 | 44345390 | 44345405 |
| 135 | AAGCTCA CATGGCC CT | RNA1{[LR](A)[sP].[dR](A)[sP]. [dR](G)[sP].[LR]([5meC])[sP]. [dR](T)[sP].[dR[(C)[sP].[LR] (A)[sP].[dR](C)[sP].[LR](A) [sP].[dR](T)[sP].[LR](G)[sP]. [LR](G)[sP].[dR](C)[sP].[dR] (C)[sP].[LR]([5meC])[sP].[LR] (T)}$$$$V2.0 | AGGGCCAT GTGAGCTT | 265 | 280 | 44345387 | 44345402 |
| 136 | CTCACAT GGCCCTG GC | RNA1{[LR]([5meC])[sP].[dR](T) [sP].[dR](C)[sP].[LR](A)[sP]. [dR](C)[sP].[LR](A)[sP].[dR] (T)[sP].[dR](G)[sP].[LR](G) [sP].[dR](C)[sP].[dR](C)[sP]. [LR]([5meC])[sP].[dR](T)[sP]. [dR](G)[sP].[LR](G)[sP].[LR] ([5meC])}$$$$V2.0 | GCCAGGGC CATGTGAG | 262 | 277 | 44345384 | 44345399 |
| 137 | ACATGGC CCTGGCG GG | RNA1{[LR](A)[sP].[dR](C)[sP]. [LR](A)[sP].[dR](T)[sP].[dR] (G)[sP].[LR](G)[sP].[dR](C) [sP].[dR](C)[sP].[LR]([5meC]) [sP].[dR](T)[sP].[dR](G)[sP]. [LR](G)[sP].[dR]([5meC])[sP]. [dR[(G)[sP].[LR](G)[sP].[LR] (G)}$$$$V2.0 | CCCGCCAG GGCCATGT | 259 | 274 | 44345381 | 44345396 |
| 138 | TGGCCCT GGCGGGC CC | RNA1{[LR](T)[sP].[dR](G)[sP]. [dR](G)[sP].[LR]([5meC])[sP]. [dR](C)[sP].[dR](C)[sP].[LR] (T)[sP].[dR](G)[sp].[dR](G) [sP].[LR]([5meC])[sP].[dR](G) [sP].[dR](G)[sP].[LR](G)[sP]. [dR](C)[sP].[LR]([5meC])[sP]. [LR]([5meC]}$$$$V2.0 | GGGCCCGC CAGGGCCA | 256 | 271 | 44345378 | 44345393 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 139 | CCCTGGCGGGCCCCTG | RNA1{[LR]([5meC])[sP].[dR](C)[sP].[dR](C)[sP].[LR](T)[sP].[dR](G)[sP].[dR](G)[sP].[LR]([5meC])[sP].[dm(G)[sP].[dR](G)[sP].[dR](C)[sP].[LR]([5meC])[sP].[dR](C)[sP].[dR](C)[sP].[LR](T)[sP].[LR](G)}$$$$V2.0 | CAGGGGCCCGCCAGGG | 253 | 268 | 44345375 | 44345390 |
| 140 | TGGCGGGCCCCTGGGC | RNA1{[LR](T)[sP].[dR](G)[sP].[dR](G)[sP].[LR]([5meC])[sP].[dR](G)[sP].[dR](G)[sP].[LR](G)[sP].[dR](C)[sP].[dR](C)[sP].[LR]([5meC])[sP].[dR](C)[sP].[dR](T)[sP].[LR](G)[sP].[dR](G)[sP].[LR]([5meC])}$$$$V2.0 | GCCCAGGGGCCCGCCA | 250 | 265 | 44345372 | 44345387 |
| 141 | CGGGCCCCTGGGCAGG | RNA1{[LR]([5meC])[sP].[dR](G)[sP].[dR](G)[sP].[LR](G)[sP].[dR](C)[sP].[dR](C)[sP].[LR]([5meC])[sP].[dm(C)[sP].[dR](T)[sP].[LR](G)[sP].[dR](G)[sP].[dR](G)[sP].[LR]([5meC])[sP].[dR](A)[sP].[LR](G)[sP].[LR](G)}$$$$V2.0 | CCTGCCCAGGGGCCCG | 247 | 262 | 44345369 | 44345384 |
| 142 | GCCCCTGGGCAGGAGC | RNA1{[LR](G)[sP].[dR](C)[sP].[dR](C)[sP].[LR]([5meC])[sP].[dR](C)[sP].[dR](T)[sP].[LR](G)[sP].[dR](G)[sp].[dR](G)[sP].[LR]([5meC])[sP].[dR](A)[sP].[dR](G)[sP].[LR](G)[sP].[dR](A)[sP].[LR](G)[sP].[LR]([5meC])}$$$$V2.0 | GCTCCTGCCAGGGGC | 244 | 259 | 44345366 | 44345381 |
| 143 | CCTGGGCAGGAGCAGG | RNA1{[LR]([5meC][sP].[dR](C)[sP].[dR](T)[sP].[LR](G)[sP].[dR](G)[sP].[dR](G)[sP].[LR]([5meC])[sP].[dR](A)[sP].[dR](G)[sP].[LR](G)[sP].[dR](A)[sP].[dR](G)[sP].[LR]([5meC])[sP].[dR](A)[sP].[LR](G)[sP].[LR](G)}$$$$V2.0 | CCTGCTCCTGCCCAGG | 241 | 256 | 44345363 | 44345378 |
| 144 | GGGCAGGAGCAGGCGA | RNA1{[LR](G)[sP].[dR](G)[sP].[dR](G)[sP].[LR]([5meC])[sP].[dR](A)[sP].[dR](G)[sP].[LR](G)[sP].[dR](A)[sP].[dR](G)[sP].[LR]([5meC])[sP].[dR](A)[sP].[dR](G)[sP].[LR](G)[sP].[dR](C)[sP].[LR](G)[sP].[LR](A)}$$$$V2.0 | TCGCCTGCTCCTGCCC | 238 | 253 | 44345360 | 44345375 |
| 145 | CAGGAGCAGGCGAGAG | RNA1{[LR]([5meC])[sP].[dR](A)[sP].[dR](G)[sP].[LR](G)[sP].[dR](A)[sP].[dR](G)[sP].[LR]([5meC])[sP].[dR](A)[sP].[dR](G)[sP].[LR](G)[sP].[dR](C)[sP].[LR](G)[sP].[dR](A)[sP].[dR](G)[sP].[LR](A)[sP].[LR](G)}$$$$V2.0 | CTCTCGCCTGCTCCTG | 235 | 250 | 44345357 | 44345372 |
| 146 | GAGCAGGCGAGAGGTC | RNA1{[LR](G)[sP].[dR](A)[sP].[dR](G)[sP].[LR]([5meC])[sP].[dR](A)[sP].[dR](G)[sP].[LR](G)[sP].[dR](C)[sP].[LR](G)[sP].[dR](A)[sP].[dR](G)[sP].[LR](A)[sP].[dR](G)[sP].[dR](G)[sP].[LR](T)[sP].[LR]([5meC])}$$$$V2.0 | GACCTCTCGCCTGCTC | 232 | 247 | 44345354 | 44345369 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 147 | CAGGCGA GAGGTCT GC | RNA1{[LR]([5meC])[sP].[dR](A) [sP].[dR](G)[sP].[LR](G)[sP]. [dR](C)[sP].[LR](G)[sP].[dR] (A)[sP].[dR](G)[sP].[LR](A) [sP].[dR](G)[sP].[dR](G)[sP]. [LR](T)[sP].[dR](C)[sP].[dR] (T)[sP].[LR](G)[sP].[LR] ([5meC])}$$$$V2.0 | GCAGACCT CTCGCCTG | 229 | 244 | 44345351 | 44345366 |
| 148 | GCGAGAG GTCTGCG CG | RNA1{[LR](G)[sP].[dR](C)[sP]. [LR](G)[sP].[dR](A)[sP].[dR] (G)[sP].[dR](A)[sP].[dR](G) [sP].[dR](G)[sP].[LR](T)[sP]. [dR](C)[sP].[dR](T)[sP].[LR] (G)[sP].[dR]([5meC])[sP].[dR] (G)[sP].[LR]([5meC])[sP].[LR] (G)}$$$$V2.0 | CGCGCAGA CCTCTCGC | 226 | 241 | 44345348 | 44345363 |
| 149 | AGAGGTC TGCGCGG CC | RNA1{[LR](A)[sP].[dR](G)[sP]. [LR](A)[sP].[dR](G)[sP].[dR] (G)[sP].[LR](T)[sP].[dR](C) [sP].[dR](T)[sP].[LR](G)[sP]. [dR]([5meC])[sP].[dR](G)[sP]. [LR]([5meC])[sP].[dR](G)[sP]. [dR](G)[sP].[LR](G)[sP]. [LR]([5meC])}$$$$V2.0 | GGCCGCGC AGACCTCT | 223 | 238 | 44345345 | 44345360 |
| 150 | GGTCTGC GCGGCCG CT | RNA1{[LR](G)[sP].[dR](G)[sP]. [LR](T)[sP].[dR](C)[sP].[dR] (T)[sP].[LR](G)[sP].[dR](C) [sP].[LR](G)[sP].[dR](C)[sP]. [LR](G)[sP].[dR](G)[sP].[dR] (C)[sP].[LR]([5meC])[sP].[dR] (G)[sP].[LR]([5meC])[sP].[LR] (T)}$$$$V2.0 | AGCGGCCG CGCAGACC | 220 | 235 | 44345342 | 44345357 |
| 151 | CTGCGCG GCCGCTC TC | RNA1{[LR]([5meC])[sP].[dR](T) [sP].[LR](G)[sP].[dR](C)[sP]. [LR](G)[sP].[dR]([5meC])[sP]. [dR](G)[sP].[LR](G)[sP].[dR] (C)[sP].[dR](C)[sP].[LR](G) [sP].[dR](C)[sP].[LR](T)[sP]. [dR](C)[sP].[LR](T)[sP].[LR] ([5meC])}$$$$V2.0 | GAGAGCGG CCGCGCAG | 217 | 232 | 44345339 | 44345354 |
| 152 | CGCGGCC GCTCTCC TA | RNA1{[LR]([5meC])[sP].[dR](G) [sP].[dR](C)[sP].[LR](G)[sP]. [dR](G)[sP].[dR](C)[sP].[LR] ([5meC])[sP].[dR](G)[sP].[dR] (C)[sP].[LR](T)[sP].[dR](C) [sP].[LR](T)[sP].[dR](C)[sP]. [dR](C)[sP].[LR](T)[sP].[LR] (A)}$$$$V2.0 | TAGGAGAG CGGCCGCG | 214 | 229 | 44345336 | 44345351 |
| 153 | GGCCGCT CTCCTAC CT | RNA1{[LR](G)[sP].[dR](G)[sP]. [dR](C)[sP].[LR]([5meC])[sP]. [dR](G)[sP].[dR](C)[sP].[LR] (T)[sP].[dR](C)[sP].[dR](T) [sP].[LR]([5meC])[sP].[dR](C) [sP].[dR](T)[sP].[LR](A)[sP]. [dR](C)[sP].[LR]([5meC])[sP]. [LR](T)}$$$$V2.0 | AGGTAGGA GAGCGGCC | 211 | 226 | 44345333 | 44345348 |
| 154 | CGCTCTC CTACCTG CG | RNA1{[LR]([5meC])[sP].[dR](G) [sP].[dR](C)[sP].[LR](T)[sP]. [dR](C)[sP].[dR](T)[sP].[LR] ([5meC])[sP].[dR](C)[sP].[dR] (T)[sP].[LR](A)[sP].[dR](C) [sP].[LR]([5meC])[sP].[dR](T) [sP].[dR](G)[sP].[LR]([5meC]) [sP].[LR](G)}$$$$V2.0 | CGCAGGTA GGAGAGCG | 208 | 223 | 44345330 | 44345345 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 155 | TCTCCTACCTGCGTCC | RNA1{[LR](T)[sP].[dR](C)[sP].[dR](T)[sP].[LR]([5meC])[sP].[dR](C)[sP].[dR](T)[sP].[LR](A)[sP].[dR](C)[sP].[dR](C)[sP].[LR](T)[sP].[dR](G)[sP].[dR](C)[sP].[LR](G)[sP].[dR](T)[sP].[LR]([5meC])[sP].[LR]([5meC])}$$$$V2.0 | GGACGCAGGTAGGAGA | 205 | 220 | 44345327 | 44345342 |
| 156 | CCTACCTGCGTCCGAC | RNA1{[LR]([5meC])[sP].[dR](C)[sP].[dR](T)[sP].[LR](A)[sP].[dR](C)[sP].[dR](C)[sP].[LR](T)[sP].[dR](G)[sP].[dR](C)[sP].[LR](G)[sP].[dR](T)[sP].[dR](C)[sP].[LR]([5meC])[sP].[dR](G)[sP].[LR](A)[sP].[LR]([5meC])}$$$$V2.0 | GTCGGACGCAGGTAGG | 202 | 217 | 44345324 | 44345339 |
| 157 | ACCTGCGTCCGACTCC | RNA1{[LR](A)[sP].[dR](C)[sP].[dR](C)[sP].[LR](T)[sP].[dR](G)[sP].[dR](C)[sP].[LR](G)[sP].[dR](T)[sP].[dR](C)[sP].[LR]([5meC])[sP].[dR](G)[sP].[LR](A)[sP].[dR](C)[sP].[dR](T)[sP].[LR]([5meC])[sP].[LR]([5meC])}$$$$V2.0 | GGAGTCGGACGCAGGT | 199 | 214 | 44345321 | 44345336 |
| 158 | GGGGAAGAAGCCAGCA | RNA1{[LR](G)[sP].[dR](G)[sP].[dR](G)[sP].[LR](G)[sP].[dR](A)[sP].[dR](A)[sP].[LR](G)[sP].[dR](A)[sP].[LR](A)[sP].[dR](G)[sP].[dR](C)[sP].[LR]([5meC])[sP].[dR](A)[sP].[dR](G)[sP].[LR]([5meC])[sP].[LR](A)}$$$$V2.0 | TGCTGGCTTCTTCCCC | 489 | 504 | 44345611 | 44345626 |
| 159 | GGGAAGAAGCCAGCAC | RNA1{[LR](G)[sP].[dR](G)[sP].[dR](G)[sP].[LR](A)[sP].[dR](A)[sP].[dR](G)[sP].[LR](A)[sP].[dR](A)[sP].[LR](G)[sP].[dR](C)[sP].[dR](C)[sP].[LR](A)[sP].[dR](G)[sP].[dR](C)[sP].[LR](A)[sP].[LR]([5meC])}$$$$V2.0 | GTGCTGGCTTCTTCCC | 488 | 503 | 44345610 | 44345625 |
| 160 | GAAGAAGCCAGCACCT | RNA1{[LR](G)[sP].[dR](A)[sP].[dR](A)[sP].[LR](G)[sP].[dR](A)[sP].[dR](A)[sP].[LR](G)[sP].[dR](C)[sP].[dR](C)[sP].[LR](A)[sP].[dR](G)[sP].[dR](C)[sP].[LR](A)[sP].[dR](C)[sP].[LR]([5meC])[sP].[LR](T)}$$$$V2.0 | AGGTGCTGGCTTCTTC | 486 | 501 | 44345608 | 44345623 |
| 161 | AAGAAGCCAGCACCTA | RNA1{[LR](A)[sP].[dR](A)[sP].[dR](G)[sP].[LR](A)[sP].[dR](A)[sP].[LR](G)[sP].[dR](C)[sP].[dR](C)[sP].[LR](A)[sP].[dR](G)[sP].[dR](C)[sP].[LR](A)[sP].[dR](C)[sP].[dR](C)[sP].[LR](T)[sP].[LR](A)}$$$$V2.0 | TAGGTGCTGGCTTCTT | 485 | 500 | 44345607 | 44345622 |
| 162 | GAAGCCAGCACCTACC | RNA1{[LR](G)[sP].[dR](A)[sP].[dR](A)[sP].[LR](G)[sP].[dR](C)[sP].[dR](C)[sP].[LR](A)[sP].[dR](G)[sP].[dR](C)[sP].[LR](A)[sP].[dR](C)[sP].[LR]([5meC])[sP].[dR](T)[sP].[dR](A)[sP].[LR]([5meC])[sP].[LR]([5meC])}$$$$V2.0 | GGTAGGTGCTGGCTTC | 483 | 498 | 44345605 | 44345620 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 163 | AAGCCAGCACCTACCG | RNA1{[LR](A)[sP].[dR](A)[sP].[LR](G)[sP].[dR](C)[sP].[dR](C)[sP].[LR](A)[sP].[dR](G)[sP].[dR](C)[sP].[LR](A)[sP].[dR](C)[sP].[dR](C)[sP].[LR](T)[sP].[dR](A)[sP].[dR](C)[sP].[LR]([5meC])[sP].[LR](G)}$$$$V2.0 | CGGTAGGTGCTGGCTT | 482 | 497 | 44345604 | 44345619 |
| 164 | GCCAGCACCTACCGAC | RNA1{[LR](G)[sP].[dR](C)[sP].[dR](C)[sP].[LR](A)[sP].[dR](G)[sP].[dR](C)[sP].[LR](A)[sP].[dR](C)[sP].[dR](C)[sP].[LR](T)[sP].[dR](A)[sP].[dR](C)[sP].[LR]([5meC])[sP].[dR](G)[sP].[dR](A)[sP].[LR]([5meC])}$$$$V2.0 | GTCGGTAGGTGCTGGC | 480 | 495 | 44345602 | 44345617 |
| 165 | CCAGCACCTACCGACA | RNA1{[LR]([5meC])[sP].[dR](C)[sP].[LR](A)[sP].[dR](G)[sP].[dR](C)[sP].[LR](A)[sP].[dR](C)[sP].[LR]([5meC])[sP].[dR](T)[sP].[LR](A)[sP].[A[sP].[dR](C)[sP].[LR](G)[sP].[dR](A)[sP].[LR]([5meC])[sP].[LR](A)}$$$$V2.0 | TGTCGGTAGGTGCTGG | 479 | 494 | 44345601 | 44345616 |
| 166 | AGCACCTACCGACAGG | RNA1{[LR](A)[sP].[dR](G)[sP].[dR](C)[sP].[LR](A)[sP].[dR](C)[sP].[LR]([5meC])[sP].[dR](T)[sP].[LR](A)[sP].[dR](C)[sP].[dR](C)[sP].[LR](G)[sP].[dR](A)[sP].[LR]([5meC])[sP].[dR](A)[sP].[LR](G)[sP].[LR](G)}$$$$V2.0 | CCTGTCGGTAGGTGCT | 477 | 492 | 44345599 | 44345614 |
| 167 | GCACCTACCGACAGGG | RNA1{[LR](G)[sP].[dR](C)[sP].[dR](A)[sP].[LR]([5meC])[sP].[dR](C)[sP].[dR](T)[sP].[LR](A)[sP].[dR](C)[sp].[dR](C)[sP].[LR](G)[sP].[dR](A)[sP].[dR](C)[sP].[LR](A)[sP].[dR](G)[sP].[LR](G)[sP].[LR](G)}$$$$V2.0 | CCCTGTCGGTAGGTGC | 476 | 491 | 44345598 | 44345613 |
| 168 | ACCTACCGACAGGGGT | RNA1{[LR](A)[sP].[dR](C)[sP].[LR]([5meC])[sP].[dR](T)[sP].[LR](A)[sP].[dR](C)[sP].[dR](C)[sP].[LR](G)[sp].IdR](A)[sP].[dR](C)[sP].[LR](A)[sP].[dR](G)[sP].[LR](G)[sP].[dR](G)[sP].[LR](G)[sP].[LR](T)}$$$$V2.0 | ACCCCTGTCGGTAGGT | 474 | 489 | 44345596 | 44345611 |
| 169 | CCTACCGACAGGGGTG | RNA1{[LR]([5meC][sP].[dR[(C)[sP].[dR](T)[sP].[LR](A)[sP].[dR](C)[sP].[dR](C)[sP].[LR](G)[sP].[dR](A)[sP].[dR](C)[sP].[LR](A)[sP].[dR](G)[sP].[LR](G)[sP].[dR](G)[sP].[dR](G)[sP].[LR](T)[sP].[LR](G)}$$$$V2.0 | CACCCCTGTCGGTAGG | 473 | 488 | 44345595 | 44345610 |
| 170 | TACCGACAGGGGTGGA | RNA1{[LR](T)[sP].[dR](A)[sP].[dR](C)[sP].[LR]([5meC])[sP].[dR](G)[sP].[LR](A)[sP].[dR](C)[sP].[dR](A)[sP].[LR](G)[sP].[dR](G)[sP].[dR](G)[sP].[LR](G)[sP].[dR](T)[sP].[dR](G)[sP].[LR](G)[sP].[LR](A)}$$$$V2.0 | TCCACCCCTGTCGGTA | 471 | 486 | 44345593 | 44345608 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 171 | ACCGACA GGGGTGG AG | RNA1{[LR](A)[sP].[dR](C)[sP]. [dR](C)[sP].[LR](G)[sP].[dR] (A)[sP].[dR](C)[sP].[LR](A) [sP].[dR](G)[sP].[dR](G)[sP]. [LR](G)[sP].[dR](G)[sP].[dR] (T)[sP].[LR](G)[sP].[dR](G) [sP].[LR](A)[sP].[LR](G)}$$$$ V2.0 | CTCCACCC CTGTCGGT | 470 | 485 | 44345592 | 44345607 |
| 172 | CGACAGG GGTGGAG CT | RNA1{[LR]([5meC])[sP].[dR](G) [sP].[LR](A)[sP].[dR](C)[sP]. [dR](A)[sP].[LR](G)[sP].[dR] (G)[sP].[dR](G)[sP].[LR](G) [sP].[dR](T)[sP].[dR](G)[sP]. [LR](G)[sP].[dR](A)[sP].[dR] (G)[sP].[LR]([5meC])[sP].[LR] (T)}$$$$V2.0 | AGCTCCAC CCCTGTCG | 468 | 483 | 44345590 | 44345605 |
| 173 | GACAGGG GTGGAGC TG | RNA1{[LR](G)[sP].[dR](A)[sP]. [dR](C)[sP].[LR](A)[sP].[dR] (G)[sP].[dR](G)[sP].[LR](G) [sP].[dR](G)[sP].[dR](T)[sP]. [LR](G)[sP].[dR](G)[sP].[dR] (A)[sP].[LR](G)[sP].[dR](C) [sP].[LR](T)[sP].[LR](G)}$$$$ V2.0 | CAGCTCCA CCCCTGTC | 467 | 482 | 44345589 | 44345604 |
| 174 | CAGGGGT GGAGCTG GG | RNA1{[LR]([5meC])[sP].[dR](A) [sP].[LR](G)[sP].[dR](G)[sP]. [dR](G)[sP].[LR](G)[sP].[dR] (T)[sP].[dR](G)[sP].[LR](G) [sP].[dR](A)[sP].[dR](G)[sP]. [LR]([5meC])[sP].[dR](T)[sP]. [dR](G)[sP].[LR](G)[sP].[LR] (G)}$$$$V2.0 | CCCAGCTC CACCCCTG | 465 | 480 | 44345587 | 44345602 |
| 175 | AGGGGTG GAGCTGG GT | RNA1{[LR](A)[sP].[dR](G)[sP]. [dR](G)[sP].[LR](G)[sP].[dR] (G)[sP].[dR](T)[sP].[LR](G) [sP].[dR](G)[sP].[dR](A)[sP]. [LR](G)[sP].[dR](C)[sP].[dR] (T)[sP].[LR](G)[sP].[dR](G) [sP].[LR](G)[sP].[LR](T)}$$$$ V2.0 | ACCCAGCT CCACCCCT | 464 | 479 | 44345586 | 44345601 |
| 176 | GGGTGGA GCTGGGT CA | RNA1{[LR](G)[sP].[dR](G)[sP]. [dR](G)[sP].[LR](T)[sP].[dR] (G)[sP].[dR](G)[sP].[LR](A) [sP].[dR](G)[sP].[dR](C)[sP]. [LR](T)[sP].[dR](G)[sP].[dR] (G)[sP].[LR](G)[sP].[dR](T) [sP].[LR]([5meC])[sP].[LR] (A)}$$$$V2.0 | TGACCCAG CTCCACCC | 462 | 477 | 44345584 | 44345599 |
| 177 | GGTGGAG CTGGGTC AA | RNA1{[LR](G)[sP].[dR](G)[sP]. [dR](T)[sP].[LR](G)[sP].[dR] (G)[sP].[dR](A)[sP].[LR](G) [sP].[dR](C)[sP].[dR](T)[sP]. [LR](G)[sP].[dR](G)[sP].[dR] (G)[sP].[LR](T)[sP].[dR](C) [sP].[LR](A)[sP].[LR](A)}$$$$ V2.0 | TTGACCCA GCTCCACC | 461 | 476 | 44345583 | 44345598 |
| 178 | TGGAGCT GGGTCAA GA | RNA1{[LR](T)[sP].[dR](G)[sP]. [dR](G)[sP].[LR](A)[sP].[dR] (G)[sP].[dR](C)[sP].[LR](T) [sP].[dR](G)[sP].[dR](G)[sP]. [LR](G)[sP].[dR](T)[sP].[dR] (C)[sP].[LR](A)[sP].[sP](A) [sP1.[LR](G)[sP].[LR](A)} $$$ $V2.0 | TCTTGACC CAGCTCCA | 459 | 474 | 44345581 | 44345596 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 179 | GGAGCTG GGTCAAG AA | RNA1{[LR](G)[sP].[dR](G)[sP].[dR](A)[sP].[LR](G)[sP].[dR](C)[sP].[dR](T)[sP].[LR](G)[sP].[dR](G)[sP].[dR](G)[sP].[LR](T)[sP].[dR](C)[sP].[LR](A)[sP].[dR](A)[sP].[dR](G)[sP].[LR](A)[sP].[LR](A)}$$$ $V2.0 | TTCTTGAC CCAGCTCC | 458 | 473 | 44345580 | 44345595 |
| 180 | CAGAAGG GGACGGC AG | RNA1{[LR]([5meC])[sP].[dR](A)[sP].[dR](G)[sP].[LR](A)[sP].[dR](A)[sP].[dR](G)[sP].[LR](G)[sP].[dR](G)[sP].[dR](G)[sP].[LR](A)[sP].[dR](C)[sP].[LR](G)[sP].[dR](G)[sP].[dR](C)[sP].[LR](A)[sP].[LR](G)}$ $$$V2.0 | CTGCCGTC CCCTTCTG | 4165 | 4180 | 44349287 | 44349302 |
| 181 | AAGGGGA CGGCAGC AG | RNA1{[LR](A)[sP].[dR](A)[sP].[dR](G)[sP].[LR](G)[sP].[dR](G)[sP].[dR](G)[sP].[LR](A)[sP].[dR](C)[sP].[LR](G)[sP].[dR](G)[sP].[dR](C)[sP].[LR](A)[sP].[dR](G)[sP].[dR](C)[sP].[LR](A)[sP].[LR](G)}$$$$ V2.0 | CTGCTGCC GTCCCCTT | 4162 | 4177 | 44349284 | 44349299 |
| 182 | GGGACGG CAGCAGC TG | RNA1{[LR](G)[sP].[dR](G)[sP].[dR](G)[sP].[LR](A)[sP].[dR](C)[sP].[LR](G)[sP].[dR](G)[sP].[dR](C)[sP].[LR](A)[sP].[dR](G)[sP].[dR](C)[sP].[LR](A)[sP].[dR](G)[sP].[dR](C)[sP].[LR](A)[sP].[dR](C)[sP].[LR](T)[sP].[LR](G)}$$$$ V2.0 | CAGCTGCT GCCGTCCC | 4159 | 4174 | 44349281 | 44349296 |
| 183 | ACGGCAG CAGCTGT AG | RNA1{[LR](A)[sP].[dR](C)[sP].[LR](G)[sP].[dR](G)[sP].[dR](C)[sP].[LR](A)[sP].[dR](G)[sP].[dR](C)[sP].[LR](A)[sP].[dR](G)[sP].[dR](C)[sP].[LR](T)[sP].[dR](G)[sP].[dR](T)[sP].[LR](A)[sP].[LR](G)}$$$$ V2.0 | CTACAGCT GCTGCCGT | 4156 | 4171 | 44349278 | 44349293 |
| 184 | GCAGCAG CTGTAGC TG | RNA1{[LR](G)[sP].[dR](C)[sP].[LR](A)[sP].[dR](G)[sP].[dR](C)[sP].[LR](A)[sP].[dR](G)[sP].[dR](C)[sP].[LR](T)[sP].[dR](G)[sP].[dR](T)[sP].[LR](A)[sP].[dR](G)[sP].[dR](C)[sP].[LR](T)[sP].[LR](G)}$$$$ V2.0 | CAGCTACA GCTGCTGC | 4153 | 4168 | 44349275 | 44349290 |
| 185 | GCAGCTG TAGCTGG CT | RNA1{[LR](G)[sP].[dR](C)[sP].[LR](A)[sP].[dR](G)[sP].[dR](C)[sP].[dR](T)[sP].[LR](G)[sP].[dR](T)[sP].[dR](A)[sP].[dR](G)[sP].[dR](C)[sP].[LR](T)[sP].[dR](G)[sP].[dR](G)[sP].[LR]([5meC])[sP].[LR](T)}$$$$V2.0 | AGCCAGCT ACAGCTGC | 4150 | 4165 | 44349272 | 44349287 |
| 186 | GCTGTAG CTGGCTC CT | RNA1{[LR](G)[sP].[dR](C)[sP].[dR](T)[sP].[LR](G)[sP].[dR](T)[sP].[dR](A)[sP].[LR](G)[sP].[dR](C)[sP].[dR](T)[sP].[LR](G)[sP].[dR](G)[sP].[dR](C)[sP].[LR](T)[sP].[dR](C)[sP].[LR]([5meC])[sP].[LR](T)}$$$$V2.0 | AGGAGCCA GCTACAGC | 4147 | 4162 | 44349269 | 44349284 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 187 | GTAGCTGGCTCCTCCG | RNA1{[LR](G)[sP].[dR](T)[sP].[dR](A)[sP].[LR](G)[sP].[dR](C)[sP].[dR](T)[sP].[LR](G)[sP].[dR](G)[sP].[dR](C)[sP].[LR](T)[sP].[dR](C)[sP].[dR](C)[sP].[LR](T)[sP].[dR](C)[sP].[LR]([5meC])[sP].[LR](G)}$$$$V2.0 | CGGAGGAGCCAGCTAC | 4144 | 4159 | 44349266 | 44349281 |
| 188 | GCTGGCTCCTCCGGGG | RNA1{[LR](G)[sP].[dR](C)[sP].[dR](T)[sP].[LR](G)[sP].[dR](G)[sP].[dR](C)[sP].[dR](T)[sP].[dR](C)[sP].[dR](C)[sP].[LR](T)[sP].[dR](C)[sP].[LR]([5meC])[sP].[dR](G)[sP].[dR](G)[sP].[LR](G)[sP].[LR](G)}$$$$V2.0 | CCCCGGAGGAGCCAGC | 4141 | 4156 | 44349263 | 44349278 |
| 189 | GGCTCCTCCGGGGTCC | RNA1{[LR](G)[sP].[dR](G)[sP].[dR](C)[sP].[LR](T)[sP].[dR](C)[sP].[dR](C)[sP].[LR](T)[sP].[dR](C)[sP].[dR](C)[sP].[LR](G)[sP].[dR](G)[sP].[dR](G)[sP].[LR](G)[sP].[dR](T)[sP].[LR]([5meC])[sP].[LR]([5meC])}$$$$V2.0 | GGACCCCGGAGGAGCC | 4138 | 4153 | 44349260 | 44349275 |
| 190 | TCCTCCGGGGTCCAGG | RNA1{[LR](T)[sP].[dR](C)[sP].[dR](C)[sP].[LR](T)[sP].[dR](C)[sP].[dR](C)[sP].[LR](G)[sP].[dR](G)[sP].[dR](G)[sP].[LR](G)[sP].[dR](T)[sP].[dR](C)[sP].[LR]([5meC])[sP].[dR](A)[sP].[LR](G)[sP].[LR](G)}$$$V2.0 | CCTGGACCCCGGAGGA | 4135 | 4150 | 44349257 | 44349272 |
| 191 | TCCGGGGTCCAGGCAG | RNA1{[LR](T)[sP].[dR](C)[sP].[dR](C)[sP].[LR](G)[sP].[dR](G)[sP].[dR](G)[sP].[LR](G)[sP].[dR](T)[sP].[dR](C)[sP].[LR]([5meC])[sP].[dR](A)[sP].[dR](G)[sP].[LR](G)[sP].[dR](C)[sP].[LR](A)[sP].[LR](G)}$$$V2.0 | CTGCCTGGACCCCGGA | 4132 | 4147 | 44349254 | 44349269 |
| 192 | GGGGTCCAGGCAGCAG | RNA1{[LR](G)[sP].[dR](G)[sP].[dR](G)[sP].[LR](G)[sP].[dR](T)[sP].[dR](C)[sP].[LR]([5meC])[sP].[dR](A)[sP].[dR](G)[sP].[LR](G)[sP].[dR](C)[sP].[LR](A)[sP].[dR](G)[sP].[dR](C)[sP].[LR](A)[sP].[LR](G)}$$$$V2.0 | CTGCTGCCTGGACCCC | 4129 | 4144 | 44349251 | 44349266 |
| 193 | GTCCAGGCAGCAGGCC | RNA1{[LR](G)[sP].[dR](T)[sP].[dR](C)[sP].[LR]([5meC])[sP].[dR](A)[sP].[dR](G)[sP].[LR](G)[sP].[dR](C)[sP].[LR](A)[sP].[dR](G)[sP].[dR](C)[sP].[LR](A)[sP].[dR](G)[sP].[dR](G)[sP].[LR]([5meC])[sP].[LR]([5meC])}$$$$V2.0 | GGCCTGCTGCCTGGAC | 4126 | 4141 | 44349248 | 44349263 |
| 194 | CAGGCAGCAGGCCACA | RNA1{[LR]([5meC])[sP].[dR](A)[sP].[dR](G)[sP].[LR](G)[sP].[dR](C)[sP].[LR](A)[sP].[dR](G)[sP].[dR](C)[sP].[LR](A)[sP].[dR](G)[sP].[dR](G)[sP].[LR]([5meC])[sP].[dR](C)[sP].[dR](A)[sP].[LR]([5meC])[sP].[LR](A)}$$$$V2.0 | TGTGGCCTGCTGCCTG | 4123 | 4138 | 44349245 | 44349260 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 195 | GCAGCAGGCCACAGGG | RNA1{[LR](G)[sP].[dR](C)[sP].[LR](A)[sP].[dR](G)[sP].[dR](C)[sP].[LR](A)[sP].[dR](G)[sP].[LR](G)[sP].[dR](C)[sP].[dR](C)[sP].[LR](A)[sP].[dR](C)[sP].[LR](A)[sP].[dR](G)[sP].[LR](G)[sP].[LR](G)}$$$$V2.0 | CCCTGTGGCCTGCTGC | 4120 | 4135 | 44349242 | 44349257 |
| 196 | GCAGGCCACAGGGCAG | RNA1{[LR](G)[sP].[dR](C)[sP].[LR](A)[sP].[dR](G)[sP].[LR](G)[sP].[dR](C)[sP].[dR](C)[sP].[LR](A)[sP].[dR](C)[sP].[LR](A)[sP].[dR](G)[sP].[dR](G)[sP].[LR](G)[sP].[dR](C)[sP].[LR](A)[sP].[LR](G)}$$$$V2.0 | CTGCCCTGTGGCCTGC | 4117 | 4132 | 44349239 | 44349254 |
| 197 | GGCCACAGGGCAGAAC | RNA1{[LR](G)[sP].[dR](G)[sP].[dR](C)[sP].[LR]([5meC])[sP].[dR](A)[sP].[dR](C)[sP].[LR](A)[sP].[dR](G)[sP].[dR](G)[sP].[LR](G)[sP].[dR](C)[sP].[LR](A)[sP].[dR](G)[sP].[dR](A)[sP].[dR](A)[sP].[LR]([5meC])}$$$$V2.0 | GTTCTGCCCTGTGGCC | 4114 | 4129 | 44349236 | 44349251 |
| 198 | CACAGGGCAGAACTGA | RNA1{[LR]([5meC])[sP].[dR](A)[sP].[dR](C)[sP].[LR](A)[sP].[dR](G)[sP].[dR](G)[sP].[LR](G)[sP].[dR](C)[sP].[LR](A)[sP].[dR](G)[sP].[dR](A)[sP].[LR](A)[sP].[dR](C)[sP].[dR](T)[sP].[LR](G)[sP].[LR](A)}$$$$V2.0 | TCAGTTCTGCCCTGTG | 4111 | 4126 | 44349233 | 44349248 |
| 199 | AGGGCAGAACTGACCA | RNA1{[LR](A)[sP].[dR](G)[sP].[dR](G)[sP].[LR](G)[sP].[dR](C)[sP].[LR](A)[sP].[dR](G)[sP].[dR](A)[sP].[LR](A)[sP].[dR](C)[sP].[dR](T)[sP].[LR](G)[sP].[dR](A)[sP].[dR](C)[sP1.[LR]([5meC])[sP].[LRKA)}$$$$V2.0 | TGGTCAGTTCTGCCCT | 4108 | 4123 | 44349230 | 44349245 |
| 200 | GCAGAACTGACCATCT | RNA1{[LR](G)[sP].[dR](C)[sP].[LR](A)[sP].[dR](G)[sP].[dR](A)[sP].[LR](A)[sP].[dR](C)[sP].[dR](T)[sP].[LR](G)[sP].[dR](A)[sP].[dR](C)[sP].[LR]([5meC])[sP].[dR](A)[sP].[dR](T)[sP].[LR]([5meC])[sP].[LR](T)}$$$$V2.0 | AGATGGTCAGTTCTGC | 4105 | 4120 | 44349227 | 44349242 |
| 201 | GAACTGACCATCTGG | RNA1{[LR](G)[sP].[dR](A)[sP].[LR](A)[sP].[dR](C)[sP].[dR](T)[sP].[LR](G)[sP].[dR](A)[sP].[dR](C)[sP].[LR]([5meC])[sP].[dR](A)[sP].[dR](T)[sP].[LR]([5meC])[sP].[dR](T)[sP].[dR](G)[sP].[LR](G)[sP].[LR](G)}$$$$V2.0 | CCCAGATGGTCAGTTC | 4102 | 4117 | 44349224 | 44349239 |
| 202 | CTGACCATCTGGGCAC | RNA1{[LR]([5meC])[sP].[dR](T)[sP].[dR](G)[sP].[LR](A)[sP].[dR](C)[sP].[dR](C)[sP].[LR](A)[sP].[dR](T)[sP].[dR](C)[sP].[LR](T)[sP].[dR](G)[sP].[dR](G)[sP].[dR](G)[sP].[dR](C)[sP].[LR](A)[sP].[LR]([5meC])}$$$$V2.0 | GTGCCCAGATGGTCAG | 4099 | 4114 | 44349221 | 44349236 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 203 | ACCATCT GGGCACC GC | RNA1{[LR](A)[sP].[dR](C)[sP].[dR](C)[sP].[LR](A)[sP].[dR](T)[sP].[dR](C)[sP].[dR](T)[sP].[dR](G)[sP].[dR](G)[sP].[LR](G)[sP].[dR](C)[sP].[LR](A)[sP].[dR](C)[sP].[dR](C)[sP].[LR](G)[sP].[LR]([5meC])}$$$$V2.0 | GCGGTGCC CAGATGGT | 4096 | 4111 | 44349218 | 44349233 |
| 204 | ATCTGGG CACCGCG TT | RNA1{[LR](A)[sP].[dR](T)[sP].[dR](C)[sP].[LR](T)[sP].[dR](G)[sP].[dR](G)[sP].[LR](G)[sP].[dR](C)[sP].[LR](A)[sP].[dR](C)[sP].[dR](C)[sP].[LR](G)[sP].[dR]([5meC])[sP].[dR](G)[sP].[LR](T)[sP].[LR](T)}$$$$V2.0 | AACGCGGT GCCCAGAT | 4093 | 4108 | 44349215 | 44349230 |
| 205 | TGGGCAC CGCGTTC CA | RNA1{[LR](T)[sP].[dR](G)[sP].[dR](G)[sP].[LR](G)[sP].[dR](C)[sP].[dR](A)[sP].[dR](C)[sP].[dR](C)[sP].[LR](G)[sP].[dR]([5meC])[sP].[dR](G)[sP].[sP].[LR](T)[sP].[dR](T)[sP].[dR](C)[sP].[LR]([5meC])[sP].[LR](A)}$$$$V2.0 | TGGAACGC GGTGCCCA | 4090 | 4105 | 44349212 | 44349227 |
| 206 | GCACCGC GTTCCAG CC | RNA1{[LR](G)[sP].[dR](C)[sP].[LR](A)[sP].[dR](C)[sP].[dR](C)[sP].[LR](G)[sP].[dR](C)[sP].[LR](G)[sP].[dR](T)[sP].[LR](T)[sP].[dR](C)[sP].[dR](C)[sP].[LR](A)[sP].[dR](G)[sP].[LR]([5meC])[sP].[LR]([5meC])}$$$$V2.0 | GGCTGGAA CGCGGTGC | 4087 | 4102 | 44349209 | 44349224 |
| 207 | CCGCGTT CCAGCCA CC | RNA1{[LR]([5meC])[sP].[dR](C)[sP].[LR](G)[sP].[dR](C)[sP].[LR](G)[sP].[dR](T)[sP].[LR](T)[sP].[dR](C)[sP].[dR](C)[sP].[LR](A)[sP].[dR](G)[sP].[sP].[dR](C)[sP].[LR]([5meC])[sP].[dR](A)[sP].[LR]([5meC])[sP].[LR]([5meC])}$$$$V2.0 | GGTGGCTG GAACGCGG | 4084 | 4099 | 44349206 | 44349221 |
| 208 | CGTTCCA GCCACCA GC | RNA1{[LR]([5meC])[sP].[dR](G)[sP].[dR](T)[sP].[LR](T)[sP].[dR](C)[sP].[dR](C)[sP].[LR](A)[sP].[dR](G)[sP].[dR](C)[sP].[LR]([5meC])[sP].[dR](A)[sP].[dR](C)[sP].[LR]([5meC])[sP].[dR](A)[sP].[LR](G)[sP].[LR]([5meC])}$$$$V2.0 | GCTGGTGG CTGGAACG | 4081 | 4096 | 44349203 | 44349218 |
| 209 | TCCAGCC ACCAGCC CT | RNA1{[LR](T)[sP].[dR](C)[sP].[dR](C)[sP].[LR](A)[sP].[dR](G)[sP].[dR](C)[sP].[LR]([5meC])[sP].[dR](A)[sp].[LR]([5meC])[sP].[dR](A)[sP].[LR](G)[sP].[dR](C)[sP].[dR](C)[sP].[LR]([5meC])[sP].[LR](T)}$$$$V2.0 | AGGGCTGG TGGCTGGA | 4078 | 4093 | 44349200 | 44349215 |
| 210 | AGCCACC AGCCCTG CT | RNA1{[LR](A)[sP].[dR](G)[sP].[dR](C)[sP].[LR]([5meC])[sP].[dR](A)[sP].[dR](C)[sP].[LR]([5meC])[sP].[dR](A)[sP].[LR](G)[sP].[dR](C)[sP].[dR](C)[sP].[LR]([5meC])[sP].[dR](T)[sP].[dR](G)[sP].[LR]([5meC])[sP].[LR](T)}$$$$V2.0 | AGCAGGGC TGGTGGCT | 4075 | 4090 | 44349197 | 44349212 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| 211 | CACCAGCCCTGCTGTT | RNA1{[LR]([5meC])[sP].[dR](A)[sP].[LR]([5meC])[sP].[dR](C)[sP].[LR](A)[sP].[dR](G)[sP].[dR](C)[sP].[LR]([5meC])[sP].[dR](C)[sP].[dR](T)[sP].[LR](G)[sP].[dR](C)[sP].[LR](T)[sP].[dR](G)[sP].[LR](T)[sP].[LR](T)}$$$$V2.0 | AACAGCAGGGCTGGTG | 4072 | 4087 | 44349194 | 44349209 |
| 212 | CAGCCCTGCTGTTAAG | RNA1{[LR]([5meC])[sP].[dR](A)[sP].[LR](G)[sP].[dR](C)[sP].[LR]([5meC])[sP].[dR](C)[sP].[dR](T)[sP].[LR](G)[sP].[dR](C)[sP].[dR](T)[sP].[LR](G)[sP].[dR](T)[sP].[dR](T)[sP].[LR](A)[sP].[LR](A)[sP].[LR](G)}$$$$V2.0 | CTTAACAGCAGGGCTG | 4069 | 4084 | 44349191 | 44349206 |
| 213 | CCCTGCTGTTAAGGCC | RNA1{[LR]([5meC][sP].[dR[(C)[sP].[LR]([5meC])[sP].[dR](T)[sP].[LR](G)[sP].[dR](C)[sP].[dR](T)[sP].[LR](G)[sP].[dR](T)[sP].[dR](T)[sP].[dR](A)[sP].[LR](A)[sP].[dR](G)[sP].[dR](G)[sP].[LR]([5meC])[sP].[LR]([5meC])}$$$$V2.0 | GGCCTTAACAGCAGGG | 4066 | 4081 | 44349188 | 44349203 |
| 214 | TGCTGTTAAGGCCACC | RNA1{[LR](T)[sP].[dR](G)[sP].[LR]([5meC])[sP].[dR](T)[sP].[LR](G)[sP].[dR](T)[sP].[dR](T)[sP].[LR](A)[sP].[dR](A)[sP].[dR](G)[sP].[LR](G)[sP].[dR](C)[sP].[dR](C)[sP].[LR](A)[sP].[LR]([5meC])[sP].[LR]([5meC])}$$$$V2.0 | GGTGGCCTTAACAGCA | 4063 | 4078 | 44349185 | 44349200 |
| 215 | TGTTAAGGCCACCCAG | RNA1{[LR](T)[sP].[dR](G)[sP].[LR](T)[sP].[dR](T)[sP].[LR](A)[sP].[dR](A)[sP].[dR](G)[sP].[LR](G)[sP].[dR](C)[sP].[dR](C)[sP].[LR](A)[sP].[dR](C)[sP].[LR]([5meC])[sP].[dR](C)[sP].[LR](A)[sP].[LR](G)}$$$$V2.0 | CTGGGTGGCCTTAACA | 4060 | 4075 | 44349182 | 44349197 |
| 216 | TAAGGCCACCCAGCTC | RNA1{[LR](T)[sP].[dR](A)[sP].[LR](A)[sP].[dR](G)[sP].[dR](G)[sP].[LR]([5meC])[sP].[dR](C)[sP].[dR](A)[sP].[LR]([5meC])[sP].[dR](C)[sP].[dR](C)[sP].[LR](A)[sP].[dR](G)[sP].[dR](C)[sP].[LR](T)[sP].[LR]([5meC])}$$$$V2.0 | GAGCTGGGTGGCCTTA | 4057 | 4072 | 44349179 | 44349194 |
| 217 | GGCCACCCAGCTCACC | RNA1{[LR](G)[sP].[dR](G)[sP].[dR](C)[sP].[LR]([5meC])[sP].[dR](A)[sP].[dR](C)[sP].[LR]([5meC])[sP].[LR](A)[sP].[dR](G)[sP].[dR](C)[sP].[LR](T)[sP].[dR](C)[sP].[dR](A)[sP].[LR]([5meC])[sP].[LR]([5meC])}$$$$V2.0 | GGTGAGCTGGGTGGCC | 4054 | 4069 | 44349176 | 44349191 |
| 218 | CACCCAGCTCACCAGG | RNA1{[LR]([5meC])[sP].[dR](A)[sP].[dR](C)[sP].[LR]([5meC])[sP].[dR](C)[sP].[LR](A)[sP].[dR](G)[sP].[dR](C)[sP].[LR](T)[sP].[dR](C)[sP].[LR](A) | CCTGGTGAGCTGGGTG | 4051 | 4066 | 44349173 | 44349188 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [sP].[dR](C)[sP].[LR]([5meC])[sP].[dR](A)[sP].[LR](G)[sP].[LR](G)}$$$$V2.0 | | | | | |
| 219 | CCAGCTCACCAGGGTC | RNA1{[LR]([5meC])[sP].[dR](C)[sP].[LR](A)[sP].[dR](G)[sP].[dR](C)[sP].[LR](T)[sP].[dR](C)[sP].[LR](A)[sP].[dR](C)[sP].[dR](C)[sP].[LR](A)[sP].[dR](G)[sP].[LR](G)[sP].[dR](G)[sP].[LR](T)[sP].[LR]([5meC])}$$$$V2.0 | GACCCTGGTGAGCTGG | 4048 | 4063 | 44349170 | 44349185 |
| 220 | GCTCACCAGGGTCCAC | RNA1{[LR](G)[sP].[dR](C)[sP].[LR](T)[sP].[dR](C)[sP].[LR](A)[sP].[dR](C)[sP].[dR](C)[sP].[LR](A)[sP].[dR](G)[sr)].[dR](G)[sP].[LR](G)[sP].[dR](T)[sP].[LR]([5meC])[sP].[dR](C)[sP].[LR](A)[sP].[LR]([5meC])}$$$$V2.0 | GTGGACCCTGGTGAGC | 4045 | 4060 | 44349167 | 44349182 |
| 221 | CACCAGGGTCCACATG | RNA1{[LR]([5meC])[sP].[dR](A)[sP].[dR](C)[sP].[LR]([5meC])[sP].[dR](A)[sP].[LR](G)[sP].[dR](G)[sP].[dR](G)[sP].[LR](T)[sP].[dR](C)[sP].[dR](C)[sP].[LR](A)[sP].[dR](C)[sP].[dR](A)[sP].[LR](T)[sP].[LR](G)}$$$$V2.0 | CATGTGGACCCTGGTG | 4042 | 4057 | 44349164 | 44349179 |
| 222 | CAGGGTCCACATGGTC | RNA1{[LR]([5meC])[sP].[dR](A)[sP].[LR](G)[sP].[dR](G)[sP].[dR](G)[sP].[LR](T)[sP].[dR](C)[sP].[dR](C)[sP].[LR](A)[sP].[dR](C)[sP].[LR](A)[sP].[dR](T)[sP].[LR](G)[sP].[dR](G)[sP].[LR](T)[sP].[LR]([5meC])}$$$$V2.0 | GACCATGTGGACCCTG | 4039 | 4054 | 44349161 | 44349176 |
| 223 | GGTCCACATGGTCTGC | RNA1{[LR](G)[sP].[dR](G)[sP].[LR](T)[sP].[dR](C)[sP].[dR](C)[sP].[LR](A)[sP].[dR](C)[sP].[LR](A)[sP].[dR](T)[sP].[LR](G)[sP].[dR](G)[sP].[LR](T)[sP].[dR](C)[sP].[dR](T)[sP].[LR](G)[sP].[LR]([5meC])}$$$$V2.0 | GCAGACCATGTGGACC | 4036 | 4051 | 44349158 | 44349173 |
| 224 | CCACATGGTCTGCCTG | RNA1{[LR]([5meC])[sP].[dR](C)[sP].[LR](A)[sP].[dR](C)[sP].[LR](A)[sP].[dR](T)[sP].[LR](G)[sP].[dR](G)[sP].[LR](T)[sP].[dR](C)[sP].[dR](T)[sP].[LR](G)[sP].[dR](C)[sP].[dR](C)[sP].[LR](T)[sP].[LR](G)}$$$$V2.0 | CAGGCAGACCATGTGG | 4033 | 4048 | 44349155 | 44349170 |
| 225 | CATGGTCTGCCTGCAA | RNA1{[LR]([5meC])[sP].[dR](A)[sP].[dR](T)[sP].[LR](G)[sP].[dR](G)[sP].[LR](T)[sP].[dR](C)[sP].[dR](T)[sP].[LR](G)[sP].[dR](C)[sP].[dR](C)[sP].[LR](T)[sP].[dR](G)[sP].[dR](C)[sP].[LR](A)[sP].[LR](A)}$$$V2.0 | TTGCAGGCAGACCATG | 4030 | 4045 | 44349152 | 44349167 |
| 226 | GGTCTGCCTGCAAAGT | RNA1{[LR](G)[sP].[dR](G)[sP].[LR](T)[sP].[dR](C)[sP].[dR](T)[sP].[LR](G)[sP].[dR](C)[sP].[dR](C)[sP].[LR](T)[sP].[dR](G)[sP].[dR](C)[sP].[LR] | ACTTTGCAGGCAGACC | 4027 | 4042 | 44349149 | 44349164 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | (A)[sP].[dR](A)[sP].[dR](A) [sP].[LR](G)[sP].[LR](T)}$$$$ V2.0 | | | | | |
| 227 | CTGCCTG CAAAGTA CC | RNA1{[LR]([5meC])[sP].[dR](T) [sP].[dR](G)[sP].[LR]([5meC]) [sP].[dR](C)[sP].[dR](T)[sP]. [LR](G)[sP].[dR](C)[sP].[LR] (A)[sP].[dR](A)[sP].[dR](A) [sP].[LR](G)[sP].[dR](T)[sP]. [](A)[sP].[LR]([5meC])[sP]. [LR]([5meC])}$$$$V2.0 | GGTACTTT GCAGGCAG | 4024 | 4039 | 44349146 | 44349161 |
| 228 | CCTGCAA AGTACCA AG | RNA1{[LR]([5meC])[sP].[dR](C) [sP].[dR](T)[sP].[LR](G)[sP]. [dR](C)[sP].[LR](A)[sP].[dR] (A)[sP].[dR](A)[sP].[dR](G) [sP].[dR](T)[sP].[LR](A)[sP]. [dR](C)[sP].[dR](C)[sP].[LR] (A)[sP].[LR](A)[sP].[LR](G)}$ $$$V2.0 | CTTGGTAC TTTGCAGG | 4021 | 4036 | 44349143 | 44349158 |
| 229 | GCAAAGT ACCAAGG AA | RNA1{[LR](G)[sP].[dR](C)[sP]. [LR](A)[sP].[dR](A)[sP].[LR] (A)[sP].[dR](G)[sP].[dR](T) [sP].[LR](A)[sP].[dR](C)[sP]. [dR](C)[sP].[LR](A)[sP].[LR] (A)[sP].[dR](G)[sP].[dR](G) [sP].[LR](A)[sP].[LR](A)}$$$$ V2.0 | TTCCTTGG TACTTTGC | 4018 | 4033 | 44349140 | 44349155 |
| 230 | AAGTACC AAGGAAC GT | RNA1{[LR](A)[sP].[dR](A)[sP]. [LR](G)[sP].[dR](T)[sP].[LR] (A)[sP].[dR](C)[sP].[dR](C) [sP].[LR](A)[sP].[dR](A)[sP]. [dR](G)[sP].[LR](G)[sP].[dR] (A)[sP].[LR](A)[sP].[dR](C) [sP].[LR](G)[sP].[LR](T)}$$$$ V2.0 | ACGTTCCT TGGTACTT | 4015 | 4030 | 44349137 | 44349152 |
| 231 | TACCAAG GAACGTC TG | RNA1{[LR](T)[sP].[dR](A)[sP]. [dR](C)[sP].[LR]([5meC])[sP]. [dR](A)[sP].[LR](A)[sP].[dR] (G)[sP].[dR](G)[sP].[LR](A) [sP].[dR](A)[sP].[dR](c)[sP]. [LR](G)[sP].[dR](T)[sP].[dR] (C)[sP].[dR](T)[sP].[LR](G)}$ $$$V2.0 | CAGACGTT CCTTGGTA | 4012 | 4027 | 44349134 | 44349149 |
| 232 | CAAGGAA CGTCTGG CA | RNA1{[LR]([5meC])[sP].[dR](A) [sP].[LR](A)[sP].[dR](G)[sP]. [dR](G)[sP].[LR](A)[sP].[dR] (A)[sP].[dR](C)[sP].[LR](G) [sP].[dR](T)[sP].[dR](C)[sP]. [LR](T)[sP].[dR](G)[sP].[dR] (G)[sP].[LR]([5meC])[sP].[LR] (A)}$$$$V2.0 | TGCCAGAC GTTCCTTG | 4009 | 4024 | 44349131 | 44349146 |
| 233 | GGAACGT CTGGCAA CT | RNA1{[LR](G)[sP].[dR](G)[sP]. [dR](A)[sP].[LR](A)[sP].[dR] ([5meC])[sP].[dR](G)[sP].[LR] (T)[sP].[dR](C)[sp].[dR](T) [sP].[LR](G)[sP].[dR](G)[sP]. [dR](C)[sP].[LR](A)[sP].[dR] (A)[sP].[LR]([5meC])[sP].[LR] (T)}$$$$V2.0 | AGTTGCCA GACGTTCC | 4006 | 4021 | 44349128 | 44349143 |
| 234 | ACGTCTG GCAACTG CT | RNA1{[LR](A)[sP].[dR]([5meC]) [sP].[dR](G)[sP].[LR](T)[sP]. [dR](C)[sP].[dR](T)[sP].[LR] (G)[sP].[dR](G)[sP].[dR](C) [sP].[LR](A)[sP].[dR](A)[sP]. | AGCAGTTG CCAGACGT | 4003 | 4018 | 44349125 | 44349140 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [LR]([5meC])[sP].[dR](T)[sP].[dR](G)[sP].[LR]([5meC])[sP].[LR](T)}$$$$V2.0 | | | | | |
| 235 | TCTGGCAACTGCTTAA | RNA1{[LR](T)[sP].[dR](C)[sP].[dR](T)[sP].[LR](G)[sP].[dR](G)[sP].[dR](C)[sP].[LR](A)[sP].[LR](A)[sP].[dR](C)[sP].[dR](T)[sP].[LR](G)[sP].[dR](C)[sP].[LR](T)[sP].[dR](T)[sP].[LR](A)[sP].[LR](A)}$$$$V2.0 | TTAAGCAGTTGCCAGA | 4000 | 4015 | 44349122 | 44349137 |
| 236 | GGCAACTGCTTAAGCC | RNA1{[LR](G)[sP].[dR](G)[sP].[dR](C)[sP].[LR](A)[sP].[LR](A)[sP].[dR](C)[sP].[dR](T)[sP].[LR](G)[sP].[dR](C)[sP].[LR](T)[sP].[dR](T)[sP].[LR](A)[sP].[LR](A)[sP].[dR](G)[sP].[LR]([5meC])[sP].[LR]([5meC])}$$$$V2.0 | GGCTTAAGCAGTTGCC | 3997 | 4012 | 44349119 | 44349134 |
| 237 | AACTGCTTAAGCCCAC | RNA1{[LR](A)[sP].[LR](A)[sP].[dR](C)[sP].[dR](T)[sP].[LR](G)[sP].[dR](C)[sP].[LR](T)[sP].[dR](T)[sP].[LR](A)[sP].[dR](A)[sP].[dR](G)[sP].[LR]([5meC])[sP].[dR](C)[sP].[dR](C)[sP].[LR](A)[sP].[LR]([5meC])}$$$$V2.0 | GTGGGCTTAAGCAGTT | 3994 | 4009 | 44349116 | 44349131 |
| 238 | TGCTTAAGCCCACGCC | RNA1{[LR](T)[sP].[dR](G)[sP].[dR](C)[sP].[LR](T)[sP].[dR](T)[sP].[LR](A)[sP].[dR](A)[sP].[dR](G)[sP].[LR]([5meC])[sP].[dR](C)[sP].[dR](C)[sP].[LR](A)[sP].[dR]([5meC])[sP].[dR](G)[sP].[LR]([5meC])[sP].[LR]([5meC])}$$$$V2.0 | GGCGTGGGCTTAAGCA | 3991 | 4006 | 44349113 | 44349128 |
| 239 | TTAAGCCCACGCCACC | RNA1{[LR](T)[sP].[dR](T)[sP].[LR](A)[sP].[LR](A)[sP].[dR](G)[sP].[LR]([5meC])[sP].[dR](C)[sP].[dR](C)[sP].[LR](A)[sP].[dR](C)[sP].[LR](G)[sP].[dR](C)[sP].[LR](C)[sP].[LR](A)[sP].[LR]([5meC])[sP].[LR]([5meC])}$$$$V2.0 | GGTGGCGTGGGCTTAA | 3988 | 4003 | 44349110 | 44349125 |
| 240 | AGCCCACGCCACCCTT | RNA1{[LR](A)[sP].[dR](G)[sP].[dR](C)[sP].[LR]([5meC])[sP].[dR](C)[sP].[LR](A)[sP].[dR](C)[sP].[LR](G)[sP].[dR](C)[sP].[dR](C)[sP].[LR](A)[sP].[dR](C)[sP].[LR](C)[sP].[LR]([5meC])[sP].[dR](C)[sP].[LR](T)[sP].[LR](T)}$$$$V2.0 | AAGGGTGGCGTGGGCT | 3985 | 4000 | 44349107 | 44349122 |
| 241 | CCACGCCACCCTTGAT | RNA1{[LR]([5meC])[sP].[dR](C)[sP].[LR](A)[sP].[dR](C)[sP].[LR](G)[sP].[dR](C)[sP].[dR](C)[sP].[LR](A)[sP].[dR](C)[sP].[LR]([5meC])[sP].[dR](C)[sP].[LR](T)[sP].[dR](T)[sP].[dR](G)[sP].[LR](A)[sP].[LR](T)}$$$$V2.0 | ATCAAGGGTGGCGTGG | 3982 | 3997 | 44349104 | 44349119 |
| 242 | CGCCACCCTTGATTCT | RNA1{[LR]([5meC])[sP].[dR](G)[sP].[dR](C)[sP].[LR]([5meC])[sP].[dR](A)[sP].[dR](C)[sP].[LR]([5meC])[sP].[dR](C)[sP].[LR](T)[sP].[dR](T)[sP].[dR] | AGAATCAAGGGTGGCG | 3979 | 3994 | 44349101 | 44349116 |

TABLE 2-continued

Compound Table

| SEQ ID NO | Oligo Sequence | Helm sequence | Target sequence | Start position in SEQ ID 276 | End position in SEQ ID 276 | chromo- some start (hg38 assembly) | Chromo- some end (hg38 assembly) |
|---|---|---|---|---|---|---|---|
| | | (G)[sP].[LR](A)[sP].[dR](T) [sP].[dR](T)[sP].[LR]([5meC]) [sP].[LR](T)}$$$$V2.0 | | | | | |
| 243 | CACCCTT GATTCTA GG | RNA1{[LR]([5meC])[sP].[dR](A) [sP].[dR](C)[sP].[LR]([5meC]) [sP].[dR](C)[sP].[LR](T)[sP]. [dR](T)[sP].[LR](G)[sP].[dR] (A)[sP].[dR](T)[sP].[LR](T) [sP].[dR](C)[sP].[LR](T)[sP]. [dR](A)[sP].[LR](G)[sP].[LR] (G)}$$$$V2.0 | CCTAGAAT CAAGGGTG | 3976 | 3991 | 44349098 | 44349113 |
| 244 | CCTTGAT TCTAGGG TC | RNA1{[LR]([5meC])[sP].[dR](C) [sP].[LR](T)[sP].[dR](T)[sP]. [LR](G)[sP].[dR](A)[sP].[dR] (T)[sP].[dR](T)[sP].[LR](C) [sP].[dR](T)[sP].[LR](A)[sP]. [dR](G)[sP].[LR](G)[sP].[dR] (G)[sP].[LR](T)[sP].[LR] ([5meC])}$$$$V2.0 | GACCCTAG AATCAAGG | 3973 | 3988 | 44349095 | 44349110 |
| 245 | TGATTCT AGGGTCA CT | RNA1{[LR](T)[sP].[dR](G)[sP]. [LR](A)[sP].[dR](T)[sP].[LR] (T)[sP].[dR](C)[sP].[dR](T) [sP].[dR](A)[sP].[dR](G)[sP]. [dR](G)[sP].[LR](G)[sP].[dR] (T)[sP].[dR](C)[sP].[dR](A) [sP].[LR]([5meC])[sP].[LR](T) }$$$$V2.0 | AGTGACCC TAGAATCA | 3970 | 3985 | 44349092 | 44349107 |
| 246 | TTCTAGG GTCACTC AG | RNA1{[LR](T)[sP].[LR](T)[sP]. [dR](C)[sP].[dR](T)[sP].[LR] (A)[sP].[dR](G)[sP].[dR](G) [sP].[LR](G)[sP].[dR](T)[sP]. [dR](C)[sP].[LR](A)[sP].[dR] (C)[sP].[LR](T)[sP].[dR](C) [sP].[LR](A)[sP].[LR](G)}$$$$ V2.0 | CTGAGTGA CCCTAGAA | 3967 | 3982 | 44349089 | 44349104 |
| 247 | TAGGGTC ACTCAGT AC | RNA1{[LR](T)[sP].[dR](A)[sP]. [dR](G)[sP].[LR](G)[sP].[dR] (G)[sP].[dR](T)[sP].[LR] ([5meC])[sP].[dR](A)[sP].[dR] (C)[sP].[LR](T)[sP].[dR](C) [sP].[LR](A)[sP].[dR](G)[sP]. [dR](T)[sP].[dR](A)[sP].[LR] ([5meC])}$$$$V2.0 | GTACTGAG TGACCCTA | 3964 | 3979 | 44349086 | 44349101 |
| 248 | GGTCACT CAGTACC CT | RNA1{[LR](G)[sP].[dR](G)[sP]. [dR](T)[sP].[LR]([5meC])[sP]. [dR](A)[sP].[dR](C)[sP].[LR] (T)[sP].[dR](C)[sP].[LR](A) [sP].[dR](G)[sP].[dR](T)[sP]. [LR](A)[sP].[dR](C)[sP].[dR] (C)[sP].[LR]([5meC])[sP].[LR] (T)}$$$$V2.0 | AGGGTACT GAGTGACC | 3961 | 3976 | 44349083 | 44349098 |
| 249 | CACTCAG TACCCTA GC | RNA1{[LR]([5meC])[sP].[dR](A) [sP].[dR](C)[sP].[LR](T)[sP]. [dR](C)[sP].[LR](A)[sP].[dR] (G)[sP].[dR](T)[sP].[LR](A) [sP].[dR](C)[sP].[dR](C)[sP]. [LR]([5meC])[sP].[dR](T)[sP]. [dR](A)[sP].[LR](G)[sP].[LR] ([5meC])}$$$$V2.0 | GCTAGGGT ACTGAGTG | 3958 | 3973 | 44349080 | 44349095 |
| 250 | TCAGTAC CCTAGCC CC | RNA1{[LR](T)[sP].[dR](C)[sP]. [LR](A)[sP].[dR](G)[sP].[dR] (T)[sP].[LR](A)[sP].[dR](C) [sP].[dR](C)[sP].[LR]([5meC]) [sP].[dR](T)[sP].[dR](A)[sP]. | GGGGCTAG GGTACTGA | 3955 | 3970 | 44349077 | 44349092 |

TABLE 2-continued

Compound Table

| SEQ ID NO | Oligo Sequence | Helm sequence | Target sequence | Start position in SEQ ID 276 | End position in SEQ ID 276 | chromo-some start (hg38 assembly) | Chromo-some end (hg38 assembly) |
|---|---|---|---|---|---|---|---|
| | | [LR](G)[sP].[dR](C)[sP].[dR](C)[sP].[LR]([5meC])[sP].[LR]([5meC])}$$$$V2.0 | | | | | |
| 251 | GTACCCTAGCCCCAGG | RNA1{[LR](G)[sP].[dR](T)[sP].[LR](A)[sP].[dR](C)[sP].[dR](C)[sP].[LR]([5meC])[sP].[dR](T)[sP].[dR](A)[sP].[LR](G)[sP].[dR](C)[sP].[dR](C)[sP].[LR]([5meC])[sP].[dR](C)[sP].[dR](A)[sP].[LR](G)[sP].[LR](G)}$$$$V2.0 | CCTGGGGCTAGGGTAC | 3952 | 3967 | 44349074 | 44349089 |
| 252 | CCCTAGCCCCAGGCCA | RNA1{[LR]([5meC])[sP].[dR](C)[sP].[dR](C)[sP].[LR](T)[sP].[dR](A)[sP].[dR](G)[sP].[LR]([5meC])[sP].[dR](C)[sP].[LR]([5meC])[sP].[dR](A)[sP].[dR](G)[sP].[LR](G)[sP].[dR](C)[sP].[LR]([5meC])[sP].[LR](A)}$$$$V2.0 | TGGCCTGGGGCTAGGG | 3949 | 3964 | 44349071 | 44349086 |
| 253 | TAGCCCCAGGCCAAGG | RNA1{[LR](T)[sP].[dR](A)[sP].[dR](G)[sP].[LR]([5meC])[sP].[dR](C)[sP].[dR](C)[sP].[LR]([5meC])[sP].[dR](A)[sP].[dR](G)[sP].[LR](G)[sP].[dR](C)[sP].[dR](C)[sP].[LR](A)[sP].[dR](A)[sP].[LR](G)[sP].[LR](G)}$$$$V2.0 | CCTTGGCCTGGGGCTA | 3946 | 3961 | 44349068 | 44349083 |
| 254 | CCCCAGGCCAAGGTCC | RNA1{[LR]([5meC])[sP].[dR](C)[sP].[dR](C)[sP].[LR]([5meC])[sP].[dR](A)[sP].[dR](G)[sP].[LR](G)[sP].[dR](C)[sP].[dR](C)[sP].[LR](A)[sP].[dR](A)[sP].[dR](G)[sP].[LR](G)[sP].[dR](T)[sP].[LR]([5meC])[sP].[LR]([5meC])}$$$$V2.0 | GGACCTTGGCCTGGGG | 3943 | 3958 | 44349065 | 44349080 |
| 255 | CAGGCCAAGGTCCTGG | RNA1{[LR]([5meC])[sP].[dR](A)[sP].[dR](G)[sP].[LR](G)[sP].[dR](C)[sP].[dR](C)[sP].[LR](A)[sP].[dR](A)[sP].[dR](G)[sP].[LR](G)[sP].[dR](T)[sP].[LR]([5meC])[sP].[dR](C)[sP].[dR](T)[sP].[LR](G)[sP].[LR](G)}$$$$V2.0 | CCAGGACCTTGGCCTG | 3940 | 3955 | 44349062 | 44349077 |
| 256 | GCCAAGGTCCTGGCC | RNA1{[LR](G)[sP].[dR](C)[sP].[dR](C)[sP].[LR](A)[sP].[dR](A)[sP].[dR](G)[sP].[LR](G)[sP].[dR](T)[sP].[LR]([5meC])[sP].[dR](C)[sP].[dR](T)[sP].[LR](G)[sP].[dR](G)[sP].[dR](C)[sP].[LR]([5meC])[sP].[LR]([5meC])}$$$$V2.0 | GGGCCAGGACCTTGGC | 3937 | 3952 | 44349059 | 44349074 |
| 257 | AAGGTCCTGGCCCAGG | RNA1{[LR](A)[sP].[dR](A)[sP].[dR](G)[sP].[LR](G)[sP].[dR](T)[sP].[LR]([5meC])[sP].[dR](C)[sP].[dR](T)[sP].[LR](G)[sP].[dR](G)[sP].[dR](C)[sP].[LR]([5meC])[sP].[dR](C)[sP].[dR](A)[sP].[LR](G)[sP].[LR](G)}$$$$V2.0 | CCTGGGCCAGGACCTT | 3934 | 3949 | 44349056 | 44349071 |
| 258 | GTCCTGGCCCAGGACT | RNA1{[LR](G)[sP].[dR](T)[sP].[dR](C)[sP].[LR]([5meC])[sP].[dR](T)[sP].[dR](G)[sP].[LR](G)[sP].[dR](C)[sP].[dR](C)[sP].[LR]([5meC])[sP].[dR](A) | AGTCCTGGGCCAGGAC | 3931 | 3946 | 44349053 | 44349068 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [sP].[dR](G)[sP].[LR](G)[sP].[dR](A)[sP].[LR]([5meC])[sP].[LR](T)}$$$$V2.0 | | | | | |
| 259 | CTGGCCC AGGACTG CC | RNA1{[LR]([5meC])[sP].[dR](T)[sP].[dR](G)[sP].[LR](G)[sP].[dR](C)[sP].[dR](C)[sP].[LR]([5meC])[sP].[dR](A)[sP].[dR](G)[sP].[LR](G)[sP].[dR](A)[sP].[LR]([5meC])[sP].[dR](T)[sP].[dR](G)[sP].[LR]([5meC])[sP].[LR]([5meC])}$$$$V2.0 | GGCAGTCC TGGGCCAG | 3928 | 3943 | 44349050 | 44349065 |
| 260 | GCCCAGG ACTGCCT GA | RNA1{[LR](G)[sP].[dR](C)[sP].[LR]([5meC])[sP].[dR](C)[sP].[LR](A)[sP].[dR](G)[sP].[dR](G)[sP].[LR](A)[sp].[dR](C)[sP].[dR](T)[sP].[LR](G)[sP].[dR](C)[sP].[LR]([5meC])[sP].[dR](T)[sP].[LR](G)[sP].[LR](A)}$$$$V2.0 | TCAGGCAG TCCTGGGC | 3925 | 3940 | 44349047 | 44349062 |
| 261 | CAGGACT GCCTGAG CC | RNA1{[LR]([5meC])[sP].[dR](A)[sP].[dR](G)[sP].[LR](G)[sP].[dR](A)[sP].[LR](C)[sP].[LR](T)[sP].[dR](G)[sP].[dR](C)[sP].[LR]([5meC])[sP].[dR](T)[sP].[LR](G)[sP].[dR](A)[sP].[dR](G)[sP].[LR]([5meC])[sP].[LR]([5meC])}$$$$V2.0 | GGCTCAGG CAGTCCTG | 3922 | 3937 | 44349044 | 44349059 |
| 262 | GACTGCC TGAGCCT TC | RNA1{[LR](G)[sP].[dR](A)[sP].[dR](C)[sP].[LR](T)[sP].[dR](G)[sP].[dR](C)[sP].[LR]([5meC])[sP].[dR](T)[sP].[LR](G)[sP].[dR](A)[sP].[dR](G)[sP].[LR]([5meC])[sP].[dR](C)[sP].[dR](T)[sP].[LR](T)[sP].[LR]([5meC])}$$$$V2.0 | GAAGGCTC AGGCAGTC | 3919 | 3934 | 44349041 | 44349056 |
| 263 | TGCCTGA GCCTTCT CA | RNA1{[LR](T)[sP].[dR](G)[sP].[dR](C)[sP].[LR]([5meC])[sP].[dR](T)[sP].[LR](G)[sP].[dR](A)[sP].[dR](G)[sP].[LR]([5meC])[sP].[dR](T)[sP].[LR](T)[sP].[dR](C)[sP].[dR](T)[sP].[LR]([5meC])[sP].[LR](A)}$$$$V2.0 | TGAGAAGG CTCAGGCA | 3916 | 3931 | 44349038 | 44349053 |
| 264 | CTGAGCC TTCTCAA CA | RNA1{[LR]([5meC])[sP].[dR](T)[sP].[LR](G)[sP].[dR](A)[sP].[dR](G)[sP].[LR]([5meC])[sP].[dR](C)[sP].[dR](T)[sP].[LR](T)[sP].[dR](C)[sP].[LR](T)[sP].[dR](C)[sP].[LR](A)[sP].[dR](A)[sP].[LR]([5meC])[sP].[LR](A)}$$$$V2.0 | TGTTGAGA AGGCTCAG | 3913 | 3928 | 44349035 | 44349050 |
| 265 | AGCCTTC TCAACAC CT | RNA1{[LR](A)[sP].[dR](G)[sP].[dR](C)[sP].[LR]([5meC])[sP].[dR](T)[sP].[LR](T)[sP].[dR](C)[sP].[LR](T)[sP].[LR](C)[sP].[LR](A)[sP].[dR](A)[sP].[dR](C)[sP].[LR](A)[sP].[dR](C)[sP].[LR]([5meC])[sP].[LR](T)}$$$$V2.0 | AGGTGTTG AGAAGGCT | 3910 | 3925 | 44349032 | 44349047 |
| 266 | CTTCTCA ACACCTC CC | RNA1{[LR]([5meC])[sP].[dR](T)[sP].[LR](T)[sP].[dR](C)[sP].[LR](T)[sP].[dR](C)[sP].[LR](A)[sP].[dR](A)[sp].RJR](C) | GGGAGGTG TTGAGAAG | 3907 | 3922 | 44349029 | 44349044 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [sP].[LR](A)[sP].[dR](C)[sP].[dR](C)[sP].[LR](T)[sP].[dR](C)[sP].[LR]([5meC])[sP].[LR]([5meC])}$$$$V2.0 | | | | | |
| 267 | CTCAACACCTCCCTGT | RNA1{[LR]([5meC])[sP].[dR](T)[sP].[dR](C)[sP].[LR](A)[sP].[dR](A)[sP].[dR](C)[sP].[LR](A)[sP].[dR](C)[sP].[dR](C)[sP].[LR](T)[sP].[dR](C)[sP].[LR]([5meC])[sP].[dR](C)[sP].[dR](T)[sP].[LR](G)[sP].[LR](T)}$$$$V2.0 | ACAGGGAGGTGTTGAG | 3904 | 3919 | 44349026 | 44349041 |
| 268 | AACACCTCCCTGTCCA | RNA1{[LR](A)[sP].[dR](A)[sP].[dR](C)[sP].[LR](A)[sP].[dR](C)[sP].[dR](C)[sP].[LR](T)[sP].[dR](C)[sP].[LR]([5meC])[sP].[dR](C)[sP].[dR](T)[sP].[LR](G)[sP].[dR](T)[sP].[dR](C)[sP].[LR]([5meC])[sP].[LR](A)}$$$$V2.0 | TGGACAGGGAGGTGTT | 3901 | 3916 | 44349023 | 44349038 |
| 269 | ACCTCCCTGTCCAGGC | RNA1{[LR](A)[sP].[dR](C)[sP].[dR](C)[sP].[LR](T)[sP].[dR](C)[sP].[LR]([5meC])[sP].[dR](C)[sP].[dR](T)[sP].[LR](G)[sP].[dR](T)[sP].[dR](C)[sP].[LR]([5meC])[sP].[dR](A)[sP].[LR](G)[sP].[LR](G)[sP].[LR]([5meC])}$$$$V2.0 | GCCTGGACAGGGAGGT | 3898 | 3913 | 44349020 | 44349035 |
| 270 | TCCCTGTCCAGGCAGG | RNA1{[LR](T)[sP].[dR](C)[sP].[LR]([5meC])[sP].[dR](C)[sP].[dR](T)[sP].[LR](G)[sP].[dR](T)[sP].[LR](C)[sP].[LR]([5meC])[sP].[dR](A)[sP].[dR](G)[sP].[LR](G)[sP].[LR](C)[sP].[dR](A)[sP].[LR](G)[sP].[LR](G)}$$$$V2.0 | CCTGCCTGGACAGGGA | 3895 | 3910 | 44349017 | 44349032 |
| 271 | CTGTCCAGGCAGGCAG | RNA11[LR]([5meC])[sP].[dR](T)[sP].[dR](G)[sP].[LR](T)[sP].[dR](C)[sP].[dR](C)[sP].[LR](A)[sP].[dR](G)[sP].[dR](G)[sP].[LR]([5meC])[sP].[dR](A)[sP].[dR](G)[sP].[LR](G)[sP].[dR](C)[sP].[LR](A)[sP].[LR](G)}$$$$V2.0 | CTGCCTGCCTGGACAG | 3892 | 3907 | 44349014 | 44349029 |
| 272 | TCCAGGCAGGCAGAAA | RNA1{[LR](T)[sP].[dR](C)[sP].[dR](C)[sP].[LR](A)[sP].[dR](G)[sP].[dR](G)[sP].[LR]([5meC])[sP].[dR](A)[sP].[dR](G)[sP].[LR](G)[sP].[dR](C)[sP].[LR](A)[sP].[dR](G)[sP].[dR](A)[sP].[LR](A)[sP].[LR](A)}$$$$V2.0 | TTTCTGCCTGCCTGGA | 3889 | 3904 | 44349011 | 44349026 |
| 273 | AGGCAGGCAGAAATCT | RNA1{[LR](A)[sP].[dR](G)[sP].[dR](G)[sP].[LR]([5meC])[sP].[dR](A)[sP].[dR](G)[sP].[LR](G)[sP].[dR](C)[sP].[LR](A)[sP].[dR](G)[sP].[dR](A)[sP].[LR](A)[sP].[dR](A)[sP].[dR](T)[sP].[LR]([5meC])[sP].[LR](T)}$$$$V2.0 | AGATTTCTGCCTGCCT | 3886 | 3901 | 44349008 | 44349023 |
| 274 | CAGGCAGAAATCTGCA | RNA1{[LR]([5meC])[sP].[dR](A)[sP].[dR](G)[sP].[LR](G)[sP].[dR](C)[sP].[dR](A)[sP].[dR](G)[sP].[dR](A)[sP].[LR](A) | TGCAGATTTCTGCCTG | 3883 | 3898 | 44349005 | 44349020 |

TABLE 2-continued

Compound Table

| SEQ ID NO | Oligo Sequence | Helm sequence | Target sequence | Start position in SEQ ID 276 | End position in SEQ ID 276 | chromosome start (hg38 assembly) | Chromosome end (hg38 assembly) |
|---|---|---|---|---|---|---|---|
| | | [sP].[dR](A)[sP].[dR](T)[sP].[LR]([5meC])[sP].[dR](T)[sP].[dR](G)[sP].[LR]([5meC])[sP].[LR](A)}$$$$V2.0 | | | | | |
| 275 | GCAGAAA TCTGCAG GG | RNA1{[LR](G)[sP].[dR](C)[sP].[LR](A)[sP].[dR](G)[sP].[dR](A)[sP].[LR](A)[sP].[dR](A)[sP].[LR](T)[sP].[dR](C)[sP].[dR](T)[sP].[LR](G)[sP].[dR](C)[sP].[LR](A)[sP].[dR](G)[sP].[LR](G)[sP].[LR](G)}$$$$V2.0 | CCCTGCAG ATTTCTGC | 3880 | 3895 | 44349002 | 44349017 |
| 289 | TCAAGAA TGGTGTG GTCC | RNA1{[MOE](T)[sP].[MOE]([5meC])[sP].[MOE](A)[sP].[MOE](A)[sP].[MOE](G)[sP].[MOE](A)[sP].[MOE](A)[sP].[MOE](T)[sP].[MOE](G)[sP].[MOE](G)[sP].[MOE](T)[sP].[MOE](G)[sP].[MOE](T)[sP].[MOE](G)[sP].[MOE](G)[sP].[MOE](T)[sP].[MOE]([5meC])[sP].[MOE]([5meC])}$$$$V2.0 | GGACCACA CCATTCTT GA | 447 | 464 | 44345569 | 44345586 |
| 290 | GGTCAAG AATGGTG TGGT | RNA1{[MOE](G)[sP].[MOE](G)[sP].[MOE](T)[sP].[MOE]([5meC])[sP].[MOE](A)[sP].[MOE](A)[sP].[MOE](G)[sP].[MOE](A)[sP].[MOE](A)[sP].[MOE](T)[sP].[MOE](G)[sP].[MOE](G)[sP].[MOE](T)[sP].[MOE](G)[sP].[MOE](T)[sP].[MOE](G)[sP].[MOE](G)[sP].[MOE](T)}$$$$V2.0 | ACCACACC ATTCTTGA CC | 449 | 466 | 44345571 | 44345588 |

Helm Annotation Key:
[LR](G) is a beta-D-oxy-LNA guanine nucleoside,
[LR](T) is a beta-D-oxy-LNA thymine nucleoside,
[LR](A) is a beta-D-oxy-LNA adenine nucleoside,
[LR]([5meC] is a beta-D-oxy-LNA 5-methyl cytosine nucleoside,
[dR](G) is a DNA guanine nucleoside,
[dR](T) is a DNA thymine nucleoside,
[dR](A) is a DNA adenine nucleoside,
[dR]([C] is a DNA cytosine nucleoside,
[mR](G) is a 2'-O-methyl RNA guanine nucleoside,
[mR](U) is a 2'-O-methyl RNA DNA uracil nucleoside,
[mR](A) is a 2'-O-methyl RNA DNA adenine nucleoside,
[mR]([C) is a 2'-O-methyl RNA DNA cytosine nucleoside,
[MOE](G) is a 2'-MOE RNA guanine nucleoside,
[MOE](T) is a 2'-MOE RNA DNA thymine nucleoside,
[MOE](A) is a 2'-MOE thyl RNA DNA adenine nucleoside,
[MOE]([C) is a 2'-MOE RNA DNA cytosine nucleoside.

We claim:

1. An antisense oligonucleotide consisting of a contiguous nucleotide sequence, which is complementary to a splice regulation site of the human progranulin pre-mRNA transcript, wherein the contiguous nucleotide is SEQ ID NO:134, and wherein the antisense oligonucleotide or contiguous nucleotide sequence thereof comprises one or more modified nucleotides or one or more modified nucleosides.

2. The antisense oligonucleotide according to claim 1, wherein the contiguous nucleotide sequence is complementary to SEQ ID NO:281.

3. The antisense oligonucleotide according to claim 1, wherein the antisense oligonucleotide is or comprises an antisense oligonucleotide mixmer or totalmer.

4. An antisense oligonucleotide having the structure:

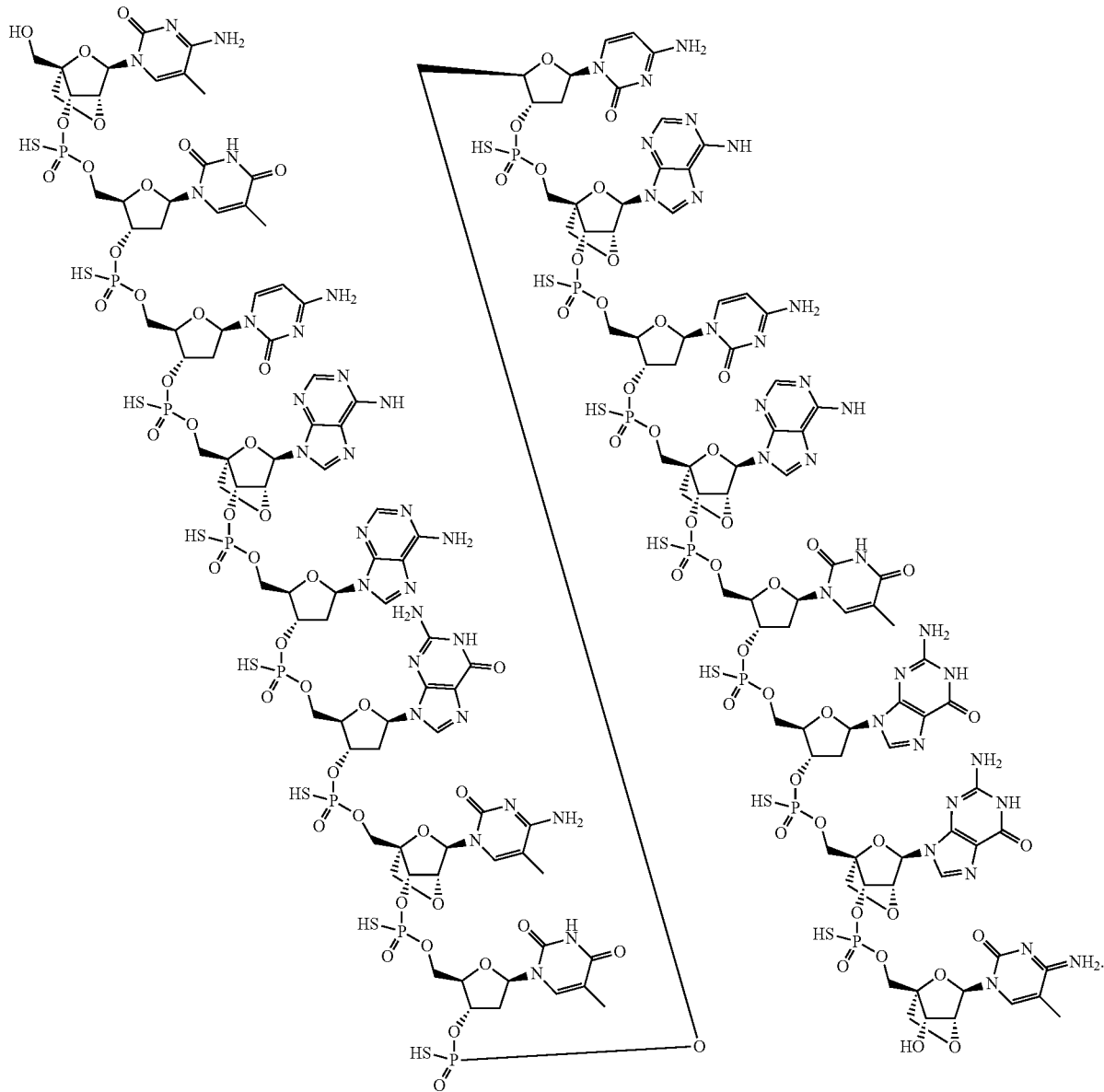

5. An antisense oligonucleotide wherein the oligonucleotide is the oligonucleotide CtcAagCtcAcAtgGC (SEQ ID NO:134) wherein capital letters represent beta-D-oxy LNA nucleosides, lowercase letters represent DNA nucleosides, all LNA C are 5-methyl cytosine, and all internucleoside linkages are phosphorothioate internucleoside linkages.

6. A pharmaceutical composition comprising the antisense oligonucleotide according to claim 1 and a pharmaceutically acceptable diluent, solvent, carrier, salt and/or adjuvant.

7. The antisense oligonucleotide according to claim 1 for use in the treatment of a neurological disease.

8. The antisense oligonucleotide according to claim 1 for use in the treatment of progranulin haploinsufficiency or a related disorder.

9. The pharmaceutical composition according to claim 6 for use in the treatment of a neurological disease.

10. The pharmaceutical composition according to claim 6 for use in the treatment of progranulin haploinsufficiency or a related disorder.

\* \* \* \* \*